US012005054B2

United States Patent
Cheruvallath et al.

(10) Patent No.: US 12,005,054 B2
(45) Date of Patent: Jun. 11, 2024

(54) PIPERIDINYL-3-(ARYLOXY)PROPANAMIDES AND PROPANOATES

(71) Applicant: Takeda Pharmaceutical Company Limited, Osaka (JP)

(72) Inventors: Zacharia Cheruvallath, San Diego, CA (US); Jason Green, San Diego, CA (US); Ben Johnson, San Diego, CA (US); Kristin Schleicher, San Diego, CA (US); Huikai Sun, San Diego, CA (US); Mingnam Tang, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 17/320,574

(22) Filed: May 14, 2021

(65) Prior Publication Data
US 2023/0021834 A1    Jan. 26, 2023

Related U.S. Application Data

(62) Division of application No. 16/289,311, filed on Feb. 28, 2019, now Pat. No. 11,045,457.

(60) Provisional application No. 62/637,295, filed on Mar. 1, 2018.

(51) Int. Cl.
| | |
|---|---|
| *A61K 31/4439* | (2006.01) |
| *A61K 31/40* | (2006.01) |
| *A61K 31/4355* | (2006.01) |
| *A61K 31/438* | (2006.01) |
| *A61K 31/4468* | (2006.01) |
| *A61K 31/4545* | (2006.01) |
| *A61K 31/497* | (2006.01) |
| *A61K 31/501* | (2006.01) |
| *A61K 31/506* | (2006.01) |
| *C07D 207/14* | (2006.01) |
| *C07D 211/58* | (2006.01) |
| *C07D 401/12* | (2006.01) |
| *C07D 401/14* | (2006.01) |
| *C07D 403/12* | (2006.01) |
| *C07D 491/048* | (2006.01) |

(52) U.S. Cl.
CPC .......... *A61K 31/4439* (2013.01); *A61K 31/40* (2013.01); *A61K 31/4355* (2013.01); *A61K 31/438* (2013.01); *A61K 31/4468* (2013.01); *A61K 31/4545* (2013.01); *A61K 31/497* (2013.01); *A61K 31/501* (2013.01); *A61K 31/506* (2013.01); *C07D 207/14* (2013.01); *C07D 211/58* (2013.01); *C07D 401/12* (2013.01); *C07D 401/14* (2013.01); *C07D 403/12* (2013.01); *C07D 491/048* (2013.01)

(58) Field of Classification Search
CPC .. C07D 211/58; C07D 207/14; C07D 401/12; C07D 401/14; C07D 403/12; C07D 491/048; A61K 31/4468; A61K 31/4439; A61K 31/4355; A61K 31/4545; A61K 31/497; A61K 31/501; A61K 31/506
See application file for complete search history.

(56) References Cited

U.S. PATENT DOCUMENTS

| | | | |
|---|---|---|---|
| 6,903,085 B1 | 6/2005 | Thom et al. | |
| 11,045,457 B2 * | 6/2021 | Cheruvallath | ....... C07D 207/14 |
| 2016/0221948 A1 * | 8/2016 | Fusano | .................. A61P 25/00 |
| 2017/0002001 A1 | 1/2017 | Zhu et al. | |
| 2017/0320838 A1 | 11/2017 | Mazzaferro et al. | |

FOREIGN PATENT DOCUMENTS

| | | |
|---|---|---|
| EP | 3045448 A1 | 7/2016 |
| JP | 2007169270 A | 7/2007 |
| WO | 2001014333 A1 | 3/2001 |

(Continued)

OTHER PUBLICATIONS

Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Gastambide et al., Hippocampal SSTR4 somatostatin receptors control the selection of memory strategies, Psychopharmacology, 202:153-163 (2009).*
Patel et al., Schizophrenia: Overview and Treatment Options, Pharmacy and Therapeutics (P&T), vol. 39, No. 9, pp. 638-645 (2014).*
Lally et al., Antipsychotic medication in schizophrenia: a review, British Medical Bulletin, 114:169-179 (2015).*

(Continued)

*Primary Examiner* — Deepak R Rao
(74) *Attorney, Agent, or Firm* — Honigman LLP; Lucy X. Yang; Jonathan P. O'Brien

(57) ABSTRACT

Disclosed are compounds of Formula 1,

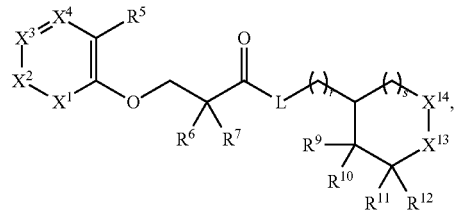

stereoisomers thereof, and pharmaceutically acceptable salts thereof, wherein L, r, s, $R^5$, $R^6$, $R^7$, $R^9$, $R^{10}$, $R^{11}$, $R^{12}$, $X^1$, $X^2$, $X^3$, $X^4$, $X^{13}$, and $X^{14}$ are defined in the specification. This disclosure also relates to materials and methods for preparing compounds of Formula 1, to pharmaceutical compositions which contain them, and to their use for treating diseases, disorders, and conditions associated with SSTR4.

19 Claims, No Drawings

(56) References Cited

FOREIGN PATENT DOCUMENTS

| WO | 2005115977 A1 | 12/2005 |
| WO | 2006091697 A1 | 8/2006 |
| WO | 2006128803 A1 | 12/2006 |
| WO | 2009026422 A2 | 2/2009 |
| WO | 2009114173 A1 | 9/2009 |
| WO | 2010059922 A1 | 5/2010 |
| WO | 2011026917 A1 | 3/2011 |
| WO | 2014184275 A1 | 11/2014 |
| WO | 2015037716 A1 | 3/2015 |
| WO | 2016075240 A1 | 5/2016 |
| WO | 2017003723 A1 | 1/2017 |

OTHER PUBLICATIONS

Borzsei et al., Exploration of Somatostatin Binding Mechanism to Somatostatin Receptor Subtype 4, International Journal of Molecular Sciences, 23, 6878, pp. 1-17 (2022).*

Kantas et al., In Silico, In Vitro and In Vivo Pharmacodynamic Characterization of Novel Analgesic Drug Candidate Somatostatin SST4 Receptor Agonists, Frontiers in Pharmacology, vol. 11, Article 601887, pp. 1-13 (2021).*

* cited by examiner

PIPERIDINYL-3-(ARYLOXY)PROPANAMIDES AND PROPANOATES

FIELD OF THE INVENTION

This invention relates to piperidinyl-3-(aryloxy)propanamide and propanoate derivatives which are modulators of somatostatin receptor 4 (SSTR4), to pharmaceutical compositions which contain them, and to their use to treat diseases, disorders, and conditions associated with SSTR4, including Alzheimer's disease.

BACKGROUND OF THE INVENTION

Somatostatin receptor 4 (SSTR4) is a G-protein coupled receptor for the peptide somatostatin. SSTR4 is coupled with Gi, inhibitory G protein, which inhibits production of cyclic AMP. SSTR4 is abundantly expressed in the central nervous system (CNS) and to a lesser extent in the dorsal root ganglia and intestine. See M. A. Meyer, "Highly Expressed Genes within Hippocampal Sector CA1: Implications for the Physiology of Memory," *Neurology International* 6(2):5388 (2014). SSTR4 is highly conserved among different species. For example, human, mouse, and rat SSTR4 protein sequences share greater than 87% identity at the amino acid level. These factors—predominant expression in the brain and high degree of sequence homology across different species—suggest that SSTR4 has an important role in physiology.

Experiments using bacTRAP technology indicate SSTR4 has its strongest expression in the pyramidal neurons in the cortex and in the CA1 region of the hippocampus. This CNS expression is conserved in humans, non-human primates, and mice. The hippocampus is important for learning and memory. See L. R. Squire and A. J. Dede, "Conscious and Unconscious Memory Systems," *Cold Spring Harbor Perspectives in Biology* 7:a021667 (2015). Indeed, the CA1 region of the hippocampus is the last station in the trisynaptic circuit that governs learning. This circuit starts in the entorhinal cortex, which also contains SSTR4, extends into the dentate gyrus, then into CA3, and finally reaches the CA1 region of the hippocampus. CA1 projects out of the hippocampus through the subiculum. This circuit encodes all types of information from the external world in order to generate memories and to learn new knowledge.

Alzheimer's disease is characterized by degeneration of neurons within this circuitry, mainly in the entorhinal cortex and CA1 region of the hippocampus. See A. Serrano-Pozo et al., "Neuropathological Alterations in Alzheimer Disease," *Cold Spring Harbor Perspectives in Medicine* 1:a006189 (2011). In addition, hippocampal sst4 appears to selectively control the use of cognitive strategies by switching from hippocampus-based multiple associations to simple striatum-based behavioral responses. See F. Gastambide et al., "Hippocampal SSTR4 Somatostatin Receptors Control the Selection of Memory Strategies," *Psychopharmacology (Berl)* 202(1-3):153-63 (2009). This finding provides a strong basis for using SSTR4 agonists as a pharmacological approach to improve striatum-based learning. Id.

Moreover, recent studies also point to hyperactivity of the hippocampus as a main driver for disease progression as well as impairment of cognitive abilities in Alzheimer's patients. See M. A. Busche et al., "Decreased Amyloid-β and Increased Neuronal Hyperactivity by Immunotherapy in Alzheimer's Models," *Nature Neuroscience* 18(12):1725-27 (2015); see also K. Yamamoto et al., "Chronic Optogenetic Activation Augments A3 Pathology in a Mouse Model of Alzheimer Disease," *Cell Reports* 11(6):859-65 (2015). Activation of SSTR4 receptor has been shown to play a role in controlling neuronal activity. See C. Qiu et al., "Somatostatin Receptor Subtype 4 Couples to the M-Current to Regulate Seizures," *Journal of Neuroscience* 28(14):3567-76 (2008). Thus agonists for the receptor will likely represent good pharmacological tools to inhibit and control neuronal activity in the cortex and hippocampus.

SSTR4 agonists are expected to be useful for treating Alzheimer's disease and other CNS disorders such as epilepsy and depression.

SUMMARY OF THE INVENTION

This invention provides piperidinyl-3-(aryloxy)propanamide and propanoate derivatives and pharmaceutically acceptable salts thereof. This invention also provides pharmaceutical compositions that contain the piperidinyl-3-(aryloxy)propanamide and propanoate derivatives and provides for their use to treat diseases, disorders and conditions associated with SSTR4, including Alzheimer's disease and other CNS disorders.

One aspect of the invention provides compounds of Formula 1:

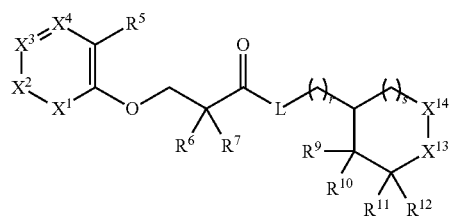

or a pharmaceutically acceptable salt thereof in which:
$X^1$ is selected from N and $CR^1$;
$X^2$ is selected from N and $CR^2$;
$X^3$ is selected from N and $CR^3$; and
$X^4$ is selected from N and $CR^4$, provided no more than two of $X^1$, $X^2$, $X^3$, and $X^4$ are N;
$X^{13}$ is $NR^{13}$ and $X^{14}$ is $CR^{15}R^{16}$ or $X^{13}$ is $CH_2$ and $X^{14}$ is $NR^{14}$;
L is selected from $NR^8$ and O;
r is selected from 0 and 1;
s is selected from 0 and 1;
$R^1$, $R^2$, and $R^3$ are each independently selected from
   (a) hydrogen, halo, hydroxy, and cyano; and
   (b) $C_{1-4}$ alkyl, $C_{3-6}$ cycloalkyl, and $C_{1-4}$ alkoxy, each substituted with 0 to 3 optional substituents independently selected from halo;
$R^4$ is selected from
   (a) hydrogen, halo, hydroxy, and cyano; and
   (b) $C_{1-4}$ alkyl, $C_{3-6}$ cycloalkyl, and $C_{1-4}$ alkoxy, each substituted with 0 to 3 optional substituents independently selected from halo;
$R^5$ is selected from
   (a) hydrogen, halo, hydroxy, and cyano; and
   (b) $C_{1-4}$ alkyl, $C_{3-6}$ cycloalkyl, and $C_{1-4}$ alkoxy, each substituted with 0 to 3 optional substituents independently selected from halo, oxo, and phenyl which is substituted with 0 to 3 optional substituents independently selected from halo; or
$R^4$ and $R^5$, together with the carbon atoms to which they are attached, form a cyclopent-1-en-1,2-diyl or a furan-2,3-diyl;

$R^6$ and $R^7$ are each independently selected from halo and $C_{1-3}$ alkyl, or $R^6$ and $R^7$, together with the carbon atom to which they are attached, form a $C_{3-4}$ cycloalkan-1,1-diyl;

$R^8$ is selected from H and $C_{1-4}$ alkyl;

$R^9$ and $R^{10}$ are each independently selected from
  (a) hydrogen, halo, hydroxy, and cyano;
  (b) $C_{1-4}$ alkyl, $C_{3-6}$ cycloalkyl, and $C_{1-4}$ alkoxy, each substituted with 0 to 3 optional substituents independently selected from halo; and
  (c) phenyl and $C_{1-5}$ heteroaryl, each substituted with 0 to 3 optional substituents independently selected from halo, $C_{1-4}$ alkyl, and $C_{1-4}$ alkoxy, wherein the $C_{1-5}$ heteroaryl substituent is a monocyclic ring with 5 to 6 ring members in which 1 to 4 ring members are heteroatoms, each of the heteroatoms independently selected from N, O, and S, provided no more than one of the ring members is O or S, and wherein the $C_{1-4}$ alkyl and $C_{1-4}$ alkoxy optional substituents on phenyl and $C_{1-5}$ heteroaryl are each independently substituted with 0 to 3 optional substituents independently selected from halo; or $R^9$ and $R^{10}$, together with the carbon atom to which they are attached, form a $C_{3-4}$ cycloalkan-1,1-diyl;

$R^{11}$ and $R^{12}$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo; or $R^{11}$ and $R^{12}$, together with the carbon atom to which they are attached, form a $C_{3-4}$ cycloalkan-1,1-diyl;

$R^{13}$ and $R^{14}$ are each independently selected from
  (a) hydrogen; and
  (b) $C_{1-4}$ alkyl, which is substituted with 0 to 3 optional substituents independently selected from cyano, oxo, and phenyl which is substituted with 0 to 3 optional substituents independently selected from halo; and $R^{15}$ and $R^{16}$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo; or $R^{15}$ and $R^{16}$, together with the carbon atom to which they are attached, form a $C_{3-4}$ cycloalkan-1,1-diyl.

Another aspect of the invention provides a compound which is selected from the group of compounds described in the examples and their pharmaceutically acceptable salts.

A further aspect of the invention provides a pharmaceutical composition which includes a compound of Formula 1 or a pharmaceutically acceptable salt thereof, or any one of the compounds or pharmaceutically acceptable salts defined in the preceding paragraph; and a pharmaceutically acceptable excipient.

An additional aspect of the invention provides a compound of Formula 1 or a pharmaceutically acceptable salt thereof, or any one of the compounds and pharmaceutically acceptable salts defined in the preceding paragraphs, for use as a medicament.

Another aspect of the invention provides a compound of Formula 1 or a pharmaceutically acceptable salt thereof, or any one of the compounds or pharmaceutically acceptable salts defined in the preceding paragraphs, for treatment of a disease, disorder or condition associated with SSTR4.

A further aspect of the invention provides a use of a compound of Formula 1 or a pharmaceutically acceptable salt thereof, or any one of the compounds or pharmaceutically acceptable salts defined in the preceding paragraphs, for the manufacture of a medicament for the treatment of a disease, disorder or condition associated with SSTR4.

An additional aspect of the invention provides a method of treating a disease, disorder or condition associated with SSTR4, the method comprising administering to the subject an effective amount of a compound of Formula 1 or a pharmaceutically acceptable salt thereof, or any one of the compounds or pharmaceutically acceptable salts defined in the preceding paragraphs.

Another aspect of the invention provides a method of treating a disease, disorder or condition in a subject, the method comprising administering to the subject an effective amount of a compound of Formula 1 or a pharmaceutically acceptable salt thereof, or any one of the compounds or pharmaceutically acceptable salts defined in the preceding paragraphs, wherein the disease, disorder or condition is selected from Alzheimer's disease, depression, anxiety, schizophrenia, bipolar disorder, autism, epilepsy, pain, and hyperactivity disorder.

A further aspect of the invention provides an effective amount of a compound of Formula 1 or a pharmaceutically acceptable salt thereof, or any one of the compounds or pharmaceutically acceptable salts defined in the preceding paragraphs; and at least one additional pharmacologically active agent.

DETAILED DESCRIPTION OF THE INVENTION

Unless otherwise indicated, this disclosure uses definitions provided below.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided that valence requirements are met and that a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-4}$ alkyl refers to an alkyl group having 1 to 4 (i.e., 1, 2, 3 or 4) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkanediyl" refers to divalent alkyl groups, where alkyl is defined above, and generally having a specified number of carbon atoms (e.g., $C_{1-4}$ alkanediyl refers to an alkanediyl group having 1 to 4 (i.e., 1, 2, 3 or 4) carbon atoms, $C_{1-6}$ alkanediyl refers to an alkanediyl group having 1 to 6 carbon atoms, and so on). Examples of alkanediyl groups include methylene, ethane-1,1-diyl, ethane-1,2-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, isobutane-1,3-diyl, isobutane-1,1-diyl, isobutane-1,2-diyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, 1-fluoroethyl, 1,1-difluoroethyl, 1-chloroethyl, 1,1-dichloroethyl, 1-fluoro-1-methylethyl, 1-chloro-1-methylethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements, and where indicated, may optionally include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkanediyl" refers to divalent cycloalkyl groups, where cycloalkyl is defined above, and generally having a specified number of carbon atoms (e.g., $C_{3-4}$ cycloalkanediyl refers to a cycloalkanediyl group having 3 to 4 (i.e., 3 or 4) carbon atoms, $C_{3-6}$ cycloalkanediyl refers to a cycloalkanediyl group having 3 to 6 carbon atoms, and so on). Examples of cycloalkanediyl groups include cyclopropan-1,1-diyl, cyclopropan-1,2-diyl, cyclobutan-1,1-diyl, cyclobutan-1,2-diyl, and the like.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom, and where indicated, may optionally include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom, and where indicated, may optionally include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-6}$ heterocyclyl refers to a heterocyclyl group having 2 to 6 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached through any ring atom, and where indicated, may optionally include one or more non-hydrogen substituents unless such attachment or substitution would violate valence requirements or result in a chemically unstable compound. Examples of heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothienyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6- dihydropyrimidinyl, 1,2,3,4-tetrahydropyrimidinyl, and 1,2-dihydropyrazolo[1,5-d][1,2,4]triazinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-6}$ heterocycle-diyl refers to a heterocycle-diyl group having 2 to 6 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom (or ring atoms for fused rings), and where indicated, may optionally include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thienyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothienyl, benzo[c]thienyl, 1H-indolyl, 3H-indolyl, isoindolyl, 1H-isoindolyl, indolinyl, isoindolinyl, benzimidazolyl, 1H-indazolyl, 2H-indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, benzo[d]thiazolyl, 2,3-dihydro-1H-pyrrolo[2,3-b]pyridinyl, [1,2,4]triazolo[1,5-a]pyridinyl, 2,3-dihydro-1H-imidazo[4,5-b]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-a]pyrazinyl, imidazo[1,2-b]pyridazinyl, and 4,5,6,7-tetrahydropyrazolo[1,5-a]pyrazinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and OH can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with SSTR4" and similar phrases relate to a disease, disorder or condition in a subject for which activation of SSTR4 may provide a therapeutic or prophylactic benefit.

The following abbreviations may be used in the specification: Ac (acetyl); ACN (acetonitrile); AIBN (azo-bisisobutyronitrile); API (active pharmaceutical ingredient); aq (aqueous); BINAP (2,2'-bis(diphenylphosphino)-1,1'-binaphthyl); Boc (tert-butoxycarbonyl); Cbz (carbobenzyloxy); dba (dibenzylideneacetone); DCC (1,3-dicyclohexylcarbodiimide); DCE (1,1-dichloroethane); DCM (dichloromethane); DIAD (diisopropyl azodicarboxylate); DIPEA (N,N-diisopropylethylamine, Hünig's Base); DMA (N,N-dimethylacetamide); DMAP (4-dimethylaminopyridine); DME (1,2-dimethoxyethane); DMF (N,N-dimethylformamide); DMSO (dimethylsulfoxide); dppf (1,1'-bis(diphenylphosphino)ferrocene); DTT (dithiothreitol); $EC_{50}$ (effective concentration at half maximal response); EDA (ethoxylated dodecyl alcohol, Brj®35); EDC (N-(3-dimethylaminopropyl)-N'-ethylcarbodiimide); EDTA (ethylenediaminetetraacetic acid); ee (enantiomeric excess); eq (equivalents); Et (ethyl); $Et_3N$ (triethylamine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); AcOH (acetic acid); HOBt (1H-benzo[d][1,2,3]triazol-1-ol); $IC_{50}$ (concentration at 50% inhibition); IPA (isopropanol); IPAc (isopropyl acetate); IPE (isopropylether); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMM (N-methylmorpholine); NMP (N-methyl-pyrrolidone); OTf (triflate); PE (petroleum ether); Ph (phenyl); $pEC_{50}$ ($-log_{10}$ ($EC_{50}$), where $EC_{50}$ is given in molar (M) units); $pIC_{50}$ ($-log_{10}(IC_{50})$, where $IC_{50}$ is given in molar (M) units); Pr (propyl); c-Pr (cyclopropyl), i-Pr (isopropyl); PTFE (polytetrafluoroethylene); RT (room temperature, approximately 20° C. to 25° C.); T3P (2,4,6-tripropyl-1,3,5,2,4,6-trioxatriphosphinane 2,4,6-trioxide); TCEP (tris(2-carboxyethyl)phosphine); TFA (trifluoroacetic acid); TFAA (2,2,2-trifluoroacetic anhydride); THE (tetrahydrofuran); TMS (trimethylsilyl); and Tris buffer (2-amino-2-hydroxymethylpropane-1,3-diol buffer).

As described, below, this disclosure concerns compounds of Formula 1 and their pharmaceutically acceptable salts. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating diseases, disorders or conditions of the CNS, including Alzheimer's disease, and other diseases, disorders or conditions associated with SSTR4.

The compounds of Formula 1 include those in which (1):
$X^1$ is selected from N and $CR^1$;
$X^2$ is selected from N and $CR^2$;
$X^3$ is selected from N and $CR^3$; and
$X^4$ is selected from N and $CR^4$, provided no more than two of $X^1$, $X^2$, $X^3$, and $X^4$ are N;
$X^{13}$ is $NR^{13}$ and $X^{14}$ is $CR^{15}R^{16}$ or $X^{13}$ is $CH_2$ and $X^{14}$ is $NR^{14}$;
L is selected from $NR^8$ and O;
r is selected from 0 and 1;
s is selected from 0 and 1;
$R^1$, $R^2$, and $R^3$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo;
$R^4$ is selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo;
$R^5$ is selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo, oxo, and phenyl which is substituted with 0 to 3 optional substituents independently selected from halo; or
$R^4$ and $R^5$, together with the carbon atoms to which they are attached, form a cyclopent-1-en-1,2-diyl or a furan-2,3-diyl;
$R^6$ and $R^7$ are each independently selected from halo and $C_{1-3}$ alkyl, or $R^6$ and $R^7$, together with the carbon atom to which they are attached, form a $C_{3-4}$ cycloalkan-1,1-diyl;
$R^8$ is selected from H and $C_{1-4}$ alkyl;
$R^9$ and $R^{10}$ are each independently selected from
  (a) hydrogen, halo, hydroxy, and cyano;
  (b) $C_{1-4}$ alkyl, $C_{3-6}$ cycloalkyl, and $C_{1-4}$ alkoxy, each substituted with 0 to 3 optional substituents independently selected from halo; and
  (c) phenyl and $C_{1-5}$ heteroaryl, each substituted with 0 to 3 optional substituents independently selected from halo, $C_{1-4}$ alkyl, and $C_{1-4}$ alkoxy, wherein the $C_{1-5}$ heteroaryl substituent is a monocyclic ring with 5 to 6 ring members in which 1 to 4 ring members are heteroatoms, each of the heteroatoms independently selected from N, O, and S, provided no more than one of the ring members is O or S, and wherein the $C_{1-4}$ alkyl and $C_{1-4}$ alkoxy optional substituents on phenyl and $C_{1-5}$ heteroaryl are each independently substituted with 0 to 3 optional substituents independently selected from halo; or $R^9$ and $R^{10}$, together with the carbon atom to which they are attached, form a $C_{3-4}$ cycloalkan-1,1-diyl;

$R^{11}$ and $R^{12}$ are each independently selected from
(a) hydrogen, halo, hydroxy, and cyano; and
(b) $C_{1-4}$ alkyl, $C_{3-6}$ cycloalkyl, and $C_{1-4}$ alkoxy, each substituted with 0 to 3 optional substituents independently selected from halo; or $R^{11}$ and $R^{12}$, together with the carbon atom to which they are attached, form a $C_{3-4}$ cycloalkan-1,1-diyl;

$R^{13}$ and $R^{14}$ are each independently selected from
(a) hydrogen; and
(b) $C_{1-4}$ alkyl, which is substituted with 0 to 3 optional substituents independently selected from cyano, oxo, and phenyl which is substituted with 0 to 3 optional substituents independently selected from halo; and $R^{15}$ and $R^{16}$ are each independently selected from
(a) hydrogen, halo, hydroxy, and cyano; and
(b) $C_{1-4}$ alkyl, $C_{3-6}$ cycloalkyl, and $C_{1-4}$ alkoxy, each substituted with 0 to 3 optional substituents independently selected from halo; or $R^{15}$ and $R^{16}$, together with the carbon atom to which they are attached, form a $C_{3-4}$ cycloalkan-1,1-diyl.

In addition to embodiment (1) in the preceding paragraph, the compounds of Formula 1 include those in which (2) $X^1$ is $CR^1$, $X^2$ is $CR^2$, $X^3$ is $CR^3$, and $X^4$ is $CR^4$.

In addition to embodiment (2) in the preceding paragraph, compounds of Formula 1 include those in which:

(3) $R^1$, $R^2$, $R^3$, and $R^4$ are each independently selected from
(a) hydrogen, halo, hydroxy, and cyano; and
(b) $C_{1-4}$ alkyl, $C_{3-6}$ cycloalkyl, and $C_{1-4}$ alkoxy, each substituted with 0 to 3 optional substituents independently selected from halo;

(4) $R^1$, $R^2$, $R^3$, and $R^4$ are each independently selected from
(a) hydrogen, halo, and cyano; and
(b) $C_{1-4}$ alkyl, $C_{3-6}$ cycloalkyl, and $C_{1-4}$ alkoxy, each substituted with 0 to 3 optional substituents independently selected from halo;

(5) $R^1$, $R^2$, $R^3$, and $R^4$ are each independently selected from
(a) hydrogen, halo, and cyano; and
(b) $C_{1-4}$ alkyl and $C_{3-6}$ cycloalkyl, each substituted with 0 to 3 optional substituents independently selected from halo;

(6) $R^1$, $R^2$, $R^3$, and $R^4$ are each independently selected from
(a) hydrogen, halo, and cyano; and
(b) methyl and cyclopropyl, each substituted with 0 to 3 optional substituents independently selected from halo;

(7) $R^1$, $R^2$, $R^3$, and $R^4$ are each independently selected from hydrogen, halo, cyano, methyl, trifluoromethyl, and cyclopropyl;

(8) $R^1$, $R^2$, $R^3$, and $R^4$ are each independently selected from hydrogen, fluoro, chloro, bromo, cyano, methyl, trifluoromethyl, and cyclopropyl;

(9) $R^1$ and $R^2$ are each independently selected from hydrogen and methyl; and
$R^3$ and $R^4$ are each independently selected from hydrogen, fluoro, chloro, bromo, cyano, methyl, trifluoromethyl, and cyclopropyl;

(10) each of $R^1$, $R^2$, $R^3$ and $R^4$ is hydrogen; or

(11) $R^4$ and $R^5$, together with the carbon atoms to which they are attached, form a cyclopent-1-en-1,2-diyl or a furan-2,3-diyl.

In addition to embodiment (1), the compounds of Formula 1 include those in which (12) $X^1$ is N, $X^2$ is $CR^2$, $X^3$ is $CR^3$, and $X^4$ is $CR^4$.

In addition to embodiment (12) in the preceding paragraph, compounds of Formula 1 include those in which:

(13) $R^2$, $R^3$, and $R^4$ are each independently selected from
(a) hydrogen, halo, hydroxy, and cyano; and
(b) $C_{1-4}$ alkyl, $C_{3-6}$ cycloalkyl, and $C_{1-4}$ alkoxy, each substituted with 0 to 3 optional substituents independently selected from halo;

(14) $R^2$, $R^3$, and $R^4$ are each independently selected from
(a) hydrogen, halo, and cyano; and
(b) $C_{1-4}$ alkyl, $C_{3-6}$ cycloalkyl, and $C_{1-4}$ alkoxy, each substituted with 0 to 3 optional substituents independently selected from halo;

(15) $R^2$, $R^3$, and $R^4$ are each independently selected from
(a) hydrogen, halo, and cyano; and
(b) $C_{1-4}$ alkyl and $C_{3-6}$ cycloalkyl, each substituted with 0 to 3 optional substituents independently selected from halo;

(16) $R^2$, $R^3$, and $R^4$ are each independently selected from
(a) hydrogen, halo, and cyano; and
(b) methyl and cyclopropyl, each substituted with 0 to 3 optional substituents independently selected from halo;

(17) $R^2$, $R^3$, and $R^4$ are each independently selected from hydrogen, halo, cyano, methyl, trifluoromethyl, and cyclopropyl;

(18) $R^2$, $R^3$, and $R^4$ are each independently selected from hydrogen, fluoro, chloro, bromo, cyano, methyl, trifluoromethyl, and cyclopropyl;

(19) $R^2$ is selected from hydrogen and methyl; and
$R^3$ and $R^4$ are each independently selected from hydrogen, fluoro, chloro, bromo, cyano, methyl, trifluoromethyl, and cyclopropyl;

(20) each of $R^2$, $R^3$ and $R^4$ is hydrogen; or

(21) $R^4$ and $R^5$, together with the carbon atoms to which they are attached, form a cyclopent-1-en-1,2-diyl or a furan-2,3-diyl.

In addition to embodiment (1), the compounds of Formula 1 include those in which (22) $X^1$ is $CR^1$, $X^2$ is N, $X^3$ is $CR^3$, and $X^4$ is $CR^4$.

In addition to embodiment (22) in the preceding paragraph, compounds of Formula 1 include those in which:

(23) $R^1$, $R^3$, and $R^4$ are each independently selected from
(a) hydrogen, halo, hydroxy, and cyano; and
(b) $C_{1-4}$ alkyl, $C_{3-6}$ cycloalkyl, and $C_{1-4}$ alkoxy, each substituted with 0 to 3 optional substituents independently selected from halo;

(24) $R^1$, $R^3$, and $R^4$ are each independently selected from
(a) hydrogen, halo, and cyano; and
(b) $C_{1-4}$ alkyl, $C_{3-6}$ cycloalkyl, and $C_{1-4}$ alkoxy, each substituted with 0 to 3 optional substituents independently selected from halo;

(25) $R^1$, $R^3$, and $R^4$ are each independently selected from
(a) hydrogen, halo, and cyano; and
(b) $C_{1-4}$ alkyl and $C_{3-6}$ cycloalkyl, each substituted with 0 to 3 optional substituents independently selected from halo;

(26) $R^1$, $R^3$, and $R^4$ are each independently selected from
(a) hydrogen, halo, and cyano; and
(b) methyl and cyclopropyl, each substituted with 0 to 3 optional substituents independently selected from halo;

(27) $R^1$, $R^3$, and $R^4$ are each independently selected from hydrogen, halo, cyano, methyl, trifluoromethyl, and cyclopropyl;

(28) $R^1$, $R^3$, and $R^4$ are each independently selected from hydrogen, fluoro, chloro, bromo, cyano, methyl, trifluoromethyl, and cyclopropyl;
(29) $R^1$ is selected from hydrogen and methyl; and
$R^3$ and $R^4$ are each independently selected from hydrogen, fluoro, chloro, bromo, cyano, methyl, trifluoromethyl, and cyclopropyl;
(30) each of $R^1$, $R^3$ and $R^4$ is hydrogen; or
(31) $R^4$ and $R^5$, together with the carbon atoms to which they are attached, form a cyclopent-1-en-1,2-diyl or a furan-2,3-diyl.

In addition to embodiment (1), the compounds of Formula 1 include those in which (32) $X^1$ is $CR^1$, $X^2$ is $CR^2$, $X^3$ is N, and $X^4$ is $CR^4$.

In addition to embodiment (32) in the preceding paragraph, compounds of Formula 1 include those in which:
(33) $R^1$, $R^2$, and $R^4$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo;
(34) $R^1$, $R^2$, and $R^4$ are each independently selected from
  (a) hydrogen, halo, and cyano; and
  (b) $C_{1-4}$ alkyl, $C_{3-6}$ cycloalkyl, and $C_{1-4}$ alkoxy, each substituted with 0 to 3 optional substituents independently selected from halo;
(35) $R^1$, $R^2$, and $R^4$ are each independently selected from
  (a) hydrogen, halo, and cyano; and
  (b) $C_{1-4}$ alkyl and $C_{3-6}$ cycloalkyl, each substituted with 0 to 3 optional substituents independently selected from halo;
(36) $R^1$, $R^2$, and $R^4$ are each independently selected from
  (a) hydrogen, halo, and cyano; and
  (b) methyl and cyclopropyl, each substituted with 0 to 3 optional substituents independently selected from halo;
(37) $R^1$, $R^2$, and $R^4$ are each independently selected from hydrogen, halo, cyano, methyl, trifluoromethyl, and cyclopropyl;
(38) $R^1$, $R^2$, and $R^4$ are each independently selected from hydrogen, fluoro, chloro, bromo, cyano, methyl, trifluoromethyl, and cyclopropyl;
(39) $R^1$ and $R^2$ are each independently selected from hydrogen and methyl; and
$R^4$ is selected from hydrogen, fluoro, chloro, bromo, cyano, methyl, trifluoromethyl, and cyclopropyl;
(40) each of $R^1$, $R^2$, and $R^4$ is hydrogen; or
(41) $R^4$ and $R^5$, together with the carbon atoms to which they are attached, form a cyclopent-1-en-1,2-diyl or a furan-2,3-diyl.

In addition to embodiment (1), the compounds of Formula 1 include those in which (42) $X^1$ is $CR^1$, $X^2$ is $CR^2$, $X^3$ is $CR^3$, and $X^4$ is N.

In addition to embodiment (42) in the preceding paragraph, compounds of Formula 1 include those in which:
(43) $R^1$, $R^2$, and $R^3$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo;
(44) $R^1$, $R^2$, and $R^3$ are each independently selected from
  (a) hydrogen, halo, and cyano; and
  (b) $C_{1-4}$ alkyl, $C_{3-6}$ cycloalkyl, and $C_{1-4}$ alkoxy, each substituted with 0 to 3 optional substituents independently selected from halo;
(45) $R^1$, $R^2$, and $R^3$ are each independently selected from
  (a) hydrogen, halo, and cyano; and
  (b) $C_{1-4}$ alkyl and $C_{3-6}$ cycloalkyl, each substituted with 0 to 3 optional substituents independently selected from halo;
(46) $R^1$, $R^2$, and $R^3$ are each independently selected from
  (a) hydrogen, halo, and cyano; and
  (b) methyl and cyclopropyl, each substituted with 0 to 3 optional substituents independently selected from halo;
(47) $R^1$, $R^2$, and $R^3$ are each independently selected from hydrogen, halo, cyano, methyl, trifluoromethyl, and cyclopropyl;
(48) $R^1$, $R^2$, and $R^3$ are each independently selected from hydrogen, fluoro, chloro, bromo, cyano, methyl, trifluoromethyl, and cyclopropyl;
(49) $R^1$ and $R^2$ are each independently selected from hydrogen and methyl; and
$R^3$ is selected from hydrogen, fluoro, chloro, bromo, cyano, methyl, trifluoromethyl, and cyclopropyl; or
(50) each of $R^1$, $R^2$, and $R^3$ is hydrogen.

In addition to embodiment (1), the compounds of Formula 1 include those in which (51) $X^1$ is N, $X^2$ is N, $X^3$ is $CR^3$, and $X^4$ is $CR^4$.

In addition to embodiment (51) in the preceding paragraph, compounds of Formula 1 include those in which:
(52) $R^3$ and $R^4$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo;
(53) $R^3$ and $R^4$ are each independently selected from
  (a) hydrogen, halo, and cyano; and
  (b) $C_{1-4}$ alkyl, $C_{3-6}$ cycloalkyl, and $C_{1-4}$ alkoxy, each substituted with 0 to 3 optional substituents independently selected from halo;
(54) $R^3$ and $R^4$ are each independently selected from
  (a) hydrogen, halo, and cyano; and
  (b) $C_{1-4}$ alkyl and $C_{3-6}$ cycloalkyl, each substituted with 0 to 3 optional substituents independently selected from halo;
(55) $R^3$ and $R^4$ are each independently selected from
  (a) hydrogen, halo, and cyano; and
  (b) methyl and cyclopropyl, each substituted with 0 to 3 optional substituents independently selected from halo;
(56) $R^3$ and $R^4$ are each independently selected from hydrogen, halo, cyano, methyl, trifluoromethyl, and cyclopropyl;
(57) $R^3$ and $R^4$ are each independently selected from hydrogen, fluoro, chloro, bromo, cyano, methyl, trifluoromethyl, and cyclopropyl;
(58) $R^3$ and $R^4$ are each independently selected from hydrogen, fluoro, chloro, bromo, cyano, methyl, trifluoromethyl, and cyclopropyl;
(59) $R^3$ and $R^4$ is hydrogen; or
(60) $R^4$ and $R^5$, together with the carbon atoms to which they are attached, form a cyclopent-1-en-1,2-diyl or a furan-2,3-diyl.

In addition to embodiment (1), the compounds of Formula 1 include those in which (61) $X^1$ is N, $X^2$ is $CR^2$, $X^3$ is N, and $X^4$ is $CR^4$.

In addition to embodiment (61) in the preceding paragraph, compounds of Formula 1 include those in which:
(62) $R^2$ and $R^4$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo;

(63) $R^2$ and $R^4$ are each independently selected from
  (a) hydrogen, halo, and cyano; and
  (b) $C_{1-4}$ alkyl, $C_{3-6}$ cycloalkyl, and $C_{1-4}$ alkoxy, each substituted with 0 to 3 optional substituents independently selected from halo;
(64) $R^2$ and $R^4$ are each independently selected from
  (a) hydrogen, halo, and cyano; and
  (b) $C_{1-4}$ alkyl and $C_{3-6}$ cycloalkyl, each substituted with 0 to 3 optional substituents independently selected from halo;
(65) $R^2$ and $R^4$ are each independently selected from
  (a) hydrogen, halo, and cyano; and
  (b) methyl and cyclopropyl, each substituted with 0 to 3 optional substituents independently selected from halo;
(66) $R^2$ and $R^4$ are each independently selected from hydrogen, halo, cyano, methyl, trifluoromethyl, and cyclopropyl;
(67) $R^2$ and $R^4$ are each independently selected from hydrogen, fluoro, chloro, bromo, cyano, methyl, trifluoromethyl, and cyclopropyl;
(68) $R^2$ is selected from hydrogen and methyl; and
  $R^4$ is selected from hydrogen, fluoro, chloro, bromo, cyano, methyl, trifluoromethyl, and cyclopropyl;
(69) each of $R^2$ and $R^4$ is hydrogen; or
(70) $R^4$ and $R^5$, together with the carbon atoms to which they are attached, form a cyclopent-1-en-1,2-diyl or a furan-2,3-diyl.

In addition to embodiment (1), the compounds of Formula 1 include those in which (71) $X^1$ is N, $X^2$ is $CR^2$, $X^3$ is $CR^3$, and $X^4$ is N.

In addition to embodiment (71) in the preceding paragraph, compounds of Formula 1 include those in which:
(72) $R^2$ and $R^3$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo;
(73) $R^2$ and $R^3$ are each independently selected from
  (a) hydrogen, halo, and cyano; and
  (b) $C_{1-4}$ alkyl, $C_{3-6}$ cycloalkyl, and $C_{1-4}$ alkoxy, each substituted with 0 to 3 optional substituents independently selected from halo;
(74) $R^2$ and $R^3$ are each independently selected from
  (a) hydrogen, halo, and cyano; and
  (b) $C_{1-4}$ alkyl and $C_{3-6}$ cycloalkyl, each substituted with 0 to 3 optional substituents independently selected from halo;
(75) $R^2$ and $R^3$ are each independently selected from
  (a) hydrogen, halo, and cyano; and
  (b) methyl and cyclopropyl, each substituted with 0 to 3 optional substituents independently selected from halo;
(76) $R^2$ and $R^3$ are each independently selected from hydrogen, halo, cyano, methyl, trifluoromethyl, and cyclopropyl;
(77) $R^2$ and $R^3$ are each independently selected from hydrogen, fluoro, chloro, bromo, cyano, methyl, trifluoromethyl, and cyclopropyl;
(78) $R^2$ is selected from hydrogen and methyl; and
  $R^3$ is selected from hydrogen, fluoro, chloro, bromo, cyano, methyl, trifluoromethyl, and cyclopropyl; or
(79) each of $R^2$ and $R^3$ is hydrogen.

In addition to embodiment (1), the compounds of Formula 1 include those in which (80) $X^1$ is $CR^1$, $X^2$ is N, $X^3$ is N, and $X^4$ is $CR^4$.

In addition to embodiment (80) in the preceding paragraph, compounds of Formula 1 include those in which:
(81) $R^1$ and $R^4$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo;
(82) $R^1$ and $R^4$ are each independently selected from
  (a) hydrogen, halo, and cyano; and
  (b) $C_{1-4}$ alkyl, $C_{3-6}$ cycloalkyl, and $C_{1-4}$ alkoxy, each substituted with 0 to 3 optional substituents independently selected from halo;
(83) $R^1$ and $R^4$ are each independently selected from
  (a) hydrogen, halo, and cyano; and
  (b) $C_{1-4}$ alkyl and $C_{3-6}$ cycloalkyl, each substituted with 0 to 3 optional substituents independently selected from halo.
(84) $R^1$ and $R^4$ are each independently selected from
  (a) hydrogen, halo, and cyano; and
  (b) methyl and cyclopropyl, each substituted with 0 to 3 optional substituents independently selected from halo;
(85) $R^1$ and $R^4$ are each independently selected from hydrogen, halo, cyano, methyl, trifluoromethyl, and cyclopropyl;
(86) $R^1$ and $R^4$ are each independently selected from hydrogen, fluoro, chloro, bromo, cyano, methyl, trifluoromethyl, and cyclopropyl;
(87) $R^1$ is selected from hydrogen and methyl; and
  $R^4$ is selected from hydrogen, fluoro, chloro, bromo, cyano, methyl, trifluoromethyl, and cyclopropyl;
(88) each of $R^1$ and $R^4$ is hydrogen; or
(89) $R^4$ and $R^5$, together with the carbon atoms to which they are attached, form a cyclopent-1-en-1,2-diyl or a furan-2,3-diyl.

In addition to embodiment (1), the compounds of Formula 1 include those in which (90) $X^1$ is $CR^1$, $X^2$ is N, $X^3$ is $CR^3$, and $X^4$ is N.

In addition to embodiment (90) in the preceding paragraph, compounds of Formula 1 include those in which:
(91) $R^1$ and $R^3$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo;
(92) $R^1$ and $R^3$ are each independently selected from
  (a) hydrogen, halo, and cyano; and
  (b) $C_{1-4}$ alkyl, $C_{3-6}$ cycloalkyl, and $C_{1-4}$ alkoxy, each substituted with 0 to 3 optional substituents independently selected from halo;
(93) $R^1$ and $R^3$ are each independently selected from
  (a) hydrogen, halo, and cyano; and
  (b) $C_{1-4}$ alkyl and $C_{3-6}$ cycloalkyl, each substituted with 0 to 3 optional substituents independently selected from halo;
(94) $R^1$ and $R^3$ are each independently selected from
  (a) hydrogen, halo, and cyano; and
  (b) methyl and cyclopropyl, each substituted with 0 to 3 optional substituents independently selected from halo;
(95) $R^1$ and $R^3$ are each independently selected from hydrogen, halo, cyano, methyl, trifluoromethyl, and cyclopropyl;
(96) $R^1$ and $R^3$ are each independently selected from hydrogen, fluoro, chloro, bromo, cyano, methyl, trifluoromethyl, and cyclopropyl;
(97) $R^1$ is selected from hydrogen and methyl; and R³ is selected from hydrogen, fluoro, chloro, bromo, cyano, methyl, trifluoromethyl, and cyclopropyl; or
(98) each of R¹ and R³ is hydrogen.

In addition to embodiment (1), the compounds of Formula 1 include those in which (99) $X^1$ is $CR^1$, $X^2$ is $CR^2$, $X^3$ is N, and $X^4$ is N.

In addition to embodiment (99) in the preceding paragraph, compounds of Formula 1 include those in which:
(100) R¹ and R² are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo;
(101) R¹ and R² are each independently selected from
  (a) hydrogen, halo, and cyano; and
  (b) $C_{1-4}$ alkyl, $C_{3-6}$ cycloalkyl, and $C_{1-4}$ alkoxy, each substituted with 0 to 3 optional substituents independently selected from halo;
(102) R¹ and R² are each independently selected from
  (a) hydrogen, halo, and cyano; and
  (b) $C_{1-4}$ alkyl and $C_{3-6}$ cycloalkyl, each substituted with 0 to 3 optional substituents independently selected from halo;
(103) R¹ and R² are each independently selected from
  (a) hydrogen, halo, and cyano; and
  (b) methyl and cyclopropyl, each substituted with 0 to 3 optional substituents independently selected from halo;
(104) R¹ and R² are each independently selected from hydrogen, halo, cyano, methyl, trifluoromethyl, and cyclopropyl;
(105) R¹ and R² are each independently selected from hydrogen, fluoro, chloro, bromo, cyano, methyl, trifluoromethyl, and cyclopropyl;
(106) R¹ and R² are each independently selected from hydrogen and methyl; or
(107) each of R¹ and R² is hydrogen.

In addition, or as an alternative, to one of embodiments (1) through (107) in the preceding paragraphs, compounds of Formula 1 include those in which:
(108) R⁵ is selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo, oxo, and phenyl which is substituted with 0 to 3 optional substituents independently selected from halo;
(109) R⁵ is selected from
  (a) halo and cyano; and
  (b) $C_{1-4}$ alkyl, $C_{3-6}$ cycloalkyl, and $C_{1-4}$ alkoxy, each substituted with 0 to 3 optional substituents independently selected from halo;
(110) R⁵ is selected from
  (a) fluoro, chloro, bromo, and cyano; and
  (b) methyl, ethyl, propyl, isopropyl, cyclopropyl, methoxy, ethoxy, propoxy, and isopropoxy, each substituted with 0 to 3 optional substituents independently selected from halo;
(111) R⁵ is selected from
  (a) fluoro, chloro, bromo, and cyano; and
  (b) methyl, ethyl, cyclopropyl, methoxy, and ethoxy, each substituted with 0 to 3 optional substituents independently selected from fluoro;
(112) R⁵ is selected from fluoro, chloro, bromo, cyano, methyl, ethyl, cyclopropyl, methoxy, ethoxy, fluoromethyl, difluoromethyl, trifluoromethyl, fluoromethoxy, difluoromethoxy, and trifluoromethoxy;
(113) R⁵ is selected from chloro, methyl, ethyl, cyclopropyl, trifluoromethyl, and trifluoromethoxy; or
(114) R⁵ is selected from methyl, cyclopropyl, trifluoromethyl, and trifluoromethoxy.

In addition, or as an alternative, to one of embodiments (1) through (114) in the preceding paragraphs, compounds of Formula 1 include those in which:
(115) R⁶ and R⁷ are each independently selected from fluoro and methyl or together with the carbon atom to which they are attached form a cyclopropan-1,1-diyl or a cyclobutan-1,1-diyl;
(116) R⁶ and R⁷ are both fluoro or both methyl or together with the carbon atom to which they are attached form a cyclopropan-1,1-diyl or a cyclobutan-1,1-diyl;
(117) R⁶ and R⁷ are both methyl; or
(118) R⁶ and R⁷ are both fluoro.

In addition, or as an alternative, to one of embodiments (1) through (118) in the preceding paragraphs, compounds of Formula 1 include those in which (119) L is $NR^8$.

In addition to embodiment (119) in the preceding paragraph, compounds of Formula 1 include those in which:
(120) R⁸ is selected from hydrogen and methyl; or
(121) R⁸ is hydrogen.

In addition, or as an alternative, to one of embodiments (1) through (118) in the preceding paragraphs, compounds of Formula 1 include those in which (122) L is O.

In addition, or as an alternative, to one of embodiments (1) through (122) in the preceding paragraphs, compounds of Formula 1 include those in which:
(123) R⁹ and R¹⁰ are each independently selected from
  (a) hydrogen, halo, hydroxy, and cyano;
  (b) $C_{1-4}$ alkyl, $C_{3-6}$ cycloalkyl, and $C_{1-4}$ alkoxy, each substituted with 0 to 3 optional substituents independently selected from halo; and
  (c) phenyl and $C_{1-5}$ heteroaryl, each substituted with 0 to 3 optional substituents independently selected from halo, $C_{1-4}$ alkyl, and $C_{1-4}$ alkoxy, wherein the $C_{1-5}$ heteroaryl substituent is a monocyclic ring with 5 to 6 ring members in which 1 to 4 ring members are heteroatoms, each of the heteroatoms independently selected from N, O, and S, provided no more than one of the ring members is O or S, and wherein the $C_{1-4}$ alkyl and $C_{1-4}$ alkoxy optional substituents on phenyl and $C_{1-5}$ heteroaryl are each independently substituted with 0 to 3 optional substituents independently selected from halo;
(124) R⁹ and R¹⁰ are each independently selected from
  (a) hydrogen and halo;
  (b) $C_{1-4}$ alkyl and $C_{1-4}$ alkoxy, each substituted with 0 to 3 optional substituents independently selected from halo; and
  (c) phenyl and $C_{1-5}$ heteroaryl, each substituted with 0 to 3 optional substituents independently selected from halo and $C_{1-4}$ alkyl, wherein the $C_{1-5}$ heteroaryl substituent is a monocyclic ring with 5 to 6 ring members in which 1 or 2 ring members are heteroatoms, each of the heteroatoms being N, and wherein the $C_{1-4}$ alkyl optional substituents on phenyl and $C_{1-5}$ heteroaryl are each independently substituted with 0 to 3 optional substituents independently selected from halo;
(125) R⁹ and R¹⁰ are each independently selected from
  (a) hydrogen and halo;
  (b) $C_{1-4}$ alkyl and $C_{1-4}$ alkoxy, each substituted with 0 to 3 optional substituents independently selected from halo; and (c) phenyl, pyridinyl, and pyrazolyl, each substituted with 0 to 3 optional substituents independently selected from halo and $C_{1-4}$ alkyl which is substituted with 0 to 3 optional substituents independently selected from halo;

(126) $R^9$ and $R^{10}$ are each independently selected from
- (a) hydrogen and halo;
- (b) methyl, ethyl, propyl, isopropyl, methoxy, and ethoxy, each substituted with 0 to 3 optional substituents independently selected from halo; and
- (c) phenyl, pyridinyl, and pyrazolyl, each substituted with 0 to 3 optional substituents independently selected from halo and methyl which is substituted with 0 to 3 optional substituents independently selected from halo;

(127) $R^9$ and $R^{10}$ are each independently selected from
- (a) hydrogen, fluoro, and chloro;
- (b) methyl, ethyl, propyl, isopropyl, methoxy, and ethoxy; and
- (c) phenyl, pyridinyl, and pyrazolyl, each substituted with 0 to 3 optional substituents independently selected from fluoro, chloro, and methyl which is substituted with 0 to 3 optional substituents independently selected from fluoro;

(128) $R^9$ and $R^{10}$ are selected from hydrogen, halo, and $C_{1-4}$ alkyl;

(129) $R^9$ and $R^{10}$ are the same and are selected from hydrogen, fluoro, and methyl;

(130) $R^9$ and $R^{10}$ is hydrogen;

(131) $R^9$ and $R^{10}$, together with the carbon atom to which they are attached, form a $C_{3-4}$ cycloalkan-1,1-diyl; or (132) $R^9$ and $R^{10}$, together with the carbon atom to which they are attached, form a cyclopropan-1,1-diyl.

In addition, or as an alternative, to one of embodiments (1) through (132) in the preceding paragraphs, compounds of Formula 1 include those in which:

(133) $R^{11}$ and $R^{12}$ are each independently selected from
- (a) hydrogen, halo, hydroxy, and cyano; and
- (b) $C_{1-4}$ alkyl, $C_{3-6}$ cycloalkyl, and $C_{1-4}$ alkoxy, each substituted with 0 to 3 optional substituents independently selected from halo;

(134) $R^{11}$ and $R^{12}$ are each independently selected from hydrogen and $C_{1-4}$ alkyl which is substituted with 0 to 3 optional substituents independently selected from halo;

(135) $R^{11}$ and $R^{12}$ are each independently selected from hydrogen and $C_{1-4}$ alkyl;

(136) $R^{11}$ and $R^{12}$ are each independently selected from hydrogen, methyl, and ethyl;

(137) $R^{11}$ and $R^{12}$ are the same and are selected from hydrogen, halo, and $C_{1-4}$ alkyl;

(138) $R^{11}$ and $R^{12}$ are the same and are selected from hydrogen and methyl;

(139) $R^{11}$ and $R^{12}$ is hydrogen;

(140) $R^{11}$ and $R^{12}$, together with the carbon atom to which they are attached, form a $C_{3-4}$ cycloalkan-1,1-diyl; or (141) $R^{11}$ and $R^{12}$, together with the carbon atom to which they are attached, form a cyclopropan-1,1-diyl.

In addition, or as an alternative, to one of embodiments (1) through (141) in the preceding paragraphs, compounds of Formula 1 include those in which (142) $X^{13}$ is $NR^{13}$ and $X^{14}$ is $CR^{15}R^{16}$.

In addition to embodiment (142) in the preceding paragraph, compounds of Formula 1 include those in which:

(143) $R^{13}$ is selected from
- (a) hydrogen; and
- (b) $C_{1-4}$ alkyl, which is substituted with 0 to 3 optional substituents independently selected from cyano, oxo, and phenyl which is substituted with 0 to 3 optional substituents independently selected from halo;

(144) $R^{13}$ is selected from hydrogen and $C_{1-4}$ alkyl which is substituted with 0 to 3 optional substituents independently selected from cyano, oxo, and phenyl which is substituted with 0 to 1 optional substituents independently selected from halo;

(145) $R^{13}$ is selected from hydrogen, methyl, cyanomethyl, and benzoylmethyl which is substituted with 0 to 1 optional substituents independently selected from halo;

(146) $R^{13}$ is selected from hydrogen, methyl, cyanomethyl, and chlorobenzoylmethyl;

(147) $R^{13}$ is selected from hydrogen and methyl; or (148) $R^{13}$ is methyl.

In addition, or as an alternative, to one of embodiments (142) through (148) in the preceding paragraphs, compounds of Formula 1 include those in which:

(149) $R^{15}$ and $R^{16}$ are each independently selected from
- (a) hydrogen, halo, hydroxy, and cyano; and
- (b) $C_{1-4}$ alkyl, $C_{3-6}$ cycloalkyl, and $C_{1-4}$ alkoxy, each substituted with 0 to 3 optional substituents independently selected from halo;

(150) $R^{15}$ and $R^{16}$ are each independently selected from hydrogen and $C_{1-4}$ alkyl which is substituted with 0 to 3 optional substituents independently selected from halo;

(151) $R^{15}$ and $R^{16}$ are each independently selected from hydrogen, methyl, and ethyl;

(152) $R^{15}$ and $R^{16}$ is hydrogen;

(153) $R^{15}$ and $R^{16}$, together with the carbon atom to which they are attached, form a $C_{3-4}$ cycloalkan-1,1-diyl; or (154) $R^{15}$ and $R^{16}$, together with the carbon atom to which they are attached, form a cyclobutan-1,1-diyl.

In addition, or as an alternative, to one of embodiments (1) through (141) in the preceding paragraphs, compounds of Formula 1 include those in which (155) $X^{13}$ is $CH_2$ and $X^{14}$ is $NR^{14}$.

In addition to embodiment (155) in the preceding paragraph, compounds of Formula 1 include those in which:

(156) $R^{14}$ is selected from
- (a) hydrogen; and
- (b) $C_{1-4}$ alkyl, which is substituted with 0 to 3 optional substituents independently selected from cyano, oxo, and phenyl which is substituted with 0 to 3 optional substituents independently selected from halo;

(157) $R^{14}$ is selected from hydrogen and $C_{1-4}$ alkyl; or (158) $R^{14}$ is $C_{1-4}$ alkyl.

In addition, or as an alternative, to one of embodiments (1) through (158) in the preceding paragraphs, compounds of Formula 1 include those in which:

(159) r is 0; or (160) r is 1.

In addition, or as an alternative, to one of embodiments (1) through (160) in the preceding paragraphs, compounds of Formula 1 include those in which:

(161) s is 0; or (162) s is 1.

Compounds of Formula 1 include embodiments (1) through (162) described in the preceding paragraphs and all compounds specifically named in the examples, and may exist as salts, complexes, solvates, hydrates, and liquid crystals. Likewise, compounds of Formula 1 that are salts may exist as complexes, solvates, hydrates, and liquid crystals.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8):1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., —$COO^-Na^+$, —$COO^-K^+$, —$SO_3^-Na^+$) or polar non-ionic moiety (such as —$N^-N^+(CH_3)_3$). See, e.g., N. H. Hartshorne and A. Stuart, *Crystals and the Polarizing Microscope* (4th ed, 1970).

Each compound of Formula 1 may exist as polymorphs, stereoisomers, tautomers, or some combination thereof, may be isotopically-labeled, may result from the administration of a prodrug, or form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., Bioreversible Carriers in Drug Design (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 may exist as stereoisomers that result from the presence of one or more stereogenic centers, one or more double bonds, or both. The stereoisomers may be pure, substantially pure, or mixtures. Such stereoisomers may also result from acid addition or base salts in which the counter-ion is optically active, for example, when the counter-ion is D-lactate or L-lysine.

Compounds of Formula 1 may exist as tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2$H and $^3$H; isotopes of carbon, such as $^{11}$C, $^{13}$C and $^{14}$C; isotopes of nitrogen, such as $^{13}$N and $^{15}$N; isotopes of oxygen, such as $^{15}$O, $^{17}$O and $^{18}$O; isotopes of sulfur, such as $^{35}$S; isotopes of fluorine, such as $^{18}$F; isotopes of chlorine, such as $^{36}$Cl, and isotopes of iodine, such as $^{123}$I and $^{125}$I. Use of isotopic variations (e.g., deuterium, $^2$H) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{18}$F, $^{15}$O and $^{13}$N, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure and claims to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane, cyclohexane, methylcyclohexane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the schemes, below, substituent identifiers (L, r, s, $R^5$, $R^6$, $R^7$, $R^9$, $R^{10}$, $R^{11}$, $R^{12}$, $X^1$, $X^2$, $X^3$, $X^4$, $X^{13}$, and $X^{14}$) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include $X^{13}$ substituent having a potentially reactive amine. In such cases, $X^{13}$ would include the moiety with or without, say, a Boc or Cbz group attached to the amine.

Scheme A shows a general method for preparing compounds of Formula 1 when L is $NR^8$ (Formula 1A). In accordance with the method, a propanoic acid derivative (A1) is reacted with a piperidinylamine (A2, r=0) or piperidinylmethanamine (A2, r=1) in which $X^{13}$=$NR^{13}$ and $X^{14}$=$CR^{15}R^{16}$ or $X^{13}$=$CH_2$ and $X^{14}$=$NR^{14}$ and both $R^{13}$ and $R^{14}$ are non-H. The reaction is carried out using standard amide coupling agents, such as HATU, DCC, EDC hydrochloride, T3P or 2-chloro-1-methylpyridin-1-ium iodide, in the presence of a non-nucleophilic base (e.g., Et$_3$N, DIPEA) and one or more compatible polar solvents (e.g. DCM, DMA, DMF, TIF). The amide coupling may be carried out at temperatures which range from room temperature to about 80° C. HOBt may be used to facilitate the reaction. Though not shown in Scheme A, the propanamide (Formula 1A, $R^8$=H) may be reacted with an alkyl halide (e.g., $R^8$I, $R^8$=$C_{1-4}$ alkyl) in the presence of a strong non-nucleophilic base (e.g. NaH) and a compatible polar aprotic solvent (e.g. DMF) to give an N-alkyl propanamide (Formula 1A, $R^8$=$C_{1-4}$ alkyl).

Scheme A

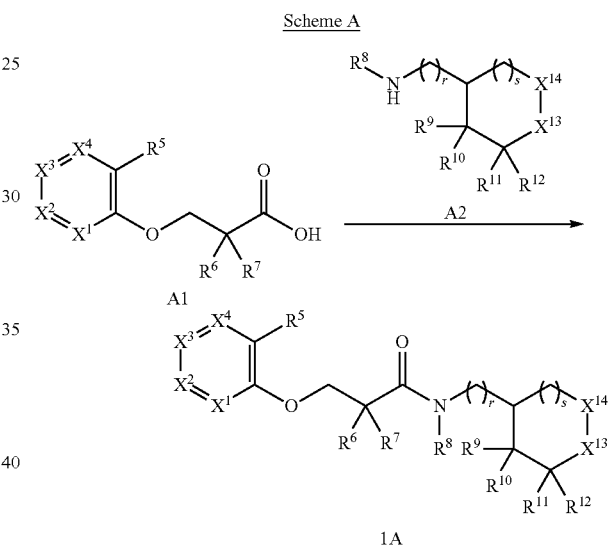

1A

Scheme B also shows a general method for preparing compounds of Formula 1 when L is $NR^8$ (Formula 1A). In accordance with the method, a propanoic acid derivative (A1) is reacted with a piperidinylamine (B1 or B2, r=0) or piperidinylmethanamine (B1 or B2, r=1) in which PG is an amine protective group, such as Boc or Cbz. The amide coupling is carried out using reagents and conditions described in Scheme A, to give a protected piperidinyl or piperidinylmethyl propanamide (B3 or B4). Following removal of PG, the de-protected piperidine derivative (B5 or B6) may be reacted with an alkyl aldehyde ($B^7$ or $B^8$) in the presence of a mild reducing agent, such as sodium cyanoborohydride or sodium triacetoxyborohydride, and a compatible solvent (e.g., DCM, MeOH) to give the compound of Formula 1A. The propanamide (Formula 1A, $R^8$=H) may be reacted with an alkyl halide (e.g., $R^8$I, $R^8$=$C_{1-4}$ alkyl) in the presence of a strong non-nucleophilic base (e.g. NaH) and a compatible polar aprotic solvent (e.g. DMF) to give an N-alkyl propanamide (Formula 1A, $R^8$=$C_{1-4}$ alkyl).

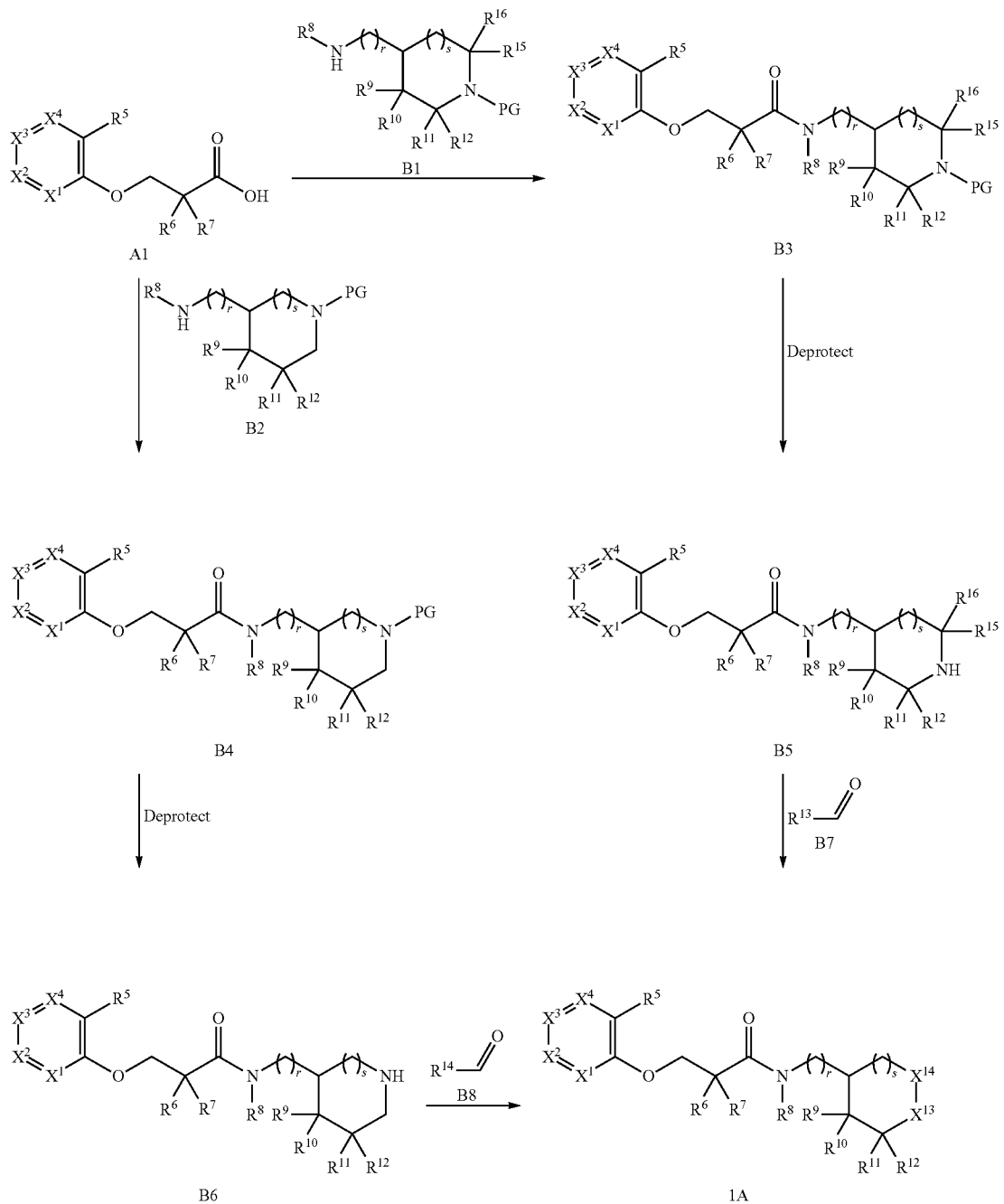

Scheme C shows a general method for preparing compounds of Formula 1 when L is O (Formula 1). In accordance with the method, a propanoic acid derivative (A1) is reacted with a hydroxypiperidine (C1, r=0) or hydroxymethylpiperidine (C1, r=1) in which $X^{13}$=$NR^{13}$ and $X^{14}$=$CR^{15}R^{16}$ or $X^{13}$=$CH_2$ and $X^{14}$=$NR^{14}$ and both $R^{13}$ and $R^{14}$ are non-H. The reaction is carried out in the presence of DCC, catalytic amount of DMAP, and one or more compatible polar solvents (e.g. DCM, DMA, DMF) at about room temperature to give the piperidinyl or piperidinylmethyl propanoate (Formula 1).

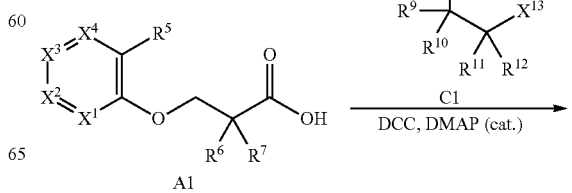

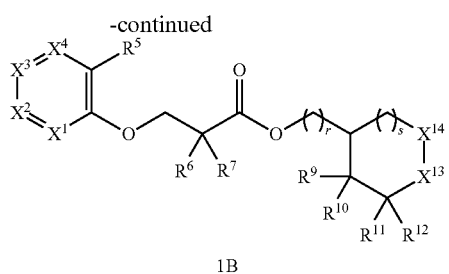

1B

Scheme D shows a method for preparing compounds of Formula 1 when L is O. In accordance with the method, a propanoic acid derivative (A1) is reacted with a hydroxypiperidine (D1 or D2, r=0) or hydroxymethylpiperidine D1 or D2, r=1) in which PG is an amine protective group, such as Boc or Cbz. The reaction is carried out in the presence of DCC, catalytic amount of DMAP, and one or more compatible polar solvents (e.g. DCM, DMA, DMF). The esterification is typically carried out at room temperature and gives a protected piperidinyl or piperidinylmethyl propanaoate (D3 or D4). Following removal of PG, the de-protected piperidine derivative (D5 or D6) may be reacted with an alkyl aldehyde ($B^7$ or $B^8$) in the presence of a mild reducing agent, such as sodium cyanoborohydride or sodium triacetoxyborohydride, and a compatible solvent (e.g., DCM, MeOH) to give the compound of Formula 1B.

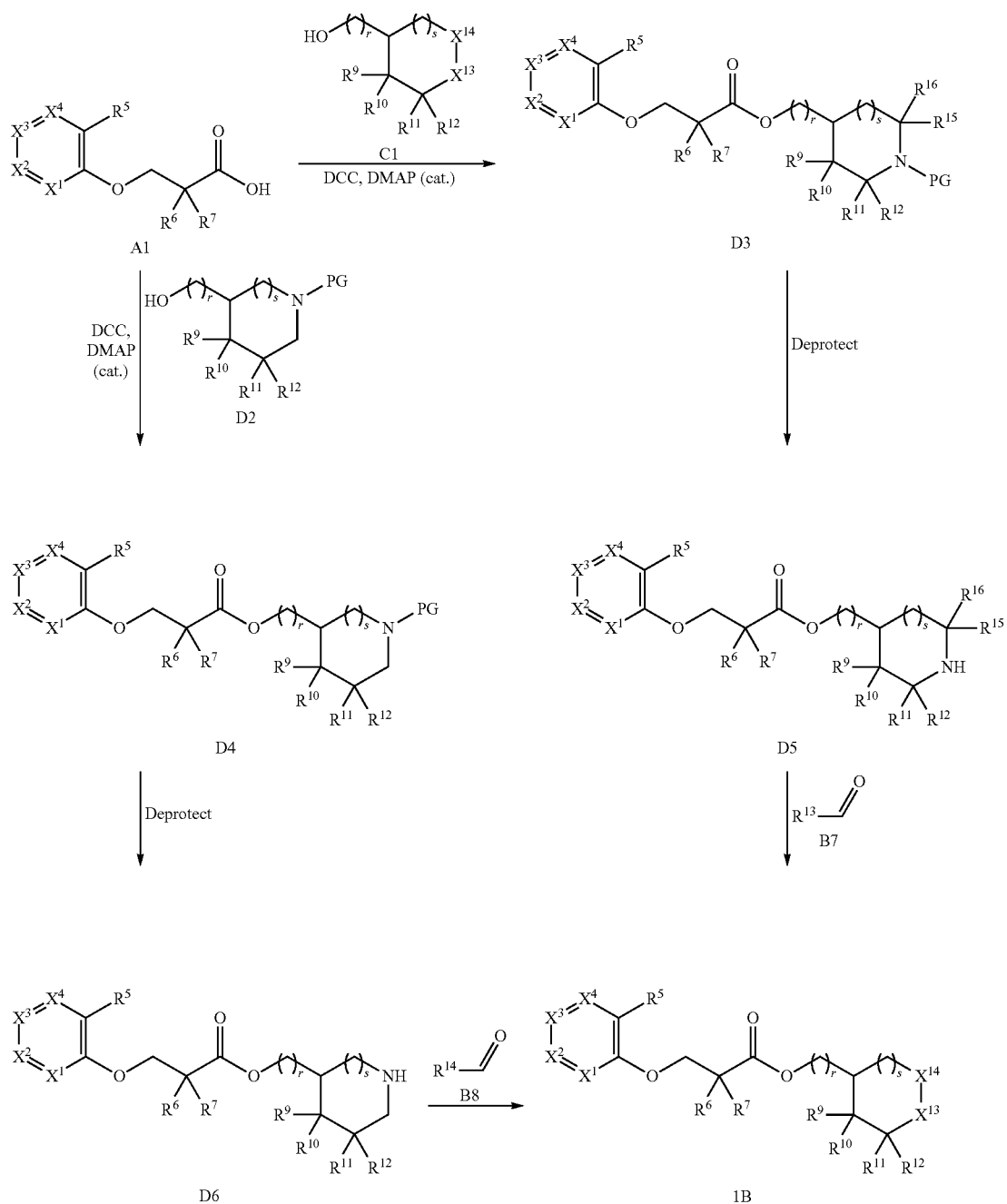

Scheme E shows a general method for preparing compounds of Formula 1. In accordance with the method, an alcohol (E1) is first treated with a strong base (e.g., NaH) in the present of a compatible solvent (e.g. DMF, THF) and then reacted with an aryl or heteroaryl halide (E2, $R^{17}$=halo) which includes a nitrogen ring atom or electron withdrawing group ortho or para to $R^{17}$. The first step is typically carried out at a temperature from 0° C. to room temperature, and the second step is typically carried out at room temperature to about 80° C. The alcohol (E1) includes a piperidinyl moiety in which $X^{13}$=$NR^{13}$ and $X^{14}$=$CR^{15}R^{16}$ or $X^{13}$=$CH_2$ and $X^{14}$=$NR^{14}$ and both $R^{13}$ and $R^{14}$ are non-H. Alternatively, the piperidinyl moiety may include an amine protective group (e.g., Boc or Cbz) which is subsequently removed to give the compound of Formula 1 in which $R^{13}$ or $R^{14}$ is H. In addition, the product (Formula 1, $R^8$=H) may be reacted with an alkyl halide (e.g., $R^8$I, $R^8$=$C_{1-4}$ alkyl) in the presence of a strong non-nucleophilic base (e.g. NaH) and a compatible polar aprotic solvent (e.g. DMF) to give an N-alkyl propanamide (Formula 1, $R^8$=$C_{1-4}$ alkyl).

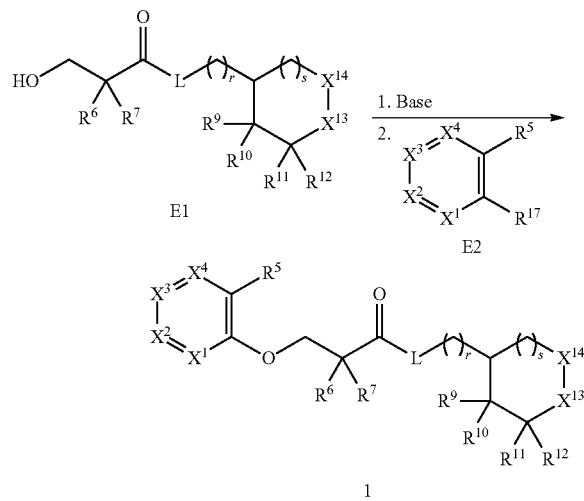

The methods depicted in the schemes may be varied as desired. For example, protecting groups may be added or removed and products may be further elaborated via, for example, alkylation, acylation, hydrolysis, oxidation, reduction, amidation, sulfonation, alkynation, and the like to give the desired final product. Furthermore, any intermediate or final product which comprises mixture of stereoisomers may be optionally purified by chiral column chromatography (e.g., supercritical fluid chromatography) or by derivatization with optically-pure reagents as described above to give a desired stereoisomer.

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more of these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic)acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10): 955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 μg to about 20 mg of the API per actuation and the actuation volume may vary from about 1 μL to about 100 μL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 μg to about 1000 μg of the API. The overall daily dose will typically range from about 100 μg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat diseases, disorders, and conditions for which activation of SSTR4 is indicated. Such diseases, disorders, and conditions generally relate to any unhealthy or abnormal state in a subject for which the activation of SSTR4 provides a therapeutic benefit. More particularly, the compounds of Formula 1 may be used to treat CNS diseases, disorders or conditions, including Alzheimer's disease, and other forms of dementia (i.e., major or mild neurocognitive disorders) associated with one or more medical conditions, including frontotemporal lobar degeneration, Lewy body disease, vascular disease, traumatic brain injury, substance or medication use, HIV infection, prion disease, Parkinson's disease, and Huntington's disease. The compounds of Formula 1 may also be used to treat major or mild neurocognitive disorders associated with depression, schizophrenia, bipolar disorder, and autism. In addition, the compounds of Formula 1 may be used to treat anxiety and to treat epilepsy.

The claimed and disclosed compounds may be combined with one or more other pharmacologically active compounds or therapies to treat one or more disorders, diseases or conditions for which SSTR4 is indicated. Such combinations may offer significant therapeutic advantages, including fewer side effects, improved ability to treat underserved patient populations, or synergistic activity. For example, compounds of Formula 1, which include compounds specifically named above, and their pharmaceutically acceptable complexes, salts, solvates and hydrates, may be administered simultaneously, sequentially or separately in combination with one or more compounds or therapies for treating Alzheimer's disease, including beta-secretase inhibitors, gamma-secretase inhibitors, HMG-CoA reductase inhibitors, nonsteroidal anti-inflammatory drugs (NSAIDs, such as apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac), vitamin E, and anti-amyloid antibodies. Specific examples of compounds used to treat Alzheimer's disease include donepezil, rivastigmine, memantine, and galantamine.

In addition to drugs used to improve cognition, the compounds of Formula 1 may be combined with sedatives, hypnotics, anxiolytics, antipsychotics, tranquilizers, and other medications that are used in the treatment of Alzheimer's disease. For example, the compounds of Formula 1 may be combined with one or more agents for treating depression (antidepressants) and/or schizophrenia (atypical or typical antipsychotics) including amitriptyline, amoxapine, aripiprazole, asenapine, bupropion, chlordiazepoxide, citalopram, chlorpromazine, clozapine, desipramine, desvenlafaxine, doxepin, duloxetine, escitalopram, fluoxetine, fluoxetine, fluphenazine, haloperidol, iloperidone, imipramine, isocarboxazid, lamotrigine, levomilnacipran, lurasidone, mirtazapine, nefazodone, nortriptyline, olanzapine, paliperidone, paroxetine, perphenazine, phenelzine, protriptyline, quetiapine, risperidone, selegiline, sertraline, tranylcypromine, trazodone, trimipramine, venlafaxine, vilazodone, and vortioxetine, and ziprasidone.

Likewise, the compounds of Formula 1 may be combined with one or more agents for treating anxiety (anxiolytics) including benzodiazepines (alprazolam, chlordiazepoxide, clobazepam, clonazepam, clorazepate, diazepam, estazolam, flurazepam, lorazepam, midazolam, oxazepam, prazepam, quazepam, temazepam, and triazolam), antihistamines (hydroxyzine), non-benzodiazepines (eszopiclone, zaleplon, zolpidem, and zopiclone) and buspirone.

The compounds of Formula 1 may also be combined with one or more agents for treating epilepsy (antiepileptics or anticonvulsants) including acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

Biological Activity

The biological activity of the compound of Formula 1 with respect to SSTR4 may be determined using the following in vitro and in vivo methods.

Inhibition of Forskolin Stimulated cAMP in Cells Overexpressing SSTR4

This cell-based assay measures the ability of compounds to inhibit forskolin stimulated cAMP in CHO-K1 cells overexpressing SSTR4. CHO-K1 cells overexpressing SSTR4 (CHO-SSTR4) are purchased from DiscoveRx (product code 95-0059C2). The CHO-SSTR4 cells are maintained in F12K media with 10% Fetal Bovine Serum (Hyclone), 1% Pen/Strep (Life Technologies), and 800 µg/mL G418 (Life Technologies). To perform the assay, 3000 cells are plated per well in white 384-well plate (Corning 3570) in 50 µL complete media and the cells are allowed to attach for 16 hours in a 37° C., 5% $CO_2$ incubator. The next day, the culture media is removed from the cells and the cells are washed (added then removed) with Kreb's Ringer Buffer (ZenBio, KRB-1000 mL). Test compounds are suspended in DMSO and diluted in stimulation buffer: Kreb's Ringer Buffer plus 0.5% BSA (Roche), 300 µM IBMX (Sigma), and 350 nM forskolin (Sigma). The cells are incubated in 10 µL compound/stimulation buffer for 30 minutes at room temperature. Cellular cAMP levels are detected with a HTRF LANCE Ultra cAMP kit (Perkin Elmer, catalog number TRF0264).

The assay is performed in accordance with the manufacturer's instructions. Five µL of diluted Eu-W8044 labeled streptavidin (dilution: 1:50 in cAMP Detection Buffer) is added to each well. Then 5 µL of diluted biotin cAMP (dilution: 1:150 in cAMP Detection Buffer) is added to each well. The plates are covered and allowed to incubate for 60 minutes at room temperature on a shaker. HTRF (665 nm/615 nm) is read on a Perkin Elmer ENVISION plate reader. The $pEC_{50}$ values are generated using Activity Base for Screening Data Management.

SSTR4 I-125 Somatostatin Competition Binding Assay

This membrane-based assay measures the ability of compounds to competitively inhibit binding of I-125 labeled somatostatin to SSTR4 in membranes from CHO-K1 that overexpress SSTR4. Membranes from CHO-K1 cells overexpressing SSTR4 are purchased from Perkin Elmer (catalog number ES-524-M400UA). Test compounds are suspended in DMSO and then diluted in assay buffer (25 mM HEPES pH 7.4, 10 mM $MgCl_2$, 1 mM $CaCl_2$), 0.5% BSA) plus 0.2 nM I-125 labeled somatostatin (Perkin Elmer catalog number NEX389). Fifty µL of compound/I-125 somatostatin in assay buffer are added per well to a 96-well poly-propylene plate. Then 1 µg of SSTR4 membranes in 50 µL assay buffer are added per well. The Plate is incubated for 60 minutes at room temperature. FilterMat A filters (Perkin Elmer catalog number 1450-421) are pre-soaked in 0.5% PEI (Sigma catalog number P3143). The contents of the assay plate are transferred to filters with a TomTech harvester and washed 5 times with 20 mM HEPES, 100 mM NaCl. The filters are dried in a microwave oven then transferred to sample bag containing a scintillator sheet (Perkin Elmer catalog number 1450-441). The scintillator sheets are melted to filters using a heat block. The filters are then read in a MicroBeta scintillation counter. Binding Ki curves are generated using Activity Base for Screening Data Management and the results are reported as $pIC_{50}$.

SSTR1 I-125 Somatostatin Competition Binding Assay for Selectivity Versus SSTR4

This membrane-based assay measures the ability of compounds to competitively inhibit binding of I-125 labeled somatostatin to SSTR1 in membranes from CHO-K1 that overexpress SSTR1. Membranes from CHO-K1 cells overexpressing SSTR1 are purchased from Perkin Elmer (catalog number ES-520-M400UA). Test compounds are suspended in DMSO and then diluted in assay buffer (25 mM HEPES pH 7.4, 10 mM $MgCl_2$, 1 mM $CaCl_2$), 0.5% BSA) plus 0.4 nM I-125 labeled somatostatin (Perkin Elmer catalog number NEX389). Fifty µL of compound/I-125 somatostatin in assay buffer are added per well to 96-well poly-propylene plate. Then 10 µg of SSTR1 membranes in 50 µL assay buffer are added per well. The plate is incubated for 60 minutes at room temperature. FilterMat A filters (Perkin Elmer catalog number 1450-421) are pre-soaked in 0.5% PEI (Sigma catalog number P3143). The contents of the assay plate are transferred to filters with a TomTech harvester and washed 5 times with 20 mM HEPES, 100 mM NaCl. The filters are dried in a microwave oven then transferred to sample bag containing a scintillator sheet (Perkin Elmer catalog number 1450-441). The scintillator sheets are melted to the filters using a heat block. The filters are then read in a MicroBeta scintillation counter. Binding Ki curves are generated using Activity Base for Screening Data Management and the results are reported as $pIC_{50}$.

In Vivo Screening Using Subcutaneous Pentylenetetrazole (PTZ)

Swiss-Webster mice, 6-8 week old are used in the subcutaneous PTZ model of seizures. PTZ is a GABAergic agent that blocks GABA receptors, thereby disinhibiting all CNS systems and inducing seizures in animals. Seizures can be assessed and quantified by observation of the animals in the study. Thus, this model provides a screening model to test compounds with anti-convulsant activity in mice, which is derived from the activity of the compound on the inhibitory receptor SSTR4. In accordance with the method, Swiss-Webster mice which are 6 to 8 weeks old are acclimatized to the study room prior to start the experiment (1 hour). Animals (n=6/group) are then blindly dosed with vehicle or test compound, and 15 minutes later are dosed subcutaneously with PTZ. Animals are scored based on the time it takes them to get a seizure that impairs their capacity to stand. The time is scored as latency to seizure. Number and degree of seizures are also scored, but not used in the final data.

EXAMPLES

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), $CD_3OD$ (deuteromethanol), $CD_3CN$ (deuteroacetonitrile), and THF-$d_8$ (deuterotetrahydrofuran). The mass spectra (m/z for $[M+H]^+$) were recorded using either electrospray ionization (ESI-MS) or atmospheric pressure chemical ionization (APCI-MS) mass spectrometry.

Where indicated, intermediate preparations and example compounds are purified by HPLC. Tables 1 to 3 list equipment, materials, and conditions for some of the HPLC separations.

TABLE 1

HPLC Method A

| | |
|---|---|
| Pump | Shimadzu LC-8A or LC-20AP |
| UV/Vis | Shimadzu SPD-20A |
| Software | LCSolution |
| Column | Phenomenex Gemini ® C18, 5 µm, ID 30 mm × 150 mm |
| Mobile Phases | ACN (0.035% TFA) in water (0.05% TFA) |
| Gradient | 10% to 100% ACN (unless indicated otherwise) |

TABLE 2

HPLC Method B

| | |
|---|---|
| Pump | Shimadzu LC-8A or LC-20AP |
| UV/Vis | Shimadzu SPD-20A |
| Software | LCSolution |
| Column | Phenomenex Gemini ® C18, 5 µm, ID 30 mm × 150 mm |
| Mobile Phases | Water/ACN (10 mM $NH_4HCO_3$ in 20/80 water/ACN, pH 9.5-10) in water (10 mM $NH_4HCO_3$, pH 9.5-10) |
| Gradient | 10% to 100% ACN (unless indicated otherwise) |

TABLE 3

HPLC Method C

| | |
|---|---|
| Pump | Waters 2525/2545 |
| UV/Vis | Waters 2487 |
| ELSD | Altech 2000 |
| MS | Waters 3100 |
| Software | MassLynx, FractionLynx |
| Column | SunFire ™ C18, 5 µm, ID 30 mm × 75 mm column |
| Mobile Phase | ACN (0.035% TFA) in water (0.05% TFA) |

The preparations and examples may employ supercritical fluid chromatography (SFC) to separate enantiomers. Table 4 lists equipment, materials, and conditions for some of the SFC separations.

TABLE 4

SFC Method A

| | |
|---|---|
| Instrument | MGII preparative SFC |
| Column | ChiralPak AD, 5 µm, ID 30 mm × 250 mm column |
| Mobile Phases | $CO_2$ and EtOH (containing 0.1% ammonium hydroxide) |

Besides HPLC, some of the preparations and examples may employ flash chromatography or preparative thin layer chromatography (TLC). Preparative TLC is typically carried out on silica gel 60 $F_{254}$ plates.

After isolation by chromatography, the solvent may be removed and the product cried in a centrifugal evaporator (e.g., GeneVac™), rotary evaporator, evacuated flask, etc. Reactions in an inert (e.g., nitrogen) or reactive (e.g., $H_2$) atmosphere are typically carried out at a pressure of about 1 atmosphere (14.7 psi).

Preparation 1: methyl 2,2-dimethyl-3-((3-methylpyridin-2-yl)oxy)propanoate

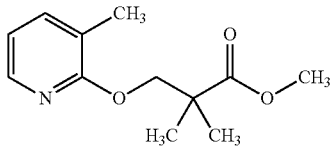

Diisopropyl azodicarboxylate (1.02 g, 5.04 mmol) was added slowly to a solution of 3-methylpyridin-2-ol (0.500 g, 4.58 mmol), methyl 3-hydroxy-2,2-dimethylpropanoate (0.606 g, 4.58 mmol) and triphenylphosphine (1.32 g, 5.04 mmol) in THF (6 mL) at 0° C. The solution was allowed to warm to room temperature and stirred overnight. The reaction mixture was diluted with EtOAc and washed with saturated aq NaHCO$_3$(2×) and brine. The organic layer was dried over Na$_2$SO$_4$, filtered, and concentrated under reduced pressure. The residue was purified by automated flash silica column chromatography, eluting with a gradient of 0-100% EtOAc in heptanes. The fractions containing the desired product were evaporated to afford the title compound (0.324 g, 33%). ESI-MS [M+H]$^+$ calc'd for C$_{12}$H$_{17}$NO$_3$, 224.12; found, 224.1.

Preparation 2: 2,2-dimethyl-3-((3-methylpyridin-2-yl)oxy)propanoic Acid

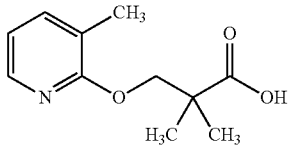

A solution of methyl 2,2-dimethyl-3-((3-methylpyridin-2-yl)oxy)propanoate (0.324 g, 1.52 mmol) in THF (8.13 mL) and water (2.71 mL) was treated with lithium hydroxide hydrate (0.183 g, 7.66 mmol). The reaction mixture was allowed to stir at room temperature overnight, and was then quenched with saturated aq NH$_4$Cl and extracted with EtOAc. The organic layer was dried over Na$_2$SO$_4$, filtered, and concentrated under reduced pressure to give the title compound (0.321 g, quantitative) which was used without further purification. ESI-MS [M+H]$^+$ calc'd for C$_{11}$H$_{15}$NO$_3$, 210.11; found, 210.1.

Preparation 3: 3-(2-ethylphenoxy)-2,2-dimethylpropanoic Acid

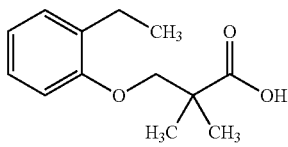 [SMILES: CCc1ccccc1OCC(C)(C)C(=O)O]

To methyl 2,2-dimethyl-3-(tosyloxy)propanoate (0.800 g, 2.79 mmol) in DMF (5 mL) was added 2-ethylphenol (0.683 g, 5.59 mmol) and Cs$_2$CO$_3$ (1.82 g, 5.59 mmol). The solution was heated at 80° C. overnight and then quenched with water, acidified to pH 2 with concentrated HCl, extracted with EtOAc, and washed with brine. The organic layer was dried over Na$_2$SO$_4$, filtered, and concentrated under reduced pressure to give the title compound as a semi-solid (0.200 g, 32%) which was used without further purification. ESI-MS [M+H]$^+$ calc'd for C$_{13}$H$_{18}$O$_3$, 223.13; found, 223.1.

Preparation 4: 2-(4-aminopiperidin-1-yl)-1-(4-chlorophenyl)ethan-1-one

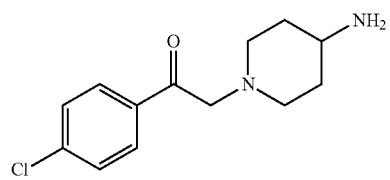 [SMILES: NC1CCN(CC(=O)c2ccc(Cl)cc2)CC1]

Step A: tert-butyl (1-(2-(4-chlorophenyl)-2-oxoethyl)piperidin-4-yl)carbamate

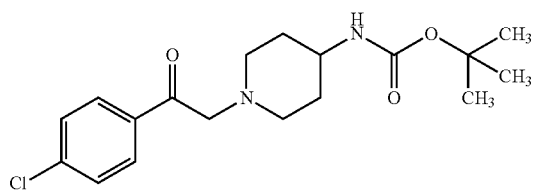 [SMILES: CC(C)(C)OC(=O)NC1CCN(CC(=O)c2ccc(Cl)cc2)CC1]

To a solution of tert-butyl piperidin-4-ylcarbamate (2.00 g, 9.99 mmol) and DIPEA (1.78 mL, 10.3 mmol) in THF (10 mL) was added 2-bromo-1-(4-chlorophenyl)ethanone (2.20 g, 9.42 mmol). The reaction mixture was heated in a sealed tube at 90° C. overnight, and was then cooled, extracted into EtOAc, and washed successively with 1 N NaOH and brine. The organic layers were combined, dried over Na$_2$SO$_4$, filtered, and concentrated under reduced pressure to give the title compound as an off-white semi-solid (3.32 g, assumed quantitative). ESI-MS [M+H]$^+$ calc'd for C$_{18}$H$_{25}$ClN$_2$O$_3$ 353.16; found, 354.3.

Step B: 2-(4-aminopiperidin-1-yl)-1-(4-chlorophenyl)ethan-1-one

To a solution of tert-butyl (1-(2-(4-chlorophenyl)-2-oxoethyl)piperidin-4-yl)carbamate (3.32 g, 9.41 mmol) in methanol (20 mL) was added 6 N HCl in methanol (7.84 mL, 47.0 mmol). The reaction mixture was stirred until the reaction was completed and then concentrated to remove excess methanol. A white precipitate formed and was collected by filtration and dried to give the title compound (1.5 g, 63%).

Preparation 5: 1-(hydroxymethyl)-N-(1-methylpiperidin-4-yl)cyclopropane-1-carboxamide

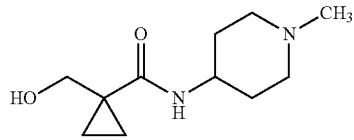

Step A: (1-((benzyloxy)methyl)cyclopropyl)methanol

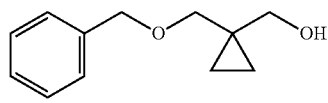 [SMILES: OCC1(COCc2ccccc2)CC1]

Sodium hydride (60 wt %, 1.261 g, 31.5 mmol) was added in one portion to a solution of cyclopropane-1,1-diyldimethanol (2.30 g, 28.7 mmol) in DMF (71.7 mL) at 0° C. The solution was stirred for 15 minutes before dropwise addition of (bromoethyl)benzene (3.38 mL, 28.3 mmol). The reaction was allowed to warm to room temperature and stir for 24 hours. The reaction was quenched with saturated aq NH$_4$Cl, extracted with Et$_2$O, dried over Na$_2$SO$_4$, filtered, and concentrated under reduced pressure. The crude material was purified by automated flash silica column chromatography, eluting with 40% EtOAc in heptanes to give the title compound (3.115 g, 57%).

Step B: 1-((benzyloxy)methyl)cyclopropane-1-carboxylic Acid

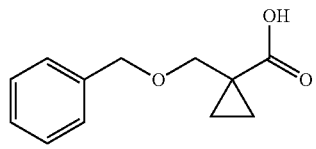 [SMILES: O=C(O)C1(COCc2ccccc2)CC1]

A 2 M solution of CrO$_3$ in aq H$_2$SO$_4$ (15.23 mL, 30.5 mmol, 2.1 eq) was slowly added dropwise to a stirred solution of (1-((benzyloxy)methyl)cyclopropyl)methanol (2.788 g, 14.50 mmol) in acetone (48.3 mL) at room temperature. The reaction mixture was allowed to stir for 30 minutes and then quenched with isopropanol (1 mL). The mixture was stirred for 10 minutes and then concentrated under reduced pressure. The crude material was taken up in water, extracted with Et$_2$O, dried over Na$_2$SO$_4$, filtered, and concentrated under reduced pressure to give the title compound as a white crystalline solid (2.688 g, 90%).

Step C: 1-((benzyloxy)methyl)-N-(1-methylpiperidin-4-yl)cyclopropane-1-carboxamide

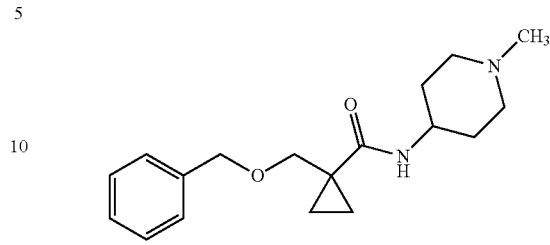

To a solution of 1-methylpiperidin-4-amine (2.232 g, 19.6 mmol) and 1-((benzyloxy)methyl)cyclopropane-1-carboxylic acid (2.688 g, 13.03 mmol) in DMF (65.2 mL) were added HATU (7.43 g, 19.6 mmol) and DIPEA (6.83 mL, 39.1 mmol). The reaction mixture was allowed to stir at room temperature for 4 hours, and was then diluted with water, extracted with EtOAc, washed with brine, dried over Na$_2$SO$_4$, filtered, and concentrated under reduced pressure. The crude material was purified by automated flash silica column chromatography, eluting with 80% EtOAc in heptanes to give the title compound as a pale yellow solid (2.805 g, 71%).

Step D: 1-(hydroxymethyl)-N-(1-methylpiperidin-4-yl)cyclopropane-1-carboxamide

A solution of 1-((benzyloxy)methyl)-N-(1-methylpiperidin-4-yl)cyclopropane-1-carboxamide (2.805 g, 9.28 mmol) and Pd—C (10 wt %, 0.987 g, 0.928 mmol) in methanol (105 mL) and EtOAc (10.54 mL) was stirred under an atmosphere of hydrogen for 3 hours. The solution was filtered through Celite© and concentrated in vacuo to give the title compound, which was used without further purification (1.97 g, assumed quantitative). $^1$H NMR (500 MHz, DMSO-d$_6$) δ 9.11 (br s, 1H), 5.06 (br s, 1H), 3.86-3.77 (m, 1H), 3.58-3.49 (m, 2H), 3.47-3.38 (m, 2H), 3.10-2.98 (m, 2H), 3.11 (s, 3H), 1.98-1.86 (m, 2H), 1.68-1.56 (m, 2H); ESI-MS [M+H]$^+$ calc'd for C$_{11}$H$_{20}$N$_2$O$_2$, 213.16; found, 213.20.

Preparation 6: methyl 2,2-dimethyl-3-(tosyloxy)propanoate

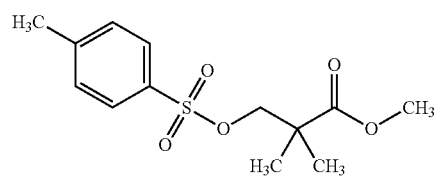

To a mixture of methyl 3-hydroxy-2,2-dimethylpropanoate (0.962 mL, 7.57 mmol) and DMAP (0.092 g, 0.76 mmol) in pyridine (20 mL) was added 4-methylbenzene-1-sulfonyl chloride (1.44 g, 7.57 mmol). The reaction mixture was left to stir at room temperature overnight. Hexane (100 mL) was added. A white precipitate was removed by filtration and the filtrate was concentrated under reduced pressure. The crude residue was taken up in hexane (50 mL) and the resulting precipitate removed by filtration. The filtrate was concentrated under reduced pressure to give the title compound as a clear oil (1.9 g, 88%). ¹H NMR (400 MHz, CDCl₃) δ ppm 1.20 (s, 6H), 1.21 (s, 1H), 2.47 (s, 3H), 3.63 (s, 3H), 4.02 (s, 2H), 7.37 (d, J=7.8 Hz, 2H), 7.77-7.81 (m, 2H); ESI-MS [M+H]⁺ calc'd for $C_{13}H_{18}O_5S$, 287.1; found, 287.1.

Preparation 7: methyl 3-(2-chlorophenoxy)-2,2-dimethylpropanoate

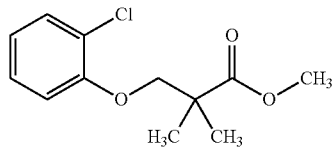 [SMILES: COC(=O)C(C)(C)COc1ccccc1Cl]

A 500 mL three-necked round-bottomed flask was charged with 2-chlorophenol (5.00 g, 38.9 mmol), methyl 3-hydroxy-2,2-dimethylpropanoate (5.14 g, 38.9 mmol), and toluene (100 mL). The resulting solution was chilled to 2° C. under nitrogen. Triphenylphosphine (10.20 g, 38.9 mmol) was added. Next, DIAD (7.56 mL, 38.9 mmol) was added over a 20-minute period. The reaction mixture was heated to 80° C. for 15 hours and then allowed to cool to room temperature. The mixture was washed with 1 M aq NaOH (20 mL) and rinsed with MTBE. The organic phase was washed with 1 M aq HCl (20 mL) and water (20 mL). The solids were removed by filtration. The filtrate was concentrated to dryness, diluted with heptanes (20 mL), and filtered to remove solids which were rinsed with heptanes (40 mL). The combined filtrate was concentrated and dried under reduced pressure to give a pale-yellow oil (9.44 g, assumed quantitative) which was used without additional purification. ESI-MS [M+H]⁺ calc'd for $C_{12}H_{15}ClO_3$, 243.079; found, 243.10.

Preparation 8: methyl 2,2-dimethyl-3-(2-(trifluoromethyl)phenoxy)propanoate

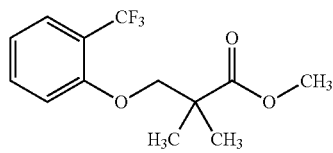

The title compound was prepared in a manner similar to PREPARATION 7, using 2-trifluoromethylphenol (0.500 g, 3.08 mmol) in place of 2-chlorophenol. The product was isolated as a pink liquid (642.9 mg, 75%). ESI-MS [M+H]⁺ calc'd for $C_{13}H_{15}F_3O_3$, 277.10; found, 277.1.

Preparation 9: methyl 3-(4-cyano-2-(trifluoromethyl)phenoxy)-2,2-dimethylpropanoate

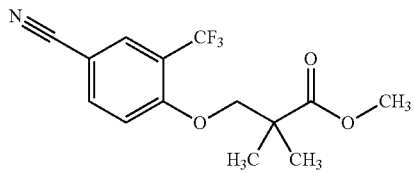 [SMILES: COC(=O)C(C)(C)COc1ccc(C#N)cc1C(F)(F)F]

The title compound (412 mg, 51%) was prepared in a manner similar to PREPARATION 7, using 4-hydroxy-3-(trifluoromethyl)benzonitrile (0.500 g, 2.67 mmol) in place of 2-chlorophenol. ESI-MS [M+H]⁺ calc'd for $C_{14}H_{14}F_3NO_3$, 302.10; found, 302.3.

Preparation 10: methyl 2,2-dimethyl-3-phenoxypropanoate

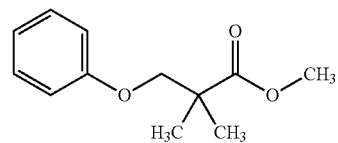

The title compound (184 mg, 17%) was prepared in a manner similar to PREPARATION 7, using phenol (0.500 g, 5.31 mmol) in place of 2-chlorophenol. ESI-MS [M+H]⁺ calc'd for $C_{12}H_{16}O_3$, 209.12; found, 209.2.

Preparation 11: 3-(2-chlorophenoxy)-2,2-dimethylpropanoic Acid

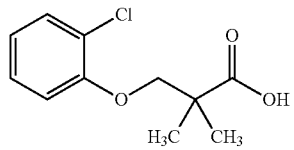

To a solution of methyl 3-(2-chlorophenoxy)-2,2-dimethylpropanoate (9.44 g, 38.9 mmol) in MeOH (50 mL) were added water (15 mL) and lithium hydroxide (1.863 g, 78.0 mmol). The reaction mixture was stirred at room temperature for 2 hours. THF (10 mL) was added to improve mixing, and the reaction mixture was stirred at room temperature for an additional 2.5 hours and at 40° C. for 1 hour. The reaction mixture was allowed to cool to room temperature and was concentrated to about 45 g under reduced pressure. The concentrate was partitioned between water and toluene and extracted with toluene. The aqueous phase was acidified to pH 1 with HCl and then extracted with EtOAc. The organic layers were combined, washed with water, concentrated and dried under reduced pressure to give the title compound as a pale-yellow crystalline solid (7.30 g, 82%). ESI-MS [M+H]⁺ calc'd for $C_{11}H_{13}ClO_3$, 229.06; found, 229.0.

Preparation 12: 2,2-dimethyl-3-(2-(trifluoromethyl)phenoxy)propanoic Acid

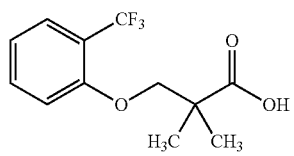

A solution of methyl 2,2-dimethyl-3-(2-(trifluoromethyl)phenoxy)propanoate (642.9 mg, 2.327 mmol) in a mixture of methanol (8.73 mL) and water (2.91 mL) was treated with lithium hydroxide hydrate (391 mg, 9.31 mmol) at room temperature. The reaction mixture was stirred at room temperature overnight, and was then acidified with 1 M aq HCl and extracted with DCM. The organic phase was washed with brine, dried over Na₂SO₄, filtered, and concentrated under reduced pressure to give the title compound (391.4 mg, 64%) as a colorless oil. ESI-MS [M+H]⁺ calc'd for $C_{12}H_{13}F_3O_3$ 263.10; found, 263.1.

Preparation 13: 3-(4-cyano-2-(trifluoromethyl)phenoxy)-2,2-dimethylpropanoic Acid

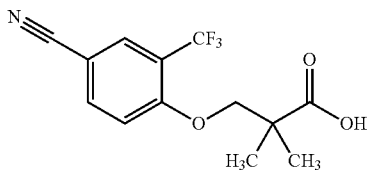 [SMILES: CC(C)(COc1ccc(C#N)cc1C(F)(F)F)C(=O)O]

To a solution of methyl 3-(4-cyano-2-(trifluoromethyl) phenoxy)-2,2-dimethylpropanoate (412 mg, 1.37 mmol) in THF (7 mL) and water (2.33 mL) was added lithium hydroxide (164 mg, 6.84 mmol). The reaction mixture was stirred at room temperature overnight, and was then acidified with 1 M aq HCl and extracted with DCM. The organic phase was washed with brine, dried over Na₂SO₄, filtered, and concentrated under reduced pressure to give the title compound (200 mg, 51%).

Preparation 14: 2,2-dimethyl-3-phenoxypropanoic Acid

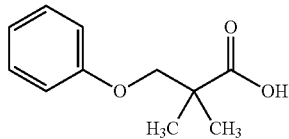

The title compound (114 mg, 66%) was prepared in a manner similar to PREPARATION 13 using methyl 2,2-dimethyl-3-phenoxypropanoate (184 mg, 0.888 mmol) in place of methyl 3-(4-cyano-2-(trifluoromethyl)phenoxy)-2,2-dimethylpropanoate.

Preparation 15: 3-hydroxy-2,2-dimethyl-N-(1-methylpiperidin-4-yl)propanamide

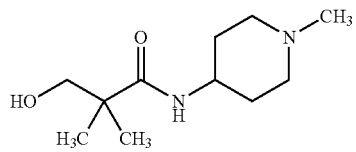

Methyl 3-hydroxy-2,2-dimethylpropanoate (1.736 g, 13.14 mmol) and 1-methylpiperidin-4-amine (1.00 g, 8.76 mmol) were combined in a 30 mL microwave vial to give a brown solution. The reaction mixture was heated at 190° C. for 3 days and then purified by automated flash silica column chromatography (60 g NH column) eluting with a gradient of 0-10% MeOH in DCM. The fractions containing the desired product were evaporated to give the title compound as a tan solid (1.0 g, 53%). ESI-MS [M+H]⁺ calc'd for $C_{11}H_{22}N_2O_2$, 215.17; found 215.2.

Preparation 16: methyl 3-((3-cyanopyridin-2-yl)oxy)-2,2-dimethylpropanoate

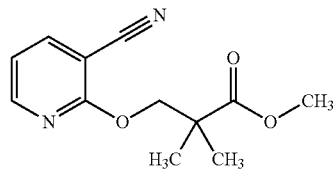 [SMILES: COC(=O)C(C)(C)COc1ncccc1C#N]

In a 125 mL round-bottomed flask were added 2-hydroxynicotinonitrile (0.300 g, 2.50 mmol), methyl 3-hydroxy-2,2-dimethylpropanoate (0.660 g, 5.00 mmol) and THF (20 mL) to give a brown solution. The reaction mixture was cooled to 0° C. Triphenylphosphine (1.31 g, 5.00 mmol) and DIAD (0.984 mL, 5.00 mmol) were added and the reaction mixture was allowed to warm to room temperature and stir overnight. The reaction mixture was treated with water and extracted with EtOAc. The organic phase was washed with brine, dried over MgSO₄, filtered, and concentrated under reduced pressure. The residue was purified by automated flash silica column chromatography (40 g column) eluting with a gradient of 20-90% EtOAc in heptanes. The fractions were evaporated to give the title compound as a colorless syrup (0.585 g, assumed quantitative).

Preparation 17: 3-((3-cyanopyridin-2-yl)oxy)-2,2-dimethylpropanoic Acid

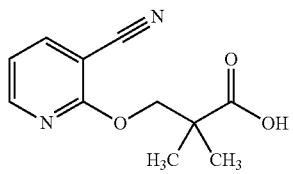 [SMILES: CC(C)(COc1ncccc1C#N)C(=O)O]

Methyl 3-((3-cyanopyridin-2-yl)oxy)-2,2-dimethylpropanoate (0.583 g, 2.49 mmol) and dioxane (12 mL) were combined in a 250 mL round-bottomed flask to give a colorless solution. To this solution was added 2 M aq LiOH (4.98 mL, 9.96 mmol). The reaction mixture was stirred at room temperature overnight, and was then acidified to pH 5 with 1 N aq HCl, and concentrated to dryness to give the title compound as a pink film (0.548 g, assumed quantitative). ESI-MS [M+H]⁺ calc'd for $C_{11}H_{12}N_2O_3$, 221.09; found, 221.1.

Preparation 18: (R)-3-hydroxy-2,2-dimethyl-N-(1-methylpyrrolidin-3-yl)propanamide

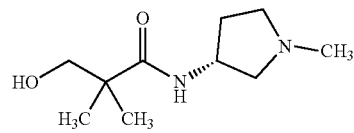

A solution of 3-hydroxy-2,2-dimethylpropanoic acid (0.517 g, 4.37 mmol), (R)-1-methylpyrrolidin-3-amine (0.438 g, 4.37 mmol), HATU (1.829 g, 4.81 mmol) and DIPEA (1.52 mL, 8.75 mmol) in DMF (5 mL) was stirred in a 100 mL round-bottomed flask at room temperature overnight. The reaction mixture was concentrated under reduced pressure and the residue was purified by automated flash silica column chromatography (30 g NH column) eluting with a gradient of 0-5% MeOH in DCM. The fractions containing the desired product were evaporated to give the title compound as a tan syrup (0.819 g, 94%). ESI-MS [M+H]$^+$ calc'd for $C_{10}H_{20}N_2O_2$, 201.16; found, 201.1.

Preparation 19: methyl 3-((5-bromopyrimidin-4-yl)oxy)-2,2-dimethylpropanoate

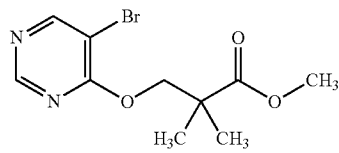

To a 100 mL round-bottomed flask containing sodium hydride (60 wt %, 0.155 g, 3.88 mmol) was added to DMF (8 mL) to give a white suspension. Methyl 3-hydroxy-2,2-dimethylpropanoate (0.342 g, 2.58 mmol) was added dropwise. After stirring for 1 hour at room temperature, a solution of 5-bromo-4-chloropyrimidine (0.500 g, 2.58 mmol) in DMF (2 mL) was added. The mixture was stirred at room temperature overnight. The reaction was quenched with saturated aq NH$_4$Cl and extracted with EtOAc. The organic phase was washed with brine, dried over MgSO$_4$, filtered, and concentrated. The residue was purified via automated flash silica column chromatography (40 g column) eluting with a gradient of 20-50% EtOAc in heptanes. The fractions containing the desired product were evaporated to give the title compound as a brown syrup (0.362 g, 48%). ESI-MS [M+H]$^+$ calc'd for $C_{10}H_{13}BrN_2O_3$, 289.02, 291.02; found 291.0.

Preparation 20: methyl 3-((5-cyclopropylpyrimidin-4-yl)oxy)-2,2-dimethylpropanoate

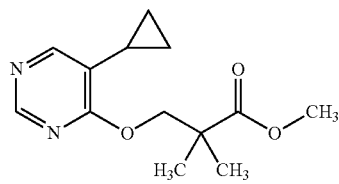 [SMILES: COC(=O)C(C)(C)COc1ncncc1C1CC1]

Methyl 3-((5-bromopyrimidin-4-yl)oxy)-2,2-dimethylpropanoate (0.362 g, 1.25 mmol), cyclopropylboronic acid (0.129 g, 1.50 mmol), 2 M aq Na$_2$CO$_3$ (2.50 mL, 5.01 mmol), Pd(dppf)Cl$_2$ (0.102 g, 0.125 mmol), 1,2-dimethoxyethane (6 mL) and water (2.5 mL) were combined in a 20 mL microwave vial to give a tan suspension. The reaction mixture was irradiated at 130° C. for 90 minutes in a Biotage® microwave reactor. The mixture was diluted with water and extracted with EtOAc. The organic phase was washed with brine, dried over MgSO$_4$, filtered, and concentrated to give the title compound crude as a tan film (0.313 g, assumed quantitative) which was used without purification. ESI-MS [M+H]$^+$ calc'd for $C_{13}H_{18}N_2O_3$, 251.13; found, 251.4.

Preparation 21: 3-((5-cyclopropylpyrimidin-4-yl)oxy)-2,2-dimethylpropanoic

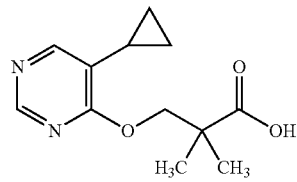 [SMILES: CC(C)(COc1ncncc1C1CC1)C(=O)O]

To a 250 mL round-bottomed flask charged with methyl 3-((5-cyclopropylpyrimidin-4-yl)oxy)-2,2-dimethylpropanoate (0.313 g, 1.25 mmol) was added 2 M aq LiOH (2.50 mL, 5.01 mmol) and dioxane (8 mL) to give a tan solution. The mixture was stirred at room temperature overnight. The reaction mixture was concentrated to dryness to give the title compound (0.296 g, assumed quantitative) which was used without further purification. ESI-MS [M+H]$^+$ calc'd for $C_{12}H_{16}N_2O_3$, 237.12; found, 237.4.

Preparation 22: 1-(hydroxymethyl)-N-(1-methylpiperidin-4-yl)cyclobutane-1-carboxamide

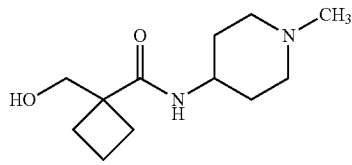 [SMILES: CN1CCC(NC(=O)C2(CO)CCC2)CC1]

In a 100 mL round-bottomed flask were combined 1-(hydroxymethyl)cyclobutanecarboxylic acid (0.500 g, 3.84 mmol), 1-methylpiperidin-4-amine (0.439 g, 3.84 mmol), HATU (1.607 g, 4.23 mmol), DIPEA (2.008 mL, 11.53 mmol) and DMF (6 mL) to give a yellow solution. The mixture was stirred at room temperature overnight and then concentrated under reduced pressure. The resulting residue was purified by automated silica column chromatography (60 g NH column) eluting with a gradient of 0-5% MeOH in DCM. The fractions containing the desired product were evaporated to give the title compound as a white film. ESI-MS [M+H]$^+$ calc'd for $C_{12}H_{22}N_2O_2$, 227.18; found, 227.2.

Preparation 23: methyl 3-((3-bromo-5-methylpyridin-2-yl)oxy)-2,2-dimethylpropanoate

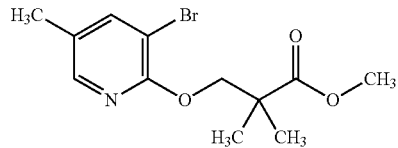

The title compound was prepared in a manner similar to PREPARATION 19, using 3-bromo-2-fluoro-5-methylpyridine (0.500 g, 2.63 mmol) in place of 5-bromo-4-chloropyrimidine. The product was isolated as a colorless syrup (0.452 g, 57%). ESI-MS [M+H]$^+$ calc'd for $C_{12}H_{16}BrNO_3$, 302.04; found, 302.1.

Preparation 24: methyl 3-((3-cyclopropyl-5-methylpyridin-2-yl)oxy)-2,2-dimethylpropanoate

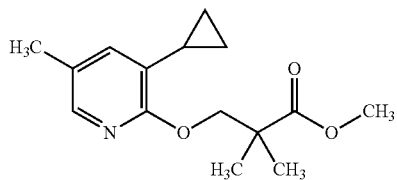

The title compound was prepared in a manner similar to PREPARATION 20, using methyl 3-((3-bromo-5-methylpyridin-2-yl)oxy)-2,2-dimethylpropanoate (0.452 g, 1.50 mmol) in place of methyl 3-((5-bromopyrimidin-4-yl)oxy)-2,2-dimethylpropanoate. The product was purified by automated flash silica column chromatography (40 g column) eluting with a gradient of 20-50% EtOAc in heptanes to give the title compound as a colorless syrup (0.277 g, 70%). ESI-MS [M+H]$^+$ calc'd for $C_{15}H_{21}NO_3$, 264.16; found, 264.5.

Preparation 25: 3-((3-cyclopropyl-5-methylpyridin-2-yl)oxy)-2,2-dimethylpropanoic Acid

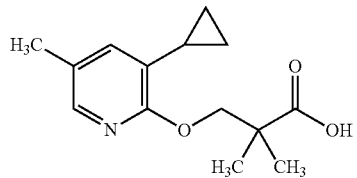 [SMILES: Cc1cnc(OCC(C)(C)C(=O)O)c(C2CC2)c1]

The title compound was prepared in a manner similar to PREPARATION 21, using methyl 3-((3-cyclopropyl-5-methylpyridin-2-yl)oxy)-2,2-dimethylpropanoate (0.277 g, 1.05 mmol) in place of methyl 3-((5-cyclopropylpyrimidin-4-yl)oxy)-2,2-dimethylpropanoate. The product (0.263 g, assumed quantitative) was used without further purification. ESI-MS [M+H]$^+$ calc'd for $C_{14}H_{19}NO_3$, 250.14; found, 250.4.

Preparation 26: methyl 3-((5-bromo-3-methylpyridin-2-yl)oxy)-2,2-dimethylpropanoate

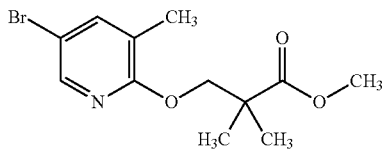 [SMILES: COC(=O)C(C)(C)COc1ncc(Br)cc1C]

The title compound was prepared in a manner similar to PREPARATION 19, using 5-bromo-2-fluoro-3-methylpyridine (0.500 g, 2.63 mmol) in place of 5-bromo-4-chloropyrimidine. The product was isolated as a colorless syrup (0.795 g, assumed quantitative) which was used without purification. ESI-MS [M+H]$^+$ calc'd for $C_{12}H_{16}BrNO_3$, 302.04; found, 302.0.

Preparation 27: methyl 3-((5-cyclopropyl-3-methylpyridin-2-yl)oxy)-2,2-dimethylpropanoate

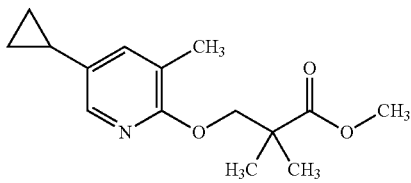 [SMILES: COC(=O)C(C)(C)COc1ncc(C2CC2)cc1C]

The title compound was prepared in a manner similar to PREPARATION 20, using methyl 3-((5-bromo-3-methylpyridin-2-yl)oxy)-2,2-dimethylpropanoate (0.795 g, 2.63 mmol) in place of methyl 3-((5-bromopyrimidin-4-yl)oxy)-2,2-dimethylpropanoate. The product was purified by automated flash silica column chromatography (40 g column) eluting with 20% EtOAc in heptanes to give a colorless film (0.114 g, 16%). ESI-MS [M+H]$^+$ calc'd for $C_{15}H_{21}NO_3$, 264.16; found, 264.4.

Preparation 28: 3-((5-cyclopropyl-3-methylpyridin-2-yl)oxy)-2,2-dimethylpropanoic Acid

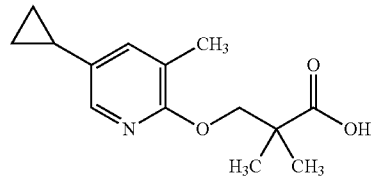 [SMILES: Cc1cc(C2CC2)cnc1OCC(C)(C)C(=O)O]

The title compound was prepared in a manner similar to PREPARATION 21, using methyl 3-((3-cyclopropyl-5-methylpyridin-2-yl)oxy)-2,2-dimethylpropanoate (0.114 g, 0.433 mmol) in place of methyl 3-((5-cyclopropylpyrimidin-4-yl)oxy)-2,2-dimethylpropanoate. The product (0.108 g, assumed quantitative) was used without further purification. ESI-MS [M+H]$^+$ calc'd for $C_{14}H_{19}NO_3$, 250.14; found, 250.4.

Preparation 29: methyl 3-((3-bromo-6-methylpyridin-2-yl)oxy)-2,2-dimethylpropanoate

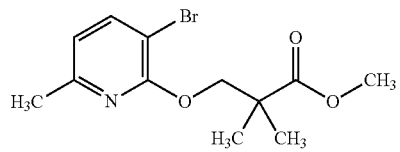

The title compound was prepared in a manner similar to PREPARATION 19, using 3-bromo-2-fluoro-6-methylpyridine (0.500 g, 2.63 mmol) in place of 5-bromo-4-chloropyrimidine. The product was isolated as a colorless syrup (0.795 g, assumed quantitative) which was used without purification. ESI-MS [M+H]+ calc'd for $C_{12}H_{16}BrNO_3$, 302.04; found, 302.0.

Preparation 30: methyl 3-((3-cyclopropyl-6-methylpyridin-2-yl)oxy)-2,2-dimethylpropanoate

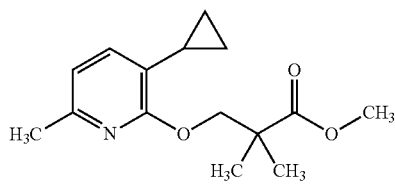

The title compound was prepared in a manner similar to PREPARATION 20, using methyl 3-((3-bromo-6-methylpyridin-2-yl)oxy)-2,2-dimethylpropanoate (0.795 g, 2.63 mmol) in place of methyl 3-((5-bromopyrimidin-4-yl)oxy)-2,2-dimethylpropanoate. The product (0.693 g, assumed quantitative) was used without further purification. ESI-MS [M+H]+ calc'd for $C_{15}H_{21}NO_3$, 264.16; found, 264.5.

Preparation 31: 3-((3-cyclopropyl-6-methylpyridin-2-yl)oxy)-2,2-dimethylpropanoic Acid

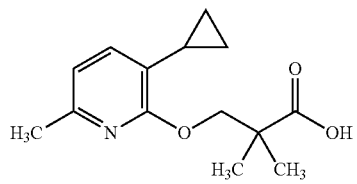

The title compound was prepared in a manner similar to PREPARATION 21, using methyl 3-((3-cyclopropyl-6-methylpyridin-2-yl)oxy)-2,2-dimethylpropanoate (0.693 g, 2.63 mmol) in place of methyl 3-((5-cyclopropylpyrimidin-4-yl)oxy)-2,2-dimethylpropanoate. The product (0.656 g, assumed quantitative) was used without further purification. ESI-MS [M+H]+ calc'd for $C_{14}H_{19}NO_3$, 250.14; found, 250.4.

Preparation 32: methyl 2,2-dimethyl-3-((3-(trifluoromethyl)pyridin-2-yl)oxy)propanoate

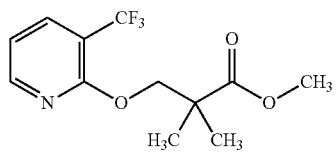

To a mixture of methyl 3-hydroxy-2,2-dimethyl-propanoate (3.60 g, 27.2 mmol) in DMF (30 mL) was added NaH (60 wt %, 1.45 g, 36.3 mmol). The mixture was allowed to stir at room temperature for 30 minutes. Next 2-fluoro-3-(trifluoromethyl)pyridine (3.00 g, 18.2 mmol) was added, the reaction mixture was allowed to stir at room temperature overnight, and was then poured into water and acidified to pH 6 with 1 M aq HCl (10 mL). The mixture was extracted with EtOAc (3×50 mL). The organic layers were combined, dried over anhydrous $Na_2SO_4$, filtered, and concentrated under reduced pressure to give crude product, which was purified by flash silica column chromatography, eluting with petroleum ether and EtOAc to give the title compound as a colorless oil (2.2 g, 43%). 1H NMR (400 MHz, CDCl3) δ ppm 1.33 (s, 6H), 3.69 (s, 3H), 4.41 (s, 2H), 6.90-7.03 (m, 1H), 7.85 (br d, J=6.8 Hz, 1H), 8.30 (br d, J=4.4 Hz, 1H); ESI-MS [M+H]+ calc'd for $C_{12}H_{14}F_3NO_3$, 278.10; found, 277.9.

Preparation 33: 2,2-dimethyl-3-((3-(trifluoromethyl)pyridin-2-yl)oxy)propanoic Acid

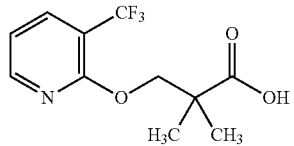

To a solution of methyl 2,2-dimethyl-3-((3-(trifluoromethyl)pyridin-2-yl)oxy)propanoate (2.2 g, 7.94 mmol) in dioxane (22 mL) was added 2 M aq lithium hydroxide (11.90 mL, 23.8 mmol). The reaction mixture was allowed to stir at room temperature overnight, and was then acidified to pH 5 with 1 M aq HCl, and extracted with EtOAc (2×50 mL). The combined organic layers were dried over $Na_2SO_4$, filtered, and concentrated under reduced pressure to give the title compound as a yellow solid (1.7 g, 80%). 1H NMR (400 MHz, CDCl3) δ ppm 1.37 (s, 6H), 4.43 (s, 2H), 6.93-7.02 (m, 1H), 7.86 (d, J=7.5 Hz, 1H), 8.30 (d, J=4.5 Hz, 1H); ESI-MS [M+H]+ calc'd for $C_{11}H_{12}F_3NO_3$, 264.08; found, 263.9.

Preparation 34: trans-3-(4-chlorophenyl)-1-methyl-4-nitropyrrolidine

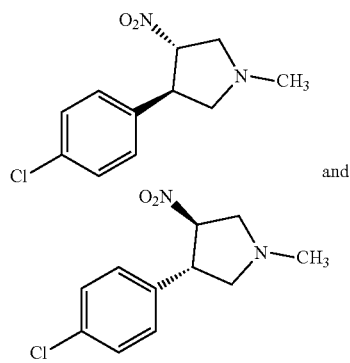

In a 250 mL round-bottomed flask were combined (E)-1-chloro-4-(2-nitrovinyl)benzene (2.00 g, 10.9 mmol), 2-(methylamino)acetic acid (2.426 g, 27.2 mmol) and paraformaldehyde (1.963 g, 65.4 mmol) in toluene (120 mL) to give a green solution. The mixture was heated under reflux for 1 hour. Solvent was removed under reduced pressure and the residue was purified by automated flash silica column chromatography (80 g column) eluting with a gradient of 20-50% EtOAc in heptanes. The fractions were evaporated to give the title compound as a light brown syrup (2.01 g, 77%). ESI-MS [M+H]⁺ calc'd for $C_{11}H_{13}ClN_2O_2$, 241.07; found, 241.1.

Preparation 35: trans-4-(4-chlorophenyl)-1-methylpyrrolidin-3-amine

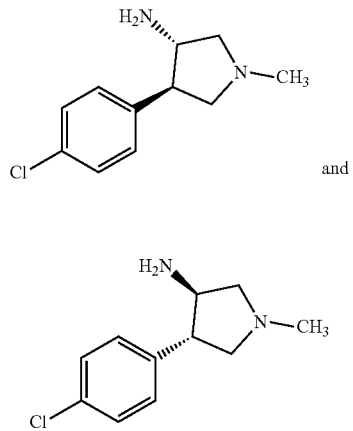

and

In a 250 mL round-bottomed flask were combined trans-3-(4-chlorophenyl)-1-methyl-4-nitropyrrolidine (2.01 g, 8.35 mmol) and zinc (4.37 g, 66.8 mmol) in ethanol (23 mL) and acetic acid (23 mL) to give a grey suspension. The mixture was stirred at 60° C. overnight and then filtered. The filtrate was concentrated under reduced pressure. The residue was taken up in DCM and treated with saturated aq NaHCO₃. The organic phase was concentrated and the residue was purified by automated flash silica column chromatography (80 g NH column) eluting with a gradient of 0-10% MeOH in DCM. The fractions were evaporated to give the title compound as a brown syrup (1.13 g, 64%). ESI-MS [M+H]⁺ calc'd for $C_{11}H_{15}ClN_2$, 211.09; found, 211.1.

Preparation 36: trans-N-(4-(4-chlorophenyl)-1-methylpyrrolidin-3-yl)-3-hydroxy-2,2-dimethylpropanamide

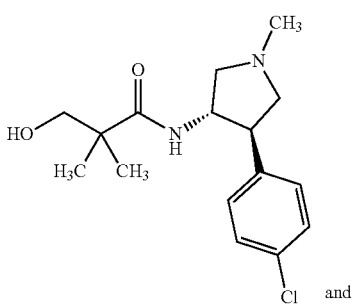

and

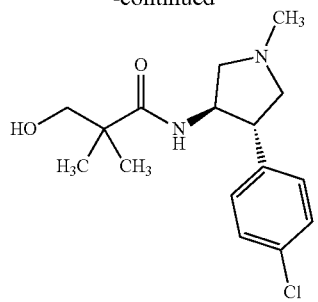

In a 250 mL round-bottomed flask were combined 3-hydroxy-2,2-dimethylpropanoic acid (0.634 g, 5.36 mmol), trans-4-(4-chlorophenyl)-1-methylpyrrolidin-3-amine (1.13 g, 5.36 mmol), HATU (2.447 g, 6.44 mmol), and DIPEA (2.80 mL, 16.1 mmol) in DMF (12 mL) to give a yellow solution. The reaction mixture was stirred at room temperature overnight. The mixture was treated with water and extracted with EtOAc. The organic phase was dried over MgSO₄ and concentrated under reduced pressure. The residue was purified by automated flash silica column chromatography (80 g column) eluting with a gradient of 0-10% MeOH in DCM. The fractions were evaporated to give the title compound as a syrup (1.36 g, 82%). ESI-MS [M+H]⁺ calc'd for $C_{16}H_{23}ClN_2O_2$, 311.14; found, 311.4.

Preparation 37: 2-nitro-1-(6-(trifluoromethyl)pyridin-3-yl)ethan-1-ol

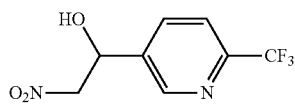

In a 250 mL round-bottomed flask, 6-(trifluoromethyl)nicotinaldehyde (5.05 g, 28.8 mmol) and triethylamine (4.02 mL, 28.8 mmol) were dissolved in nitromethane (37.1 mL, 681 mmol) to give a yellow solution. The mixture was stirred at room temperature for 1.5 hours, and was then concentrated under reduced pressure and purified by automated flash silica column chromatography (80 g column) eluting with a gradient of 0-5% MeOH in DCM. The fractions were evaporated to give the title compound as an off-white solid (6.47 g, 95%). ESI-MS [M+H]⁺ calc'd for $C_8H_7F_3N_2O_3$, 237.05; found, 237.1.

Preparation 38: (E)-5-(2-nitrovinyl)-2-(trifluoromethyl)pyridine

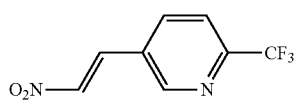

In a 250 mL round-bottomed flask, 2-nitro-1-(6-(trifluoromethyl)pyridin-3-yl)ethan-1-ol (6.47 g, 27.4 mmol) was dissolved in DCM (100 mL) to give a yellow solution. Acetic anhydride (2.59 mL, 27.4 mmol) and N,N-dimethylpyridin-4-amine (0.167 g, 1.37 mmol) were added sequentially. The mixture was stirred at room temperature for 2 hours and then treated with saturated aq NaHCO₃. The organic phase was separated and the aqueous phase was extracted with DCM. The organic phases were combined, concentrated under reduced pressure, and purified by automated flash column chromatography (80 g column) eluting with a gradient of 10-20% EtOAc in heptanes. The fractions were evaporated to give the title compound as a yellow solid (5.74 g, 96%). ESI-MS [M+H]⁺ calc'd for $C_8H_5F_3N_2O_2$, 219.03; found, 219.04.

Preparation 39: trans-5-(1-methyl-4-nitropyrrolidin-3-yl)-2-(trifluoromethyl)pyridine

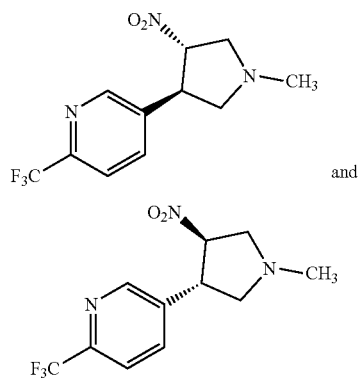

The title compound was prepared in a manner similar to PREPARATION 34, using (E)-5-(2-nitrovinyl)-2-(trifluoromethyl)pyridine (5.74 g, 23.6 mmol) in place of (E)-1-chloro-4-(2-nitrovinyl)benzene. The product was isolated as a tan syrup (5.88 g, 81%). ESI-MS [M+H]⁺ calc'd for $C_{11}H_{12}F_3N_3O_2$, 276.09; found, 276.2.

Preparation 40: trans-1-methyl-4-(6-(trifluoromethyl)pyridin-3-yl)pyrrolidin-3-amine

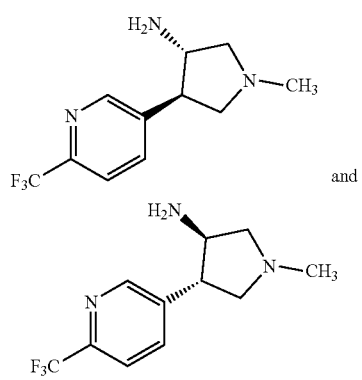

The title compound (3.94 g, 75%) was prepared in a manner similar to PREPARATION 35, using trans-5-(1-methyl-4-nitropyrrolidin-3-yl)-2-(trifluoromethyl)pyridine (5.88 g, 21.4 mmol) in place of trans-3-(4-chlorophenyl)-1-methyl-4-nitropyrrolidine. ESI-MS [M+H]⁺ calc'd for $C_{11}H_{14}F_3N_3$, 246.11; found, 246.1.

Preparation 41: trans-3-hydroxy-2,2-dimethyl-N-(1-methyl-4-(6-(trifluoromethyl)pyridin-3-yl)pyrrolidin-3-yl)propanamide

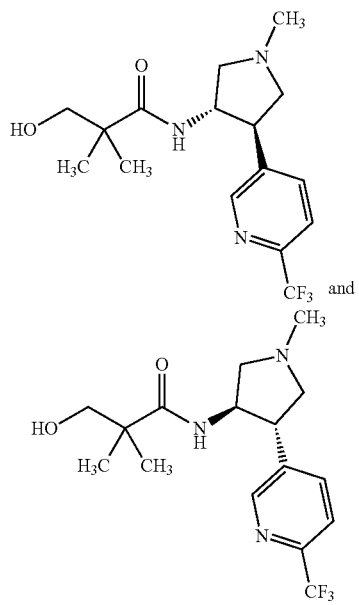

The title compound was prepared in a manner similar to PREPARATION 36, using trans-1-methyl-4-(6-(trifluoromethyl)pyridin-3-yl)pyrrolidin-3-amine (2.0 g, 5.3 mmol) in place of trans-4-(4-chlorophenyl)-1-methylpyrrolidin-3-amine. The product was isolated as a brown film (1.5 g, 82%). ESI-MS [M+H]⁺ calc'd for $C_{16}H_{22}F_3N_3O_2$, 346.17; found, 346.5.

Preparation 42: 1-(6-methylpyridin-3-yl)-2-nitroethan-1-ol

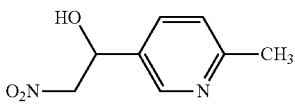

The title compound was prepared in a manner similar to PREPARATION 37, using 6-methylnicotinaldehyde (4.90 g, 40.5 mmol) and triethylamine (5.64 mL, 40.5 mmol) in nitromethane (52.1 mL, 955 mmol). The product was isolated as an off-white solid (6.1 g, 83%). ESI-MS [M+H]⁺ calc'd for $C_8H_{10}N_2O_3$, 183.07; found, 183.01.

Preparation 43: (E)-2-methyl-5-(2-nitrovinyl)pyridine

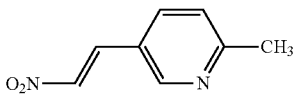

The title compound was prepared in a manner similar to PREPARATION 38, using 1-(6-methylpyridin-3-yl)-2-nitroethan-1-ol (6.10 g, 33.5 mmol) in place of 2-nitro-1-(6-(trifluoromethyl)pyridin-3-yl)ethan-1-ol. The product was isolated as a yellow solid (4.35 g, 79%). ESI-MS [M+H]+ calc'd for $C_8H_8N_2O_2$, 165.06; found, 165.1.

Preparation 44: trans-2-methyl-5-(1-methyl-4-nitro-pyrrolidin-3-yl)pyridine

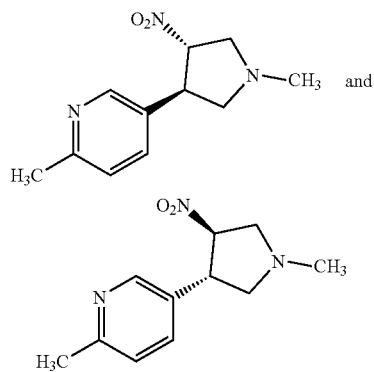

The title compound was prepared in a manner similar to PREPARATION 34, using (E)-2-methyl-5-(2-nitrovinyl)pyridine (4.35 g, 26.5 mmol) in place of (E)-1-chloro-4-(2-nitrovinyl)benzene. The product was isolated as a tan syrup (4.23 g, 72%). ESI-MS [M+H]+ calc'd for $C_{11}H_{15}N_3O_2$, 222.12; found, 222.1.

Preparation 45: trans-1-methyl-4-(6-methylpyridin-3-yl)pyrrolidin-3-amine

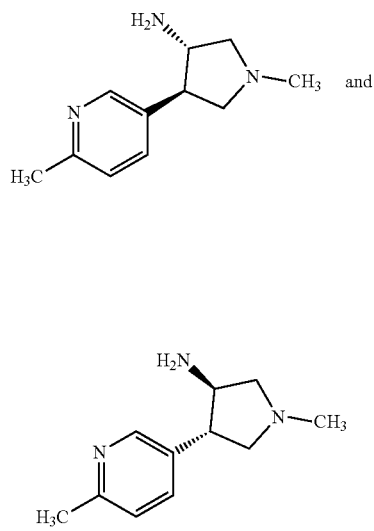

The title compound was prepared in a manner similar to PREPARATION 35, using trans-2-methyl-5-(1-methyl-4-nitropyrrolidin-3-yl)pyridine (4.23 g, 19.1 mmol) in place of trans-3-(4-chlorophenyl)-1-methyl-4-nitropyrrolidine. The product was isolated as a tan syrup (2.15 g, 59%). ESI-MS [M+H]+ calc'd for $C_{11}H_{17}N_3$, 192.14; found, 192.1.

Preparation 46: trans-3-hydroxy-2,2-dimethyl-N-(1-methyl-4-(6-methylpyridin-3-yl)pyrrolidin-3-yl)propanamide

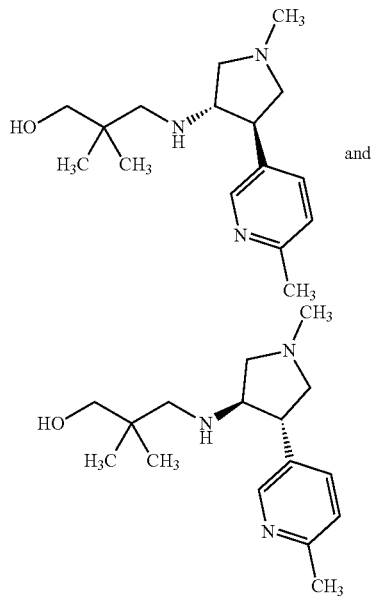

The title compound was prepared in a manner similar to PREPARATION 36, using trans-1-methyl-4-(6-methylpyridin-3-yl)pyrrolidin-3-amine (1.02 g, 5.33 mmol) in place of trans-4-(4-chlorophenyl)-1-methylpyrrolidin-3-amine. The product was isolated as a tan syrup (1.14 g, 73%). ESI-MS [M+H]+ calc'd for $C_{16}H_{25}N_3O_2$, 292.19; found, 292.2.

Preparation 47: trans-1-methyl-4-(1-methyl-1H-pyrazol-4-yl)pyrrolidin-3-amine

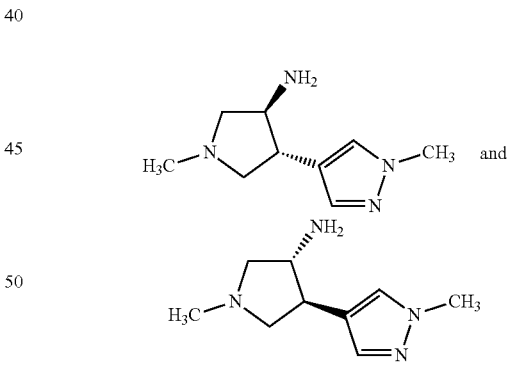

Step A: 1-(1-methyl-1H-pyrazol-4-yl)-2-nitroethan-1-ol

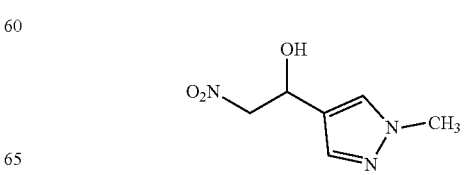

In a 250 mL round-bottomed flask, 1-methyl-1H-pyrazole-4-carbaldehyde (5.00 g, 45.4 mmol) was dissolved in nitromethane (55 mL) to give a light yellow solution. Triethylamine (6.33 mL, 45.4 mmol) was added. The reaction mixture was stirred at room temperature for 1.5 hours. Excess nitromethane was removed to give the title compound as a crude residue that was used without further purification (7.77 g, assumed quantitative). ESI-MS [M+H]$^+$ calc'd for $C_6H_9N_3O_3$, 172.07; found, 172.2.

Step B: (E)-1-methyl-4-(2-nitrovinyl)-1H-pyrazole

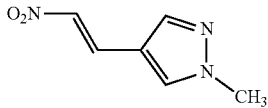

In a 250 mL round-bottomed flask, 1-(1-methyl-1H-pyrazol-4-yl)-2-nitroethan-1-ol (7.77 g, 45.4 mmol) was dissolved in DCM (100 mL) to give a brown solution. Acetic anhydride (4.29 mL, 45.4 mmol) and DMAP (0.277 g, 2.27 mmol) were added. The reaction mixture was stirred at room temperature for 2 hours and then quenched with water. The organic layer was separated and the aqueous phase was extracted with DCM (40 mL). The organic layers were combined, washed with saturated aq NH$_4$Cl, dried over MgSO$_4$, filtered, and concentrated under reduced pressure to give the title compound as a brown solid (6.66 g, 96%) which was used without further purification. ESI-MS [M+H]$^+$ calc'd for $C_6H_7N_3O_2$, 154.05; found, 154.2.

Step C: 4-(trans-1-benzyl-4-nitropyrrolidin-3-yl)-1-methyl-1H-pyrazole

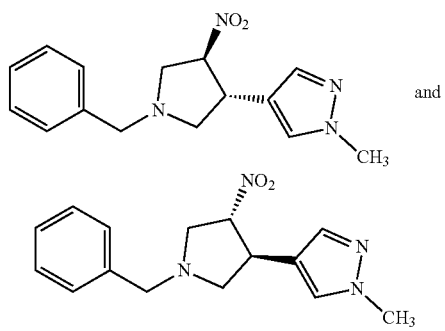

In a 250 mL round-bottomed flask were combined (E)-1-methyl-4-(2-nitrovinyl)-1H-pyrazole (3.00 g, 19.6 mmol) and N-benzyl-1-methoxy-N-((trimethylsilyl)methyl)methanamine (7.07 g, 29.8 mmol) in DCM (35 mL) to give a tan solution. The reaction mixture was cooled to 0° C. and TFA (0.150 mL, 1.96 mmol) was added dropwise. The reaction mixture was stirred at 0° C. for 30 minutes and then at room temperature for 2 hours. The reaction mixture was concentrated under reduced pressure and the residue was purified by HPLC Method A to give the title compound as a colorless syrup (0.862 g, 15%). ESI-MS [M+H]$^+$ calc'd for $C_{15}H_{18}N_4O_2$ 287.15; found, 287.4.

Step D: trans-1-benzyl-4-(1-methyl-1H-pyrazol-4-yl)pyrrolidin-3-amine

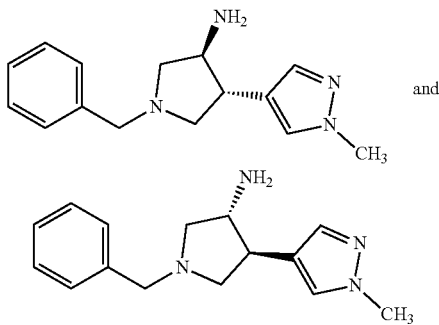

In a 125 mL round-bottomed flask, a grey suspension of 4-(trans-1-benzyl-4-nitropyrrolidin-3-yl)-1-methyl-1H-pyrazole (0.862 g, 3.01 mmol) and zinc dust (1.575 g, 24.08 mmol) in methanol (8 mL) and acetic acid (8 mL) was stirred at 60° C. for 1 hour. The reaction mixture was cooled to room temperature and filtered. The filtrate was concentrated under reduced pressure. The residue was taken up in DCM, neutralized with aqueous ammonium hydroxide and concentrated under reduced pressure. The residue was purified by automated flash silica column chromatography (30 g NH column) eluting with a gradient of 0-10% methanol in DCM. The fractions were evaporated to give the title compound (0.772 g, assumed quantitative). ESI-MS [M+H]$^+$ calc'd for $C_{15}H_{20}N_4$, 257.18; found, 257.3.

Step E: tert-butyl (trans-1-benzyl-4-(1-methyl-1H-pyrazol-4-yl)pyrrolidin-3-yl)carbamate

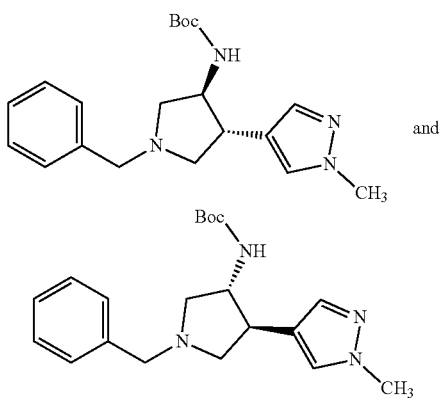

In a 250 mL round-bottomed flask, trans-1-benzyl-4-(1-methyl-1H-pyrazol-4-yl)pyrrolidin-3-amine (0.772 g, 3.01 mmol) and di-tert-butyl dicarbonate (0.657 g, 3.01 mmol) were dissolved in THF (10 mL) to give a tan solution. Triethylamine (0.629 mL, 4.52 mmol) was added and the mixture was stirred at room temperature for 6 hours. The reaction mixture was treated with water and extracted with EtOAc. The organic phase was dried over MgSO$_4$, filtered, and concentrated to give the title compound as a brown syrup (1.073 g, assumed quantitative) which was used without further purification. ESI-MS [M+H]$^+$ calc'd for $C_{20}H_{28}N_4O_2$, 357.23; found, 357.4.

Step F: tert-butyl (trans-4-(1-methyl-1H-pyrazol-4-yl)pyrrolidin-3-yl)carbamate

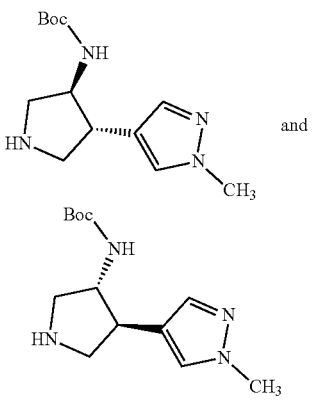

and

In a 250 mL round-bottomed flask, tert-butyl (trans-1-benzyl-4-(1-methyl-1H-pyrazol-4-yl)pyrrolidin-3-yl)carbamate (1.073 g, 3.01 mmol) was dissolved in methanol (50 mL) to give a brown solution. The reaction mixture was treated with ammonium formate (0.949 g, 15.0 mmol) and palladium on carbon (10%, 0.128 g, 0.120 mmol). The reaction mixture was stirred under nitrogen atmosphere at room temperature for 2 hours. Additional ammonium formate (0.949 g, 15.0 mmol) was added and the reaction mixture was stirred under nitrogen atmosphere at 90° C. for 1 hour. The reaction mixture was filtered. The filtrate was concentrated under reduced pressure to give the title compound as a purple solid (0.802 g, assumed quantitative). ESI-MS [M+H]+ calc'd for $C_{13}H_{22}N_4O_2$ 267.18; found, 267.3.

Step G: tert-butyl (trans-1-methyl-4-(1-methyl-1H-pyrazol-4-yl)pyrrolidin-3-yl)carbamate

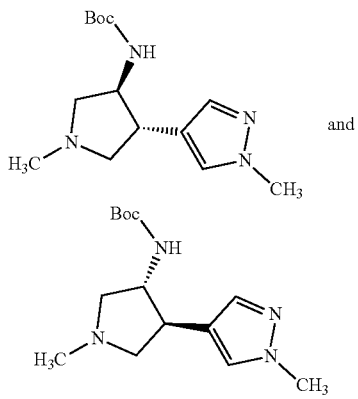

and

In a 250 mL round-bottomed flask, tert-butyl (trans-4-(1-methyl-1H-pyrazol-4-yl)pyrrolidin-3-yl)carbamate (0.802 g, 3.01 mmol) and formaldehyde (37% aq, 0.658 mL, 8.43 mmol) were dissolved in methanol (30 mL) to give a brown solution. The reaction mixture was treated with NaBH4 (0.342 g, 9.03 mmol) and stirred at room temperature for 1 hour. The reaction mixture was treated with water and extracted with EtOAc. The organic phase was washed with brine, dried over MgSO4, filtered, and concentrated. The residue was purified by automated flash silica column chromatography (30 g NH column) eluting with a gradient of 0%-5% methanol in DCM. The fractions were evaporated to give the title compound as a tan film (0.544 g, 64%). ESI-MS [M+H]+ calc'd for $C_{14}H_{24}N_4O_2$, 281.20; found [M−55], 225.2.

Step H: trans-1-methyl-4-(1-methyl-1H-pyrazol-4-yl)pyrrolidin-3-amine

In a 250 mL round bottomed flask, a solution of tert-butyl (trans-1-methyl-4-(1-methyl-1H-pyrazol-4-yl)pyrrolidin-3-yl)carbamate (0.544 g, 1.94 mmol) in dioxane (2 mL) was treated with HCl (4 M in dioxane, 1.94 mL, 7.76 mmol). The reaction mixture was stirred at room temperature for 1 hour and then concentrated to dryness to give an HCl salt of the title compound (0.433 g, quantitative) which was used without further purification. ESI-MS [M+H]+ calc'd for $C_9H_{16}N_4$, 181.14; found, 181.2.

Preparation 48: trans-5-(1-benzyl-4-nitropyrrolidin-3-yl)-2-methylpyridine

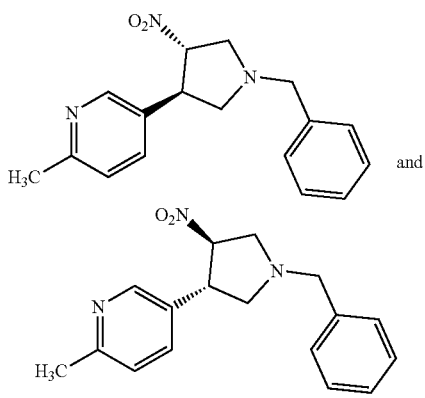

and

In a 250 mL round-bottomed flask were combined (E)-2-methyl-5-(2-nitrovinyl)pyridine (2.50 g, 15.2 mmol) and N-benzyl-1-methoxy-N-((trimethylsilyl)methyl)methanamine (5.50 g, 23.1 mmol) in DCM (30 mL) to give a tan solution. The reaction mixture was cooled to 0° C. and TFA (0.117 mL, 1.52 mmol) was added. After stirring for 30 minutes at 0° C., the reaction mixture was stirred at room temperature for 2 hours. The reaction mixture was concentrated and the residue was purified by automated flash silica column chromatography (80 g column) eluting with a gradient of 0-EtOAc in heptanes. The fractions were evaporated to give the title compound as a light brown syrup (4.47 g, 99%). ESI-MS [M+H]+ calc'd for $C_{17}H_{19}N_3O_2$, 298.15; found, 298.3.

Preparation 49: trans-1-benzyl-4-(6-methylpyridin-3-yl)pyrrolidin-3-amine

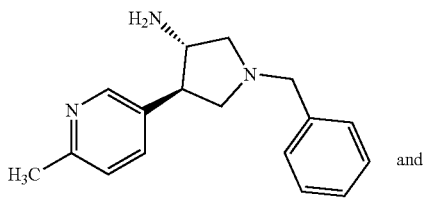

and

-continued

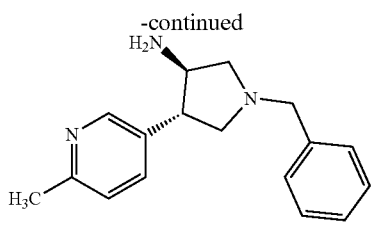

The title compound was prepared in a manner similar to PREPARATION 35, using trans-5-(1-benzyl-4-nitropyrrolidin-3-yl)-2-methylpyridine (4.47 g, 15.03 mmol) in place of trans-3-(4-chlorophenyl)-1-methyl-4-nitropyrrolidine. The product was isolated as a light yellow syrup (1.47 g, 37%). ESI-MS [M+H]$^+$ calc'd for $C_{17}H_{21}N_3$, 268.17; found, 268.3.

Preparation 50: trans-N-(1-benzyl-4-(6-methylpyridin-3-yl)pyrrolidin-3-yl)-2,2-dimethyl-3-((3-(trifluoromethyl)pyridin-2-yl)oxy)propanamide

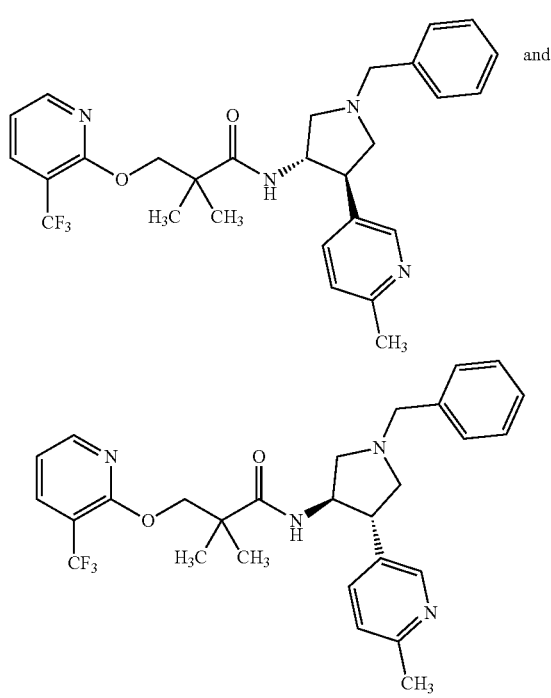

In a 250 mL round-bottomed flask were combined 2,2-dimethyl-3-((3-(trifluoromethyl)pyridin-2-yl)oxy)propanoic acid (0.150 g, 0.422 mmol), trans-1-benzyl-4-(6-methylpyridin-3-yl)pyrrolidin-3-amine (0.113 g, 0.422 mmol), HATU (0.192 g, 0.506 mmol) and DIPEA (0.220 mL, 1.265 mmol) in DMF (6 mL) to give a yellow solution. The reaction mixture was stirred at room temperature overnight, and was then treated with water and extracted with EtOAc. The organic phase was dried over MgSO$_4$ and concentrated under reduced pressure. The residue was purified by automated flash silica column chromatography (40 g column) eluting with a gradient of 30-90% hexanes in EtOAc. The fractions were evaporated to give the title compound (0.15 g, 69%). ESI-MS [M+H]$^+$ calc'd for $C_{28}H_{31}F_3N_4O_2$, 513.24; found, 513.6.

Preparation 51: trans-2,2-dimethyl-N-(4-(6-methylpyridin-3-yl)pyrrolidin-3-yl)-3-((3-(trifluoromethyl)pyridin-2-yl)oxy)propanamide

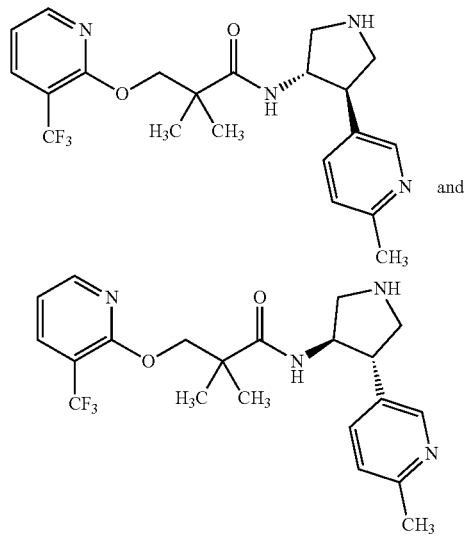

In a 250 mL round-bottomed flask, trans-N-(1-benzyl-4-(6-methylpyridin-3-yl)pyrrolidin-3-yl)-2,2-dimethyl-3-((3-(trifluoromethyl)pyridin-2-yl)oxy)propanamide (0.15 g, 0.29 mmol) was dissolved in methanol (8 mL) to give a colorless solution. Ammonium formate (0.092 g, 1.5 mmol) and palladium on activated carbon (10 wt %, 0.012 g, 0.012 mmol) were added. The reaction mixture was stirred at 90° C. under nitrogen for 1 hour and then filtered. The filtrate was concentrated to give the title compound as a colorless film (0.108 g, 87%) which was used without further purification. ESI-MS [M+H]$^+$ calc'd for $C_{21}H_{25}F_3N_4O_2$, 423.19; found, 423.5.

Preparation 52: methyl 2,2-dimethyl-3-((3-methylpyridin-2-yl)oxy)propanoate (Alternative Procedure)

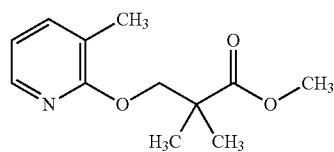 [SMILES: COC(=O)C(C)(C)COc1ncccc1C]

Methyl 3-hydroxy-2,2-dimethylpropanoate (2.97 g, 22.5 mmol) was dissolved in DMF (20 mL) to give a colorless solution. Sodium hydride (60 wt %, 1.12 g, 28.1 mmol) was added. After stirring for 30 minutes at room temperature, 2-fluoro-3-methylpyridine (2.08 g, 18.7 mmol) was added. After completion of the reaction, the mixture was treated with saturated aq NH$_4$Cl and extracted with EtOAc. The organic phase was dried over MgSO$_4$, filtered, and concentrated. The residue was purified by automated flash silica column chromatography (80 g column) eluting with a gradient of 0-20% EtOAc in heptanes. The fractions containing product were evaporated to give the title compound as a colorless oil (0.77 g, 18%). ESI-MS [M+H]+ calc'd for C$_{12}$H$_{17}$NO$_3$, 224.13; found, 224.2.

Preparation 53: 2,2-dimethyl-3-((3-methylpyridin-2-yl)oxy)propanoic Acid

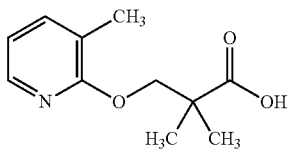

Methyl 2,2-dimethyl-3-((3-methylpyridin-2-yl)oxy)propanoate (0.77 g, 3.45 mmol) was dissolved in dioxane (14 mL) to give a colorless solution. Lithium hydroxide (2 M, 6.90 mL, 13.8 mmol) was added and the reaction mixture was stirred at room temperature overnight. The reaction mixture was concentrated to dryness to give the lithium salt of the title compound as a white solid (1.04 g, assumed quantitative) which was used without further purification. ESI-MS [M+H]+ calc'd for C$_{11}$H$_{15}$NO$_3$, 210.11; found, 210.2.

Preparation 54: (E)-1,3-dimethyl-4-(2-nitrovinyl)-1H-pyrazole

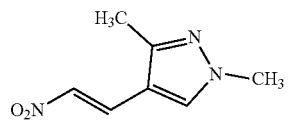

To a solution of 1,3-dimethyl-1H-pyrazole-4-carbaldehyde (1.00 g, 8.06 mmol) in nitromethane (35 mL) was added ammonium acetate (0.155 g, 2.01 mmol). The reaction mixture was heated at reflux overnight. Excess nitromethane was removed under reduced pressure. The residue was purified by automated flash silica column chromatography (40 g column) eluting with a gradient of 20-50% EtOAc in heptanes. The fractions were evaporated to give the title compound as a yellow solid (1.31 g, 97%). ESI-MS [M+H]+ calc'd for C$_7$H$_9$N$_3$O$_2$, 168.08; found, 168.2.

Preparation 55: trans-4-(1,3-dimethyl-1H-pyrazol-4-yl)-1-methylpyrrolidin-3-amine

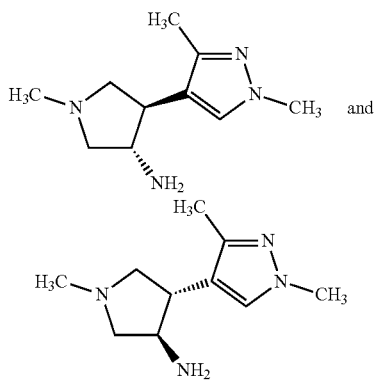

An HCl salt of the title compound (0.274 g) was prepared in a manner similar to STEPS C-H of PREPARATION 47, using (E)-1,3-dimethyl-4-(2-nitrovinyl)-1H-pyrazole (1.31 g, 7.84 mmol) in place of (E)-1-methyl-4-(2-nitrovinyl)-1H-pyrazole. ESI-MS [M+H]+ calc'd for C$_{10}$H$_{18}$N$_4$, 195.16; found, 195.2.

Preparation 56: methyl 3-((3-cyclopropylpyridin-2-yl)oxy)-2,2-dimethylpropanoate

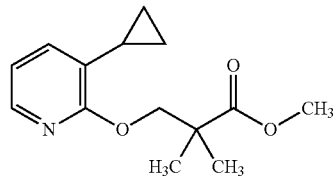 [SMILES: COC(=O)C(C)(C)COc1ncccc1C1CC1]

The title compound was prepared in a manner similar to PREPARATION 52, using 3-cyclopropyl-3-fluoropyridine (2.00 g, 14.6 mmol) in place of 2-fluoro-3-methylpyridine. The product was isolated as a brown oil (3.63 g, assumed quantitative) which was used without further purification.

Preparation 57: 3-((3-cyclopropylpyridin-2-yl)oxy)-2,2-dimethylpropanoic

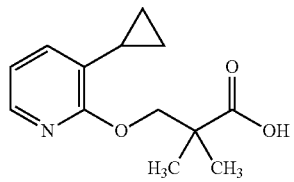 [SMILES: CC(C)(COc1ncccc1C1CC1)C(=O)O]

In a 250 mL round-bottomed flask, methyl 3-((3-cyclopropylpyridin-2-yl)oxy)-2,2-dimethylpropanoate (3.63 g, 14.6 mmol) and 2 M aq lithium hydroxide (29.2 mL, 58.3 mmol) were combined in dioxane (50 mL) to give a brown solution. The reaction mixture was stirred at room temperature overnight, and was then acidified to pH 5 with 1 N HCl and extracted with EtOAc. The organic phase was dried over MgSO$_4$, filtered, and concentrated to give the title compound as a light brown syrup (3.43 g, assumed quantitative) which was used without further purification. ESI-MS [M+H]+ calc'd for C$_{13}$H$_{17}$NO$_3$, 236.13; found, 236.2.

Preparation 58: (E)-1,5-dimethyl-4-(2-nitrovinyl)-1H-pyrazole

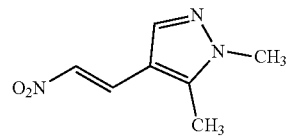

The title compound was prepared in a manner similar to PREPARATION 54, using 1,5-dimethyl-1H-pyrazole-4-carbaldehyde (0.83 g, 6.7 mmol) in place of 1,3-dimethyl-1H-pyrazole-4-carbaldehyde. The product was isolated as a colorless oil (1.118 g, assumed quantitative). ESI-MS [M+H]+ calc'd for $C_7H_9N_3O_2$ 168.08; found, 168.2.

Preparation 59: trans-4-(1,5-dimethyl-1H-pyrazol-4-yl)-1-methylpyrrolidin-3-amine

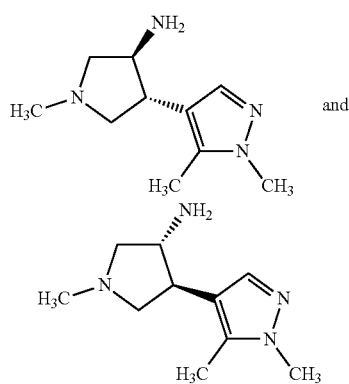

An HCl salt of the title compound (0.629 g) was prepared in a manner similar to STEPS C-H of PREPARATION 47, using (E)-1,5-dimethyl-4-(2-nitrovinyl)-1H-pyrazole (1.118 g, 6.69 mmol) in place of (E)-1-methyl-4-(2-nitrovinyl)-1H-pyrazole. ESI-MS [M+H]+ calc'd for $C_{10}H_{18}N_4$, 195.16; found, 195.2.

Preparation 60: tert-butyl 4-amino-3-ethylpiperidine-1-carboxylate

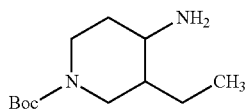 [SMILES: CCC1CN(C(=O)OC(C)(C)C)CCC1N]

A solution of tert-butyl 3-ethyl-4-oxopiperidine-1-carboxylate (1.00 g, 4.40 mmol) and ammonium formate (1.11 g, 17.6 mmol) in methanol (30 mL) was stirred for 10 minutes at room temperature. Palladium on carbon (10 wt %, 0.140 g, 0.132 mmol) was added and the reaction mixture was stirred at 60° C. for 2 hours. The reaction mixture was filtered. The filtrate was concentrated under reduced pressure to give the title compound as a light brown syrup (0.962 g, 96%) which was used without further purification.

Preparation 61: tert-butyl 4-amino-3,3-dimethylpiperidine-1-carboxylate

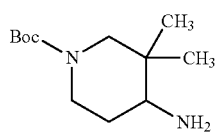

The title compound was prepared in a manner similar to PREPARATION 60, using tert-butyl 3,3-dimethyl-4-oxopiperidine-1-carboxylate (1.00 g, 4.40 mmol) in place of tert-butyl 3-ethyl-4-oxopiperidine-1-carboxylate. The product was used without further purification (0.998 g, 99%).

Preparation 62: tert-butyl 4-amino-3-fluoropiperidine-1-carboxylate

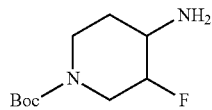

Step A: tert-butyl 4-(benzylamino)-3-fluoropiperidine-1-carboxylate

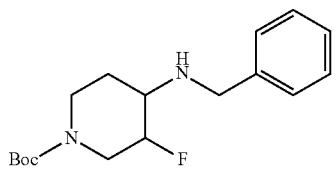 [SMILES: CC(C)(C)OC(=O)N1CCC(NCc2ccccc2)C(F)C1]

A colorless solution of tert-butyl 3-fluoro-4-oxopiperidine-1-carboxylate (1.05 g, 4.83 mmol) and phenylmethanamine (0.581 mL, 5.32 mmol) in DCM (20 mL) was treated with sodium triacetoxyborohydride (1.537 g, 7.25 mmol). The reaction mixture was stirred at room temperature for 2 hours, and was then treated with saturated aq $NaHCO_3$, neutralized with $NaCO_3$, and extracted with EtOAc. The organic phase was washed with brine, dried over $MgSO_4$, filtered, and concentrated to give the title compound as a colorless syrup (1.49 g, quantitative) which was used without further purification. ESI-MS [M+H]+ calc'd for $C_{17}H_{25}FN_2O_2$, 309.20; found [M−55], 253.2.

Step B: tert-butyl 4-amino-3-fluoropiperidine-1-carboxylate

The title compound was prepared in a manner similar to PREPARATION 60, using tert-butyl 4-(benzylamino)-3-fluoropiperidine-1-carboxylate (1.49 g, 4.83 mmol) in place of tert-butyl 3-ethyl-4-oxopiperidine-1-carboxylate. The product was isolated as a white solid (1.05 g, quantitative) which was used without further purification. ESI-MS [M+H]+ calc'd for $C_{10}H_{19}FN_2O_2$, 219.15; found [M-tert-butoxy], 145.1.

Preparation 63: tert-butyl 8-amino-5-azaspiro[2.5]octane-5-carboxylate

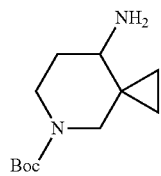

The title compound was prepared in a manner similar to PREPARATION 60, using tert-butyl 8-oxo-5-azaspiro[2.5]octane-5-carboxylate (1.00 g, 4.44 mmol) in place of tert-butyl 3-ethyl-4-oxopiperidine-1-carboxylate. The product was isolated as a white solid (0.226 g, 22%) which was used without further purification. ESI-MS [M+H]⁺ calc'd for $C_{12}H_{22}N_2O_2$, 227.32; found [M−55], 171.2.

Preparation 64: tert-butyl 4-amino-3-chloropiperidine-1-carboxylate

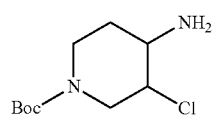

The title compound was prepared in a manner similar to PREPARATION 62 using tert-butyl 3-chloro-4-oxopiperidine-1-carboxylate (1.00 g, 4.28 mmol) in place of tert-butyl 3-fluoro-4-oxopiperidine-1-carboxylate. The product was isolated as a white solid (1.005 g, assumed quantitative) which was used without further purification. ESI-MS [M+H]⁺ calc'd for $C_{10}H_{19}ClN_2O_2$, 235.12; found [M−55], 179.1.

Preparation 65: methyl 2,2-dimethyl-3-((3-(trifluoromethoxy)pyridin-2-yl)oxy)propanoate

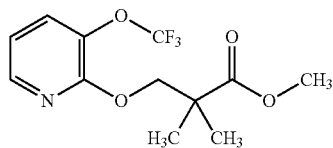

To a solution of methyl 3-hydroxy-2,2-dimethylpropanoate (5.02 g, 38.0 mmol) in DMF (6 mL) was added sodium hydride (60 wt %, 2.02 g, 50.6 mmol). After stirring for 1 hour at room temperature, 2-chloro-3-(trifluoromethoxy)pyridine (5.00 g, 25.3 mmol) was added. The mixture was heated at 100° C. overnight, and was then concentrated to ⅓ volume, treated with saturated aq NH₄Cl, and extracted with EtOAc. The organic phase was dried over MgSO₄, filtered, and concentrated to give the title compound crude as a tan oil (7.42 g, assumed quantitative) which was used without further purification. ESI-MS [M+H]⁺ calc'd for $C_{12}H_{14}F_3NO_4$, 294.09; found, 294.3.

Preparation 66: 2,2-dimethyl-3-((3-(trifluoromethoxy)pyridin-2-yl)oxy)propanoic Acid

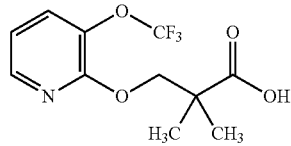 [SMILES: CC(C)(COc1ncccc1OC(F)(F)F)C(=O)O]

In a 250 mL round-bottomed flask, methyl 2,2-dimethyl-3-((3-(trifluoromethoxy)pyridin-2-yl)oxy)propanoate (6.89 g, 23.5 mmol) and lithium hydroxide (2 M, 47.0 mL, 94 mmol) were combined in dioxane (50 mL) to give a brown solution. The reaction mixture was stirred at room temperature overnight, and was then concentrated to ⅓ volume, acidified with 1 N aq HCl, and extracted with EtOAc. The organic phase was dried over MgSO₄, filtered, and concentrated under reduced pressure. The residue was purified by automated flash silica column chromatography (120 g column) eluting with a gradient of 0-50% EtOAc in heptanes. The fractions were evaporated to give the title compound as a colorless oil (3.17 g, 48%). ESI-MS [M+H]⁺ calc'd for $C_{11}H_{12}F_3NO_4$, 280.07; found, 280.13.

Preparation 67: tert-butyl 4-amino-3-(1-(difluoromethyl)-1H-pyrazol-4-yl)piperidine-1-carboxylate

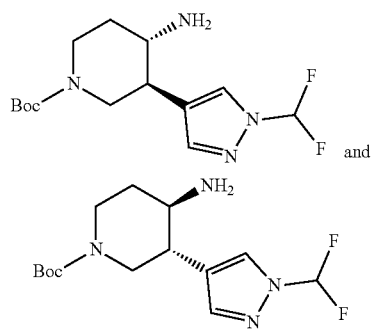

Step A: 1-(tert-butyl) 4-ethyl 5-(1-(difluoromethyl)-1H-pyrazol-4-yl)-3,6-dihydropyridine-1,4(2H)-dicarboxylate

In a 125 mL round-bottomed flask, RuPhos Pd G3 (0.143 g, 0.171 mmol), cesium carbonate (2.225 g, 6.83 mmol), 1-(tert-butyl) 4-ethyl 5-((((trifluoromethyl)sulfonyl)oxy)-3,6-dihydropyridine-1,4(2H)-dicarboxylate (1.548 g, 3.41 mmol), and 1-(difluoromethyl)-4-(4,4,5,5-tetramethyl-1,3,2-dioxaborolan-2-yl)-1H-pyrazole (1.00 g, 4.10 mmol) were combined in dioxane (20.09 mL) to give an orange solution. Nitrogen was bubbled through the reaction mixture for 5 minutes, which was then heated at 75° C. overnight. The mixture was subsequently diluted with EtOAc and filtered. The filtrate was concentrated and the resulting residue was purified by automated flash silica column chromatography (40 g column) eluting with a gradient of 0-50% EtOAc in heptanes. The fractions were evaporated to give the title compound as a yellow syrup (1.16 g, 91%). ESI-MS [M+H]⁺ calc'd for $C_{17}H_{23}F_2N_3O_4$, 372.17; found, 372.4.

Step B: cis-1-(tert-butyl) 4-ethyl 3-(1-(difluoromethyl)-1H-pyrazol-4-yl)piperidine-1,4-dicarboxylate

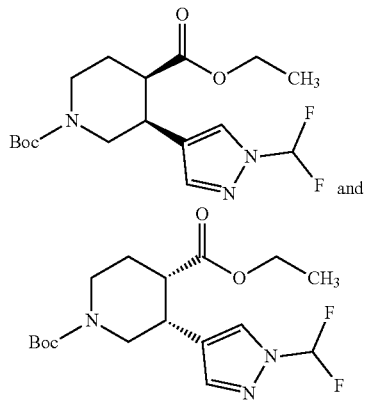

A mixture of 1-(tert-butyl) 4-ethyl 5-(1-(difluoromethyl)-1H-pyrazol-4-yl)-3,6-dihydropyridine-1,4(2H)-dicarboxylate (1.16 g, 3.12 mmol), dihydroxypalladium on carbon (20 wt %, 0.219 g, 0.312 mmol), and ammonium formate (0.788 g, 12.5 mmol) was combined in ethanol (31.2 mL) to give a black suspension. The reaction mixture was stirred at 90° C. overnight and was then filtered. The filtrate was concentrated to give the title compound (1.145 g, 98%). ESI-MS [M+H]$^+$ calc'd for $C_{17}H_{25}F_2N_3O_4$, 374.19; found [M−55], 318.2.

Step C: trans-1-(tert-butyl) 4-ethyl 3-(1-(difluoromethyl)-1H-pyrazol-4-yl)piperidine-1,4-dicarboxylate

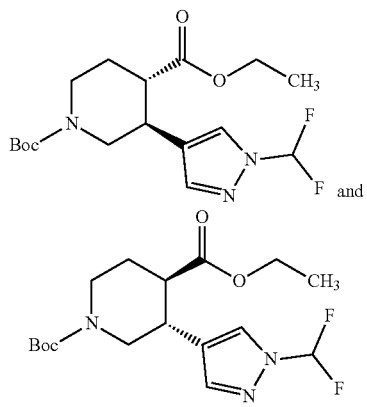

In a 50 mL round-bottomed flask, sodium metal (0.141 g, 6.13 mmol) was stirred in ethanol (18.4 mL) under nitrogen atmosphere until the metal disappeared. The solution was transferred to a flask containing a solution of cis-1-(tert-butyl) 4-ethyl 3-(1-(difluoromethyl)-1H-pyrazol-4-yl)piperidine-1,4-dicarboxylate (1.145 g, 3.07 mmol) in ethanol (12.3 mL). The reaction mixture was stirred at 85° C. overnight and was then allowed to cool to room temperature. The mixture was concentrated and the residue was treated with dilute aq HCl and extracted with EtOAc. The organic phase was dried over MgSO$_4$, filtered, and concentrated to give the title compound as a brown syrup (1.145 g, assumed quantitative) which was used without further purification. ESI-MS [M+H]$^+$ calc'd for $C_{17}H_{25}F_2N_3O_4$, 374.19; found [M−55], 318.2.

Step D: trans-1-(tert-butoxycarbonyl)-3-(1-(difluoromethyl)-1H-pyrazol-4-yl)piperidine-4-carboxylic Acid

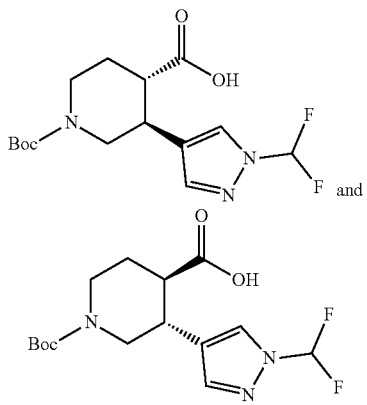

To a brown solution of trans-1-(tert-butyl) 4-ethyl 3-(1-(difluoromethyl)-1H-pyrazol-4-yl)piperidine-1,4-dicarboxylate (1.145 g, 3.07 mmol) in ethanol (8 mL) was added sodium hydroxide (10 M, 0.737 mL, 7.37 mmol). The reaction mixture was stirred at 90° C. for 1 hour, and was then acidified to pH 5 with 1 N aq HCl and extracted with EtOAc. The organic phase was dried over MgSO$_4$, filtered, and concentrated to give the title compound as a tan syrup (1.06 g, assumed quantitative) which was used without further purification. ESI-MS [M+H]$^+$ calc'd for $C_{15}H_{21}F_2N_3O_4$, 346.16; found, 346.3.

Step E: trans-tert-butyl 4-amino-3-(1-(difluoromethyl)-1H-pyrazol-4-yl)piperidine-1-carboxylate In a 250 mL round-bottomed flask, trans-1-(tert-butoxycarbonyl)-3-(1-(difluoromethyl)-1H-pyrazol-4-yl)piperidine-4-carboxylic acid (1.06 g, 3.07 mmol), diphenyl phosphorazidite (1.00 mL, 4.91 mmol), and triethylamine (0.642 mL, 4.61 mmol) were combined in toluene (18 mL) to give a brown solution. The reaction mixture was heated at 100° C. for 1 hour and was then cooled to room temperature. Sodium hydroxide (10 M, 3.07 mL, 30.7 mmol) was added and the reaction mixture was stirred at room temperature for 3 hours. The mixture was treated with water and extracted with EtOAc. The organic phase was washed with water and brine, dried over MgSO$_4$, filtered, and concentrated. The residue was purified by automated flash silica column chromatography (60 g NH column) eluting with a gradient of 0-100% EtOAc in heptanes. The fractions were evaporated to give the title compound as a colorless film (0.56 g, 58%). ESI-MS [M+H]$^+$ calc'd for $C_{14}H_{22}F_2N_4O_2$, 317.18; found [M−55], 261.2.

Preparation 68: tert-butyl trans-4-amino-3-ethylpiperidine-1-carboxylate

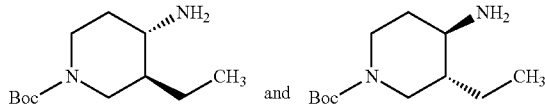 [SMILES: CC[C@H]1CN(C(=O)OC(C)(C)C)CC[C@@H]1N ; CC[C@@H]1CN(C(=O)OC(C)(C)C)CC[C@H]1N]

Step A: ethyl 1-benzyl-3-ethylpiperidine-4-carboxylate

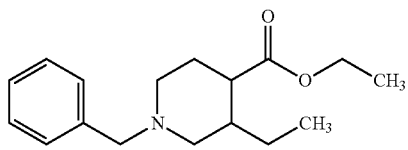 [SMILES: CCOC(=O)C1CCN(Cc2ccccc2)CC1CC]

In a 250 mL round-bottomed flask, a grey suspension of copper(I) iodide (3.14 g, 16.5 mmol) in diethyl ether (15 mL) was cooled to −40° C. (dry ice in acetonitrile). Ethylmagnesium bromide (1 M in THF, 46.9 mL, 46.9 mmol) was added dropwise. After stirring for 30 minutes, a solution of ethyl 1-benzyl-1,2,3,6-tetrahydropyridine-4-carboxylate (2.02 g, 8.23 mmol) in diethyl ether (10 mL) was added dropwise. The reaction mixture was stirred at −40° C. for 6 hours and was then quenched with saturated aq NH$_4$Cl. The organic layer was separated and the aqueous layer was extracted with EtOAc. The organic layers were combined, washed with brine, dried over MgSO$_4$, filtered, and concentrated. The residue was purified by automated flash silica column chromatography (80 g column) eluting with a gradient of 0-20% EtOAc in heptanes. The fractions were collected to give a colorless syrup, which was treated with water and extracted with EtOAc. The combined organics were washed with brine, dried over MgSO$_4$, filtered, and concentrated. The residue was purified by automated flash silica column chromatography (60 g NH column) eluting with a gradient of 0-100% EtOAc in heptanes. The fractions were evaporated to give the title compound as a colorless film (1.21 g, 53%). ESI-MS [M+H]$^+$ calc'd for C$_{17}$H$_{25}$NO$_2$, 276.20; found, 276.3.

Step B: ethyl 3-ethylpiperidine-4-carboxylate

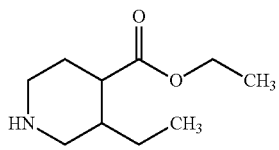

A black suspension of ethyl 1-benzyl-3-ethylpiperidine-4-carboxylate (1.21 g, 4.39 mmol) and dihydroxypalladium on carbon (20 wt %, 0.309 g, 0.439 mmol) in THF (20 mL) and ethanol (20 mL) was evacuated and backfilled with hydrogen gas three times. The reaction mixture was stirred at room temperature under hydrogen atmosphere (balloon) overnight. The reaction mixture was filtered, and the filtrate was concentrated to give the title compound as a colorless syrup (0.814 g, assumed quantitative) which was used without further purification. ESI-MS [M+H]$^+$ calc'd for C$_{10}$H$_{19}$NO$_2$, 186.15; found, 186.3.

Step C: 1-(tert-butyl) 4-ethyl 3-ethylpiperidine-1,4-dicarboxylate

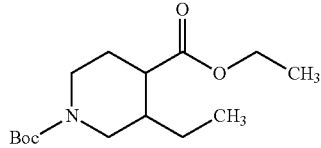

A colorless solution of ethyl 3-ethylpiperidine-4-carboxylate (0.814 g, 4.39 mmol), di-tert-butyl dicarbonate (1.102 g, 5.05 mmol) and triethylamine (0.918 mL, 6.59 mmol) in DCM (40 mL) was stirred at room temperature for 7 hours. The reaction mixture was treated with water and extracted with DCM. The organics were washed with brine, dried over MgSO$_4$, filtered, and concentrated to give the title compound as a colorless syrup (1.25 g, assumed quantitative) which was used without further purification. ESI-MS [M+H]$^+$ calc'd for C$_{15}$H$_{27}$NO$_4$, 286.20; found [M-Boc], 186.0.

Step D: 1-(tert-butyl) trans-4-ethyl 3-ethylpiperidine-1,4-dicarboxylate

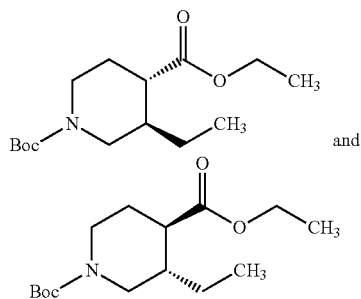

To a colorless solution of 1-(tert-butyl) 4-ethyl 3-ethylpiperidine-1,4-dicarboxylate (1.25 g, 4.39 mmol) in ethanol (17.6 mL) was added a freshly made solution of sodium metal (0.202 g, 8.78 mmol) in ethanol (26.3 mL). The reaction mixture was stirred at 85° C. overnight. The reaction mixture was treated with water and extracted with EtOAc. The organic phase was washed with brine, dried over MgSO$_4$, filtered, and concentrated to give crude title compound as a tan syrup (1.25 g, assumed quantitative) which was used without further purification.

Step E: trans-1-(tert-butoxycarbonyl)-3-ethylpiperidine-4-carboxylic Acid

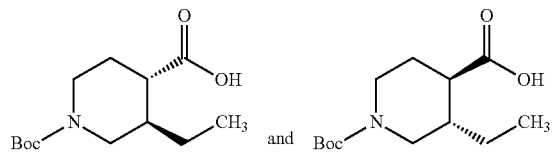 [SMILES: CC[C@H]1CN(C(=O)OC(C)(C)C)CC[C@@H]1C(=O)O ; CC[C@@H]1CN(C(=O)OC(C)(C)C)CC[C@H]1C(=O)O]

A brown solution of 1-(tert-butyl) trans-4-ethyl 3-ethylpiperidine-1,4-dicarboxylate (1.25 g, 4.39 mmol) and lithium hydroxide (2 M, 8.78 mL, 17.6 mmol) in dioxane (16 mL) was stirred at room temperature overnight. The reaction mixture was acidified to pH 5 with dilute aq HCl and extracted with EtOAc. The organic phase was dried over MgSO$_4$, filtered, and concentrated to give the title compound as a light brown syrup (1.05 g, 93%) which was used without further purification.

Step F: tert-butyl trans-4-amino-3-ethylpiperidine-1-carboxylate

A brown solution of trans-1-(tert-butoxycarbonyl)-3-ethylpiperidine-4-carboxylic acid (1.05 g, 4.08 mmol), diphenyl phosphorazidite (1.33 mL, 6.53 mmol) and triethylamine (0.853 mL, 6.12 mmol) in toluene (27.2 mL) was heated at 100° C. for 1 hour. The reaction mixture was cooled to room temperature and sodium hydroxide (10 M, 4.08 mL, 40.8 mmol) was added. The reaction mixture was stirred at room temperature for 3 hours and then extracted with DCM. The organic phase was dried over MgSO$_4$, filtered, and concentrated to give the title compound as a light brown syrup (0.622 g, 67%) which was used without further purification. ESI-MS [M+H]$^+$ calc'd for C$_{12}$H$_{24}$N$_2$O$_2$, 229.19; found, 229.2.

Preparation 69: tert-butyl 4-amino-2,2-dimethylpiperidine-1-carboxylate

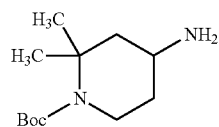 [SMILES: CC(C)(C)OC(=O)N1CCC(N)CC1(C)C]

A colorless solution of tert-butyl 2,2-dimethyl-4-oxopiperidine-1-carboxylate (1.00 g, 4.40 mmol) and ammonium formate (1.11 g, 17.6 mmol) in methanol (29.3 mL) was stirred for 10 minutes at room temperature and then treated with palladium on carbon (10 wt %, 0.140 g, 0.132 mmol). The reaction mixture was stirred at 60° C. for 2 hours. Extra ammonium formate (1.11 g, 17.6 mmol) was added and the reaction mixture was stirred at 60° C. for an additional 1 hour. The reaction mixture was filtered and the filtrate was concentrated to give the title compound as a white solid (1.00 g, assumed quantitative) which was used without further purification. ESI-MS [M+H]$^+$ calc'd for C$_{12}$H$_{24}$N$_2$O$_2$, 229.19; found [M−55], 173.1.

Preparation 70: 1,5,5-trimethylpyrrolidin-3-amine

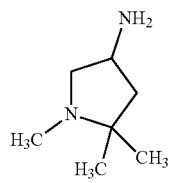

A black suspension of 1,5,5-trimethylpyrrolidin-3-one (1.00 g, 7.86 mmol), ammonium formate (1.983 g, 31.4 mmol), and palladium on carbon (10 wt %, 0.251 g, 0.236 mmol) in methanol (52.4 mL) was stirred at 60° C. for 2 hours. The reaction mixture was filtered through a pad of Celite©. The filtrate was concentrated to give the title compound as a yellow syrup (0.63 g, 62%) which was used without further purification. ESI-MS [M+H]$^+$ calc'd for C$_7$H$_{16}$N$_2$, 129.14; found, 129.1.

Preparation 71: 4-benzyl-4-azaspiro[2.5]octan-7-amine

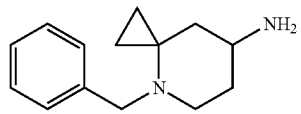 [SMILES: NC1CCN(Cc2ccccc2)C2(CC2)C1]

A yellow solution of 4-benzyl-4-azaspiro[2.5]octan-7-one (0.690 g, 3.20 mmol), ammonium acetate (1.235 g, 16.02 mmol), and sodium cyanoborohydride (0.060 g, 0.96 mmol) in methanol (21.4 mL) was heated to reflux for 64 hours. The reaction mixture was concentrated. The residue was purified by automated flash silica column chromatography (40 g NH column) eluting with a gradient of 0-50% EtOAc in heptanes. The fractions were evaporated to give the title compound as a brown film (0.308 g, 44%). ESI-MS [M+H]$^+$ calc'd for C$_{14}$H$_{20}$N$_2$, 217.17; found, 217.2.

Preparation 72: tert-butyl 3-(o-tolyl)-4-(N,2,2-trimethyl-3-((3-(trifluoromethyl)pyridin-2-yl)oxy)propanamido)piperidine-1-carboxylate

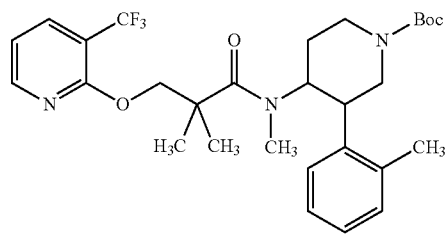 [SMILES: Cc1ccccc1C1CN(C(=O)OC(C)(C)C)CCC1N(C)C(=O)C(C)(C)COc1ncccc1C(F)(F)F]

Step A: tert-butyl 4-oxo-3-(o-tolyl)piperidine-1-carboxylate

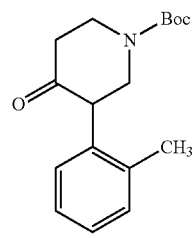 [SMILES: Cc1ccccc1C1CN(C(=O)OC(C)(C)C)CCC1=O]

A glass vial was purged with nitrogen and charged with anhydrous THF (6.3 mL), diacetoxypalladium (28.2 mg, 0.125 mmol) and sodium tert-butoxide (362 mg, 3.76 mmol). The mixture was stirred for 15 minutes until the sodium tert-butoxide was dissolved. Tri-tert-butylphosphine (1.0 M in toluene, 251 μL, 0.251 mmol), 1-bromo-2-methylbenzene (332 µL, 2.76 mmol) and tert-butyl 4-oxopiperidine-1-carboxylate (500 mg, 2.51 mmol) were added. The reaction mixture was slowly heated at 45-50° C. over a period of 4 hours and was then poured into saturated aq NaHCO$_3$(5 mL) and extracted with EtOAc (8 mL). The organic layer was separated, dried over Na$_2$SO$_4$, concentrated under reduced pressure, and purified by flash silica column chromatography, eluting with a gradient of 15-100% EtOAc in heptanes to give the title compound as a colorless oil (172 mg, 24%).

Step B: tert-butyl 4-(methylamino)-3-(o-tolyl)piperidine-1-carboxylate

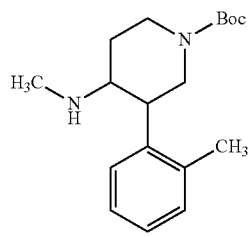 [SMILES: CNC1CCN(C(=O)OC(C)(C)C)CC1c1ccccc1C]

A mixture of tert-butyl 4-oxo-3-(o-tolyl)piperidine-1-carboxylate (270 mg, 0.933 mmol), methanamine (33% in EtOH, 134 µL, 1.07 mmol) and sodium triacetoxyhydroborate (989 mg, 4.67 mmol) in DCM (4.7 mL) was stirred at room temperature for 3 days. To the reaction mixture was added EtOAc (15 mL) followed by saturated aq NaHCO$_3$. The resulting mixture was stirred at room temperature for 1 hour. The organic layer was separated and the aqueous layer was extracted with EtOAc (15 mL). The combined organic layers were washed with brine, dried over Na$_2$SO$_4$, filtered, and concentrated to give the title compound as a light yellow oil (260 mg, 92%) which was directly used without further purification.

Step C: tert-butyl 3-(o-tolyl)-4-(N,2,2-trimethyl-3-((3-(trifluoromethyl)pyridin-2-yl)oxy)propanamido)piperidine-1-carboxylate To a solution of 2,2-dimethyl-3-((3-(trifluoromethyl)pyridin-2-yl)oxy)propanoic acid (73.5 mg, 0.279 mmol) and HATU (106 mg, 0.279 mmol) in DMF (1.4 mL) was added DIPEA (146 µL, 0.838 mmol). The resulting solution was stirred at room temperature for 10 minutes. Next tert-butyl 4-(methylamino)-3-(o-tolyl)piperidine-1-carboxylate (100 mg, 0.279 mmol) was added and the reaction mixture was stirred for 6 hours at room temperature and subsequently heated at 60° C. overnight. The reaction mixture was purified by preparative HPLC (Method A) to give a TFA salt of the title compound as a light brown oil (17 mg, 9.2%). ESI-MS [M+H]$^+$ calc'd for C$_{29}$H$_{38}$F$_3$N$_3$O$_4$, 550.28; found, 550.1.

Preparation 73: trans-tert-butyl 4-(2,2-dimethyl-3-((3-(trifluoromethyl)pyridin-2-yl)oxy)propanamido)-3-(o-tolyl)piperidine-1-carboxylate

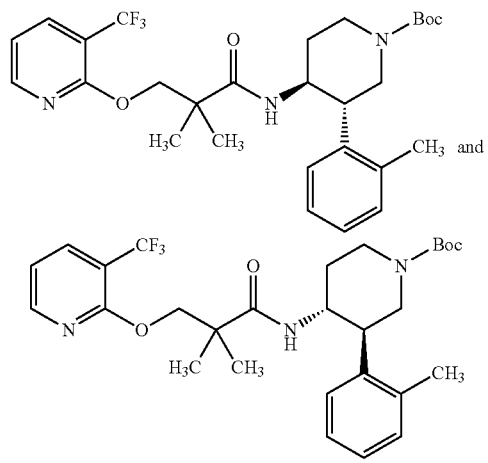

Step A: tert-butyl 4-amino-3-(o-tolyl)piperidine-1-carboxylate

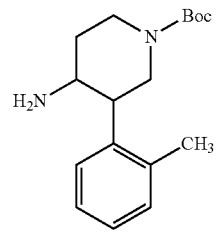 [SMILES: Cc1ccccc1C1CN(C(=O)OC(C)(C)C)CCC1N]

Sodium cyanotrihydroborate (36.9 mg, 0.587 mmol) was added in 2 portions at 10 minute intervals to a solution of tert-butyl 4-oxo-3-(o-tolyl)piperidine-1-carboxylate (170 mg, 0.587 mmol) and ammonium acetate (453 mg, 5.87 mmol) in dry methanol (3.0 mL). The reaction was subsequently quenched with saturated aq NaHCO$_3$(5.0 mL) and then extracted with EtOAc (2×10 mL). The organic layers were dried over anhydrous Na$_2$SO$_4$ and the solvent removed to give the title compound as a colorless oil (175 mg, assumed quantitative) which was used without further purification.

Step B: trans-tert-butyl 4-(2,2-dimethyl-3-((3-(trifluoromethyl)pyridin-2-yl)oxy)propanamido)-3-(o-tolyl)piperidine-1-carboxylate To a solution of HATU (79 mg, 0.21 mmol), 2,2-dimethyl-3-((3-(trifluoromethyl)pyridin-2-yl)oxy)propanoic acid (54.4 mg, 0.207 mmol) in DMF (1.0 mL) was added DIPEA (108 µL, 0.620 mmol). The solution was stirred at room temperature for 5 minutes. Next tert-butyl 4-amino-3-(o-tolyl)piperidine-1-carboxylate (60 mg, 0.21 mmol) was added and the solution was stirred at room temperature for 4 hours. The product was purified by preparative HPLC (Method A) to give title compound as a colorless oil (34 mg, 31%). ESI-MS [M+H]$^+$ calc'd for C$_{28}$H$_{36}$F$_3$N$_3$O$_4$, 536.27; found, 536.1.

Preparation 74: tert-butyl 4-amino-3-phenylpiperidine-1-carboxylate

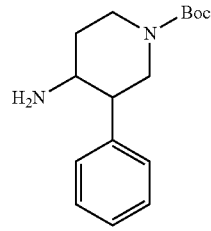 [SMILES: CC(C)(C)OC(=O)N1CCC(N)C(c2ccccc2)C1]

Step A: tert-butyl (E)-4-(hydroxyimino)-3-phenylpiperidine-1-carboxylate

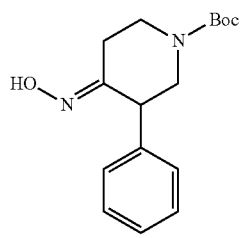

To a mixture of tert-butyl 4-oxo-3-phenyl-piperidine-1-carboxylate (1.1 g, 4.00 mmol) and NH$_2$OH·HCl (420 mg, 6.04 mmol) in EtOH (15 mL) was added NaOAc (700 mg, 8.53 mmol). The reaction mixture was allowed to stir at room temperature overnight and was then poured into water and extracted with EtOAc. The organic phase was washed with saturated aq NaHCO$_3$, dried over Na$_2$SO$_4$, filtered, and concentrated under reduced pressure to give the title compound (1.1 g, 95%) which was used without further purification. ESI-MS [M+H]$^+$ calc'd for C$_{16}$H$_{22}$N$_2$O$_3$, 291.17; found, 291.2.

Step B: tert-butyl 4-amino-3-phenylpiperidine-1-carboxylate

To a mixture of tert-butyl (E)-4-(hydroxyimino)-3-phenylpiperidine-1-carboxylate (700 mg, 2.41 mmol) in 1:1 THF/EtOH (25 mL) was added Raney Nickel (0.2 g). The suspension was degassed under vacuum and purged with H$_2$ several times. The mixture was stirred under H$_2$ (60 psi) at 70° C. for 24 hours and was then filtered through a pad of Celite®, which was rinsed with EtOAc. The filtrate was dried over Na$_2$SO$_4$, filtered, and concentrated under reduced pressure to give the title compound (0.75 g, 87%) which was used without further purification (77% purity). ESI-MS [M+H]$^+$ calc'd for C$_{16}$H$_{24}$N$_2$O$_2$, 277.19; found [M-t-Bu], 221.1.

Preparation 75: trans-tert-butyl 4-(2,2-dimethyl-3-((3-(trifluoromethyl)pyridin-2-yl)oxy)propanamido)-3-phenylpiperidine-1-carboxylate

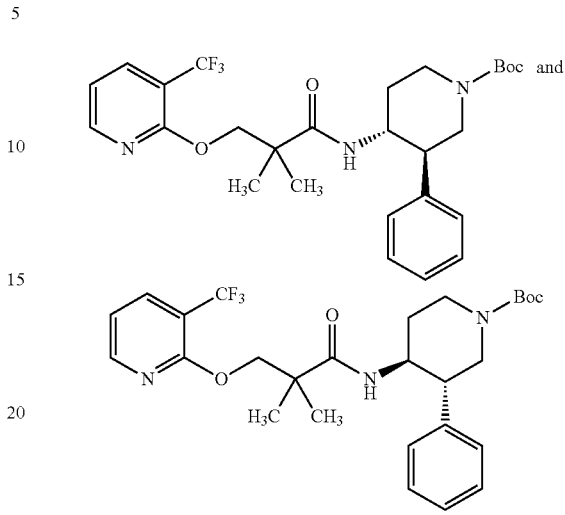

To a mixture of 2,2-dimethyl-3-((3-(trifluoromethyl)pyridin-2-yl)oxy)propanoic acid (300 mg, 1.14 mmol) and tert-butyl 4-amino-3-phenylpiperidine-1-carboxylate (380 mg, 1.376 mmol) in DMF (10 mL) was added HATU (650 mg, 1.71 mmol) and DIPEA (442 mg, 3.42 mmol) at 25° C. under nitrogen. The reaction mixture was allowed to stir at room temperature overnight and was then partitioned between EtOAc and brine. The organic phase was separated, washed with brine, dried, filtered, and concentrated under reduced pressure. The crude product was purified by preparative HPLC (Phenomenex Gemini 10 μm, 25 mm ID×150 mm column) eluting with a gradient of 60-80% ACN in water (containing 0.05% HCl) to give the title compound (240 mg, 38%) as a light yellow solid (94% purity). ESI-MS [M+H]$^+$ calc'd for C$_{27}$H$_{34}$F$_3$N$_3$O$_4$, 522.26; found, 522.0.

Preparation 76: trans-tert-butyl 3-phenyl-4-(N,2,2-trimethyl-3-((3-(trifluoromethyl)pyridin-2-yl)oxy)propanamido)piperidine-1-carboxylate

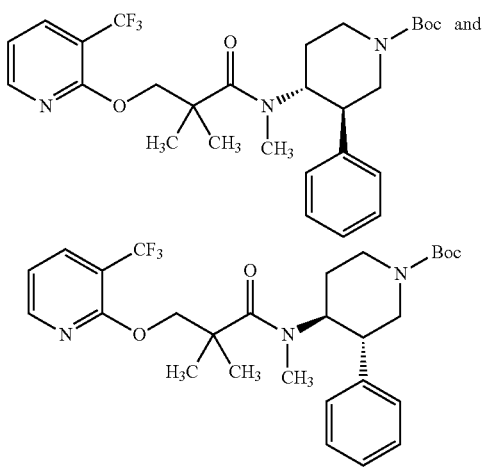

To a solution of trans-tert-butyl 4-((2,2-dimethyl-3-((3-(trifluoromethyl)-2-pyridyl)oxy) propanoyl)amino)-3-phenyl-piperidine-1-carboxylate (50 mg, 95 μmol) in DMF (2 mL) was added MeI (1.0 g, 7.05 mmol) at room temperature. NaH (60 wt %, 11.4 mg, 285 μmol) was added to the mixture and stirred overnight. The mixture was added to brine, and extracted with EtOAc. The organic phase was dried over anhydrous Na$_2$SO$_4$, filtered, and concentrated to give the crude product. The crude product was purified by preparative TLC using 3:1 petroleum ether/EtOAc as the eluent to afford the title compound as a colorless oil (35 mg, 69%). ESI-MS [M+H]$^+$ calc'd for C$_{27}$H$_{34}$F$_3$N$_3$O$_4$, 536.27; found, 536.3.

Preparation 77: 2,2-dimethyl-N-(3-phenylpiperidin-4-yl)-3-((3-(trifluoromethyl)pyridin-2-yl)oxy)propanamide

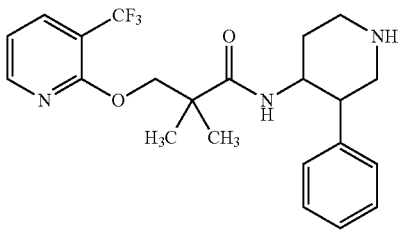 [SMILES: CC(C)(COc1ncccc1C(F)(F)F)C(=O)NC1CCNCC1c1ccccc1]

Step A: tert-butyl 4-oxo-3-phenylpiperidine-1-carboxylate

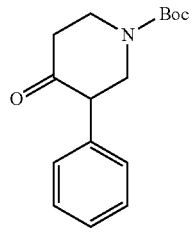 [SMILES: CC(C)(C)OC(=O)N1CCC(=O)C(c2ccccc2)C1]

A glass vial was purged with nitrogen and charged with anhydrous THF (10 mL), diacetoxypalladium (0.056 g, 0.251 mmol) and sodium tert-butoxide (0.724 g, 7.53 mmol). The mixture was stirred for 15 minutes until the sodium tert-butoxide was dissolved. Tri-tert-butylphosphine (50 wt % in toluene, 0.239 mL, 0.502 mmol), bromobenzene (0.579 mL, 5.27 mmol) and tert-butyl 4-oxopiperidine-1-carboxylate (1.00 g, 5.02 mmol) were added. The reaction mixture was slowly heated at 45-50° C. for 4 hours and was then poured into saturated aq NaHCO$_3$(5 mL) and extracted with EtOAc (8 mL). The organic layer was separated, dried over anhydrous Na$_2$SO$_4$, concentrated under reduced pressure, and purified by automated flash silica column chromatography, eluting with a gradient of 10-100% EtOAc in heptanes to give the title compound as a colorless oil (570 mg, 41%). ESI-MS [M+H]$^+$ calc'd for C$_{16}$H$_{21}$NO$_3$, 276.34; found [M−55], 220.1.

Step B: tert-butyl 4-amino-3-phenylpiperidine-1-carboxylate

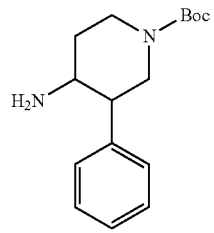

Sodium cyanotrihydroborate (103 mg, 1.64 mmol) was added in 2 portions at 10 minute intervals to a solution of tert-butyl 4-oxo-3-phenylpiperidine-1-carboxylate (430 mg, 1.56 mmol) and ammonium acetate (1204 mg, 15.62 mmol) in dry methanol (7.8 mL). The resulting solution was stirred at room temperature overnight and was then quenched with saturated aq NaHCO$_3$(5.0 mL) and extracted with EtOAc (2×10 mL). The organic layers were combined and dried over anhydrous Na$_2$SO$_4$. The solvent was removed to give the title compound as a colorless oil (420 mg, 97% yield) which was used without further purification. ESI-MS [M+H]$^+$ calc'd for C$_{16}$H$_{24}$N$_2$O$_2$, 277.34; found [M−55], 221.1.

Step C: tert-butyl 4-(2,2-dimethyl-3-((3-(trifluoromethyl)pyridin-2-yl)oxy)propanamido)-3-phenylpiperidine-1-carboxylate

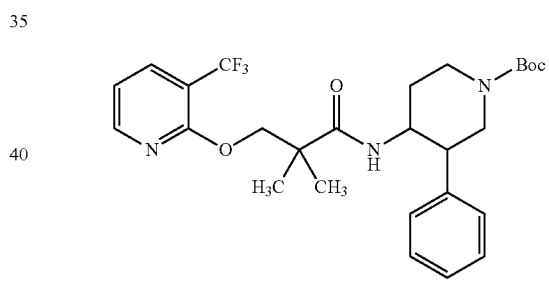

The title compound was prepared in a manner similar to PREPARATION 75, using a mixture of cis- and trans-stereoisomers of tert-butyl 4-amino-3-phenylpiperidine-1-carboxylate (150 mg, 0.543 mmol, 1 eq). The product was purified by preparative HPLC (Method A) to give the title compound as a colorless oil (102 mg, 30%). ESI-MS [M+H]$^+$ calc'd for C$_{27}$H$_{34}$F$_3$N$_3$O$_4$, 522.25; found, 522.1.

Step D: 2,2-dimethyl-N-(3-phenylpiperidin-4-yl)-3-((3-(trifluoromethyl)pyridin-2-yl)oxy)propanamide The title compound was prepared in a manner similar to EXAMPLE 162, using tert-butyl 4-(2,2-dimethyl-3-((3-(trifluoromethyl)pyridin-2-yl)oxy)propanamido)-3-phenylpiperidine-1-carboxylate (102 mg, 0.162 mmol, 1 eq) in place of trans-tert-butyl 3-phenyl-4-(N,2,2-trimethyl-3-((3-(trifluoromethyl)pyridin-2-yl)oxy)propanamido)piperidine-1-carboxylate. The solvent was removed to give a TFA salt of the title compound (87 mg, quantitative) which was used without further purification. ESI-MS [M+H]$^+$ calc'd for C$_{22}$H$_{26}$F$_3$N$_3$O$_2$, 422.20; found, 422.1.

Preparation 78: tert-butyl cis-4-(2,2-dimethyl-3-((3-(trifluoromethoxy)pyridin-2-yl)oxy)propanamido)-3-phenylpiperidine-1-carboxylate

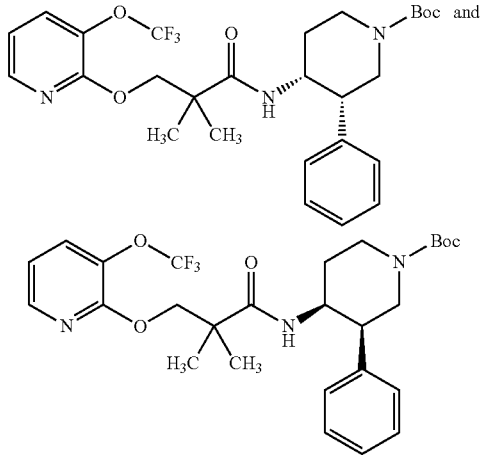

Preparation 79: tert-butyl trans-4-(2,2-dimethyl-3-((3-(trifluoromethoxy)pyridin-2-yl)oxy)propanamido)-3-phenylpiperidine-1-carboxylate

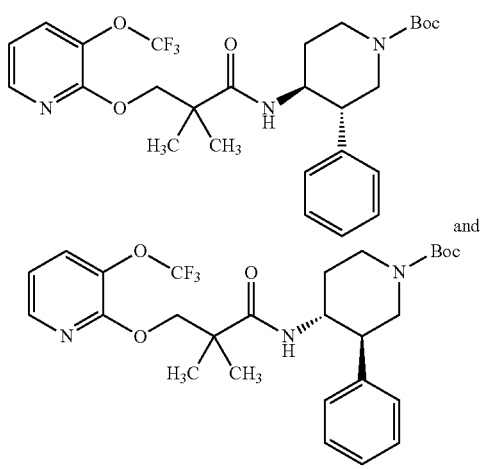

To a solution of 2,2-dimethyl-3-((3-(trifluoromethoxy)pyridin-2-yl)oxy)propanoic acid (152 mg, 0.543 mmol) and HATU (206 mg, 0.543 mmol) in DMF (5427 μL) was added DIPEA (284 μL, 1.628 mmol). The reaction mixture was stirred at room temperature for 10 minutes after which tert-butyl 4-amino-3-phenylpiperidine-1-carboxylate (150 mg, 0.543 mmol) was added. The resulting solution was stirred at room temperature for 3 hours and subsequently purified by preparative HPLC (Method A) to give the title cis-stereoisomer and trans-stereoisomer as colorless oils. The major peak was arbitrarily assigned to be the cis-stereoisomer (52 mg, 18%) and the minor peak was arbitrarily assigned to be the trans-stereoisomer (44 mg, 15%). Major peak: ESI-MS [M+H]$^+$ calc'd for $C_{27}H_{34}N_3O_5$, 538.25; found, 538.1. Minor peak: ESI-MS [M+H]$^+$ calc'd for $C_{27}H_{34}N_3O_5$, 538.25; found, 538.1.

Preparation 80: trans-1-methyl-4-(1-methyl-1H-pyrazol-4-yl)piperidin-3-amine

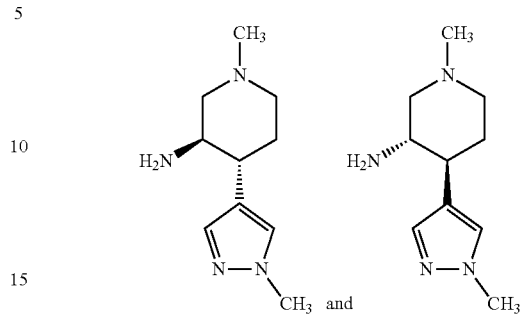

Step A: 1-(tert-butyl) 3-ethyl 4-(1-methyl-1H-pyrazol-4-yl)-5,6-dihydropyridine-1,3(2H)-dicarboxylate

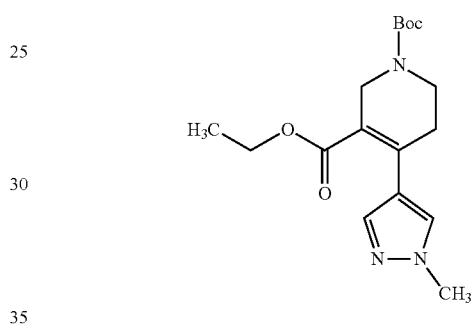

To a round bottom flask containing 1-(tert-butyl) 3-ethyl 4-(((trifluoromethyl)sulfonyl)oxy)-5,6-dihydropyridine-1,3(2H)-dicarboxylate (45.0 g, 112 mmol), 1-methyl-4-(4,4,5,5-tetramethyl-1,3,2-dioxaborolan-2-yl)pyrazole (27.85 g, 133.9 mmol), $K_3PO_4$ (59.20 g, 278.9 mmol) and Pd(dppf)Cl$_2$ (8.16 g, 11.2 mmol) was added dioxane (500 mL). The reaction mixture was stirred at 90° C. for 16 hours under nitrogen and then concentrated under reduced pressure. The crude product was purified by flash silica column chromatography, eluting with petroleum ether/EtOAc to give the title compound (42.7 g, 97%) as a red oil (85% purity). ESI-MS [M+H]$^+$ calc'd for $C_{17}H_{25}N_3O_4$, 336.19; found [M−55], 280.0.

Step B: 1-(tert-butyl) 3-ethyl 4-(1-methyl-1H-pyrazol-4-yl)piperidine-1,3-dicarboxylate

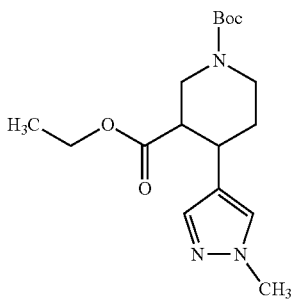 [SMILES: CCOC(=O)C1CN(C(=O)OC(C)(C)C)CCC1c1cnn(C)c1]

To a solution of 1-(tert-butyl) 3-ethyl 4-(1-methyl-1H-pyrazol-4-yl)-5,6-dihydropyridine-1,3(2H)-dicarboxylate (30.0 g, 89.4 mmol) in MeOH (400 mL) was added Mg (13.05 g, 536.7 mmol). The suspension was stirred at 15° C. for 2 hours under a nitrogen atmosphere. The mixture was then diluted with EtOAc and washed with 1M aq HCl and brine. The organic layer was dried, filtered, and concentrated under reduced pressure. The crude product was purified by automated flash silica column chromatography (120 g column) eluting with a gradient of 0-60% EtOAc in petroleum ether to give the title compound as light yellow gum (27 g, 93%, cis:trans=1.8:1). ESI-MS [M+H]$^+$ calc'd for $C_{17}H_{27}N_3O_4$, 338.21; found [M−55], 282.0.

Step C: 1-(tert-butyl) trans-3-ethyl 4-(1-methyl-1H-pyrazol-4-yl)piperidine-1,3-dicarboxylate

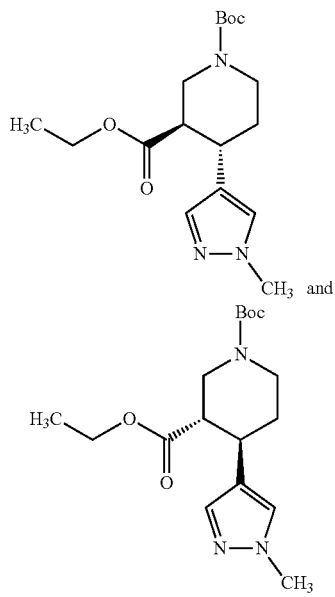

A solution of 1-(tert-butyl) 3-ethyl 4-(1-methyl-1H-pyrazol-4-yl)piperidine-1,3-dicarboxylate (mixture of cis and trans isomers, 10.0 g, 29.6 mmol) in EtOH (10 mL) was stirred at room temperature. A solution of EtONa in ethanol (6.5 M, 10 mL) was added. The mixture was stirred at reflux for 16 hours and was then diluted with EtOAc and saturated aq NH$_4$Cl. The organic layer was separated and dried, filtered, and concentrated under reduced pressure. The crude product was purified by automated flash silica column chromatography (120 g column) eluting with a gradient of 0-1% methanol in DCM to give the title compound as a light yellow gum (3.5 g, 35%). ESI-MS [M+H]$^+$ calc'd for $C_{17}H_{27}N_3O_4$, 338.21; found [M−55], 282.0.

Step D: ethyl trans-4-(1-methyl-1H-pyrazol-4-yl)piperidine-3-carboxylate

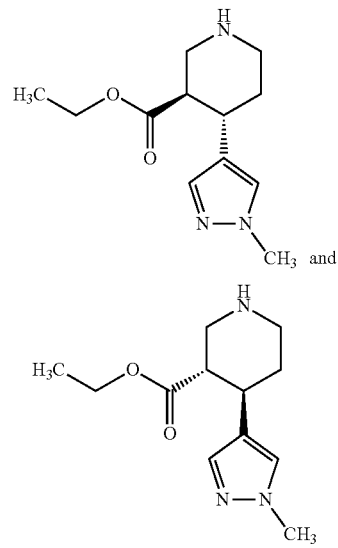

To a round bottom flask containing 1-(tert-butyl) trans-3-ethyl 4-(1-methyl-1H-pyrazol-4-yl)piperidine-1,3-dicarboxylate (3.50 g, 10.4 mmol) in DCM (50 mL) was added TFA (23.10 g, 202.6 mmol). The reaction mixture was stirred at 15° C. for 2 hours and then concentrated under reduced pressure. The resulting TFA salt of the crude product was dissolved in water and washed with EtOAc. The aqueous layer was treated with saturated aq Na$_2$CO$_3$ to adjust its pH to 9-10 and was then stirred at room temperature for 10 minutes and extracted with DCM (2×50 mL). The organic layers were combined, dried over Na$_2$SO$_4$, filtered, and concentrated under reduced pressure to give the title compound as a light yellow gum (1.35 g, 56%). ESI-MS [M+H]$^+$ calc'd for $C_{12}H_{19}N_3O_2$, 238.16; found, 238.0.

Step E: ethyl trans-1-methyl-4-(1-methyl-1H-pyrazol-4-yl)piperidine-3-carboxylate

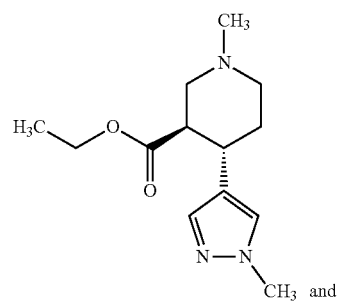

-continued

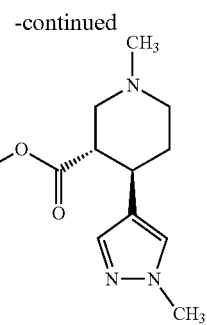

To a round bottom flask containing ethyl trans-4-(1-methyl-1H-pyrazol-4-yl)piperidine-3-carboxylate (1.35 g, 5.69 mmol) in DCE (10 mL) was added formaldehyde (40% aq, 1.71 g, 22.8 mmol) and NaBH(OAc)$_3$ (4.82 g, 22.8 mmol). The reaction mixture was stirred at room temperature for 2 hours and was then quenched with water and saturated aq Na$_2$CO$_3$ (20 mL) and extracted with DCM (2×30 mL). The combined organic layers were washed with brine, dried over Na$_2$SO$_4$, filtered, and concentrated under reduced pressure to give the crude product. The crude product was purified by preparative HPLC (Phenomenex Synergi Max-RP 10 μm, 50 mm ID×250 mm column) eluting with a gradient of 1-30% ACN in water (containing 0.1% TFA). The resulting TFA salt was basified with aq Na$_2$CO$_3$, extracted with EtOAc, dried, and concentrated to give the title compound as a light yellow oil (1.0 g, 83%). ESI-MS [M+H]$^+$ calc'd for C$_{13}$H$_{21}$N$_3$O$_2$, 252.17; found, 252.2.

Step F: trans-1-methyl-4-(1-methyl-1H-pyrazol-4-yl)piperidine-3-carboxylic acid

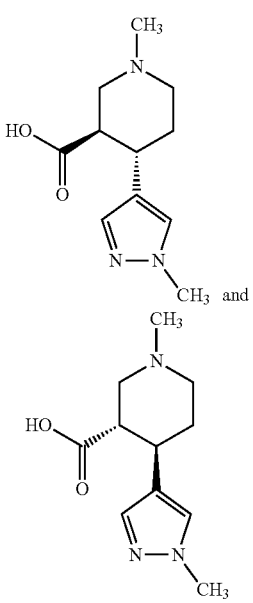

To a solution of ethyl trans-1-methyl-4-(1-methyl-1H-pyrazol-4-yl)piperidine-3-carboxylate (500 mg, 1.99 mmol) in THF (6 mL) were added lithium hydroxide monohydrate (150.3 mg, 3.58 mmol) and water (2 mL) at room temperature. The mixture was stirred at 60° C. for 24 hours and was then washed with MTBE (3×3 mL). The aqueous phase was acidified with 1M aq HCl to pH 6-7 and lyophilized to give the title compound (with LiCl) as a white solid (620 mg). ESI-MS [M+H]$^+$ calc'd for C$_{11}$H$_{17}$N$_3$O$_2$, 224.14; found, 224.1.

Step G: butyl (trans-1-methyl-4-(1-methyl-1H-pyrazol-4-yl)piperidin-3-yl)carbamate

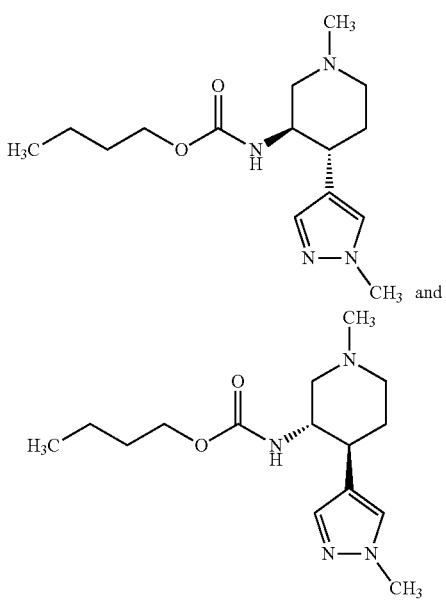

A mixture of trans-1-methyl-4-(1-methyl-1H-pyrazol-4-yl)piperidine-3-carboxylic acid (200 mg, 0.896 mmol), Et$_3$N (272 mg, 2.69 mmol) and diphenyl phosphorazidite (493 mg, 1.79 mmol) in n-BuOH (2 mL) was heated at 110° C. for 40 hours. The reaction mixture was subsequently diluted with water (10 mL) and extracted with DCM (2×30 mL). The organic layers were combined, dried over Na$_2$SO$_4$, filtered, and concentrated under reduced pressure. The crude product was purified by preparative HPLC (Phenomenex Gemini 10 μm, 25 mm ID×150 mm column) eluting with a gradient of 24-54% ACN in water (containing 0.05% ammonium hydroxide) to give the title compound as a yellow oil (120 mg, 23%). ESI-MS [M+H]$^+$ calc'd for C$_{15}$H$_{26}$N$_4$O$_2$, 295.21; found, 295.2.

Step H: trans-1-methyl-4-(1-methyl-1H-pyrazol-4-yl)piperidin-3-amine

To a round bottom flask containing butyl (trans-1-methyl-4-(1-methyl-1H-pyrazol-4-yl)piperidin-3-yl)carbamate (100 mg, 0.340 mmol) in ethylene glycol dimethyl ether (1 mL) was added KOH (57.2 mg, 1.02 mmol). The reaction mixture was stirred at 90° C. for 16 hours and then filtered. The filtrate was concentrated under reduced pressure and the resulting concentrate was purified by automated flash silica column chromatography (4 g column) eluting with a gradient of 0-20% methanol in DCM to give the title compound as a yellow oil (55 mg, 81%). ESI-MS [M+H]$^+$ calc'd for C$_{10}$H$_{18}$N$_4$, 195.16; found, 195.2.

Preparation 81: tert-butyl 4-amino-2-ethylpiperidine-1-carboxylate

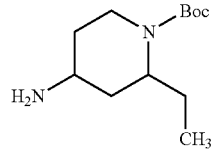

The title compound was prepared in a manner similar to PREPARATION 70, using tert-butyl 2-ethyl-4-oxopiperidine-1-carboxylate (1.00 g, 4.40 mmol, 1 eq) in place of 1,5,5-trimethylpyrrolidin-3-one to give a white solid (1.005 g, assumed quantitative) which was used without further purification. ESI-MS [M+H]$^+$ calc'd for $C_{12}H_{24}N_2O_2$, 229.19; found [M−72], 155.7.

Preparation 82: 2,2-difluoro-3-((3-(trifluoromethyl)pyridin-2-yl)oxy)propanoic Acid

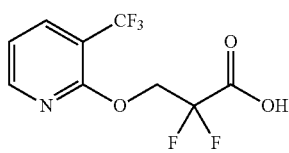 [SMILES: O=C(O)C(F)(F)COc1ncccc1C(F)(F)F]

To a solution of ethyl 2,2-difluoro-3-hydroxypropanoate (0.336 g, 2.18 mmol) in DMF (8 mL) was added NaH (60 wt %, 0.145 g, 3.63 mmol). The mixture was allowed to stir at room temperature for 30 minutes. Next, 2-fluoro-3-(trifluoromethyl)pyridine (0.300 g, 1.817 mmol) was added. The reaction mixture was stirred at room temperature for 1 hour and then treated with dilute aq HCl and extracted with EtOAc. The aqueous layer was concentrated and the residue was re-dissolved in ethanol. The precipitate was filtered off and the filtrate was concentrated to give the title compound as a brown syrup (0.407 g, 83%) which was used without further purification. ESI-MS [M+H]$^+$ calc'd for $C_9H_6F_5NO_3$, 272.03; found, 272.1.

Preparation 83: 3-((3-cyclopropylpyridin-2-yl)oxy)-2,2-difluoropropanoic Acid

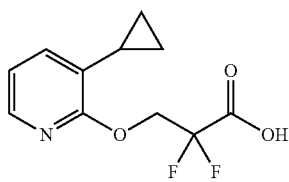 [SMILES: O=C(O)C(F)(F)COc1ncccc1C1CC1]

To a solution of ethyl 2,2-difluoro-3-hydroxypropanoate (0.405 g, 2.62 mmol) in DMF (8 mL), was added NaH (60 wt %, 0.131 g, 3.28 mmol). After stirring for 1 hour, 3-cyclopropyl-2-fluoropyridine (0.300 g, 2.19 mmol) was added. The mixture was stirred overnight and then treated with dilute aq HCl to pH 5 and extracted with EtOAc. The aqueous layer was concentrated and the residue was re-dissolved in EtOH/EtOAc (3:1) and filtered. The filtrate was concentrated to give the title compound as a brown syrup (0.527 g, 99%) which was used without further purification. ESI-MS [M+H]$^+$ calc'd for $C_{11}H_{11}F_2NO_3$, 244.08; found, 244.2.

Preparation 84: ethyl 2,2-difluoro-3-((3-(trifluoromethoxy)pyridin-2-yl)oxy)propanoate

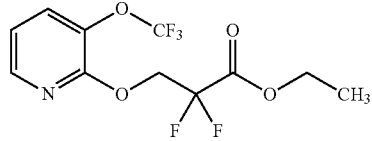 [SMILES: CCOC(=O)C(F)(F)COc1ncccc1OC(F)(F)F]

In a 100 mL round-bottomed flask, ethyl 2,2-difluoro-3-hydroxypropanolate (0.468 g, 3.04 mmol) was dissolved in DMF (8 mL) to give a colorless solution. NaH (60 wt %, 91 mg, 3.8 mmol) was added and the reaction mixture was stirred for 1 hour at room temperature. Next 2-chloro-3-(trifluoromethoxy)pyridine (0.500 g, 2.53 mmol) was added. The reaction mixture was stirred at 100° C. overnight, then removed from heat, treated with dilute aq HCl, and extracted with EtOAc. The organic phase was dried over MgSO$_4$, filtered, and concentrated to give crude title compound as a colorless oil (0.797 g, assumed quantitative). ESI-MS [M+H]$^+$ calc'd for $C_{11}H_{10}F_5NO_4$, 316.06; found, 316.3.

Preparation 85: 2,2-difluoro-3-((3-(trifluoromethoxy)pyridin-2-yl)oxy)propanoic Acid

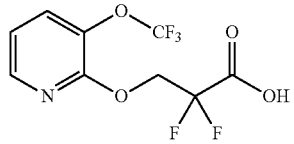 [SMILES: O=C(O)C(F)(F)COc1ncccc1OC(F)(F)F]

A solution of ethyl 2,2-difluoro-3-((3-(trifluoromethoxy)pyridin-2-yl)oxy)propanoate (0.797 g, 2.53 mmol) and LiOH (2M aq, 5.06 mL, 10.1 mmol) in dioxane (15 mL) was stirred at 50° C. for 2 hours. The reaction mixture was then treated with dilute aq HCl and extracted with EtOAc. The organic phase was dried over MgSO$_4$, filtered, and concentrated to give crude title compound as a brown syrup (0.726 g, assumed quantitative) which was used without further purification. ESI-MS [M+H]$^+$ calc'd for $C_9H_6F_5NO_4$, 288.03; found, 288.2.

Preparation 86: ethyl 2,2-difluoro-3-((3-methylpyridin-2-yl)oxy)propanoate

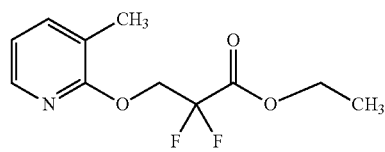 [SMILES: CCOC(=O)C(F)(F)COc1ncccc1C]

To a solution of ethyl 2,2-difluoro-3-hydroxypropanoate (0.458 g, 2.97 mmol) in DMF (8 mL) was added sodium hydride (60 wt %, 0.097 g, 4.0 mmol). After stirring for 1 hour at room temperature, 2-fluoro-3-methylpyridine (0.300 g, 2.70 mmol) was added. The mixture was stirred at room temperature overnight, then treated with dilute aq HCl and extracted with EtOAc. The organic phase was dried over MgSO$_4$, filtered, and concentrated to give crude title compound as a colorless oil (0.662 g, assumed quantitative) which was used without further purification. ESI-MS [M+H]$^+$ calc'd for C$_{11}$H$_{13}$F$_2$NO$_3$, 246.09; found, 246.2.

Preparation 87: 2,2-difluoro-3-((3-methylpyridin-2-yl)oxy)propanoic Acid

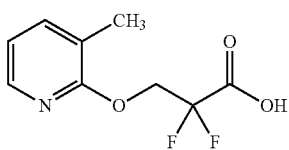

A solution of ethyl 2,2-difluoro-3-((3-methylpyridin-2-yl)oxy)propanoate (0.662 g, 2.70 mmol) and LiOH (2M aq, 5.40 mL, 10.8 mmol) in dioxane (15 mL) was stirred at 50° C. for 2 hours. The reaction mixture was then treated with dilute aq HCl to pH 5 and extracted with EtOAc. The organic phase was dried over MgSO$_4$, filtered, and concentrated to give crude title compound as a colorless oil (0.23 g, 39%) which was used without further purification. ESI-MS [M+H]$^+$ calc'd for C$_9$H$_9$F$_2$NO$_3$, 218.06; found, 218.2.

Preparation 88: tert-butyl (3S,4S)-4-(3-(2-chlorophenoxy)-2,2-dimethylpropanamido)-3-fluoropiperidine-1-carboxylate

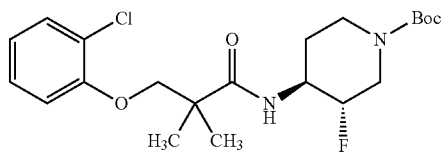 [SMILES: CC(C)(C)OC(=O)N1CC[C@H](NC(=O)C(C)(C)COc2ccccc2Cl)[C@@H](F)C1]

A solution of 3-(2-chlorophenoxy)-2,2-dimethylpropanoic acid (69 mg, 0.30 mmol), tert-butyl (3S,4S)-4-amino-3-fluoropiperidine-1-carboxylate (86 mg, 0.392 mmol), HATU (152 mg, 0.392 mmol) and triethylamine (168 µL, 1.21 mL) in THF (1.51 mL) was stirred at room temperature for 12 hours. The reaction mixture was filtered through a hydrophilic PTFE 0.45 m filter (Millipore® Millex-LCR) which was rinsed with methanol. The filtrate was purified by preparative HPLC (Method A) to give the title compound as a white solid (95 mg, 73%). ESI-MS [M+H]$^+$ calc'd for C$_{21}$H$_{30}$ClFN$_2$O$_4$, 429.20; found, 429.4.

Preparation 89: tert-butyl (3S,4S)-4-(3-(2-chlorophenoxy)-2,2-dimethylpropanamido)-3-methylpiperidine-1-carboxylate

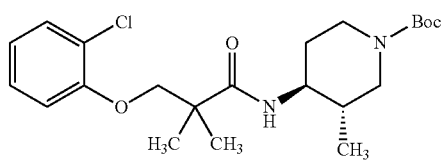 [SMILES: C[C@H]1CN(C(=O)OC(C)(C)C)CC[C@@H]1NC(=O)C(C)(C)COc1ccccc1Cl]

A solution of 3-(2-chlorophenoxy)-2,2-dimethylpropanoic acid (104 mg, 0.455 mmol), tert-butyl (3S,4S)-4-amino-3-methylpiperidine-1-carboxylate (117 mg, 0.546 mmol), HATU (212 mg, 0.546 mmol) and Et$_3$N (254 µL, 1.82 mmol) in DMA (2.27 mL) was stirred at room temperature for 12 hours. The reaction mixture was filtered through a hydrophilic PTFE 0.45 m filter (Millipore® Millex-LCR) which was rinsed with methanol. The filtrate was purified by preparative HPLC (Method A) to give the title compound as a white solid (150 mg, 78%). ESI-MS [M+H]$^+$ calc'd for C$_{22}$H$_{33}$ClN$_2$O$_4$, 425.22; found, 425.5.

Preparation 90: tert-butyl 4-(3-(2-chlorophenoxy)-2,2dimethylpropanamido)piperidine-1-carboxylate

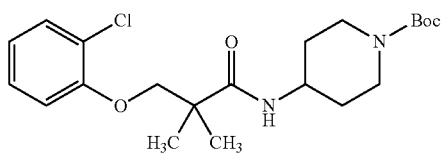 [SMILES: CC(C)(C)OC(=O)N1CCC(NC(=O)C(C)(C)COc2ccccc2Cl)CC1]

A solution of 3-(2-chlorophenoxy)-2,2-dimethylpropanoic acid (502 mg, 2.20 mmol), tert-butyl 4-aminopiperidine-1-carboxylate (550 mg, 2.63 mmol), HATU (1.02 g, 2.63 mmol) and Et$_3$N (1.22 mL, 8.78 mmol) in DMA (11 mL) was stirred at room temperature for 12 hours. The reaction mixture was filtered through a hydrophilic PTFE 0.45 m filter (Millipore® Millex-LCR) which was rinsed with methanol. The filtrate was purified by preparative HPLC (Method A) to give the title compound as a white semisolid (578 mg, 64%). ESI-MS [M+H]$^+$ calc'd for C$_{21}$H$_{31}$ClN$_2$O$_4$, 411.20; found, 411.5.

Preparation 91: methyl 3-(4-chlorophenoxy)-2,2-dimethylpropanoate

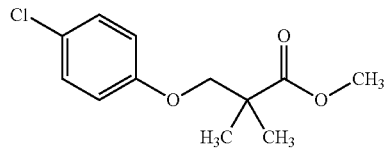 [SMILES: COC(=O)C(C)(C)COc1ccc(Cl)cc1]

A solution of methyl 2,2-dimethyl-3-((methylsulfonyl)oxy)propanoate (510 mg, 2.43 mmol), 4-chlorophenol (720 µL, 7.28 mmol), and cesium carbonate (2.37 g, 7.28 mmol) in DMA (6.06 mL) was stirred on a hot plate at 100° C. for 12 hours. The reaction mixture was suction filtered and the solvent was removed under reduced pressure. The residue was purified by automated flash silica column chromatography (12 g column) eluting with 10% EtOAc in heptanes to give the title compound as a light-yellow liquid (218 mg, 37%). $^1$H NMR (400 MHz, CDCl$_3$) δ ppm 1.32 (s, 6H), 3.70 (s, 3H), 3.94 (s, 2H), 6.81-6.85 (m, 2H), 7.20-7.25 (m, 2H); ESI-MS [M+H]$^+$ calc'd for C$_{12}$H$_{15}$ClO$_3$, 243.08; found 243.2.

Preparation 92: 3-(4-chlorophenoxy)-2,2-dimethylpropanoic Acid

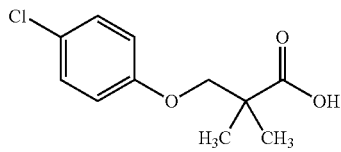

A solution of methyl 3-(4-chlorophenoxy)-2,2-dimethylpropanoate (215 mg, 0.886 mmol) in MeOH (2.22 mL) was treated with 3M aq LiOH (886 μL, 2.66 mmol) at room temperature. The resulting reaction mixture was stirred for 48 hours and the acidified to pH 2-3 by the dropwise addition of 1N aq HCl. The acidified solution was extracted with EtOAc and DCM (2×). The organic layers were combined, dried over $Na_2SO_4$, filtered, and concentrated under reduced pressure to give the title compound as a white solid (195 mg, 96%) which was used without further purification. $^1$H NMR (400 MHz, DMSO-$d_6$) δ ppm 1.20 (s, 6H), 3.94 (s, 2H), 6.92-6.98 (m, 2H), 7.27-7.34 (m, 2H), 12.31 (s, 1H); ESI-MS $[M+H]^+$ calc'd for $C_{11}H_{13}ClO_3$, 229.06; found [M–OH], 211.2.

Preparation 93: ethyl 2,2-difluoro-3-(tosyloxy)propanoate

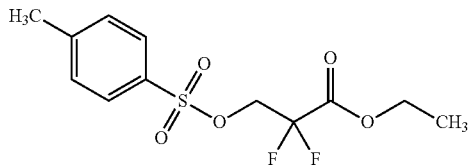 [SMILES: CCOC(=O)C(F)(F)COS(=O)(=O)c1ccc(C)cc1]

A solution of ethyl 2,2-difluoro-3-hydroxypropanoate (250 mg, 1.62 mmol) in DCM (8.11 mL) was treated with triethylamine (452 μL, 3.24 mmol) and 4-methylbenzenesulfonyl chloride (464 mg, 2.43 mmol). The resulting reaction mixture was stirred overnight, then diluted with brine and extracted with DCM. The organic phase was concentrated under reduced pressure and the residue was purified by automated flash silica column chromatography (24 g column) eluting with a gradient of 0-50% EtOAc in heptanes to give the title compound as a clear oil (181 mg, 36%).

Preparation 94: ethyl 3-(2-chlorophenoxy)-2,2-difluoropropanoate

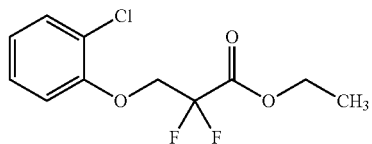 [SMILES: CCOC(=O)C(F)(F)COc1ccccc1Cl]

To a solution of ethyl 2,2-difluoro-3-(tosyloxy)propanoate (181 mg, 0.587 mmol) in DMF (1.96 mL) was added sodium hydride (60 wt %, 35.2 mg, 0.880 mmol). The reaction mixture was stirred for 1 hour. Next 2-chlorophenol (83 mg, 66.9 μL, 0.646 mmol) was added. The reaction mixture was stirred overnight, then concentrated under reduced pressure and purified by automated flash silica column chromatography (24 g column) eluting with a gradient of 0-100% EtOAc in heptanes to give the title compound (97 mg, 62%).

Preparation 95: 3-(2-chlorophenoxy)-2,2-difluoropropanoic Acid

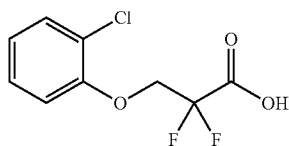 [SMILES: O=C(O)C(F)(F)COc1ccccc1Cl]

A solution of ethyl 3-(2-chlorophenoxy)-2,2-difluoropropanoate (97 mg, 0.37 mmol) in dioxane (1.10 mL) was treated with 1M aq lithium hydroxide (1.10 mL, 1.100 mmol). The mixture was stirred for 5 minutes and concentrated in vacuo to remove dioxane. The residual aqueous layer was acidified to pH 1-2 and extracted with EtOAc (3×20 mL). The organic layers were combined, dried over $Na_2SO_4$, filtered, and concentrated under reduced pressure. The resulting oil was diluted with heptane (20 mL) and concentrated under reduced pressure to give the title compound as a white solid (84 mg, 97%).

Preparation 96: tert-butyl (3S,4S)-4-(3-(2-chlorophenoxy)-2,2-difluoropropanamido)-3-methylpiperidine-1-carboxylate

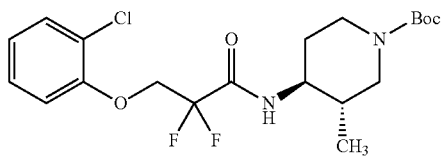 [SMILES: C[C@H]1CN(C(=O)OC(C)(C)C)CC[C@@H]1NC(=O)C(F)(F)COc1ccccc1Cl]

To a mixture of 3-(2-chlorophenoxy)-2,2-difluoropropanoic acid (30.0 mg, 0.127 mmol) in DCE (0.5 mL) and DMF (3 drops) was added oxalyl chloride (22 μL, 0.25 mmol). The mixture was stirred for 1 hour at room temperature. Next a solution of tert-butyl (3S,4S)-4-amino-3-methylpiperidine-1-carboxylate (54.3 mg, 0.254 mmol) in DCE (1 mL) and DIPEA (66 μL, 0.38 mmol) was added. The reaction mixture was heated to 70° C. for 1 hour, then cooled to room temperature and concentrated under reduced pressure. The mixture was partitioned between DCM and brine. The organic phase was concentrated and purified by automated flash silica column chromatography (24 g column) eluting with a gradient of 0-100% EtOAc in heptanes to give the title compound (6.0 mg, 11%). ESI-MS $[M+H]^+$ calc'd for $C_{20}H_{27}ClF_2N_2O_4$, 433.17; found [M-Boc], 333.3.

Example 1: 2,2-dimethyl-N-(1-methylpiperidin-4-yl)-3-((3-methylpyridin-2-yl)oxy)propanamide

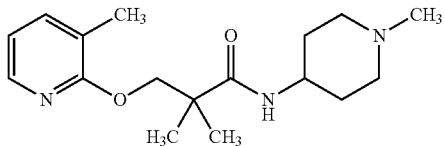

To a 20 mL vial containing 2,2-dimethyl-3-((3-methylpyridin-2-yl)oxy)propanoic acid (0.050 g, 0.239 mmol) in DMF (2 mL) were added 1-methylpiperidin-4-amine (0.033 g, 0.287 mmol), HATU (0.109 g, 0.287 mmol), and DIPEA (0.077 g, 0.597 mmol). The resulting yellow solution was allowed to stir at room temperature overnight. The reaction mixture was then filtered through a hydrophilic PTFE 0.45 m filter (Millipore® Millex-LCR) which was rinsed with methanol. The filtrate was purified by preparative HPLC (Method C) eluting with a gradient of 5-30% ACN in water. The product-containing fractions were evaporated to give a TFA salt of the title compound as a clear oil (64 mg, 64%). $^1$H NMR (400 MHz, CD$_3$OD) δ ppm 1.29-1.35 (m, 6H), 1.74-1.90 (m, 2H), 1.99-2.10 (m, 2H), 2.17 (s, 3H), 2.82-2.87 (m, 3H), 3.02-3.15 (m, 2H), 3.47-3.58 (m, 2H), 3.89-4.08 (m, 1H), 4.29-4.39 (m, 2H), 6.85-6.94 (m, 1H), 7.49-7.59 (m, 1H), 7.90-7.98 (m, 1H); ESI-MS [M+H]$^+$ calc'd for C$_{17}$H$_{27}$N$_3$O$_2$, 306.21; found, 306.2.

Example 2: 2,2-dimethyl-3-((3-methylpyridin-2-yl)oxy)-N-(1-methylpyrrolidin-3-yl)propanamide

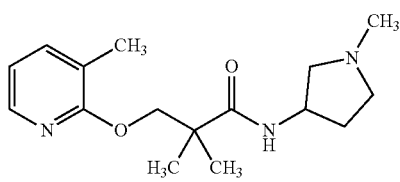 [SMILES: Cc1cccnc1OCC(C)(C)C(=O)NC1CCN(C)C1]

A TFA salt of the title compound was prepared in a manner similar to EXAMPLE 1, using 1-methylpyrrolidin-3-amine (0.029 g, 0.287 mmol, 1.2 eq) in place of 1-methylpiperidin-4-amine. The product was isolated as a light brown oil (64 mg, 72%). $^1$H NMR (400 MHz, CD$_3$OD) δ ppm 1.29-1.35 (m, 6H), 2.04-2.14 (m, 1H), 2.17 (s, 3H), 2.28-2.62 (m, 1H), 2.92 (br s, 3H), 3.02-3.16 (m, 1H), 3.32-3.43 (m, 1H), 3.53-3.97 (m, 2H), 4.26-4.36 (m, 2H), 4.44 (br s, 1H), 6.88 (dd, J=7.1, 5.0 Hz, 1H), 7.48-7.56 (m, 1H), 7.93 (dd, J=5.0, 1.0 Hz, 1H); ESI-MS [M+H]$^+$ calc'd for C$_{16}$H$_{25}$N$_3$O$_2$, 292.19; found, 292.2.

Example 3: 3-((3-cyanopyridin-2-yl)oxy)-2,2-dimethyl-N-(1-methylpiperidin-4-yl)propanamide

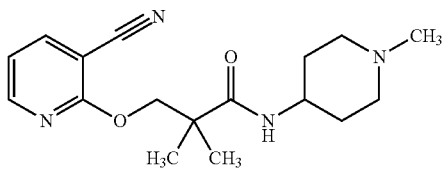

The title compound was prepared in a manner similar to EXAMPLE 1, using 3-((3-cyanopyridin-2-yl)oxy)-2,2-dimethylpropanoic acid (273 mg, 1.24 mmol) in place of 2,2-dimethyl-3-((3-methylpyridin-2-yl)oxy)propanoic acid. The product was purified by preparative HPLC (Method A) to give a TFA salt of the title compound as a white solid (79.3 mg, 15%). $^1$H NMR (500 MHz, CD$_3$OD) δ ppm 1.32 (s, 6H), 1.81-1.92 (m, 2H), 2.09-2.17 (m, 2H), 2.85 (s, 3H), 3.05-3.15 (m, 2H), 3.50-3.59 (m, 2H), 3.92-4.03 (m, 1H), 4.44 (s, 2H), 7.07-7.14 (m, 1H), 8.01-8.08 (m, 1H), 8.36-8.41 (m, 1H); ESI-MS [M+H]$^+$ calc'd for C$_{17}$H$_{24}$N$_4$O$_2$, 317.19; found, 317.23.

Example 4: (R)-3-((5-cyclopropylpyrimidin-4-yl)oxy)-2,2-dimethyl-N-(1-methylpyrrolidin-3-yl)propanamide

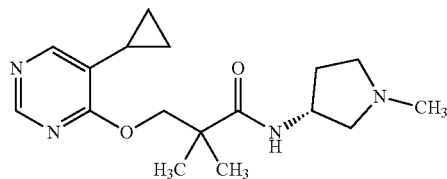 [SMILES: CN1CC[C@@H](NC(=O)C(C)(C)COc2ncncc2C2CC2)C1]

The title compound was prepared in a manner similar to EXAMPLE 1, using 3-((5-cyclopropylpyrimidin-4-yl)oxy)-2,2-dimethylpropanoic acid (148 mg, 0.626 mmol) in place of 2,2-dimethyl-3-((3-methylpyridin-2-yl)oxy)propanoic acid, and (R)-1-methylpyrrolidin-3-amine (62.7 mg, 0.626 mmol) in place of 1-methylpiperidin-4-amine. The product was purified by preparative HPLC (Method B) to give the title compound as a tan film (40.4 mg, 20%). $^1$H NMR (500 MHz, CD$_3$OD) δ ppm 0.79 (dd, J=5.6, 1.7 Hz, 2H), 0.96 (dd, J=8.3, 2.0 Hz, 2H), 1.31 (app d, J=1.5 Hz, 6H), 1.64-1.73 (m, 1H), 1.86-1.94 (m, 1H), 2.22-2.31 (m, 1H), 2.35 (s, 3H), 2.41-2.50 (m, 2H), 2.69-2.78 (m, 2H), 4.36-4.42 (m, 1H), 4.43 (s, 2H), 8.11 (s, 1H), 8.52 (s, 1H); ESI-MS [M+H]$^+$ calc'd for C$_{17}$H$_{26}$N$_4$O$_2$, 318.21; found, 319.38.

Example 5: 3-((5-cyclopropylpyrimidin-4-yl)oxy)-2,2-dimethyl-N-(1-methylpiperidin-4-yl)propanamide

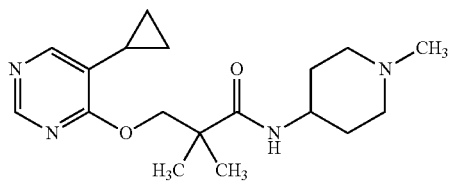 [SMILES: CN1CCC(NC(=O)C(C)(C)COc2ncncc2C2CC2)CC1]

The title compound was prepared in a manner similar to EXAMPLE 1, using 3-((5-cyclopropylpyrimidin-4-yl)oxy)-2,2-dimethylpropanoic acid (148 mg, 0.626 mmol, 1 eq) in place of 2,2-dimethyl-3-((3-methylpyridin-2-yl)oxy)propanoic acid. The product was purified by preparative HPLC (Method B) to give the title compound as a tan film (49.4 mg, 0.149 mmol). $^1$H NMR (500 MHz, CD$_3$OD) δ ppm 0.79 (dd, J=5.4, 2.0 Hz, 2H), 0.92-0.98 (m, 2H), 1.31 (s, 6H), 1.51-1.61 (m, 2H), 1.75-1.81 (m, 2H), 1.85-1.92 (m, 1H), 2.05-2.12 (m, 2H), 2.26 (s, 3H), 2.82-2.88 (m, 2H), 3.65-

3.74 (m, 1H), 4.44 (s, 2H), 8.06-8.14 (m, 1H), 8.50-8.53 (m, 1H); ESI-MS [M+H]+ calc'd for $C_{18}H_{28}N_4O_2$, 333.22; found, 333.24.

Example 6: 3-((3-cyclopropyl-5-methylpyridin-2-yl)oxy)-2,2-dimethyl-N-(1-methylpiperidin-4-yl)propanamide

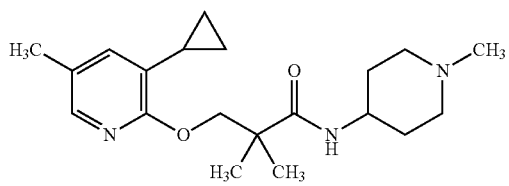

The title compound was prepared in a manner similar to EXAMPLE 1, using 3-((3-cyclopropyl-5-methylpyridin-2-yl)oxy)-2,2-dimethylpropanoic acid (131 mg, 0.526 mmol, 1 eq) in place of 2,2-dimethyl-3-((3-methylpyridin-2-yl)oxy)propanoic acid. The product was purified by preparative HPLC (Method A) to give a TFA salt of the title compound as a light blue solid (106.8 mg, 44%). $^1$H NMR (500 MHz, CD$_3$OD) δ ppm 0.68 (dd, J=4.9, 2.0 Hz, 2H), 0.89-0.96 (m, 2H), 1.32 (s, 6H), 1.77-1.89 (m, 2H), 1.99 (s, 1H), 2.03 (br s, 2H), 2.20 (s, 3H), 2.85 (s, 3H), 3.04-3.14 (m, 2H), 3.50-3.58 (m, 2H), 3.92-4.02 (m, 1H), 4.31 (s, 2H), 7.16 (d, J=2.4 Hz, 1H), 7.69-7.73 (m, 1H); ESI-MS [M+H]+ calc'd for $C_{20}H_{31}N_3O_2$, 346.24; found, 346.4.

Example 7: (R)-3-((3-cyclopropyl-5-methylpyridin-2-yl)oxy)-2,2-dimethyl-N-(1-methylpyrrolidin-3-yl)propanamide

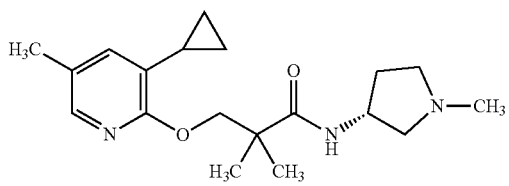

The title compound was prepared in a manner similar to EXAMPLE 1, using 3-((3-cyclopropyl-5-methylpyridin-2-yl)oxy)-2,2-dimethylpropanoic acid (131 mg, 0.526 mmol) in place of 2,2-dimethyl-3-((3-methylpyridin-2-yl)oxy)propanoic acid, and (R)-1-methylpyrrolidin-3-amine (52.7 mg, 0.526 mmol) in place of 1-methylpiperidin-4-amine. The product was purified by preparative HPLC (Method A) to give a TFA salt of the title compound as a colorless film (53.8 mg, 0.121 mmol). $^1$H NMR (500 MHz, CD$_3$OD) δ ppm 0.67 (dd, J=5.4, 2.0 Hz, 2H), 0.92 (dd, J=8.3, 2.0 Hz, 2H), 1.32 (app d, J=2.9 Hz, 6H), 1.93-2.02 (m, 1H), 2.04-2.16 (m, 1H), 2.20 (s, 3H), 2.46-2.58 (m, 1H), 2.93 (s, 3H), 3.04-3.14 (m, 1H), 3.33-3.38 (m, 1H), 3.55-3.62 (m, 1H), 3.78-3.87 (m, 1H), 4.25-4.33 (m, 2H), 4.41-4.53 (m, 1H), 7.09-7.17 (m, 1H), 7.65-7.73 (m, 1H); ESI-MS [M+H]+ calc'd for $C_{19}H_{29}N_3O_2$, 332.23; found, 332.4.

Example 8: 3-((5-cyclopropyl-3-methylpyridin-2-yl)oxy)-2,2-dimethyl-N-(1-methylpiperidin-4-yl)propanamide

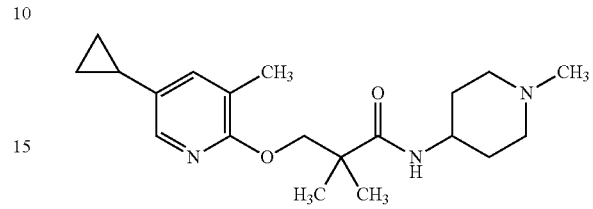

The title compound was prepared in a manner similar to EXAMPLE 1, using 3-((5-cyclopropyl-3-methylpyridin-2-yl)oxy)-2,2-dimethylpropanoic acid (108 mg, 0.433 mmol, 1 eq) in place of 2,2-dimethyl-3-((3-methylpyridin-2-yl)oxy)propanoic acid. The product was purified by preparative HPLC (Method B) to give the title compound as a light brown film (51.9 mg, 35%). $^1$H NMR (500 MHz, CD$_3$OD) δ ppm 0.58-0.62 (m, 2H), 0.91 (dd, J=8.5, 1.7 Hz, 2H), 1.28 (s, 6H), 1.50-1.60 (m, 2H), 1.79 (dd, J=14.4, 9.0 Hz, 3H), 2.04-2.11 (m, 2H), 2.13 (s, 3H), 2.25 (s, 3H), 2.78-2.85 (m, 2H), 3.64-3.74 (m, 1H), 4.26 (s, 2H), 7.13-7.18 (m, 1H), 7.70-7.74 (m, 1H); ESI-MS [M+H]+ calc'd for $C_{20}H_{31}N_3O_2$, 346.24; found, 346.3.

Example 9: 3-((3-cyclopropyl-6-methylpyridin-2-yl)oxy)-2,2-dimethyl-N-(1-methylpiperidin-4-yl)propanamide

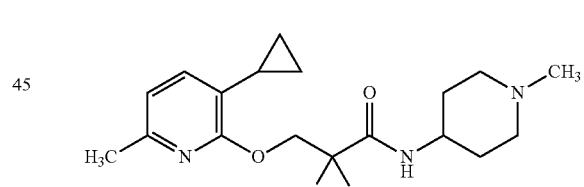

The title compound was prepared in a manner similar to EXAMPLE 1, using 3-((3-cyclopropyl-6-methylpyridin-2-yl)oxy)-2,2-dimethylpropanoic acid (218 mg, 0.876 mmol, 1 eq) in place of 2,2-dimethyl-3-((3-methylpyridin-2-yl)oxy)propanoic acid. The product was purified by preparative HPLC (Method A) to give a TFA salt of the title compound as a colorless film (78.9 mg, 20%). $^1$H NMR (500 MHz, CD$_3$OD) δ ppm 0.62 (dd, J=5.4, 2.0 Hz, 2H), 0.86-0.91 (m, 2H), 1.32 (s, 6H), 1.77-1.87 (m, 2H), 1.92-1.98 (m, 1H), 2.01-2.07 (m, 2H), 2.39 (s, 3H), 2.84 (s, 3H), 3.03-3.13 (m, 2H), 3.50-3.56 (m, 2H), 3.92-4.04 (m, 1H), 4.36 (s, 2H), 6.74 (s, 1H), 7.11-7.21 (m, 1H); ESI-MS [M+H]+ calc'd for $C_{20}H_{31}N_3O_2$, 346.24; found, 346.5.

Example 10: (R)-3-((3-cyclopropyl-6-methylpyridin-2-yl)oxy)-2,2-dimethyl-N-(1-methylpyrrolidin-3-yl)propanamide

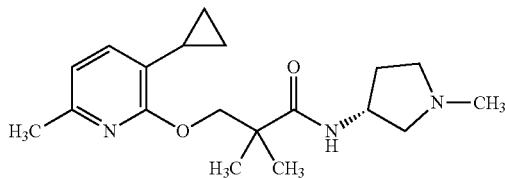

The title compound was prepared in a manner similar to EXAMPLE 1, using 3-((3-cyclopropyl-6-methylpyridin-2-yl)oxy)-2,2-dimethylpropanoic acid (217 mg, 0.872 mmol) in place of 2,2-dimethyl-3-((3-methylpyridin-2-yl)oxy)propanoic acid, and (R)-1-methylpyrrolidin-3-amine (87 mg, 0.87 mmol) in place of 1-methylpiperidin-4-amine. The product was purified by preparative HPLC (Method A) to give a TFA salt of the title compound as a colorless film (38.7 mg, 10%). $^1$H NMR (500 MHz, CD$_3$OD) δ ppm 0.61 (dd, J=5.4, 2.0 Hz, 2H), 0.84-0.92 (m, 2H), 1.32 (app d, J=2.0 Hz, 6H), 1.89-1.98 (m, 1H), 2.05-2.17 (m, 1H), 2.35 (s, 3H), 2.46-2.57 (m, 1H), 2.92 (s, 3H), 3.03-3.12 (m, 1H), 3.32-3.38 (m, 1H), 3.52-3.63 (m, 1H), 3.76-3.86 (m, 1H), 4.28-4.36 (m, 2H), 4.40-4.48 (m, 1H), 6.69 (d, J=7.8 Hz, 1H), 7.05-7.14 (m, 1H). ESI-MS [M+H]$^+$ calc'd for C$_{19}$H$_{29}$N$_3$O$_2$, 332.23; found, 332.5.

Example 11: trans-N-(1,3-dimethylpiperidin-4-yl)-2,2-dimethyl-3-((3-(trifluoromethyl)pyridin-2-yl)oxy)propanamide

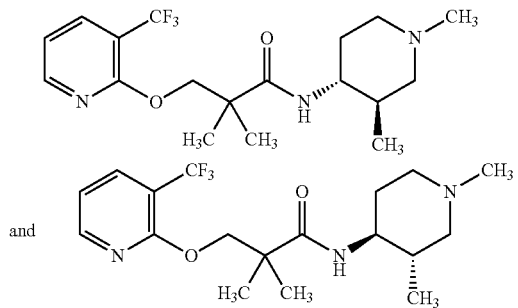

Example 12: cis-N-(1,3-dimethylpiperidin-4-yl)-2,2-dimethyl-3-((3-(trifluoromethyl)pyridin-2-yl)oxy)propanamide

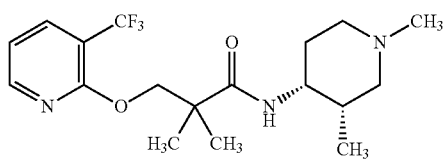

-continued

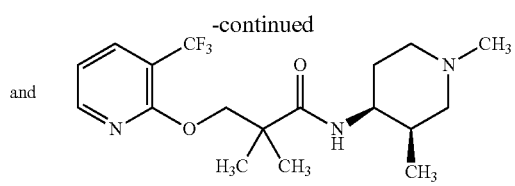

The title trans- and cis-stereoisomers were prepared in a manner similar to EXAMPLE 1, using 2,2-dimethyl-3-((3-(trifluoromethyl)pyridin-2-yl)oxy)propanoic acid (0.100 g, 0.380 mmol) in place of 2,2-dimethyl-3-((3-methylpyridin-2-yl)oxy)propanoic acid, and 1,3-dimethylpiperidin-4-amine, 2 HCl (0.076 g, 0.38 mmol) in place of 1-methylpiperidin-4-amine. The products were purified by preparative HPLC (Method B) to give the trans-stereoisomer (first eluting peak) as a colorless film (29.5 mg, 21%) and the cis-stereoisomer (second eluting peak) as a colorless film (19.8 mg, 14%). Peak 1: $^1$H NMR (500 MHz, CD$_3$OD) δ ppm 0.83 (d, J=5.9 Hz, 3H), 1.31 (app d, J=3.9 Hz, 6H), 1.48-1.60 (m, 1H), 1.71-1.80 (m, 3H), 2.00-2.11 (m, 1H), 2.26 (s, 3H), 2.80-2.94 (m, 2H), 3.38-3.47 (m, 1H), 4.45 (d, J=7.3 Hz, 2H), 7.04-7.11 (m, 1H), 7.92-8.02 (m, 1H), 8.30-8.38 (m, 1H); ESI-MS [M+H]$^+$ calc'd for C$_{18}$H$_{26}$F$_3$N$_3$O$_2$, 374.20; found, 374.4. Peak 2: $^1$H NMR (500 MHz, CD$_3$OD) δ ppm 0.90 (d, J=6.8 Hz, 3H), 1.29-1.35 (m, 6H), 1.59-1.69 (m, 1H), 1.73-1.85 (m, 1H), 2.01-2.12 (m, 1H), 2.22 (s, 3H), 2.26 (s, 4H), 3.88-4.01 (m, 1H), 4.46 (d, J=3.9 Hz, 2H), 7.10 (dd, J=7.3, 4.9 Hz, 1H), 7.94-8.04 (m, 1H), 8.30-8.38 (m, 1H); ESI-MS [M+H]$^+$ calc'd for C$_{18}$H$_{26}$F$_3$N$_3$O$_2$, 374.20; found, 374.4.

Example 13: trans-N-(1,3-dimethylpiperidin-4-yl)-2,2-dimethyl-3-((3-(trifluoromethoxy)pyridin-2-yl)oxy)propanamide

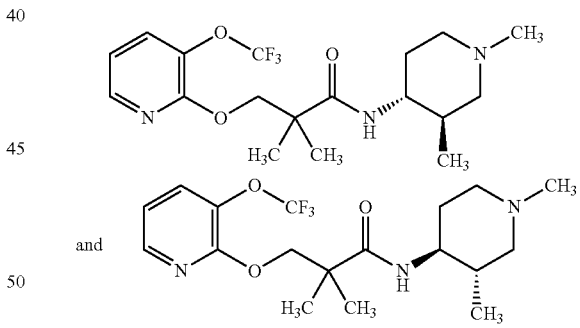

Example 14: cis-N-(1,3-dimethylpiperidin-4-yl)-2,2-dimethyl-3-((3-(trifluoromethoxy)pyridin-2-yl)oxy)propanamide

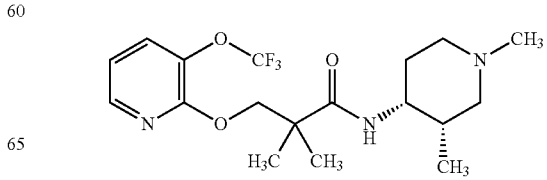

-continued

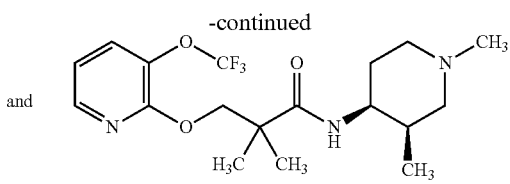

The title trans- and cis-stereoisomers were prepared in a manner similar to EXAMPLE 1, using 2,2-dimethyl-3-((3-(trifluoromethoxy)pyridin-2-yl)oxy)propanoic acid (0.100 g, 0.272 mmol) in place of 2,2-dimethyl-3-((3-methylpyridin-2-yl)oxy)propanoic acid, and 1,3-dimethylpiperidin-4-amine, 2 HCl (0.055 g, 0.27 mmol) in place of 1-methylpiperidin-4-amine. The products were purified by preparative HPLC (Method B) to give the trans-stereoisomer (first eluting peak) as a colorless film (21.7 mg, 20%) and the cis-stereoisomer (second eluting peak) as a colorless film (16.7 mg, 16%). Peak 1: $^1$H NMR (500 MHz, CD$_3$OD) δ ppm 0.84 (d, J=6.4 Hz, 3H), 1.31 (app d, J=2.4 Hz, 6H), 1.51-1.62 (m, 1H), 1.68-1.80 (m, 3H), 2.02-2.11 (m, 1H), 2.26 (s, 3H), 2.82-2.92 (m, 2H), 3.38-3.49 (m, 1H), 4.41 (d, J=2.0 Hz, 2H), 6.99-7.06 (m, 1H), 7.61-7.68 (m, 1H), 8.05-8.14 (m, 1H); ESI-MS [M+H]$^+$ calc'd for C$_{18}$H$_{26}$F$_3$N$_3$O$_3$, 390.19; found, 390.4. Peak 2: $^1$H NMR (500 MHz, CD$_3$OD) δ ppm 0.90 (d, J=6.8 Hz, 3H), 1.28-1.34 (m, 6H), 1.62-1.71 (m, 1H), 1.75-1.85 (m, 1H), 1.98-2.12 (m, 1H), 2.22 (m, 7H), 3.93-4.03 (m, 1H), 4.42 (d, J=1.0 Hz, 2H), 7.02-7.08 (m, 1H), 7.63-7.71 (m, 1H), 8.07-8.16 (m, 1H); ESI-MS [M+H]$^+$ calc'd for C$_{18}$H$_{26}$F$_3$N$_3$O$_3$, 390.19; found, 390.4.

Example 15: trans-N-(4-isopropyl-1-methylpyrrolidin-3-yl)-2,2-dimethyl-3-((3-(trifluoromethyl)pyridin-2-yl)oxy)propanamide

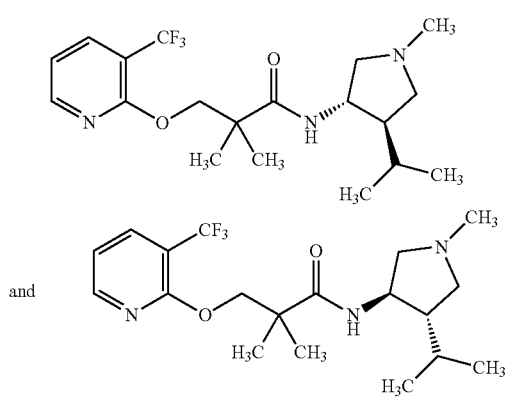

The title compound was prepared in a manner similar to EXAMPLE 1, using 2,2-dimethyl-3-((3-(trifluoromethyl) pyridin-2-yl)oxy)propanoic acid (0.110 g, 0.420 mmol) in place of 2,2-dimethyl-3-((3-methylpyridin-2-yl)oxy)propanoic acid, and trans-4-isopropyl-1-methylpyrrolidin-3-amine, HCl (0.075 g, 0.42 mmol) in place of 1-methylpiperidin-4-amine. The product was purified by preparative HPLC (Method B) to give the title compound as a colorless film (9.9 mg, 6.1%). $^1$H NMR (500 MHz, CD$_3$OD) δ ppm 0.83-0.94 (m, 6H), 1.29 (app d, J=10.2 Hz, 6H), 1.52-1.60 (m, 1H), 1.75-1.86 (m, 1H), 2.02-2.11 (m, 1H), 2.33 (s, 3H), 2.50-2.63 (m, 2H), 2.96-3.05 (m, 1H), 4.13-4.21 (m, 1H), 4.36-4.49 (m, 2H), 7.05-7.13 (m, 1H), 7.94-8.03 (m, 1H), 8.32-8.38 (m, 1H); ESI-MS [M+H]$^+$ calc'd for C$_{19}$H$_{28}$F$_3$N$_3$O$_2$, 388.21; found, 388.4.

Example 16: trans-N-(4-isopropyl-1-methylpyrrolidin-3-yl)-2,2-dimethyl-3-((3-(trifluoromethoxy)pyridin-2-yl)oxy)propanamide

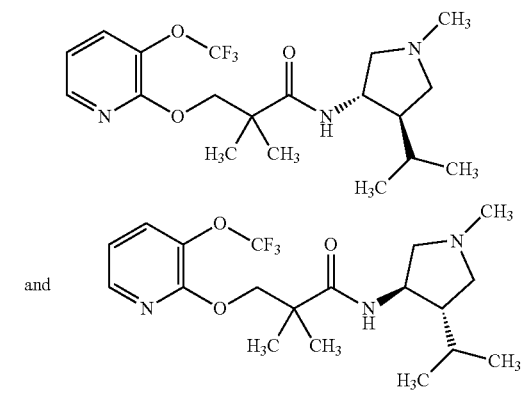

The title compound was prepared in a manner similar to EXAMPLE 1, using 2,2-dimethyl-3-((3-(trifluoromethoxy) pyridin-2-yl)oxy)propanoic acid (0.117 g, 0.420 mmol) in place of 2,2-dimethyl-3-((3-methylpyridin-2-yl)oxy)propanoic acid, and trans-4-isopropyl-1-methylpyrrolidin-3-amine, HCl (0.075 g, 0.42 mmol) in place of 1-methylpiperidin-4-amine. The product was purified by preparative HPLC (Method B) to give the title compound as a colorless film (8.5 mg, 5.0%). $^1$H NMR (500 MHz, CD$_3$OD) δ ppm 0.88 (t, J=6.1 Hz, 6H), 1.29 (app d, J=4.4 Hz, 6H), 1.50-1.63 (m, 1H), 1.75-1.87 (m, 1H), 2.02-2.12 (m, 1H), 2.33 (s, 3H), 2.50-2.64 (m, 2H), 2.96-3.04 (m, 1H), 4.15-4.22 (m, 1H), 4.39 (d, J=3.4 Hz, 2H), 6.99-7.06 (m, 1H), 7.58-7.72 (m, 1H), 8.05-8.16 (m, 1H). ESI-MS [M+H]$^+$ calc'd for C$_{19}$H$_{28}$F$_3$N$_3$O$_3$, 404.21; found, 404.4.

Example 17: trans-N-(1,3-dimethylpiperidin-4-yl)-2,2-dimethyl-3-((3-methylpyridin-2-yl)oxy)propanamide

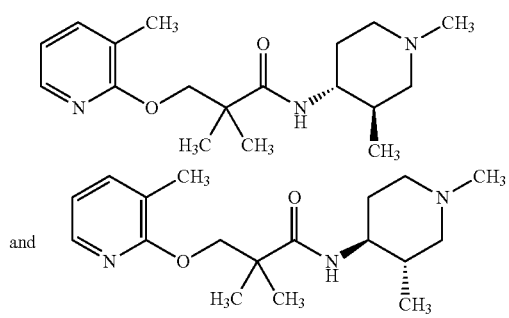

The title compound was prepared in a manner similar to EXAMPLE 1, using 1,3-dimethylpiperidin-4-amine, HCl (0.049 g, 0.297 mmol, 1 eq) in place of 1-methylpiperidin-4-amine. The product was purified by preparative HPLC (Method B) to give the title compound as a colorless film (30.5 mg, 32%). $^1$H NMR (500 MHz, CD$_3$OD) δ ppm 0.82 (d, J=6.4 Hz, 3H), 1.31 (s, 6H), 1.49-1.59 (m, 1H), 1.68-1.79

(m, 3H), 2.00-2.10 (m, 1H), 2.16 (s, 3H), 2.26 (s, 3H), 2.80-2.91 (m, 2H), 3.38-3.47 (m, 1H), 4.32 (s, 2H), 6.84 (dd, J=7.1, 5.1 Hz, 1H), 7.42-7.50 (m, 1H), 7.88-7.94 (m, 1H).); ESI-MS [M+H]$^+$ calc'd for $C_{18}H_{29}N_3O_2$, 320.23; found, 320.4.

Example 18: trans-2,2-dimethyl-N-(1-methyl-4-(1-methyl-1H-pyrazol-4-yl)pyrrolidin-3-yl)-3-((3-methylpyridin-2-yl)oxy)propanamide

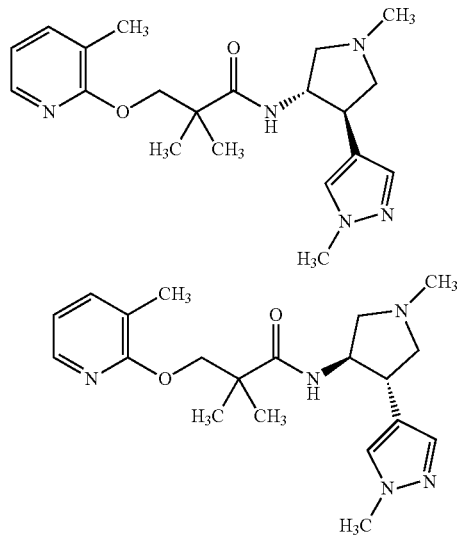

The title compound was prepared in a manner similar to EXAMPLE 1, using trans-1-methyl-4-(1-methyl-1H-pyrazol-4-yl)pyrrolidin-3-amine, HCl (0.064 g, 0.30 mmol, 1 eq) in place of 1-methylpiperidin-4-amine. The product was purified by preparative HPLC (Method A) to give a TFA salt of the title compound as a colorless film (40.2 mg, 28%). $^1$H NMR (500 MHz, CD$_3$OD) δ ppm 1.04-1.34 (m, 6H), 2.02-2.15 (m, 3H), 2.94-3.08 (m, 3H), 3.14-3.26 (m, 1H), 3.54-3.72 (m, 2H), 3.78 (s, 3H), 3.92-4.02 (m, 1H), 4.13-4.19 (m, 1H), 4.26-4.35 (m, 1H), 4.41-4.49 (m, 1H), 6.85-6.92 (m, 1H), 7.38-7.44 (m, 1H), 7.48-7.56 (m, 2H), 7.90-7.95 (m, 1H); ESI-MS [M+H]$^+$ calc'd for $C_{20}H_{29}N_5O_2$, 372.23; found, 372.4.

Example 19: trans-2,2-dimethyl-N-(1-methyl-4-(1-methyl-1H-pyrazol-4-yl)pyrrolidin-3-yl)-3-((3-(trifluoromethyl)pyridin-2-yl)oxy)propanamide

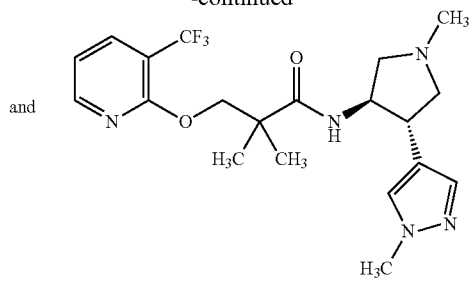

The title compound was prepared in a manner similar to EXAMPLE 1, using 2,2-dimethyl-3-((3-(trifluoromethyl)pyridin-2-yl)oxy)propanoic acid (0.070 g, 0.27 mmol) in place of 2,2-dimethyl-3-((3-methylpyridin-2-yl)oxy)propanoic acid, and trans-1-methyl-4-(1-methyl-1H-pyrazol-4-yl)pyrrolidin-3-amine, HCl (0.058 g, 0.27 mmol) in place of 1-methylpiperidin-4-amine. The product was purified by preparative HPLC (Method A) to give a TFA salt of the title compound as a colorless film (33.4 mg, 23%). $^1$H NMR (500 MHz, CD$_3$OD) δ ppm 0.99-1.32 (m, 6H), 2.98 (br s, 3H), 3.15-3.26 (m, 1H), 3.53-3.73 (m, 2H), 3.78-3.86 (m, 4H), 3.95-4.13 (m, 1H), 4.21-4.31 (m, 1H), 4.43 (s, 2H), 7.06-7.13 (m, 1H), 7.37-7.45 (m, 1H), 7.51-7.58 (m, 1H), 7.91-8.00 (m, 1H), 8.30-8.39 (m, 1H); ESI-MS [M+H]$^+$ calc'd for $C_{20}H_{26}F_3N_5O_2$, 426.20; found, 426.4.

Example 20: trans-3-((3-cyclopropylpyridin-2-yl)oxy)-N-(1,3-dimethylpiperidin-4-yl)-2,2-dimethyl-propanamide

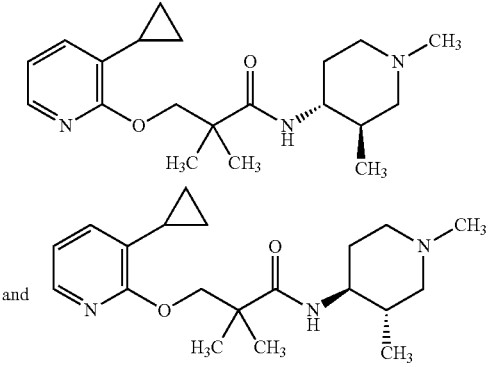

Example 21: cis-3-((3-cyclopropylpyridin-2-yl)oxy)-N-(1,3-dimethylpiperidin-4-yl)-2,2-dimethyl-propanamide

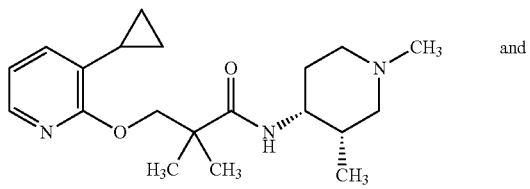

-continued

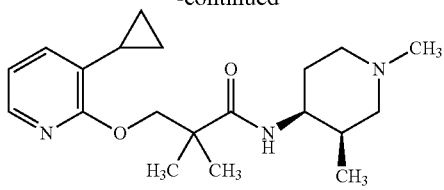

The title trans- and cis-stereoisomers were prepared in a manner similar to EXAMPLE 1, using 3-((3-cyclopropylpyridin-2-yl)oxy)-2,2-dimethylpropanoic acid (0.084 g, 0.33 mmol) in place of 2,2-dimethyl-3-((3-methylpyridin-2-yl)oxy)propanoic acid, and 1,3-dimethylpiperidin-4-amine, HCl (0.055 g, 0.33 mmol) in place of 1-methylpiperidin-4-amine. The products were purified by preparative HPLC (Method B) to give the trans-stereoisomer (first eluting peak) as a light brown film (25.7 mg, 22%) and the cis-stereoisomer (second eluting peak) as a light brown film (13.3 mg, 12%). Peak 1: $^1$H NMR (500 MHz, CD$_3$OD) δ ppm 0.61-0.67 (m, 2H), 0.82 (d, J=5.9 Hz, 3H), 0.88-0.94 (m, 2H), 1.33 (app d, J=1.5 Hz, 6H), 1.48-1.59 (m, 1H), 1.66-1.81 (m, 3H), 1.99-2.10 (m, 2H), 2.26 (s, 3H), 2.80-2.91 (m, 2H), 3.39-3.48 (m, 1H), 4.33 (d, J=2.9 Hz, 2H), 6.80-6.87 (m, 1H), 7.17-7.26 (m, 1H), 7.85-7.90 (m, 1H); ESI-MS [M+H]$^+$ calc'd for C$_{20}$H$_{31}$N$_3$O$_2$, 346.24; found, 346.4. Peak 2: $^1$H NMR (500 MHz, CD$_3$OD) δ ppm 0.62-0.71 (m, 2H), 0.83-0.99 (m, 5H), 1.34 (m, 7H), 1.59-1.69 (m, 1H), 1.73-1.82 (m, 1H), 1.99-2.08 (m, 2H), 2.18 (s, 3H), 2.26 (s, 3H), 3.94-4.01 (m, 1H), 4.37 (m, 2H), 6.83-6.90 (m, 1H), 7.22-7.28 (m, 1H), 7.87-7.93 (m, 1H); ESI-MS [M+H]$^+$ calc'd for C$_{20}$H$_{31}$N$_3$O$_2$, 346.24; found, 346.4.

Example 22: trans-3-((3-cyclopropylpyridin-2-yl)oxy)-2,2-dimethyl-N-(1-methyl-4-(1-methyl-1H-pyrazol-4-yl)pyrrolidin-3-yl)propanamide

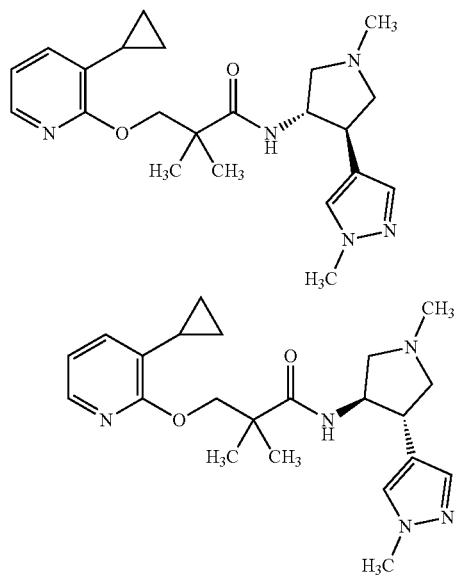

The title compound was prepared in a manner similar to EXAMPLE 1, using 3-((3-cyclopropylpyridin-2-yl)oxy)-2,2-dimethylpropanoic acid (0.080 g, 0.34 mmol) in place of 2,2-dimethyl-3-((3-methylpyridin-2-yl)oxy)propanoic acid, and trans-1-methyl-4-(1-methyl-1H-pyrazol-4-yl)pyrrolidin-3-amine, HCl (0.074 mg, 0.34 mmol) in place of 1-methylpiperidin-4-amine. The product was purified by preparative HPLC (Method A) to give a TFA salt of the title compound as a colorless film (15.4 mg, 8.8%). $^1$H NMR (500 MHz, CD$_3$OD) δ ppm 0.54-0.67 (m, 2H), 0.79-0.86 (m, 2H), 1.03-1.18 (m, 1H), 1.33 (app d, J=4.4 Hz, 6H), 1.80-1.97 (m, 1H), 2.93-3.07 (m, 4H), 3.54-3.72 (m, 3H), 3.77 (s, 3H), 3.93-4.02 (m, 1H), 4.32 (d, J=12.2 Hz, 2H), 6.86 (dd, J=6.8, 5.4 Hz, 1H), 7.21-7.28 (m, 1H), 7.40 (s, 1H), 7.45-7.51 (m, 1H), 7.83-7.92 (m, 1H); ESI-MS [M+H]$^+$ calc'd for C$_{22}$H$_{31}$N$_5$O$_2$, 398.25; found, 398.4.

Example 23: trans-N-(4-(1,3-dimethyl-1H-pyrazol-4-yl)-1-methylpyrrolidin-3-yl)-2,2-dimethyl-3-((3-methylpyridin-2-yl)oxy)propanamide

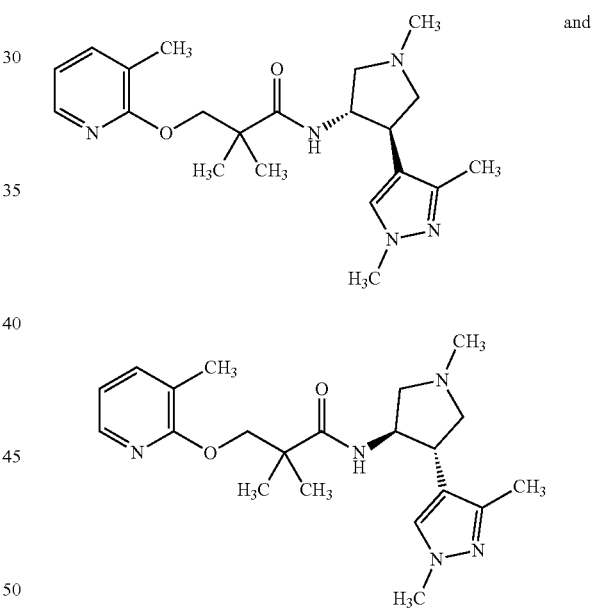

The title compound was prepared in a manner similar to EXAMPLE 1, using trans-4-(1,3-dimethyl-1H-pyrazol-4-yl)-1-methylpyrrolidin-3-amine (57.3 mg, 0.295 mmol, 1 eq) in place of 1-methylpiperidin-4-amine. The product was purified by preparative HPLC (Method A) to give a TFA salt of the title compound as a colorless film (92.8 mg, 63%). $^1$H NMR (500 MHz, CD$_3$OD) δ ppm 1.30 (app d, J=3.9 Hz, 6H), 2.01 (br s, 3H), 2.12 (s, 3H), 2.99 (m, 4H), 3.71 (m, 6H), 3.91-4.02 (m, 1H), 4.30 (s, 2H), 4.48-4.61 (m, 1H), 6.87 (dd, J=7.1, 5.1 Hz, 1H), 7.47-7.55 (m, 2H), 7.89-7.95 (m, 1H); ESI-MS [M+H]$^+$ calc'd for C$_{21}$H$_{31}$N$_5$O$_2$, 386.25; found, 386.4.

Example 24: trans-3-((3-cyclopropylpyridin-2-yl)oxy)-N-(4-(1,3-dimethyl-1H-pyrazol-4-yl)-1-methylpyrrolidin-3-yl)-2,2-dimethylpropanamide

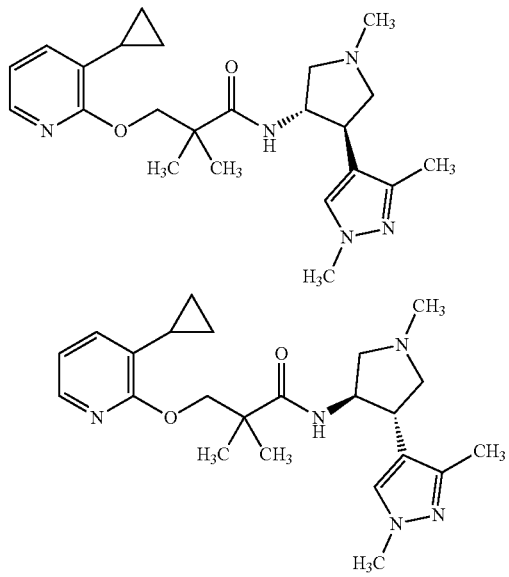

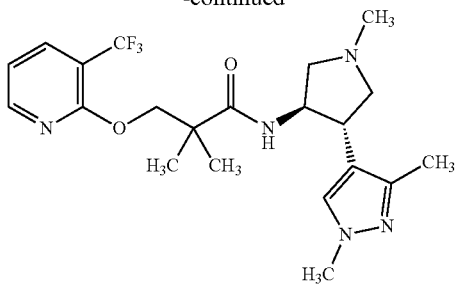

The title compound was prepared in a manner similar to EXAMPLE 1, using 3-((3-cyclopropylpyridin-2-yl)oxy)-2,2-dimethylpropanoic acid (73.8 mg, 0.295 mmol) in place of 2,2-dimethyl-3-((3-methylpyridin-2-yl)oxy)propanoic acid, and trans-4-(1,3-dimethyl-1H-pyrazol-4-yl)-1-methylpyrrolidin-3-amine (57.3 mg, 0.295 mmol) in place of 1-methylpiperidin-4-amine. The product was purified by preparative HPLC (Method A) to give a TFA salt of the title compound as a colorless film (54.4 mg, 35%). $^1$H NMR (500 MHz, CD$_3$OD) δ ppm 0.60 (d, J=5.4 Hz, 2H), 0.79-0.86 (m, 2H), 1.32 (app d, J=3.4 Hz, 6H), 1.80-1.88 (m, 1H), 2.11 (s, 3H), 2.98 (br s, 3H), 3.06-3.18 (m, 1H), 3.65 (m, 3H), 3.72 (br s, 3H), 3.92-4.03 (m, 1H), 4.25-4.35 (m, 2H), 4.40-4.51 (m, 1H), 6.87 (dd, J=7.3, 4.9 Hz, 1H), 7.23-7.28 (m, 1H), 7.48-7.53 (m, 1H), 7.88 (dd, J=5.1, 1.7 Hz, 1H); ESI-MS [M+H]$^+$ calc'd for C$_{23}$H$_{33}$N$_5$O$_2$, 412.26; found, 412.4.

Example 25: trans-N-(4-(1,3-dimethyl-1H-pyrazol-4-yl)-1-methylpyrrolidin-3-yl)-2,2-dimethyl-3-((3-(trifluoromethyl)pyridin-2-yl)oxy)propanamide

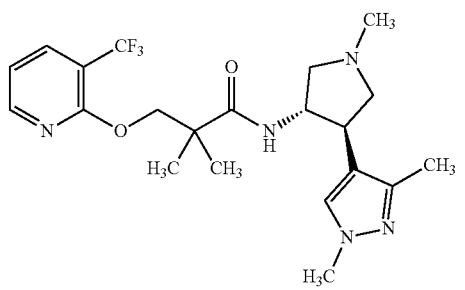

The title compound was prepared in a manner similar to EXAMPLE 1, using 2,2-dimethyl-3-((3-(trifluoromethyl)pyridin-2-yl)oxy)propanoic acid (78 mg, 0.295 mmol) in place of 2,2-dimethyl-3-((3-methylpyridin-2-yl)oxy)propanoic acid, and trans-4-(1,3-dimethyl-1H-pyrazol-4-yl)-1-methylpyrrolidin-3-amine (57.3 mg, 0.295 mmol) in place of 1-methylpiperidin-4-amine. The product was purified by preparative HPLC (Method A) to give a TFA salt of the title compound as a colorless film (39.3 mg, 24%). $^1$H NMR (500 MHz, CD$_3$OD) δ ppm 1.10 (s, 1H), 1.24-1.33 (m, 6H), 2.15 (s, 3H), 2.98 (m, 4H) 3.76 (m, 6H), 3.93-4.01 (m, 1H), 4.41 (s, 2H), 7.05-7.12 (m, 1H), 7.48-7.55 (m, 1H), 7.92-8.00 (m, 1H), 8.30-8.38 (m, 1H); ESI-MS [M+H]$^+$ calc'd for C$_{21}$H$_{28}$F$_3$N$_5$O$_2$, 440.22; found, 440.3.

Example 26: trans-N-(4-(1,5-dimethyl-1H-pyrazol-4-yl)-1-methylpyrrolidin-3-yl)-2,2-dimethyl-3-((3-methylpyridin-2-yl)oxy)propanamide The title compound was prepared in a manner similar to EXAMPLE 1, using trans-4-(1,5-dimethyl-1H-pyrazol-4-yl)-1-methylpyrrolidin-3-amine, HCl (131 mg, 0.295 mmol, 1 eq) in place of 1-methylpiperidin-4-amine. The product was purified by preparative HPLC (Method A) to give a TFA salt of the title compound as a colorless film (37.7 mg, 26%). $^1$H NMR (500 MHz, CD$_3$OD) δ ppm 1.29 (s, 6H), 2.01 (br s, 3H), 2.14 (s, 3H), 2.98 (br s, 3H), 3.11-3.25 (m, 1H), 3.70 (m, 6H), 3.85-3.97 (m, 1H), 4.27 (d, J=4.4 Hz, 2H), 4.45-4.57 (m, 1H), 6.85-6.91 (m, 1H), 7.43-7.54 (m, 2H), 7.88-7.95 (m, 1H); ESI-MS [M+H]$^+$ calc'd for C$_{21}$H$_{31}$N$_5$O$_2$, 386.25; found, 386.4.

Example 27: trans-3-((3-cyclopropylpyridin-2-yl)oxy)-N-(4-(1,5-dimethyl-1H-pyrazol-4-yl)-1-methylpyrrolidin-3-yl)-2,2-dimethylpropanamide

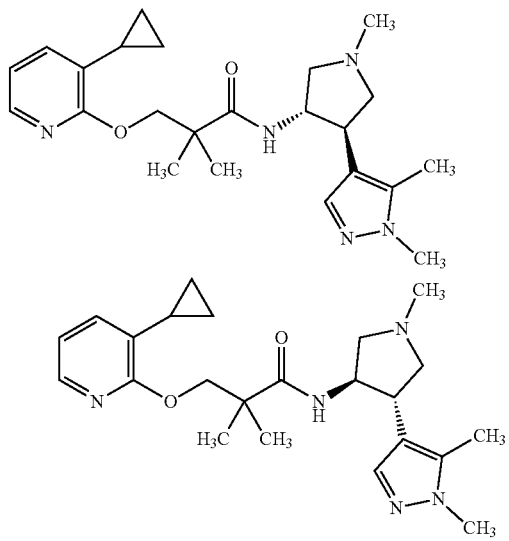

The title compound was prepared in a manner similar to EXAMPLE 1, using 3-((3-cyclopropylpyridin-2-yl)oxy)-2,2-dimethylpropanoic acid (73.8 mg, 0.295 mmol) in place of 2,2-dimethyl-3-((3-methylpyridin-2-yl)oxy)propanoic acid, and trans-4-(1,5-dimethyl-1H-pyrazol-4-yl)-1-methylpyrrolidin-3-amine, HCl (131 mg, 0.295 mmol) in place of 1-methylpiperidin-4-amine. The product was purified by preparative HPLC (Method A) to give a TFA salt of the title compound as a colorless film (24.4 mg, 16%). $^1$H NMR (500 MHz, CD$_3$OD) δ ppm 0.53-0.68 (m, 2H), 0.79-0.88 (m, 2H), 1.31 (s, 6H), 1.79-1.90 (m, 1H), 2.12 (s, 3H), 2.98 (br s, 3H), 3.12-3.23 (m, 1H), 3.70 (m, 6H), 3.85-3.95 (m, 1H), 4.29 (s, 2H), 4.34-4.45 (m, 1H), 6.83-6.90 (m, 1H), 7.23-7.32 (m, 1H), 7.43-7.49 (m, 1H), 7.84-7.92 (m, 1H); ESI-MS [M+H]$^+$ calc'd for C$_{23}$H$_{33}$N$_5$O$_2$, 412.26; found, 412.4.

Example 28: trans-N-(4-(1,5-dimethyl-1H-pyrazol-4-yl)-1-methylpyrrolidin-3-yl)-2,2-dimethyl-3-((3-(trifluoromethyl)pyridin-2-yl)oxy)propanamide

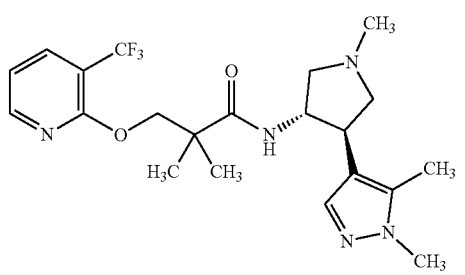

and

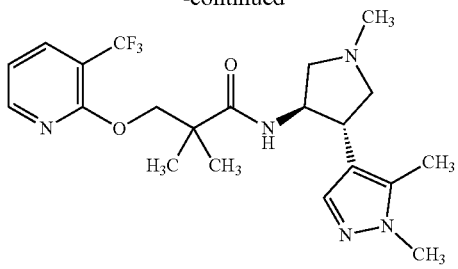

The title compound was prepared in a manner similar to EXAMPLE 1, using 2,2-dimethyl-3-((3-(trifluoromethyl)pyridin-2-yl)oxy)propanoic acid (78 mg, 0.295 mmol) in place of 2,2-dimethyl-3-((3-methylpyridin-2-yl)oxy)propanoic acid, and trans-4-(1,5-dimethyl-1H-pyrazol-4-yl)-1-methylpyrrolidin-3-amine, HCl (131 mg, 0.295 mmol) in place of 1-methylpiperidin-4-amine. The product was purified by preparative HPLC (Method A) to give a TFA salt of the title compound as a colorless film (57.1 mg, 35%). $^1$H NMR (500 MHz, CD$_3$OD) δ ppm 1.23-1.33 (m, 6H), 2.21 (s, 3H), 2.98 (br s, 3H), 3.16-3.26 (m, 1H), 3.74 (m, 6H), 3.85-4.02 (m, 1H), 4.40 (s, 3H), 7.04-7.12 (m, 1H), 7.40-7.55 (m, 1H), 7.93-8.02 (m, 1H), 8.28-8.37 (m, 1H); ESI-MS [M+H]$^+$ calc'd for C$_{21}$H$_{28}$F$_3$N$_5$O$_2$, 440.22; found, 440.3.

Example 29: trans-N-(4-(1,3-dimethyl-1H-pyrazol-4-yl)-1-methylpyrrolidin-3-yl)-2,2-dimethyl-3-((3-(trifluoromethoxy)pyridin-2-yl)oxy)propanamide

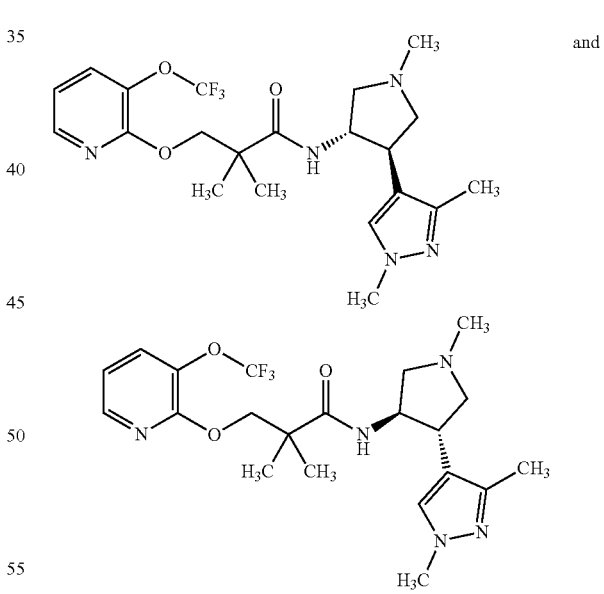

The title compound was prepared in a manner similar to EXAMPLE 1, using 2,2-dimethyl-3-((3-(trifluoromethyl)pyridin-2-yl)oxy)propanoic acid (82 mg, 0.295 mmol) in place of 2,2-dimethyl-3-((3-methylpyridin-2-yl)oxy)propanoic acid, and trans-4-(1,3-dimethyl-1H-pyrazol-4-yl)-1-methylpyrrolidin-3-amine (57.3 mg, 0.295 mmol) in place of 1-methylpiperidin-4-amine. The product was purified by preparative HPLC (Method A) to give a TFA salt of the title compound as a colorless film (25.7 mg, 15%). $^1$H NMR (500 MHz, CD$_3$OD) δ ppm 1.30 (s, 6H), 2.15 (s, 3H), 2.98 (m, 4H), 3.66 (m, 3H), 3.75 (br s, 3H), 3.98 (br s, 1H), 4.07-4.29 (m, 1H), 4.31-4.44 (m, 2H), 6.97-7.08 (m, 1H), 7.42-7.56 (m, 1H), 7.60-7.70 (m, 1H), 8.01-8.13 (m, 1H); ESI-MS [M+H]$^+$ calc'd for $C_{21}H_{28}F_3N_5O_3$, 456.21; found, 456.4.

Example 30: trans-N-(4-(1,5-dimethyl-1H-pyrazol-4-yl)-1-methylpyrrolidin-3-yl)-2,2-dimethyl-3-((3-(trifluoromethoxy)pyridin-2-yl)oxy)propanamide

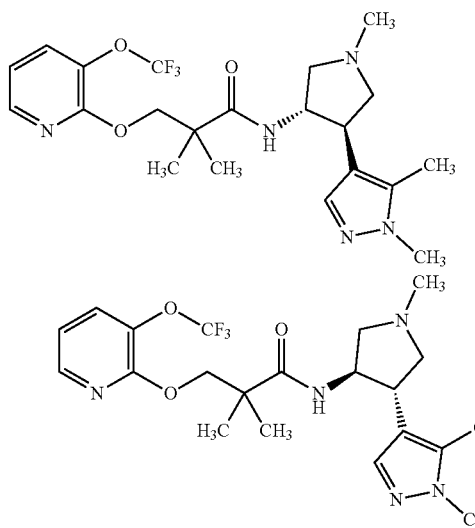

The title compound was prepared in a manner similar to EXAMPLE 1, using 2,2-dimethyl-3-((3-(trifluoromethyl)pyridin-2-yl)oxy)propanoic acid (82 mg, 0.295 mmol) in place of 2,2-dimethyl-3-((3-methylpyridin-2-yl)oxy)propanoic acid, and trans-4-(1,5-dimethyl-1H-pyrazol-4-yl)-1-methylpyrrolidin-3-amine, HCl (131 mg, 0.295 mmol) in place of 1-methylpiperidin-4-amine. The product was purified by preparative HPLC (Method A) to give a TFA salt of the title compound as a colorless film (50.5 mg, 30%). $^1$H NMR (500 MHz, CD$_3$OD) δ ppm 1.24-1.33 (m, 6H), 2.21 (s, 3H), 2.99 (br s, 3H), 3.16-3.27 (m, 1H), 3.74 (m, 6H), 3.86-3.97 (m, 1H), 4.37 (br s, 3H), 6.97-7.07 (m, 1H), 7.42-7.52 (m, 1H), 7.61-7.71 (m, 1H), 7.99-8.12 (m, 1H); ESI-MS [M+H]$^+$ calc'd for $C_{21}H_{28}F_3N_5O_3$, 456.21; found, 456.4.

Example 31: trans-N-(1,3-dimethylpiperidin-4-yl)-3-((3,5-dimethylpyridin-2-yl)oxy)-2,2-dimethylpropanamide

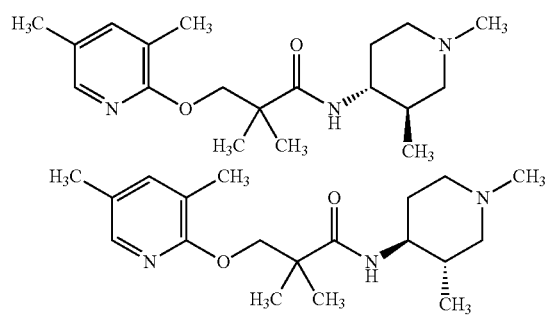

Example 32: cis-N-(1,3-dimethylpiperidin-4-yl)-3-((3,5-dimethylpyridin-2-yl)oxy)-2,2-dimethylpropanamide

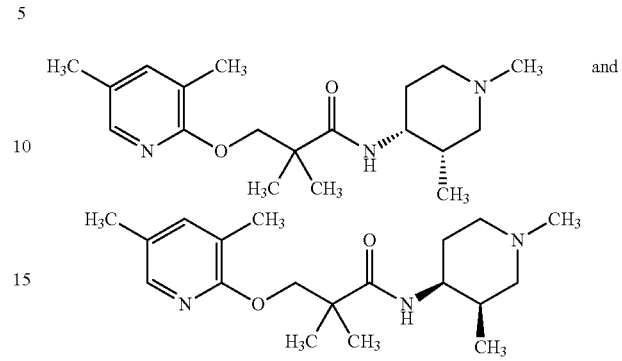

The title trans- and cis-stereoisomers were prepared in a manner similar to EXAMPLE 1, using 3-((3,5-dimethylpyridin-2-yl)oxy)-2,2-dimethylpropanoic acid (0.100 g, 0.448 mmol) in place of 2,2-dimethyl-3-((3-methylpyridin-2-yl)oxy)propanoic acid 3-dimethylpiperidin-4-amine (0.057 g, 0.45 mmol) in place of 1-methylpiperidin-4-amine. The products were purified by preparative HPLC (Method B) to give the trans-stereoisomer (first eluting peak) as a light brown film (64.0 mg, 43%) and the cis-stereoisomer (second eluting peak) as a light yellow film (32.9 mg, 22%). Peak 1: $^1$H NMR (500 MHz, CD$_3$OD) δ ppm 0.82 (d, J=6.1 Hz, 3H), 1.30 (s, 6H), 1.48-1.59 (m, 1H), 1.66-1.80 (m, 3H), 1.99-2.09 (m, 1H), 2.13 (s, 3H), 2.19 (s, 3H), 2.26 (s, 3H), 2.81-2.90 (m, 2H), 3.39-3.47 (m, 1H), 4.27 (s, 2H), 7.28-7.34 (m, 1H), 7.68-7.75 (m, 1H); ESI-MS [M+H]$^+$ calc'd for $C_{19}H_{31}N_3O_2$, 334.24; found, 334.4. Peak 2: $^1$H NMR (500 MHz, CD$_3$OD) δ ppm 0.87 (d, J=6.8 Hz, 3H), 1.31 (m, 7H), 1.61-1.70 (m, 1H), 1.73-1.83 (m, 1H), 2.00-2.08 (m, 1H), 2.10-2.25 (m, 10H), 2.29-2.44 (m, 2H), 3.92-4.01 (m, 1H), 4.30 (s, 2H), 7.32-7.37 (m, 1H), 7.68-7.77 (m, 1H); ESI-MS [M+H]$^+$ calc'd for $C_{19}H_{31}N_3O_2$, 334.24; found, 334.4.

Example 33: trans-N-(3-isopropyl-1-methylpiperidin-4-yl)-2,2-dimethyl-3-((3-(trifluoromethyl)pyridin-2-yl)oxy)propanamide

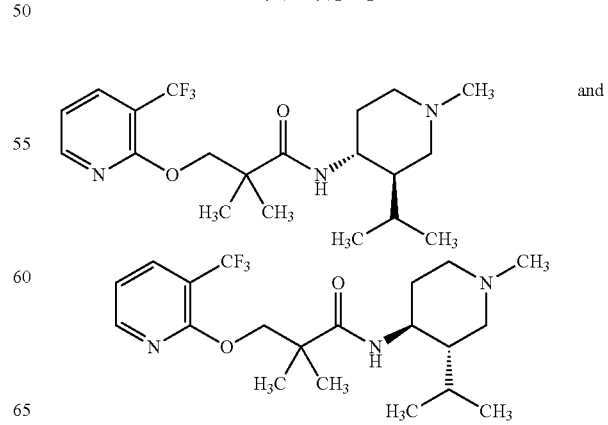

Example 34: cis-N-(3-isopropyl-1-methylpiperidin-4-yl)-2,2-dimethyl-3-((3-(trifluoromethyl)pyridin-2-yl)oxy)propanamide

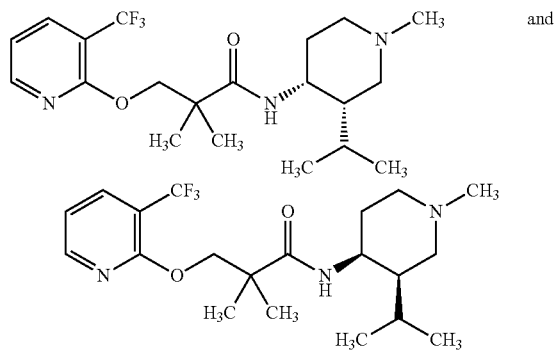

The title trans- and cis-stereoisomers were prepared in a manner similar to EXAMPLE 1, using 2,2-dimethyl-3-((3-(trifluoromethyl)pyridin-2-yl)oxy)propanoic acid (0.060 g, 0.23 mmol) in place of 2,2-dimethyl-3-((3-methylpyridin-2-yl)oxy)propanoic acid, and 3-isopropyl-1-methylpiperidin-4-amine, 2HCl (0.052 g, 0.23 mmol) in place of 1-methylpiperidin-4-amine. The products were purified by preparative HPLC (Method A) to give, upon evaporation, TFA salts of the trans-stereoisomer (first eluting peak) as a colorless film (1.7 mg, 1.5%) and the cis-stereoisomer (second eluting peak) as a tan film (12.1 mg, 10%). Peak 1: $^1$H NMR (500 MHz, CD$_3$OD) δ ppm 0.80 (d, J=6.8 Hz, 3H), 0.94 (d, J=7.1 Hz, 3H), 1.31 (app d, J=6.4 Hz, 6H), 1.70-1.82 (m, 1H), 1.89-2.08 (m, 3H), 2.87 (s, 3H), 2.90-2.96 (m, 1H), 3.04-3.11 (m, 1H), 3.45-3.53 (m, 2H), 3.92-4.04 (m, 1H), 4.38-4.55 (m, 2H), 7.06-7.14 (m, 1H), 7.56-7.64 (m, 1H), 7.95-8.03 (m, 1H), 8.31-8.39 (m, 1H); ESI-MS [M+H]$^+$ calc'd for C$_{20}$H$_{30}$F$_3$N$_3$O$_2$, 402.23; found, 402.4. Peak 2: $^1$H NMR (500 MHz, CD$_3$OD) δ ppm 0.80 (d, J=6.8 Hz, 3H), 0.94 (d, J=7.1 Hz, 3H), 1.31 (app d, J=6.4 Hz, 6H), 1.70-1.82 (m, 1H), 1.89-2.08 (m, 3H), 2.87 (s, 3H), 2.90-2.96 (m, 1H), 3.04-3.11 (m, 1H), 3.45-3.53 (m, 2H), 3.92-4.04 (m, 1H), 4.38-4.55 (m, 2H), 7.06-7.14 (m, 1H), 7.56-7.64 (m, 1H), 7.95-8.03 (m, 1H), 8.31-8.39 (m, 1H); ESI-MS [M+H]$^+$ calc'd for C$_{20}$H$_{30}$F$_3$N$_3$O$_2$, 402.23; found, 402.4.

Example 35: 2,2-dimethyl-3-((3-(trifluoromethyl)pyridin-2-yl)oxy)-N-(1,5,5-trimethylpyrrolidin-3-yl)propanamide

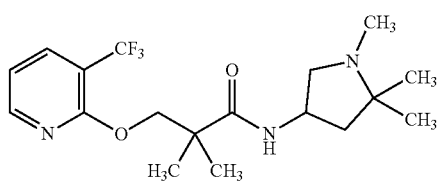 [SMILES: CN1CC(NC(=O)C(C)(C)COc2ncccc2C(F)(F)F)CC1(C)C]

The title compound was prepared in a manner similar to EXAMPLE 1, using 2,2-dimethyl-3-((3-(trifluoromethyl)pyridin-2-yl)oxy)propanoic acid (0.113 g, 0.450 mmol) in place of 2,2-dimethyl-3-((3-methylpyridin-2-yl)oxy)propanoic acid, and 1,5,5-trimethylpyrrolidin-3-amine (0.055 g, 0.43 mmol) in place of 1-methylpiperidin-4-amine. The product was purified by preparative HPLC (Method A) to give a TFA salt of the title compound as a brown film (19.4 mg, 9.3%). $^1$H NMR (400 MHz, CD$_3$OD) δ ppm 1.31 (s, 9H), 1.50 (s, 3H), 2.06-2.17 (m, 1H), 2.40-2.52 (m, 1H), 2.76 (s, 3H), 3.50-3.69 (m, 2H), 4.43 (s, 3H), 7.05-7.13 (m, 1H), 7.91-8.03 (m, 1H), 8.31-8.39 (m, 1H); ESI-MS [M+H]$^+$ calc'd for C$_{18}$H$_{26}$F$_3$N$_3$O$_2$, 374.20; found, 374.4.

Example 36: (R)-2,2-dimethyl-N-((1-methylpyrrolidin-3-yl)methyl)-3-((3-(trifluoromethyl)pyridin-2-yl)oxy)propanamide

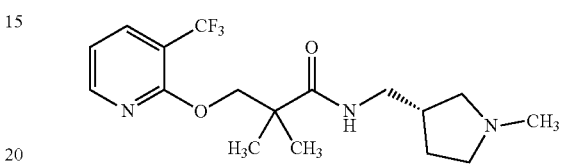

The title compound was prepared in a manner similar to EXAMPLE 1, using 2,2-dimethyl-3-((3-(trifluoromethyl)pyridin-2-yl)oxy)propanoic acid (0.060 g, 0.23 mmol) and (R)-(1-methylpyrrolidin-3-yl)methanamine (0.026 g, 0.23 mmol) in place of 2,2-dimethyl-3-((3-methylpyridin-2-yl)oxy)propanoic acid and 1-methylpiperidin-4-amine. The product was purified by preparative HPLC (Method A) to give a TFA salt of the title compound as a colorless film (71.5 mg, 66%). $^1$H NMR (400 MHz, CD$_3$OD) δ ppm 1.31 (app d, J=1.8 Hz, 6H), 1.68-1.97 (m, 1H), 2.06-2.34 (m, 1H), 2.55-2.86 (m, 2H), 2.91 (s, 3H), 3.01-3.17 (m, 1H), 3.22-3.28 (m, 1H), 3.33-3.49 (m, 1H), 3.56-3.81 (m, 2H), 4.43 (d, J=0.9 Hz, 2H), 7.00-7.16 (m, 1H), 7.92-8.01 (m, 1H), 8.30-8.42 (m, 1H); ESI-MS [M+H]$^+$ calc'd for C$_{17}$H$_{24}$F$_3$N$_3$O$_2$, 360.19; found, 360.3.

Example 37: (S)-2,2-dimethyl-N-((1-methylpyrrolidin-3-yl)methyl)-3-((3-(trifluoromethyl)pyridin-2-yl)oxy)propanamide

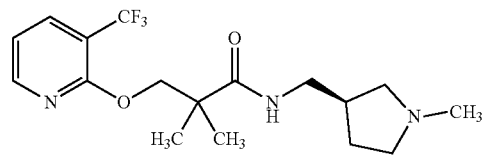 [SMILES: CN1CC[C@@H](CNC(=O)C(C)(C)COc2ncccc2C(F)(F)F)C1]

The title compound was prepared in a manner similar to EXAMPLE 1, using 2,2-dimethyl-3-((3-(trifluoromethyl)pyridin-2-yl)oxy)propanoic acid (0.060 g, 0.23 mmol) and (S)-(1-methylpyrrolidin-3-yl)methanamine (0.026 g, 0.23 mmol) in place of 2,2-dimethyl-3-((3-methylpyridin-2-yl)oxy)propanoic acid and 1-methylpiperidin-4-amine. The product was purified by preparative HPLC (Method A) to give a TFA salt of the title compound as a light brown film (86.5 mg, 80%). $^1$H NMR (400 MHz, CD$_3$OD) δ ppm 1.31 (app d, J=1.8 Hz, 6H), 1.66-1.98 (m, 1H), 2.05-2.31 (m, 1H), 2.55-2.83 (m, 2H), 2.90 (s, 3H), 3.03-3.28 (m, 2H), 3.34-3.47 (m, 1H), 3.55-3.76 (m, 2H), 4.43 (d, J=1.0 Hz, 2H), 7.03-7.14 (m, 1H), 7.94-8.02 (m, 1H), 8.35 (dd, J=5.0, 1.1 Hz, 1H); ESI-MS [M+H]$^+$ calc'd for C$_{17}$H$_{24}$F$_3$N$_3$O$_2$, 360.19; found, 360.3.

Example 38: 3-((3-chloropyridin-2-yl)oxy)-2,2-dimethyl-N-(1-methylpiperidin-4-yl)propanamide

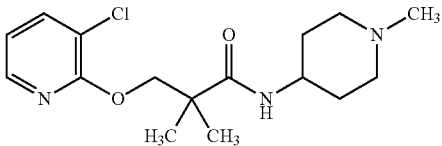 [SMILES: CN1CCC(NC(=O)C(C)(C)COc2ncccc2Cl)CC1]

In a 20 mL vial was dissolved 3-hydroxy-2,2-dimethyl-N-(1-methylpiperidin-4-yl)propanamide (0.138 g, 0.380 mmol) in DMF (1.5 mL) to give a colorless solution. Sodium hydride (60 wt %, 0.035 g, 0.87 mmol) was added. After stirring for 30 minutes at room temperature, 3-chloro-2-fluoropyridine (0.050 g, 0.38 mmol) was added. The mixture was stirred at room temperature overnight. The reaction mixture was filtered through a hydrophilic PTFE 0.45 m filter (Millipore® Millex-LCR) which was rinsed with methanol. The filtrate was purified by preparative HPLC (Method A). The product-containing fractions were evaporated to give a TFA salt of the title compound as a clear film (69.0 mg, 41%). $^1$H NMR (500 MHz, CDCl$_3$) δ ppm 1.28 (s, 6H), 1.95-2.11 (m, 4H), 2.83 (m, 5H), 3.56-3.66 (m, 2H), 3.98-4.11 (m, 1H), 4.25 (s, 2H), 6.31-6.37 (m, 1H), 6.67-6.72 (m, 1H), 7.50-7.58 (m, 1H), 8.01-8.11 (m, 1H); ESI-MS [M+H]$^+$ calc'd for C$_{16}$H$_{24}$ClN$_3$O$_2$, 326.16; found, 326.19.

Example 39: 3-((3-fluoropyridin-2-yl)oxy)-2,2-dimethyl-N-(1-methylpiperidin-4-yl)propanamide

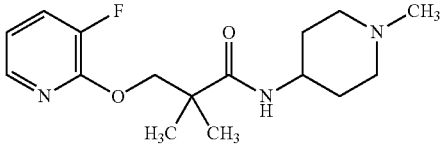 [SMILES: CN1CCC(NC(=O)C(C)(C)COc2ncccc2F)CC1]

The title compound was prepared in a manner similar to EXAMPLE 38, using 2,3-difluoropyridine (0.050 g, 0.43 mmol, 1 eq) in place of 3-chloro-2-fluoropyridine. The product was purified by preparative HPLC (Method B) to give the title compound as a light brown film (26.1 mg, 19%). $^1$H NMR (500 MHz, CDCl$_3$) δ ppm 1.30 (s, 6H), 1.41-1.52 (m, 2H), 1.84-1.94 (m, 2H), 2.10-2.16 (m, 2H), 2.25 (s, 3H), 2.65-2.77 (m, 2H), 3.71-3.86 (m, 1H), 4.34 (s, 2H), 6.16-6.26 (m, 1H), 6.83-6.93 (m, 1H), 7.29-7.38 (m, 1H), 7.86-7.93 (m, 1H); ESI-MS [M+H]$^+$ calc'd for C$_{16}$H$_{24}$FN$_3$O$_2$, 310.19; found, 310.5.

Example 40: 3-((3,5-difluoropyridin-2-yl)oxy)-2,2-dimethyl-N-(1-methylpiperidin-4-yl)propanamide

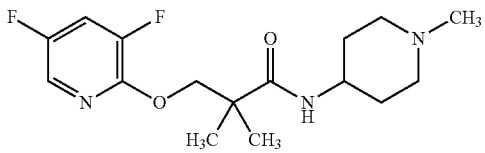

The title compound was prepared in a manner similar to EXAMPLE 38, using 2,3,5-trifluoropyridine (0.050 g, 0.38 mmol, 1 eq) in place of 3-chloro-2-fluoropyridine. The product was purified by preparative HPLC (Method B) to give the title compound as a light brown film (23.7 mg, 19%). $^1$H NMR (500 MHz, CDCl$_3$) δ ppm 1.26-1.32 (m, 6H), 1.40-1.52 (m, 2H), 1.85-1.95 (m, 2H), 2.06-2.15 (m, 2H), 2.21-2.30 (m, 3H), 2.67-2.79 (m, 2H), 3.72-3.85 (m, 1H), 4.30 (s, 2H), 6.03-6.13 (m, 1H), 7.16-7.24 (m, 1H), 7.78-7.85 (m, 1H); ESI-MS [M+H]$^+$ calc'd for C$_{16}$H$_{23}$F$_2$N$_3$O$_2$, 328.18; found, 328.4.

Example 41: 2,2-dimethyl-N-(1-methylpiperidin-4-yl)-3-((3-(trifluoromethyl)pyridin-2-yl)oxy)propanamide

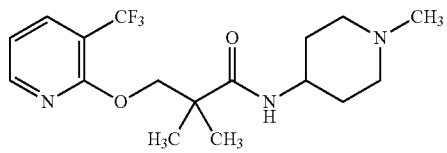

The title compound was prepared in a manner similar to EXAMPLE 38, using 2-fluoro-3-(trifluoromethyl)pyridine (0.12 g, 0.73 mmol, 1 eq) in place of 3-chloro-2-fluoropyridine. The product was purified by preparative HPLC (Method B) to give the title compound as a pale green film (68.7 mg, 26%). $^1$H NMR (500 MHz, CDCl$_3$) δ ppm 1.30 (s, 6H), 1.45 (dd, J=12.2, 3.9 Hz, 2H), 1.83-1.92 (m, 2H) 2.06 (td, J=11.6, 1.7 Hz, 2H), 2.25 (s, 3H), 2.77 (d, J=11.7 Hz, 2H), 3.71-3.81 (m, 1H), 4.39 (s, 2H), 5.98-6.08 (m, 1H), 6.93-7.03 (m, 1H), 7.84-7.92 (m, 1H), 8.23-8.36 (m, 1H); ESI-MS [M+H]$^+$ calc'd for C$_{17}$H$_{24}$F$_3$N$_3$O$_2$, 360.18; found, 360.5.

Example 42: 2,2-dimethyl-N-(1-methylpiperidin-4-yl)-3-((4-(trifluoromethyl)pyridin-3-yl)oxy)propanamide

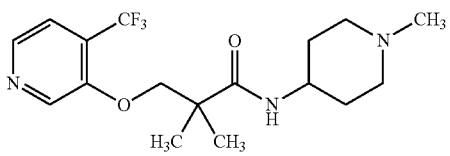 [SMILES: CN1CCC(NC(=O)C(C)(C)COc2cnccc2C(F)(F)F)CC1]

The title compound was prepared in a manner similar to EXAMPLE 38, using 3-fluoro-4-(trifluoromethyl)pyridine (0.12 g, 0.73 mmol, 1 eq) in place of 3-chloro-2-fluoropyridine. The product was purified by preparative HPLC (Method B) to give the title compound as a light brown film (87.2 mg, 67%). $^1$H NMR (500 MHz, CDCl$_3$) δ ppm 1.33 (s, 6H), 1.41-1.54 (m, 2H), 1.86-1.93 (m, 2H), 2.03-2.14 (m, 2H), 2.26 (s, 3H), 2.78 (d, J=11.7 Hz, 2H), 3.69-3.84 (m, 1H), 4.15 (s, 2H), 5.82-5.92 (m, 1H), 7.45 (d, J=4.9 Hz, 1H), 8.37-8.42 (m, 1H), 8.44-8.52 (m, 1H); ESI-MS [M+H]$^+$ calc'd for C$_{17}$H$_{24}$F$_3$N$_3$O$_2$, 360.18; found, 360.5.

Example 43: 2,2-dimethyl-N-(1-methylpiperidin-4-yl)-3-((3-(trifluoromethyl)pyridin-4-yl)oxy)propanamide

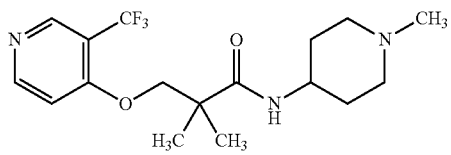 [SMILES: CN1CCC(NC(=O)C(C)(C)COc2ccncc2C(F)(F)F)CC1]

The title compound was prepared in a manner similar to EXAMPLE 38, using 4-chloro-3-(trifluoromethyl)pyridine (0.070 g, 0.39 mmol, 1 eq) in place of 3-chloro-2-fluoropyridine. The product was purified by preparative HPLC (Method B) to give the title compound as a light brown film (39.4 mg, 28%). $^1$H NMR (500 MHz, CDCl$_3$) δ ppm 1.32 (s, 6H), 1.41-1.52 (m, 2H), 1.82-1.92 (m, 2H), 2.04-2.07 (m, 2H), 2.26 (s, 3H), 2.70-2.83 (m, 2H), 3.69-3.81 (m, 1H), 4.08 (s, 2H), 5.76-5.86 (m, 1H), 6.88-6.98 (m, 1H), 8.58-8.64 (m, 1H), 8.65-8.70 (m, 1H); ESI-MS [M+H]$^+$ calc'd for C$_{17}$H$_{24}$F$_3$N$_3$O$_2$, 360.18; found, 360.5.

Example 44: 3-((4-chloro-3-fluoropyridin-2-yl)oxy)-2,2-dimethyl-N-(1-methylpiperidin-4-yl)propanamide

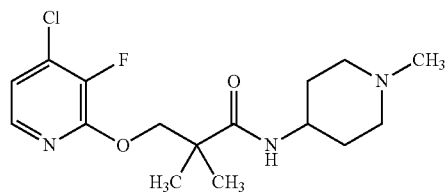 [SMILES: CN1CCC(NC(=O)C(C)(C)COc2nccc(Cl)c2F)CC1]

The title compound was prepared in a manner similar to EXAMPLE 38, using 4-chloro-2,3-difluoropyridine (0.12 g, 0.80 mmol, 2 eq) in place of 3-chloro-2-fluoropyridine. The product was purified by preparative HPLC (Method B) to give the title compound as a brown film (66.2 mg, 48%). $^1$H NMR (500 MHz, CDCl$_3$) δ ppm 1.30 (s, 6H), 1.48 (br s, 2H), 1.86-1.95 (m, 2H), 2.11 (br s, 2H), 2.27 (s, 3H), 2.73 (d, J=9.8 Hz, 2H), 3.75-3.85 (m, 1H), 4.35 (s, 2H), 6.01-6.09 (m, 1H), 6.94 (dd, J=5.4, 4.4 Hz, 1H), 7.80 (dd, J=5.4, 1.0 Hz, 1H); ESI-MS [M+H]$^+$ calc'd for C$_{16}$H$_{23}$ClFN$_3$O$_2$, 344.15; found, 344.4.

Example 45: 3-((3-chloro-5-fluoropyridin-2-yl)oxy)-2,2-dimethyl-N-(1-methylpiperidin-4-yl)propanamide

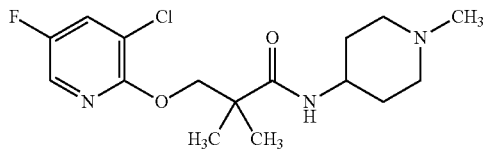 [SMILES: CN1CCC(NC(=O)C(C)(C)COc2ncc(F)cc2Cl)CC1]

The title compound was prepared in a manner similar to EXAMPLE 38, using 3-chloro-2,5-difluoropyridine (0.094 g, 0.63 mmol, 1.7 eq) in place of 3-chloro-2-fluoropyridine. The product was purified by preparative HPLC (Method B) to give the title compound as a pink solid (39.2 mg, 31%). $^1$H NMR (500 MHz, CDCl$_3$) δ ppm 1.31 (s, 6H), 1.39-1.52 (m, 2H), 1.84-1.93 (m, 2H), 2.05-2.14 (m, 2H), 2.25 (s, 3H), 2.68-2.77 (m, 2H), 3.69-3.83 (m, 1H), 4.03 (s, 2H), 5.75-5.87 (m, 1H), 6.46-6.50 (m, 1H), 7.81-7.90 (m, 1H); ESI-MS [M+H]$^+$ calc'd for C$_{16}$H$_{23}$ClFN$_3$O$_2$, 344.15; found, 344.2.

Example 46: 3-((6-chloro-2-methylpyridin-3-yl)oxy)-2,2-dimethyl-N-(1-methylpiperidin-4-yl)propanamide

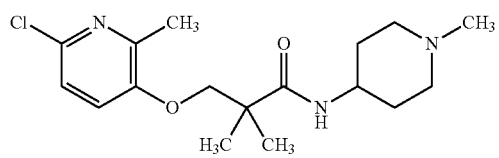 [SMILES: Cc1nc(Cl)ccc1OCC(C)(C)C(=O)NC1CCN(C)CC1]

The title compound was prepared in a manner similar to EXAMPLE 38, using 6-chloro-3-fluoro-2-methylpyridine (0.092 g, 0.63 mmol, 1.7 eq) in place of 3-chloro-2-fluoropyridine. The reaction mixture was heated at 100° C. and the product was purified by preparative HPLC (Method B) to give the title compound as a brown film (12.1 mg, 9.6%). $^1$H NMR (500 MHz, CDCl$_3$) δ ppm 1.30 (s, 6H), 1.41-1.52 (m, 2H), 1.87-1.95 (m, 2H), 2.06-2.16 (m, 2H), 2.28 (s, 3H), 2.35 (s, 3H), 2.73 (br s, 2H), 3.74-3.86 (m, 1H), 3.95 (s, 2H), 5.77-5.86 (m, 1H), 7.07-7.14 (m, 1H), 7.85-7.93 (m, 1H); ESI-MS [M+H]$^+$ calc'd for C$_{17}$H$_{26}$ClN$_3$O$_2$, 340.17; found, 340.3.

Example 47: 3-((3-cyclopropylpyridin-2-yl)oxy)-2,2-dimethyl-N-(1-methylpiperidin-4-yl)propanamide

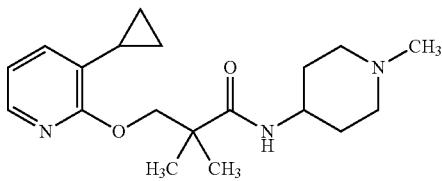 [SMILES: CN1CCC(NC(=O)C(C)(C)COc2ncccc2C2CC2)CC1]

The title compound was prepared in a manner similar to EXAMPLE 38, using 3-cyclopropyl-2-fluoropyridine (0.050 g, 0.36 mmol, 1 eq) in place of 3-chloro-2-fluoropyridine. The product was purified by preparative HPLC (Method B) to give the title compound as a light brown film (21.4 mg, 18%). $^1$H NMR (500 MHz, CD$_3$OD) δ ppm 0.63-0.70 (m, 2H), 0.87-0.96 (m, 2H), 1.29-1.34 (m, 6H), 1.50-1.61 (m, 2H), 1.76-1.85 (m, 2H), 1.97-2.05 (m, 1H), 2.05-2.16 (m, 2H), 2.27 (dd, J=2.7, 1.7 Hz, 3H), 2.79-2.89 (m, 2H), 3.66-3.76 (m, 1H), 4.29-4.35 (m, 2H), 6.80-6.88 (m, 1H), 7.20-7.28 (m, 1H), 7.86-7.91 (m, 1H); ESI-MS [M+H]$^+$ calc'd for C$_{19}$H$_{29}$N$_3$O$_2$, 332.23; found, 332.40.

Example 48: 3-((5-chloro-3-methylpyridin-2-yl)oxy)-2,2-dimethyl-N-(1-methylpiperidin-4-yl)propanamide

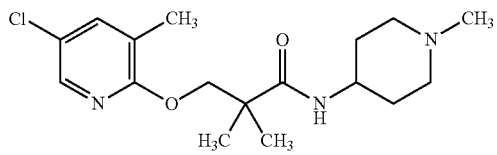 [SMILES: Cc1cc(Cl)cnc1OCC(C)(C)C(=O)NC1CCN(C)CC1]

The title compound was prepared in a manner similar to EXAMPLE 38, using 2,5-dichloro-3-methylpyridine (0.060 g, 0.37 mmol, 1 eq) in place of 3-chloro-2-fluoropyridine. The reaction mixture was heated at 100° C. and the product was purified by preparative HPLC (Method B) to give the title compound as a brown film (23.4 mg, 19%). $^1$H NMR (500 MHz, CD$_3$OD) δ ppm 1.28 (s, 6H), 1.51-1.60 (m, 2H), 1.75-1.81 (m, 2H), 2.06-2.13 (m, 2H), 2.15 (s, 3H), 2.26 (s, 3H), 2.80-2.87 (m, 2H), 3.65-3.74 (m, 1H), 4.29 (s, 2H), 7.48-7.52 (m, 1H), 7.88-7.91 (m, 1H); ESI-MS [M+H]$^+$ calc'd for C$_{17}$H$_{26}$ClN$_3$O$_2$, 340.17; found, 340.47.

Example 49: 3-((3-methoxypyridin-2-yl)oxy)-2,2-dimethyl-N-(1-methylpiperidin-4-yl)propanamide

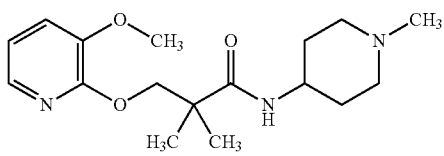

The title compound was prepared in a manner similar to EXAMPLE 38, using 2-fluoro-methoxypyridine (0.050 g, 0.39 mmol, 1 eq) in place of 3-chloro-2-fluoropyridine. The reaction mixture was heated at 100° C. and the product was purified by preparative HPLC (Method B) to give the title compound as a colorless film (43.0 mg, 34%). $^1$H NMR (500 MHz, CD$_3$OD) δ ppm 1.27 (s, 6H), 1.50-1.60 (m, 2H), 1.79-1.85 (m, 2H), 2.08-2.18 (m, 2H), 2.27 (s, 3H), 2.79-2.86 (m, 2H), 3.65-3.73 (m, 1H), 3.84 (s, 3H), 4.29 (s, 2H), 6.88-6.93 (m, 1H), 7.21-7.26 (m, 1H), 7.62-7.66 (m, 1H); ESI-MS [M+H]$^+$ calc'd for C$_{17}$H$_{27}$N$_3$O$_3$, 322.21; found, 322.41.

Example 50: 2,2-dimethyl-N-(1-methylpiperidin-4-yl)-3-((3-methylpyridin-4-yl)oxy)propanamide

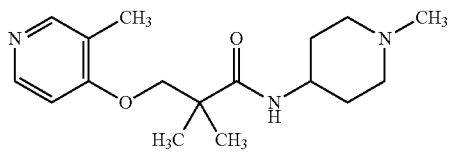 [SMILES: Cc1cnccc1OCC(C)(C)C(=O)NC1CCN(C)CC1]

The title compound was prepared in a manner similar to EXAMPLE 38, using 4-fluoro-3-methylpyridine (0.050 g, 0.45 mmol, 1 eq) in place of 3-chloro-2-fluoropyridine. The product was purified by preparative HPLC (Method B) to give the title compound as a colorless film (41.2 mg, 30%). $^1$H NMR (500 MHz, CD$_3$OD) δ ppm 1.32 (s, 6H), 1.53-1.64 (m, 2H), 1.74-1.85 (m, 2H), 2.06-2.13 (m, 2H), 2.16 (s, 3H), 2.27 (s, 3H), 2.81-2.89 (m, 2H), 3.65-3.78 (m, 1H), 4.09 (s, 2H), 6.92-7.01 (m, 1H), 8.12-8.18 (m, 1H), 8.21-8.27 (m, 1H); ESI-MS [M+H]$^+$ calc'd for C$_{17}$H$_{27}$N$_3$O$_2$, 306.21; found, 306.31.

Example 51: 3-((5-cyano-3-methylpyridin-2-yl)oxy)-2,2-dimethyl-N-(1-methylpiperidin-4-yl)propanamide

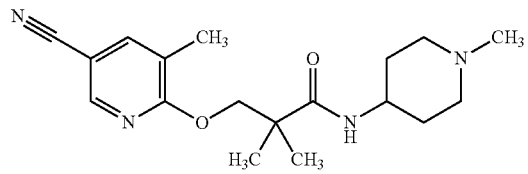 [SMILES: Cc1cc(C#N)cnc1OCC(C)(C)C(=O)NC1CCN(C)CC1]

The title compound was prepared in a manner similar to EXAMPLE 38, using 6-fluoro-5-methylnicotinonitrile (0.050 g, 0.37 mmol, 1 eq) in place of 3-chloro-2-fluoropyridine. The product was purified by preparative HPLC (Method B) to give the title compound as a colorless film (27.6 mg, 23%). $^1$H NMR (500 MHz, CD$_3$OD) δ ppm 1.30 (s, 6H), 1.50-1.61 (m, 2H), 1.74-1.81 (m, 2H), 2.05-2.13 (m, 2H), 2.19 (s, 3H), 2.26 (s, 3H), 2.82-2.88 (m, 2H), 3.65-3.74 (m, 1H), 4.40 (s, 2H), 7.76-7.80 (m, 1H), 8.32-8.37 (m, 1H); ESI-MS [M+H]$^+$ calc'd for C$_{18}$H$_{26}$N$_4$O$_2$, 331.21; found, 331.3.

Example 52: 2,2-dimethyl-N-(1-methylpiperidin-4-yl)-3-((2-(trifluoromethyl)pyridin-3-yl)oxy)propanamide

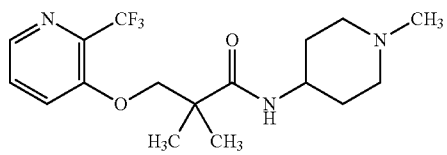

The title compound was prepared in a manner similar to EXAMPLE 38, using 3-fluoro-2-(trifluoromethyl)pyridine (0.060 g, 0.36 mmol, 1 eq) in place of 3-chloro-2-fluoropyridine. The product was purified by preparative HPLC (Method B) to give the title compound as a colorless film (28.0 mg, 21%). $^1$H NMR (500 MHz, CD$_3$OD) δ ppm 1.32 (s, 6H), 1.53-1.63 (m, 2H), 1.77-1.84 (m, 2H), 2.06-2.15 (m, 2H), 2.27 (s, 3H), 2.83-2.89 (m, 2H), 3.66-3.74 (m, 1H), 4.15 (s, 2H), 7.61 (dd, J=8.5, 4.6 Hz, 1H), 7.67-7.72 (m, 1H), 8.17-8.21 (m, 1H); ESI-MS [M+H]$^+$ calc'd for C$_{17}$H$_{24}$F$_3$N$_3$O$_2$, 360.18; found, 360.3.

Example 53: (R)-3-((3-cyclopropylpyridin-2-yl)oxy)-2,2-dimethyl-N-(1-methylpyrrolidin-3-yl)propanamide

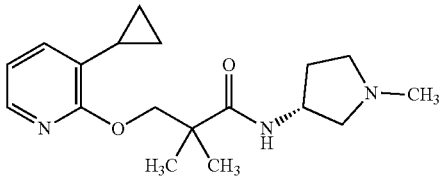 [SMILES: CN1CC[C@@H](NC(=O)C(C)(C)COc2ncccc2C2CC2)C1]

The title compound was prepared in a manner similar to EXAMPLE 38, using (R)-3-hydroxy-2,2-dimethyl-N-(1-methylpyrrolidin-3-yl)propanamide (0.088 g, 0.44 mmol) in place of 3-hydroxy-2,2-dimethyl-N-(1-methylpiperidin-4-yl)propanamide, and 3-cyclopropyl-2-fluoropyridine (0.060 g, 0.44 mmol) in place of 3-chloro-2-fluoropyridine. The product was purified by preparative HPLC (Method B) to give the title compound as a brown film (20.3 mg, 15%). $^1$H NMR (500 MHz, CD$_3$OD) δ ppm 0.62-0.70 (m, 2H), 0.92 (dd, J=8.5, 1.7 Hz, 2H), 1.31 (app d, J=1.5 Hz, 6H), 1.61-1.73 (m, 1H), 1.98-2.05 (m, 1H), 2.20-2.30 (m, 1H), 2.33 (s, 3H), 2.39-2.48 (m, 2H), 2.73 (s, 2H), 4.31 (s, 2H), 4.36-4.45 (m, 1H), 6.81-6.87 (m, 1H), 7.19-7.28 (m, 1H), 7.81-7.93 (m, 1H); ESI-MS [M+H]$^+$ calc'd for C$_{18}$H$_{27}$N$_3$O$_2$, 318.21; found, 318.26.

Example 54: 3-((3-ethoxypyridin-2-yl)oxy)-2,2-dimethyl-N-(1-methylpiperidin-4-yl)propanamide

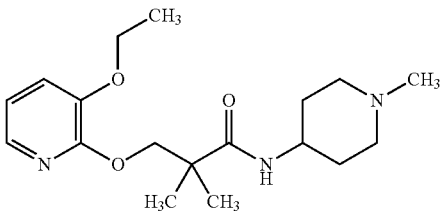 [SMILES: CCOc1cccnc1OCC(C)(C)C(=O)NC1CCN(C)CC1]

The title compound was prepared in a manner similar to EXAMPLE 38, using 3-ethoxy-2-fluoropyridine (0.060 g, 0.42 mmol, 1 eq) in place of 3-chloro-2-fluoropyridine. The product was purified by preparative HPLC (Method B) to give the title compound as a colorless foam (86.2 mg, 60%). $^1$H NMR (500 MHz, CD$_3$OD) δ ppm 1.28 (s, 6H), 1.35-1.43 (m, 3H), 1.50-1.61 (m, 2H), 1.74-1.86 (m, 2H), 2.02-2.14 (m, 2H), 2.25 (s, 3H), 2.76-2.85 (m, 2H), 3.61-3.76 (m, 1H), 4.06 (d, J=6.8 Hz, 2H), 4.30 (s, 2H), 6.82-6.90 (m, 1H), 7.15-7.24 (m, 1H), 7.60-7.66 (m, 1H); ESI-MS [M+H]$^+$ calc'd for C$_{18}$H$_{29}$N$_3$O$_3$, 336.22; found, 336.6.

Example 55: trans-N-(4-(4-chlorophenyl)-1-methylpyrrolidin-3-yl)-2,2-dimethyl-3-((3-methylpyridin-2-yl)oxy)propanamide

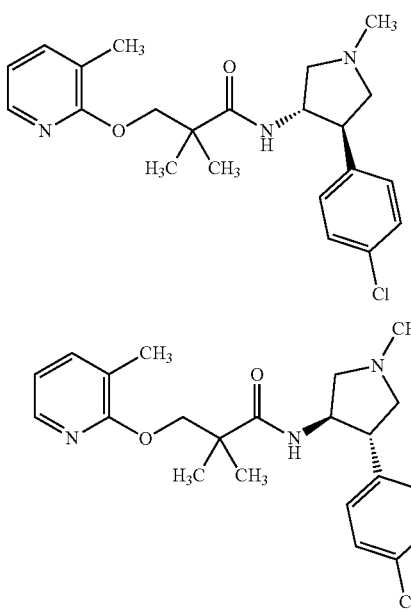

and

The title compound was prepared in a manner similar to EXAMPLE 38, using trans-N-(4-(4-chlorophenyl)-1-methylpyrrolidin-3-yl)-3-hydroxy-2,2-dimethylpropanamide (0.160 g, 0.360 mmol) in place of 3-hydroxy-2,2-dimethyl-N-(1-methylpiperidin-4-yl)propanamide, and 2-fluoro-3-methylpyridine (0.040 g, 0.36 mmol) in place of 3-chloro-2-fluoropyridine. The product was purified by preparative HPLC (Method B) to give the title compound as a brown solid (61.0 mg, 42%). $^1$H NMR (500 MHz, CD$_3$OD) δ ppm 1.27 (app d, J=3.91 Hz, 6H), 2.00 (s, 3H), 2.39 (s, 3H), 2.51-2.59 (m, 1H), 2.60-2.70 (m, 1H), 2.84-2.98 (m, 1H), 3.13-3.19 (m, 1H), 4.26 (d, J=6.4 Hz, 2H), 4.45-4.53 (m, 1H), 6.77-6.87 (m, 1H), 7.15-7.22 (m, 4H), 7.39-7.47 (m, 1H), 7.90 (dd, J=4.4, 2.0 Hz, 1H); ESI-MS [M+H]$^+$ calc'd for C$_{22}$H$_{28}$ClN$_3$O$_2$, 402.19; found, 402.4.

Example 56: trans-N-(4-(4-chlorophenyl)-1-methylpyrrolidin-3-yl)-2,2-dimethyl-3-((3-(trifluoromethyl)pyridin-2-yl)oxy)propanamide

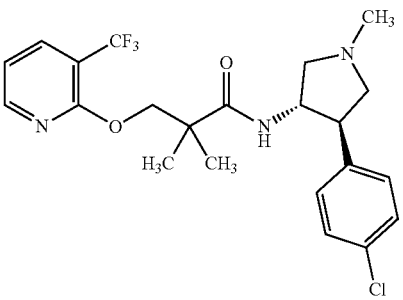

and

-continued

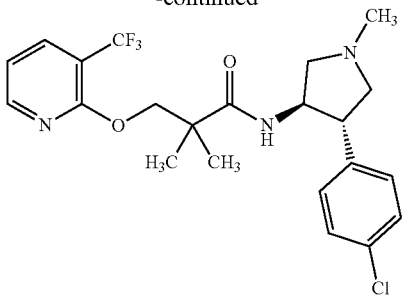

The title compound was prepared in a manner similar to EXAMPLE 38, using trans-N-(4-(4-chlorophenyl)-1-methylpyrrolidin-3-yl)-3-hydroxy-2,2-dimethylpropanamide (0.147 g, 0.331 mmol) in place of 3-hydroxy-2,2-dimethyl-N-(1-methylpiperidin-4-yl)propanamide, and 2-chloro-3-(trifluoromethyl)pyridine (0.060 g, 0.33 mmol) in place of 3-chloro-2-fluoropyridine. The product was purified by preparative HPLC (Method B) to give the title compound as a brown film (59.2 mg, 39%). $^1$H NMR (500 MHz, CD$_3$OD) δ ppm 1.27 (app d, J=12.7 Hz, 6H), 2.40 (s, 3H), 2.55 (s, 1H), 2.65-2.73 (m, 1H), 2.86-2.96 (m, 1H), 3.12-3.21 (m, 1H), 3.26-3.30 (m, 1H), 4.34-4.44 (m, 2H), 4.44-4.54 (m, 1H), 7.04-7.10 (m, 1H), 7.22 (d, J=1.5 Hz, 4H), 7.90-8.01 (m, 1H), 8.32 (dd, J=5.1, 1.2 Hz, 1H), 8.81-8.83 (m, 1H); ESI-MS [M+H]$^+$ calc'd for C$_{22}$H$_{25}$ClF$_3$N$_3$O$_2$, 456.16; found, 456.4.

Example 57: trans-2,2-dimethyl-N-(1-methyl-4-(6-(trifluoromethyl)pyridin-3-yl)pyrrolidin-3-yl)-3-((3-methylpyridin-2-yl)oxy)propanamide

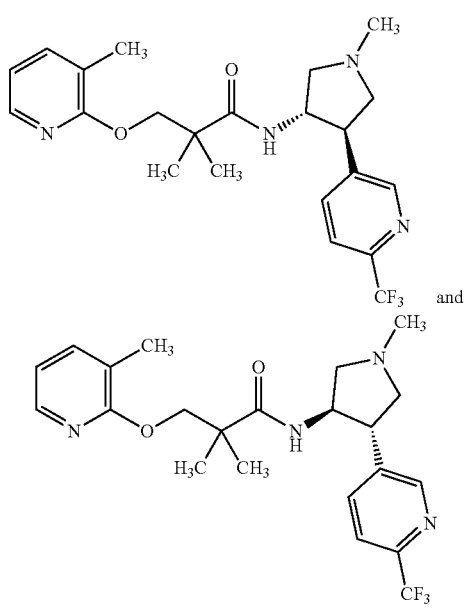

A TFA salt of the title compound was prepared in a manner similar to EXAMPLE 38, using trans-3-hydroxy-2,2-dimethyl-N-(1-methyl-4-(6-(trifluoromethyl)pyridin-3-yl)pyrrolidin-3-yl)propanamide (0.155 g, 0.450 mmol) in place of 3-hydroxy-2,2-dimethyl-N-(1-methylpiperidin-4-yl)propanamide, and 2-fluoro-3-methylpyridine (0.050 g, 0.45 mmol) in place of 3-chloro-2-fluoropyridine. The product was isolated as a colorless film (4.6 mg, 1.8%). $^1$H NMR (500 MHz, CD$_3$OD) δ ppm 1.29 (s, 6H), 1.96-2.07 (m, 3H), 3.05 (br s, 3H), 3.38-3.49 (m, 1H), 3.61-3.70 (m, 1H), 3.72-3.81 (m, 1H), 3.85-3.97 (m, 1H), 4.03-4.14 (m, 1H), 4.24-4.32 (m, 2H), 4.48-4.59 (m, 1H), 6.80-6.90 (m, 1H), 7.39-7.50 (m, 1H), 7.67-7.77 (m, 1H), 7.87-7.93 (m, 1H), 7.95-8.05 (m, 1H), 8.58-8.68 (m, 1H); ESI-MS [M+H]$^+$ calc'd for C$_{22}$H$_{27}$F$_3$N$_4$O$_2$, 437.21; found, 437.3.

Example 58: trans-3-((3-cyclopropylpyridin-2-yl)oxy)-2,2-dimethyl-N-(1-methyl-4-(6-(trifluoromethyl)pyridin-3-yl)pyrrolidin-3-yl)propanamide

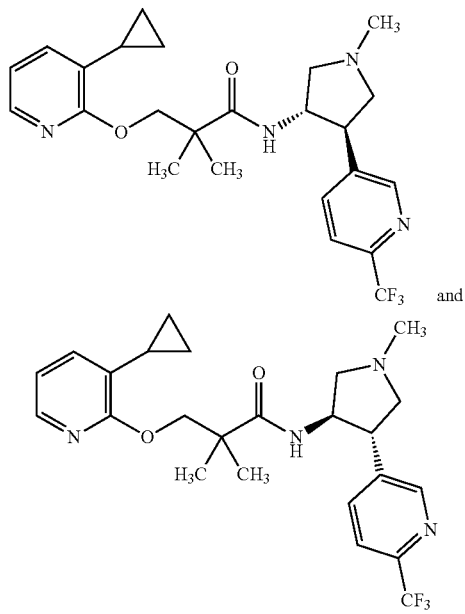

A TFA salt of the title compound was prepared in a manner similar to EXAMPLE 38, using trans-3-hydroxy-2,2-dimethyl-N-(1-methyl-4-(6-(trifluoromethyl)pyridin-3-yl)pyrrolidin-3-yl)propanamide (0.151 g, 0.450 mmol) in place of 3-hydroxy-2,2-dimethyl-N-(1-methylpiperidin-4-yl)propanamide, and 3-cyclopropyl-2-fluoropyridine (0.060 g, 0.44 mmol) in place of 3-chloro-2-fluoropyridine. The product was isolated as a colorless film (1.4 mg, 0.5%). $^1$H NMR (500 MHz, CD$_3$OD) δ ppm 0.52-0.68 (m, 2H), 0.77-0.85 (m, 2H), 0.88-0.93 (m, 1H), 0.97-1.02 (m, 1H), 1.32 (br s, 6H), 2.99-3.09 (m, 3H), 3.60-3.70 (m, 1H), 3.75-3.83 (m, 1H), 3.90-4.00 (m, 1H), 4.08-4.16 (m, 1H), 4.27-4.33 (m, 2H), 4.37-4.43 (m, 1H), 6.79-6.90 (m, 1H), 7.19-7.27 (m, 1H), 7.68-7.76 (m, 1H), 7.83-7.90 (m, 1H), 7.93-8.00 (m, 1H), 8.56-8.68 (m, 1H); ESI-MS [M+H]$^+$ calc'd for C$_{24}$H$_{29}$F$_3$N$_4$O$_2$, 463.22; found, 463.4.

Example 59: trans-2,2-dimethyl-N-(1-methyl-4-(6-(trifluoromethyl)pyridin-3-yl)pyrrolidin-3-yl)-3-((3-(trifluoromethyl)pyridin-2-yl)oxy)propanamide

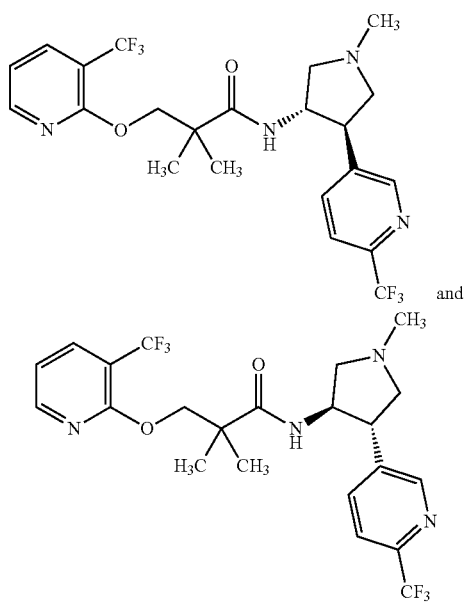

and

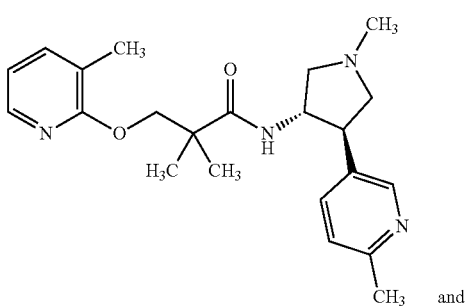

The title compound was prepared in a manner similar to EXAMPLE 38, using trans-3-hydroxy-2,2-dimethyl-N-(1-methyl-4-(6-(trifluoromethyl)pyridin-3-yl)pyrrolidin-3-yl)propanamide (0.152 g, 0.441 mmol) in place of 3-hydroxy-2,2-dimethyl-N-(1-methylpiperidin-4-yl)propanamide, and 2-chloro-3-(trifluoromethyl)pyridine (0.080 g, 0.44 mmol) in place of 3-chloro-2-fluoropyridine. The product was purified by preparative HPLC (Method B) to give the title compound as a colorless film (16.9 mg, 7.8%). $^1$H NMR (500 MHz, CD$_3$OD) δ ppm 0.71-0.80 (m, 1H), 0.95-1.00 (m, 1H), 1.28 (app d, J=5.9 Hz, 6H), 2.44 (s, 3H), 2.66-2.73 (m, 1H), 2.99-3.07 (m, 1H), 3.18-3.25 (m, 1H), 3.38-3.45 (m, 1H) 4.39 (d, J=2.0 Hz, 1H), 4.45-4.54 (m, 1H), 7.03-7.12 (m, 1H), 7.66-7.75 (m, 1H), 7.92-8.01 (m, 2H), 8.27-8.35 (m, 1H), 8.51-8.63 (m, 1H); ESI-MS [M+H]$^+$ calc'd for C$_{22}$H$_{24}$F$_6$N$_4$O$_2$, 491.18; found, 491.4.

Example 60: trans-2,2-dimethyl-N-(1-methyl-4-(6-methylpyridin-3-yl)pyrrolidin-3-yl)-3-((3-methylpyridin-2-yl)oxy)propanamide

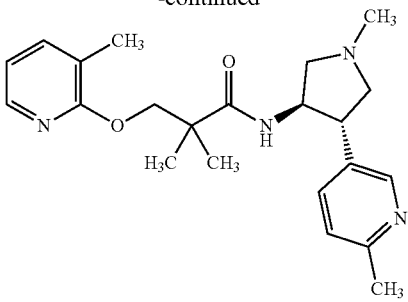

and

-continued

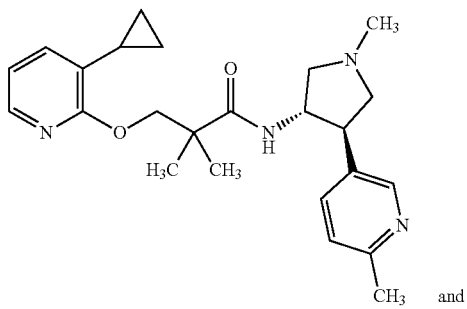

A TFA salt of the title compound was prepared in a manner similar to EXAMPLE 38, using trans-3-hydroxy-2,2-dimethyl-N-(1-methyl-4-(6-methylpyridin-3-yl)pyrrolidin-3-yl)propanamide (0.131 g, 0.450 mmol) in place of 3-hydroxy-2,2-dimethyl-N-(1-methylpiperidin-4-yl)propanamide, and 2-fluoro-3-methylpyridine (0.050 g, 0.45 mmol) in place of 3-chloro-2-fluoropyridine. The product was isolated as a colorless film (23.1 mg, 10%). $^1$H NMR (500 MHz, CD$_3$OD) δ ppm 1.29 (s, 6H), 2.02-2.13 (m, 3H), 2.65-2.76 (m, 3H), 3.05 (s, 3H), 3.44-3.82 (m, 2H), 4.01 (d, J=2.4 Hz, 3H), 4.26 (d, J=2.0 Hz, 2H), 4.75-4.84 (m, 1H), 6.83-6.90 (m, 1H), 7.46-7.52 (m, 1H), 7.76-7.84 (m, 1H), 7.88-7.95 (m, 1H), 8.37-8.45 (m, 1H), 8.69-8.73 (m, 1H); ESI-MS [M+H]$^+$ calc'd for C$_{22}$H$_{30}$N$_4$O$_2$, 383.24; found, 383.4.

Example 61: trans-3-((3-cyclopropylpyridin-2-yl)oxy)-2,2-dimethyl-N-(1-methyl-4-(6-methylpyridin-3-yl)pyrrolidin-3-yl)propanamide

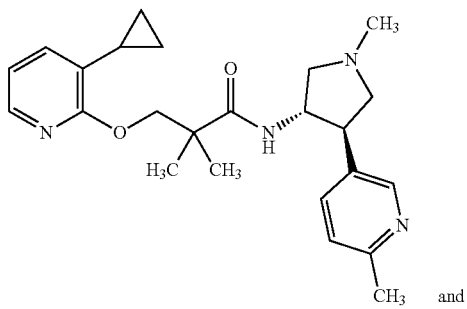

and

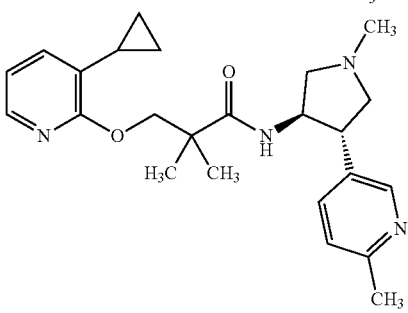

The title compound was prepared in a manner similar to EXAMPLE 38, using trans-3-hydroxy-2,2-dimethyl-N-(1-methyl-4-(6-methylpyridin-3-yl)pyrrolidin-3-yl)propanamide (0.124 g, 0.437 mmol) in place of 3-hydroxy-2,2-dimethyl-N-(1-methylpiperidin-4-yl)propanamide, and 3-cyclopropyl-2-fluoropyridine (0.060 g, 0.44 mmol) in place of 3-chloro-2-fluoropyridine. The product was purified by preparative HPLC (Method B) to give the title compound as a pale green film (35.2 mg, 20%). $^1$H NMR (500 MHz, CD$_3$OD) δ ppm 0.58 (d, J=5.4 Hz, 2H), 0.76-0.83 (m, 2H), 1.29 (s, 6H), 1.82-1.93 (m, 1H), 2.40 (s, 3H), 2.46 (s, 3H), 2.54-2.59 (m, 1H), 2.62-2.69 (m, 1H), 2.94 (s, 1H), 3.11-3.19 (m, 1H), 3.25-3.29 (m, 1H), 4.29 (s, 2H), 4.45-4.53 (m, 1H), 6.80-6.86 (m, 1H), 7.14-7.19 (m, 1H), 7.20-7.23 (m, 1H), 7.61-7.69 (m, 1H), 7.83-7.91 (m, 1H), 8.21-8.27 (m, 1H); ESI-MS [M+H]$^+$ calc'd for C$_{24}$H$_{32}$N$_4$O$_2$, 409.25; found, 409.4.

Example 62: trans-2,2-dimethyl-N-(1-methyl-4-(6-methylpyridin-3-yl)pyrrolidin-3-yl)-3-((3-(trifluoromethyl)pyridin-2-yl)oxy)propanamide

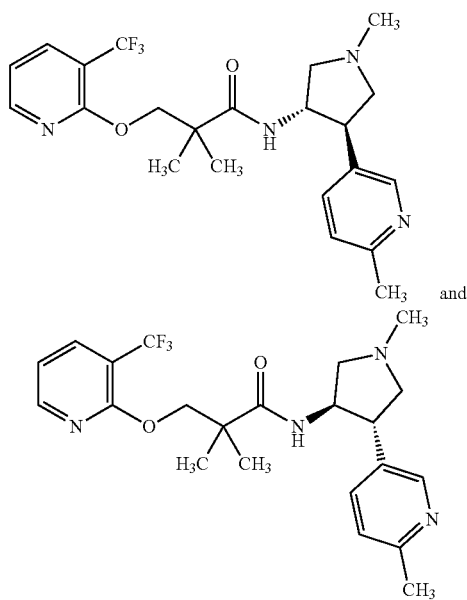

A TFA salt of the title compound was prepared in a manner similar to EXAMPLE 38, using trans-3-hydroxy-2,2-dimethyl-N-(1-methyl-4-(6-methylpyridin-3-yl)pyrrolidin-3-yl)propanamide (0.127 g, 0.424 mmol) in place of 3-hydroxy-2,2-dimethyl-N-(1-methylpiperidin-4-yl)propanamide, and 2-fluoro-3-(trifluoromethyl)pyridine (0.070 g, 0.42 mmol) in place of 3-chloro-2-fluoropyridine. The product was isolated as a colorless film (2.2 mg, 0.9%). $^1$H NMR (500 MHz, CD$_3$OD) δ ppm 1.28 (app d, J=11.7 Hz, 6H), 2.72 (s, 3H), 3.05 (s, 3H), 3.09-3.16 (m, 1H), 3.45 (d, J=1.5 Hz, 1H), 3.66-3.79 (m, 1H), 3.87-3.97 (m, 1H), 3.99-4.12 (m, 1H), 4.39 (s, 2H), 4.59-4.71 (m, 1H), 7.04-7.13 (m, 1H), 7.75-7.82 (m, 1H), 7.91-8.01 (m, 1H), 8.29-8.37 (m, 2H), 8.62-8.68 (m, 1H); ESI-MS [M+H]$^+$ calc'd for C$_{22}$H$_{27}$F$_3$N$_4$O$_2$, 437.21; found, 437.4.

Example 63: N-(1-methylpiperidin-4-yl)-1-(((3-methylpyridin-2-yl)oxy)methyl)cyclopropane-1-carboxamide

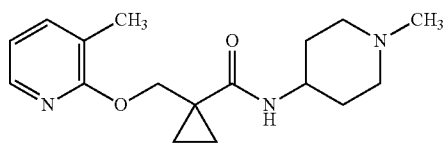 [SMILES: Cc1cccnc1OCC1(C(=O)NC2CCN(C)CC2)CC1]

Sodium hydride (60 wt %, 0.067 g, 1.7 mmol) was added to a solution of 2-fluoro-3-methylpyridine (0.124 g, 1.11 mmol) and 1-(hydroxymethyl)-N-(1-methylpiperidin-4-yl)cyclopropane-1-carboxamide (0.118 g, 0.145 mmol) in DMF (2.78 mL). The reaction mixture was stirred at room temperature for 1 hour and then diluted with methanol, filtered through a hydrophilic PTFE 0.45 m filter (Millipore® Millex-LCR), and purified by preparative HPLC (Method B) to give the title compound as a clear oil (0.044 g, 26%). $^1$H NMR (500 MHz, CD$_3$OD) δ 0.84-0.97 (m, 2H), 1.15-1.28 (m, 2H), 1.45-1.63 (m, 2H), 1.78-1.90 (m, 2H), 2.06-2.14 (m, 2H), 2.20 (s, 3H), 2.25 (s, 3H), 2.81 (d, J=11.7 Hz, 2H), 3.72 (tt, J=11.0, 4.4 Hz, 1H), 4.50 (s, 2H), 6.88 (dd, J=7.3, 4.9 Hz, 1H), 7.47-7.55 (m, 1H), 7.93-7.99 (m, 1H); ESI-MS [M+H]$^+$ calc'd for C$_{17}$H$_{25}$N$_3$O$_2$, 304.20; found, 304.20.

Example 64: 2,2-dimethyl-N-(1-methylpiperidin-4-yl)-3-(2-(trifluoromethyl)phenoxy)propanamide

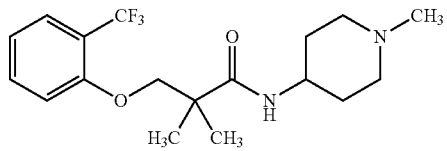

A solution of 2,2-dimethyl-3-(2-(trifluoromethyl)phenoxy)propanoic acid (65.6 mg, 0.250 mmol) in DMF (1.25 mL) was treated with triethylamine (34.8 μL, 0.250 mmol) and HATU (95.0 mg, 0.250 mmol). After stirring for 5 minutes, 1-methylpiperidin-4-amine (28.5 mg, 0.250 mmol) was added, and the reaction mixture was allowed to stir at room temperature for 1 hour. The reaction mixture was filtered through a hydrophilic PTFE 0.45 m Millipore® filter which was rinsed with MeOH. The filtrate was purified by preparative HPLC (Method A) eluting with a slow ramp gradient of 10-50% ACN in water. The product-containing fractions were evaporated, then taken up in MeOH and filtered through an Agilent PL-HCO$_3$ 500 mg basic cartridge. The filtrate was evaporated and dried under vacuum to give the title compound as a colorless oil (25.5 mg, 28%). $^1$H NMR (500 MHz, CD$_3$OD) δ ppm 1.32 (s, 6H), 1.59 (qd, J=12.2, 3.9 Hz, 2H), 1.78-1.88 (m, 2H), 2.12 (td, J=12.2, 2.4 Hz, 2H), 2.28 (s, 3H), 2.87 (d, J=12.2 Hz, 2H), 3.72 (tt, J=11.3, 4.3 Hz, 1H), 4.09 (s, 2H), 7.06 (t, J=7.6 Hz, 1H), 7.17 (d, J=8.8 Hz, 1H), 7.53-7.60 (m, 2H); ESI-MS [M+H]$^+$ calc'd for C$_{18}$H$_{25}$F$_3$N$_2$O$_2$, 359.20; found, 359.7.

Example 65: (R)-2,2-dimethyl-N-(1-methylpyrrolidin-3-yl)-3-(2-(trifluoromethyl)phenoxy)propanamide

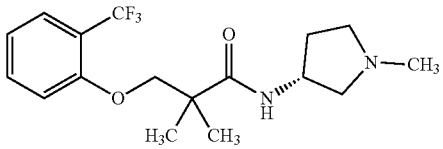 [SMILES: CN1CC[C@@H](NC(=O)C(C)(C)COc2ccccc2C(F)(F)F)C1]

The title compound was prepared in a manner similar to EXAMPLE 64, using (R)-1-methylpyrrolidin-3-amine (25.0 mg, 0.250 mmol, 1 eq) in place of 1-methylpiperidin-4-amine. The product was isolated as a colorless oil (25.6 mg, 30%). $^1$H NMR (500 MHz, DMSO-$d_6$) δ ppm 1.20 (d, J=1.0 Hz, 6H), 1.56-1.65 (m, 1H), 1.99-2.09 (m, 1H), 2.20 (s, 3H), 2.26 (dd, J=9.3, 4.9 Hz, 1H), 2.33 (td, J=8.2, 6.6 Hz, 1H), 2.52-2.55 (m, 1H), 2.57 (dd, J=9.3, 7.3 Hz, 1H), 4.07 (s, 2H), 4.14-4.25 (m, 1H), 7.08 (t, J=7.6 Hz, 1H), 7.23 (d, J=8.3 Hz, 1H), 7.45 (d, J=7.3 Hz, 1H), 7.57-7.65 (m, 2H); ESI-MS [M+H]$^+$ calc'd for $C_{17}H_{23}F_3N_2O_2$, 345.18; found, 345.6.

Example 66: 3-(2-chlorophenoxy)-2,2-dimethyl-N-(1-methylpiperidin-4-yl)propanamide

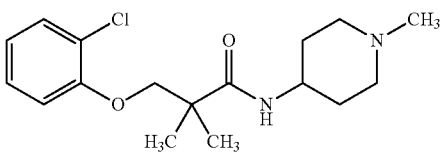 [SMILES: CN1CCC(NC(=O)C(C)(C)COc2ccccc2Cl)CC1]

A 250 mL round-bottomed flask was charged with 3-(2-chlorophenoxy)-2,2-dimethylpropanoic acid (6.50 g, 28.4 mmol), absolute EtOH (65 mL), and 1-methylpiperidin-4-amine (3.25 g, 28.4 mmol). The resulting solution was chilled to 8° C. and 4-(4,6-dimethyl-1,3,5-triazin-2-yl)-4-methylmorpholin-4-ium chloride hydrate (9.22 g, 31.3 mmol) was added. The reaction mixture was allowed to warm to room temperature and was stirred overnight. Following reaction, the mixture was filtered to remove solids and rinsed with MTBE. The filtrate was concentrated under reduced pressure to give an oil (22.5 g). The oil was dissolved in MTBE (65 mL) and washed twice with 1M aq NaOH (30 mL, then 50 mL) and then with water (50 mL). The organic phase was concentrated and dried under vacuum to give the title compound (free form) as an oil (9.23 g, assumed quantitative). A portion of the free form (2.00 g, 5.85 mmol) was dissolved in EtOH (10 mL) and transferred to a 100 mL round-bottomed flask fitted with a stir bar. A solution of citric acid (1.124 g, 5.85 mmol) in EtOH (6 mL) was added at room temperature, rinsing with EtOH (4 mL). The reaction mixture was stirred at room temperature for 1.75 hours. A resulting precipitate was collected by filtration, washed with EtOH, and suction dried. The product was dried further at 40° C. in a vacuum oven for 5 hours to give a citrate salt of the title compound as a white solid (2.09 g, 69.2%). $^1$H NMR (400 MHz, DMSO-$d_6$) δ ppm 1.14-1.33 (m, 6H), 1.59-1.75 (m, 2H), 1.76-1.89 (m, 2H), 2.46-2.72 (m, 8H), 2.87 (td, J=12.1, 2.2 Hz, 2H), 3.25 (br d, J=12.4 Hz, 2H), 3.59-3.64 (m, 1H), 4.02 (s, 2H), 6.88-6.99 (m, 1H), 7.12 (dd, J=8.2, 1.0 Hz, 1H), 7.20-7.34 (m, 1H), 7.35-7.53 (m, 2H); ESI-MS [M+H]$^+$ calc'd for $C_{17}H_{25}ClN_2O_2$, 325.17; found, 325.10.

Example 67: 3-(2-bromophenoxy)-2,2-dimethyl-N-(1-methylpiperidin-4-yl)propanamide

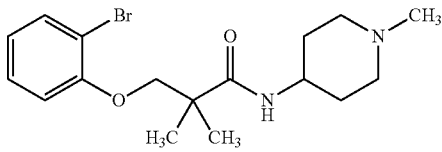

A solution of 3-(2-bromophenoxy)-2,2-dimethylpropanoic acid (328 mg, 1.2 mmol) in DMF (6 mL) was treated with Et$_3$N (167 μL, 1.20 mmol) and HATU (456 mg, 1.20 mmol). After stirring for 5 minutes, 1-methylpiperidin-4-amine (137 mg, 1.20 mmol) was added. The reaction mixture was stirred at room temperature for 2 hours, then diluted with water and saturated aq NaCl, and extracted with DCM. The organic phase was dried over Na$_2$SO$_4$, filtered, and concentrated under reduced pressure. The residue was dry loaded on silica and purified by automated flash silica column chromatography (ISCO® 40 g column) eluting with a 0-20% gradient of MeOH in DCM. The product-containing fractions were evaporated to give the title compound as a colorless oil (327.3 mg, 73.9%). (327.3 mg, 74%). $^1$H NMR (500 MHz, CD$_3$OD) δ ppm 1.34 (s, 6H), 1.69-1.84 (m, 2H), 1.97-2.07 (m, 2H), 2.64 (s, 3H), 2.76 (t, J=11.7 Hz, 2H), 3.25 (d, J=12.2 Hz, 2H), 3.89 (tt, J=11.2, 4.2 Hz, 1H), 4.04 (s, 2H), 6.83-6.89 (m, 1H), 7.03 (dd, J=8.3, 1.5 Hz, 1H), 7.27-7.33 (m, 1H), 7.51 (dd, J=8.0, 1.7 Hz, 1H); ESI-MS [M+H]$^+$ calc'd for $C_{17}H_{25}BrN_2O_2$, 369.12; found, 369.10.

Example 68: (R)-3-(2-chlorophenoxy)-2,2-dimethyl-N-(1-methylpyrrolidin-3-yl)propanamide

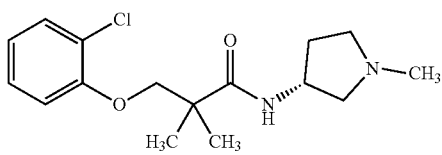

A solution of 3-(2-chlorophenoxy)-2,2-dimethylpropanoic acid (57.2 mg, 0.25 mmol) in DMF (1.25 mL) was treated with Et$_3$N (34.8 μL, 0.250 mmol) and HATU (95 mg, 0.250 mmol). After stirring for 5 minutes, (R)-1-methylpyrrolidin-3-amine (25.04 mg, 0.250 mmol) was added. The reaction mixture was stirred at room temperature for 1 hour and then filtered through a hydrophilic PTFE 0.45 m Millipore® filter, rinsing with MeOH. The filtrate was purified by preparative HPLC (Method A and then Method B). The product-containing fractions were evaporated and dried under vacuum to give the title compound as a colorless oil (24.4 mg, 31.4%). $^1$H NMR (500 MHz, CD$_3$OD) δ ppm 1.33 (s, 6H), 1.69-1.79 (m, 1H), 2.24-2.33 (m, 1H), 2.36 (s, 3H), 2.40-2.49 (m, 1H), 2.53 (dd, J=9.8, 4.4 Hz, 1H), 2.70-2.81 (m, 2H), 4.03 (s, 2H), 4.42 (ddt, J=9.0, 7.2, 4.6, 4.6 Hz, 1H), 6.90-6.95 (m, 1H), 7.06 (dd, J=8.3, 1.0 Hz, 1H), 7.26 (td, J=7.8, 1.5 Hz, 1H), 7.35 (dd, J=8.0, 1.7 Hz, 1H); ESI-MS [M+H]⁺ calc'd for $C_{16}H_{23}ClN_2O_2$, 311.15; found, 311.10.

Example 69: (R)-3-(2-bromophenoxy)-2,2-dimethyl-N-(1-methylpyrrolidin-3-yl)propanamide

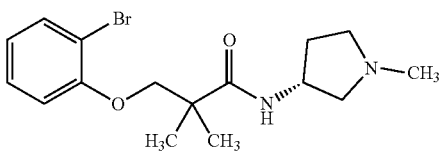 [SMILES: CN1CC[C@@H](NC(=O)C(C)(C)COc2ccccc2Cl)C1]

A solution of 3-(2-bromophenoxy)-2,2-dimethylpropanoic acid (410 mg, 1.501 mmol) in DMF (7.506 mL) was treated with Et₃N (152 mg, 1.50 mmol) and HATU (571 mg, 1.50 mmol). After stirring for 10 minutes, (R)-1-methylpyrrolidin-3-amine (150 mg, 1.50 mmol) was added. The reaction mixture was stirred at room temperature overnight, then diluted with water and extracted with DCM. The organic phase was dried over Na₂SO₄, filtered, and concentrated under reduced pressure. The residue was purified by automated flash silica column chromatography (ISCO® 40 g column) eluting with a 0-20% gradient of MeOH in DCM. The product-containing fractions were evaporated to give the title compound as an orange solid (458.4 mg, 86%). ¹H NMR (500 MHz, DMSO-d₆) δ ppm 1.23 (s, 6H), 1.58-1.68 (m, 1H), 2.01-2.11 (m, 1H), 2.21 (s, 3H), 2.28-2.36 (m, 2H), 2.53-2.62 (m, 2H), 4.01 (s, 2H), 4.21 (dtt, J=9.5, 7.2, 7.2, 4.9, 4.9 Hz, 1H), 6.89 (td, J=7.6, 1.5 Hz, 1H), 7.09 (dd, J=8.3, 1.0 Hz, 1H), 7.34 (td, J=7.8, 1.5 Hz, 1H), 7.45 (d, J=7.3 Hz, 1H), 7.56 (dd, J=8.0, 1.7 Hz, 1H); ESI-MS [M+H]⁺ calc'd for $C_{16}H_{23}BrN_2O_2$, 355.10; found, 355.10.

Example 70: 3-(2-cyclopropylphenoxy)-2,2-dimethyl-N-(1-methylpiperidin-4-yl)propanamide

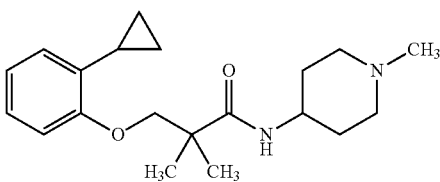 [SMILES: CN1CCC(NC(=O)C(C)(C)COc2ccccc2C2CC2)CC1]

A 5 mL microwave vial equipped with a stir bar was charged with 3-(2-bromophenoxy)-2,2-dimethyl-N-(1-methylpiperidin-4-yl)propanamide (111 mg, 0.300 mmol), potassium cyclopropyltrifluoroborate (53.3 mg, 0.360 mmol), and potassium phosphate (159 mg, 0.750 mmol) in toluene (1.25 mL) and water (0.25 mL). The mixture was degassed under vacuum and refilled with nitrogen three times. RuPhos Pd G3 (25.09 mg, 0.030 mmol) was added and the mixture was degassed under vacuum and refilled with nitrogen two more times before the vial was sealed. The reaction mixture was irradiated at 120° C. for 2 hours in a Biotage® microwave reactor and then filtered through a hydrophilic PTFE 0.45 μm Millipore® filter which was rinsed with MeOH. The filtrate was concentrated under reduced pressure. The residue was taken up in MeOH and purified by preparative HPLC (Method A) eluting with a slow ramp gradient of 10-50% ACN in water. The product-containing fractions were evaporated and then taken up in MeOH and filtered through an Agilent PL-HCO₃ 500 mg basic cartridge. The filtrate was evaporated and dried under vacuum to give the title compound as a colorless oil (32.8 mg, 33%). ¹H NMR (500 MHz, CD₃OD) δ ppm 0.55-0.64 (m, 2H), 0.83-0.92 (m, 2H), 1.32 (s, 6H), 1.55 (qd, J=12.2, 3.9 Hz, 2H), 1.76-1.86 (m, 2H), 2.03-2.16 (m, 3H), 2.25 (s, 3H), 2.82 (d, J=11.7 Hz, 2H), 3.72 (tt, J=11.4, 4.0 Hz, 1H), 3.98 (s, 2H), 6.80-6.84 (m, 2H), 6.86 (d, J=7.8 Hz, 1H), 7.04-7.11 (m, 1H); ESI-MS [M+H]⁺ calc'd for $C_{20}H_{30}N_2O_2$, 331.24; found, 331.20.

Example 71: (R)-3-(2-cyclopropylphenoxy)-2,2,-dimethyl-N-(1-methylpyrrolidin-3-yl)propanamide

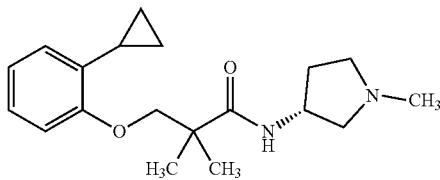

The title compound was prepared in a manner similar to EXAMPLE 70, using (R)-3-(2-bromophenoxy)-2,2-dimethyl-N-(1-methylpyrrolidin-3-yl)propanamide (107 mg, 0.300 mmol, 1 eq) in place of 3-(2-bromophenoxy)-2,2-dimethyl-N-(1-methylpiperidin-4-yl)propanamide. The product was isolated as a colorless oil (15.3 mg, 16%). ¹H NMR (500 MHz, DMSO-d₆) δ ppm 0.56-0.63 (m, 2H), 0.81-0.89 (m, 2H), 1.22 (s, 6H), 1.55-1.66 (m, 1H), 1.98-2.13 (m, 2H), 2.23-2.35 (m, 2H), 2.57 (dd, J=9.3, 7.3 Hz, 1H), 3.94 (s, 2H), 4.21 (dtt, J=9.5, 7.0, 7.0, 5.1, 5.1 Hz, 1H), 6.78-6.85 (m, 2H), 6.88 (d, J=7.8 Hz, 1H), 7.09 (ddd, J=8.3, 6.1, 2.7 Hz, 1H), 7.47 (d, J=7.3 Hz, 1H); ESI-MS [M+H]⁺ calc'd for $C_{19}H_{28}N_2O_2$, 317.22; found, 317.3.

Example 72: 3-(2-ethylphenoxy)-2,2-dimethyl-N-(1-methylpiperidin-4-yl)propanamide

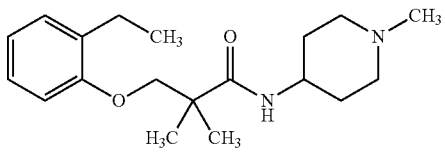 [SMILES: CCc1ccccc1OCC(C)(C)C(=O)NC1CCN(C)CC1]

In a 20 mL vial, 3-(2-ethylphenoxy)-2,2-dimethylpropanoic acid (100 mg, 0.450 mmol) and 2-chloro-1-methylpyridin-1-ium iodide (345 mg, 1.35 mmol) were combined in DMF (2 mL) to form an activated intermediate. After 30 minutes, 1-methylpiperidin-4-amine (51.4 mg, 0.450 mmol) and triethylamine (314 μL, 2.25 mmol) were added. The reaction mixture was stirred overnight at room temperature and then purified by preparative HPLC (Method C) eluting with a gradient of 25-50% ACN in water to give the title compound as a colorless oil (66 mg, 46%). ¹H NMR (400 MHz, CD₃OD) δ ppm 1.20 (t, J=7.6 Hz, 3H), 1.32-1.42 (m, 6H), 1.79-2.02 (m, 2H), 2.12 (d, J=14.2 Hz, 2H), 2.65 (q, J=7.5 Hz, 2H), 2.86-2.92 (m, 3H), 3.14 (td, J=13.1, 2.4 Hz, 2H), 3.53-3.63 (m, 2H), 3.94-4.11 (m, 3H), 6.83-6.99 (m, 2H), 7.09-7.22 (m, 2H); ESI-MS [M+H]⁺ calc'd for $C_{19}H_{30}N_2O_2$, 319.24; found, 319.5.

Example 73: 3-(4-cyano-2-(trifluoromethyl)phenoxy)-2,2-dimethyl-N-(1-methylpiperidin-4-yl)propanamide

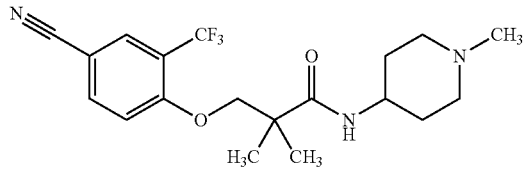 [SMILES: CN1CCC(NC(=O)C(C)(C)COc2ccc(C#N)cc2C(F)(F)F)CC1]

The title compound was prepared in a manner similar to EXAMPLE 72, using 3-(4-cyano-2-(trifluoromethyl)phenoxy)-2,2-dimethylpropanoic acid (200 mg, 0.696 mmol, 1 eq) in place of 3-(2-ethylphenoxy)-2,2-dimethylpropanoic acid. The product was isolated as a white solid (70 mg, 26%). $^1$H NMR (400 MHz, CD$_3$OD) δ ppm 1.33-1.41 (m, 6H), 1.81-2.04 (m, 2H), 2.11 (d, J=13.9 Hz, 2H), 2.90 (s, 3H), 3.14 (td, J=13.1, 2.6 Hz, 2H), 3.47-3.63 (m, 2H), 3.94-4.12 (m, 1H), 4.22-4.29 (m, 2H), 7.41 (d, J=6.7 Hz, 1H), 7.97-8.04 (m, 2H); ESI-MS [M+H]$^+$ calc'd for C$_{19}$H$_{24}$F$_3$N$_3$O$_2$, 384.19; found, 384.5.

Example 74: 2,2-dimethyl-N-(1-methylpiperidin-4-yl)-3-phenoxypropanamide

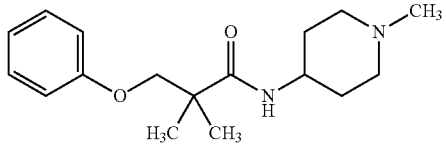 [SMILES: CN1CCC(NC(=O)C(C)(C)COc2ccccc2)CC1]

The title compound was prepared in a manner similar to EXAMPLE 72, using 2,2-dimethyl-3-phenoxypropanoic acid (114 mg, 0.587 mmol, 1 eq) in place of 3-(2-ethylphenoxy)-2,2-dimethylpropanoic acid. The product was isolated as a yellow-orange oil (106 mg, 62%). $^1$H NMR (400 MHz, CD$_3$OD) δ ppm 1.29-1.39 (m, 6H), 1.79-2.01 (m, 2H), 2.11 (d, J=12.9 Hz, 2H), 2.84-2.92 (m, 3H), 3.13 (t, J=12.6 Hz, 2H), 3.36 (br s, 1H), 3.57 (d, J=12.6 Hz, 2H), 3.92-4.10 (m, 3H), 6.89-7.01 (m, 3H), 7.29 (t, J=7.8 Hz, 2H); ESI-MS [M+H]$^+$ calc'd for C$_{17}$H$_{26}$N$_2$O$_2$ 291.21; found, 291.4.

Example 75: 3-(3-cyano-2-methylphenoxy)-2,2-dimethyl-N-(1-methylpiperidin-4-yl)propanamide

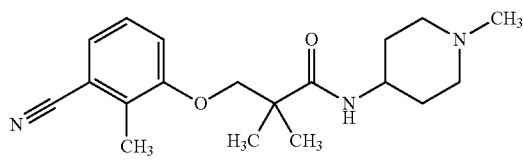 [SMILES: Cc1c(C#N)cccc1OCC(C)(C)C(=O)NC1CCN(C)CC1]

Step A: methyl 3-(3-cyano-2-methylphenoxy)-2,2-dimethylpropanoate

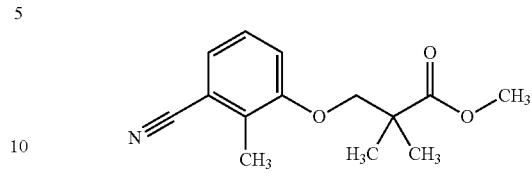

A mixture of methyl 2,2-dimethyl-3-(tosyloxy)propanoate (0.300 g, 1.05 mmol), 3-hydroxy-2-methylbenzonitrile (0.209 g, 1.57 mmol) and Cs$_2$CO$_3$ (0.512 g, 1.57 mmol) in DMF (4 mL) was heated at 100° C. overnight. The reaction mixture was then cooled, diluted with water (20 mL) and extracted with EtOAc. The combined organics were dried over MgSO$_4$, filtered, and concentrated under reduced pressure. The residue was purified by automated flash silica column chromatography, eluting with a gradient of 0-70% EtOAc in heptanes to give the title compound as a clear oil (0.15 g, 58%). ESI-MS [M+H]$^+$ calc'd for C$_{14}$H$_{17}$NO$_3$, 248.13; found, 248.2.

Step B: 3-(3-cyano-2-methylphenoxy)-2,2-dimethylpropanoic Acid

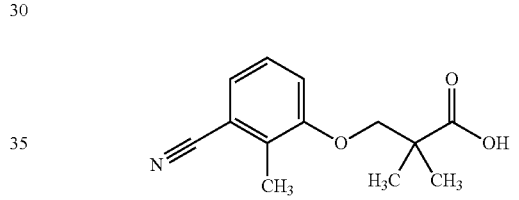

To a solution of methyl 3-(3-cyano-2-methylphenoxy)-2,2-dimethylpropanoate (0.15 g, 0.61 mmol) in methanol (5 mL) was added 2 M aqueous LiOH (0.455 mL, 0.910 mmol). The reaction mixture was allowed to stir overnight at 60° C., and was then concentrated, diluted with water, and extracted with EtOAc. The aqueous layer was acidified by the addition of 1 M aq HCl and then extracted with EtOAc. The extracts from the acidic aqueous layer were combined, dried over MgSO$_4$, filtered, and concentrated under reduced pressure to give the title compound as a yellow oil (0.123 g, 87%). ESI-MS [M+H]$^+$ calc'd for C$_{13}$H$_{15}$NO$_3$, 234.12; found, 234.2.

Step C: 3-(3-cyano-2-methylphenoxy)-2,2-dimethyl-N-(1-methylpiperidin-4-yl)propanamide To a solution of 3-(3-cyano-2-methylphenoxy)-2,2-dimethylpropanoic acid (0.123 g, 0.527 mmol) in DCM (5 mL) were added triethylamine (0.220 mL, 1.58 mmol) and 2-chloro-1-methylpyridin-1-ium iodide (0.269 g, 1.06 mmol). The reaction mixture was allowed to stir at room temperature for 20 minutes. Next 1-methylpiperidin-4-amine (0.072 mL, 0.63 mmol) was added and the reaction mixture was allowed to stir overnight at room temperature. Water (10 mL) was added. The organic and aqueous layers were separated and the aqueous layer extracted with DCM. The organic layers were combined, dried over MgSO$_4$, filtered, and concentrated under reduced pressure. The residue was taken up in MeOH and purified by preparative HPLC (Method B) to give the title compound as a white solid (0.098 g, 56%). ¹H NMR (400 MHz, CD₃CN) δ ppm 1.28 (s, 6H), 1.43-1.57 (m, 2H), 1.71-1.80 (m, 2H), 1.97 (br d, J=2.5 Hz, 2H), 2.15-2.21 (m, 3H), 2.37-2.39 (m, 3H), 2.73 (br d, J=11.9 Hz, 2H), 3.59-3.70 (m, 1H), 3.94-4.05 (m, 2H), 6.15-6.36 (m, 1H), 7.18 (dd, J=8.1, 1.0 Hz, 1H), 7.24-7.27 (m, 1H), 7.28-7.33 (m, 1H); ESI-MS [M+H]⁺ calc'd for C₁₉H₂₇N₃O₂, 330.22; found, 330.6.

Example 76: 2,2-dimethyl-N-(1-methylpiperidin-4-yl)-3-(o-tolyloxy)propanamide

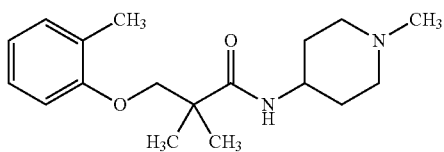

The title compound was prepared in a manner similar to EXAMPLE 75, using 2-methyl phenol in place of 3-hydroxy-2-methylbenzonitrile (STEP A). The final product was isolated as a white solid (0.035 g). ¹H NMR (400 MHz, CDCl₃) δ ppm 1.22-1.32 (m, 6H), 1.39-1.59 (m, 2H), 1.73-1.81 (m, 2H), 1.98-2.06 (m, 2H), 2.19 (s, 3H), 2.21 (s, 3H), 2.72 (br d, J=11.9 Hz, 2H), 3.59-3.71 (m, 1H), 3.95 (s, 2H), 6.29 (br s, 1H), 6.81-6.95 (m, 2H), 7.11-7.20 (m, 2H); ESI-MS [M+H]⁺ calc'd for C₁₉H₂₇N₃O₂, 305.23; found, 306.5.

Example 77: 3-(2-cyano-6-methylphenoxy)-2,2-dimethyl-N-(1-methylpiperidin-4-yl)propanamide

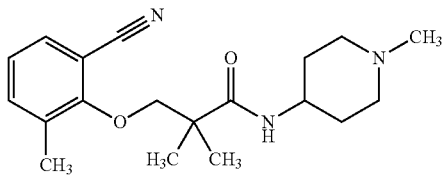 [SMILES: Cc1cccc(C#N)c1OCC(C)(C)C(=O)NC1CCN(C)CC1]

The title compound was prepared in a manner similar to EXAMPLE 75, using 2-hydroxy-3-methylbenzonitrile in place of 3-hydroxy-2-methylbenzonitrile (STEP A). The final product was isolated as a yellow oil (0.072 g). ¹H NMR (400 MHz, CD₃CN) δ ppm 1.21-1.36 (m, 6H), 1.44-1.61 (m, 2H), 1.73-1.84 (m, 2H), 1.99-2.04 (m, 1H), 2.16-2.20 (m, 3H), 2.26-2.30 (m, 3H), 2.42 (br s, 2H), 2.74 (br d, J=11.9 Hz, 2H), 3.60-3.71 (m, 1H), 4.01-4.11 (m, 2H), 6.25-6.41 (m, 1H), 7.15 (t, J=7.7 Hz, 1H), 7.45-7.53 (m, 2H); ESI-MS [M+H]⁺ calc'd for C₁₉H₂₇N₃O₂, 330.21; found, 331.5.

Example 78: 3-(2-ethoxyphenoxy)-2,2-dimethyl-N-(1-methylpiperidin-4-yl)propanamide

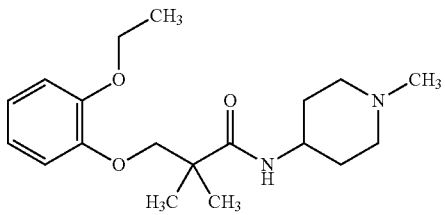 [SMILES: CCOc1ccccc1OCC(C)(C)C(=O)NC1CCN(C)CC1]

The title compound was prepared in a similar manner to EXAMPLE 75, using 2-ethoxyphenol in place of 3-hydroxy-2-methylbenzonitrile (STEP A). The final product was isolated as a yellow oil (0.038 g). ¹H NMR (400 MHz, DMSO-d₆) δ ppm 1.20 (s, 6H), 1.31 (t, J=7.0 Hz, 1H), 1.42-1.54 (m, 2H), 1.60-1.73 (m, 2H), 1.78-1.99 (m, 2H), 2.02-2.18 (m, 3H), 2.70 (br d, J=11.9 Hz, 2H), 3.46-3.64 (m, 1H), 3.92 (s, 2H), 4.00 (q, J=7.1 Hz, 2H), 6.82-6.92 (m, 2H), 6.92-7.02 (m, 2H), 7.24 (d, J=7.8 Hz, 1H); ESI-MS [M+H]⁺ calc'd for C₁₉H₃₀N₂O₃, 335.24; found, 335.4.

Example 79: 3-((2,3-dihydro-1H-inden-4-yl)oxy)-2,2-dimethyl-N-(1-methylpiperidin-4-yl)propanamide

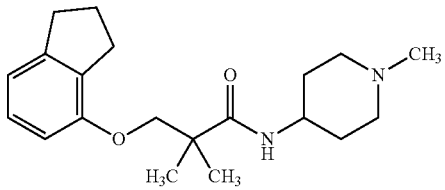 [SMILES: CN1CCC(NC(=O)C(C)(C)COc2cccc3c2CCC3)CC1]

The title compound was prepared in a similar manner to EXAMPLE 75, using 2,3-dihydro-1H-inden-4-ol in place of 3-hydroxy-2-methylbenzonitrile (STEP A). The final product was isolated as a yellow oil (0.012 g). ¹H NMR (400 MHz, DMSO-d₆) δ ppm 1.12-1.30 (m, 6H), 1.49 (qd, J=11.9, 3.7 Hz, 2H), 1.57-1.67 (m, 2H), 1.89-2.06 (m, 4H), 2.16 (s, 3H), 2.68-2.79 (m, 4H), 2.85 (t, J=7.4 Hz, 2H), 3.47-3.66 (m, 1H), 3.86-3.98 (m, 2H), 6.70 (d, J=7.7 Hz, 1H), 6.82 (d, J=7.1 Hz, 1H), 7.08 (t, J=7.4 Hz, 1H), 7.25 (br d, J=7.8 Hz, 1H); ESI-MS [M+H]⁺ calc'd for C₂₀H₃₀N₂O₂, 331.24; found, 331.4.

Example 80: 3-((3-cyclopropylpyrazin-2-yl)oxy)-2,2-dimethyl-N-(1-methylpiperidin-4-yl)propanamide

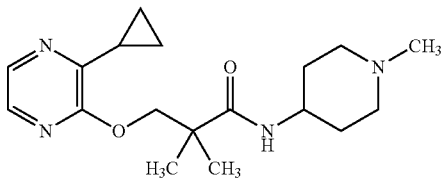 [SMILES: CN1CCC(NC(=O)C(C)(C)COc2nccnc2C2CC2)CC1]

The title compound was prepared in a manner similar to EXAMPLE 75, using 3-cyclopropylpyrazin-2-ol in place of 3-hydroxy-2-methylbenzonitrile (STEP A). The final product was isolated as a yellow oil (0.033 g, 20%). $^1$H NMR (400 MHz, CD$_3$CN) δ ppm 0.93-1.07 (m, 4H), 1.28 (s, 6H), 1.44-1.58 (m, 2H), 1.71-1.80 (m, 2H), 2.10 (td, J=11.6, 2.3 Hz, 2H), 2.24 (s, 3H), 2.30-2.42 (m, 1H), 2.80 (br d, J=11.9 Hz, 2H), 3.03 (br s, 2H), 3.63-3.73 (m, 1H), 4.30 (s, 2H), 6.30 (br d, J=6.3 Hz, 1H), 7.83 (d, J=2.8 Hz, 1H), 7.94 (d, J=2.8 Hz, 1H); ESI-MS [M+H]$^+$ calc'd for C$_{18}$H$_{28}$N$_4$O$_2$, 333.23; found, 333.2.

Example 81: 1-((2-chlorophenoxy)methyl)-N-(1-methylpiperidin-4-yl)cyclopropane-1-carboxamide

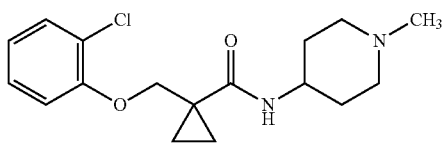 [SMILES: CN1CCC(NC(=O)C2(COc3ccccc3Cl)CC2)CC1]

Diisopropyl azodicarboxylate (0.244 mL, 1.24 mmol) was added dropwise to a solution of triphenylphosphine (0.320 g, 1.22 mmol), 2-chlorophenol (0.127 g, 0.990 mmol), and 1-(hydroxymethyl)-N-(1-methylpiperidin-4-yl)cyclopropane-1-carboxamide (0.236 g, 1.16 mmol) in toluene (9.90 mL). The solution was heated to 80° C. for 6 hours and then concentrated under reduced pressure. The residue was diluted with DMF and methanol, filtered through a hydrophilic PTFE 0.45 m filter (Millipore® Millex-LCR) and purified by preparative HPLC (Method B) to give the title compound (0.012 g, 4%). $^1$H NMR (500 MHz, CD$_3$OD) δ 0.89 (m, 2H), 1.24 (m, 2H), 1.58 (m, 2H), 1.80 (m, 2H), 2.16 (m, 2H), 2.24 (s, 3H), 2.81 (m, 2H), 3.69 (m, 1H), 4.19 (m, 2H), 6.95 (m, 1H), 7.16 (m, 1H), 7.29 (m, 1H), 7.40 (m, 1H); ESI-MS [M+H]$^+$ calc'd for C$_{17}$H$_{23}$ClN$_2$O$_2$, 323.15; found, 323.30.

Example 82: 3-((3-chloro-5-methylpyridin-2-yl)oxy)-2,2-dimethyl-N-(1-methylpiperidin-4-yl)propanamide

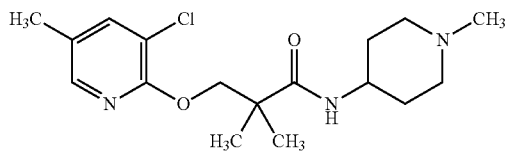

In a 20 mL vial, 3-hydroxy-2,2-dimethyl-N-(1-methylpiperidin-4-yl)propanamide (0.142 g, 0.432 mmol) was dissolved in DMF (1.5 mL) to give a colorless solution. Sodium hydride (60 wt %, 0.040 g, 0.99 mmol) was added. After stirring for 1 hour at room temperature, 2,3-dichloro-5-methylpyridine (0.070 g, 0.43 mmol) was added. The reaction mixture was heated at 100° C. overnight and was then filtered through a hydrophilic PTFE 0.45 m filter (Millipore® Millex-LCR) which was rinsed with methanol. The filtrate was purified by preparative HPLC (Method B) and the product-containing fractions were evaporated to give the title compound as a clear film (17.9 mg, 12%). $^1$H NMR (500 MHz, CD$_3$OD) δ ppm 1.28 (s, 6H), 1.49-1.62 (m, 2H), 1.73-1.82 (m, 2H), 2.05-2.13 (m, 2H), 2.15 (s, 3H), 2.27 (s, 3H), 2.80-2.91 (m, 2H), 3.65-3.77 (m, 1H), 4.29 (s, 2H), 7.47-7.53 (m, 1H), 7.88-7.93 (m, 1H); ESI-MS [M+H]$^+$ calc'd for C$_{17}$H$_{26}$ClN$_3$O$_2$, 340.17; found, 340.24.

Example 83: 3-((3,6-dimethylpyridin-2-yl)oxy)-2,2-dimethyl-N-(1-methylpiperidin-4-yl)propanamide

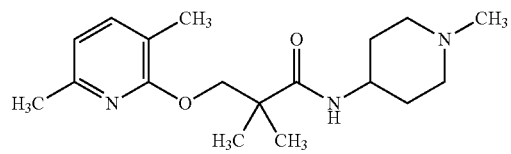

The title compound was prepared in a manner similar to EXAMPLE 82, using 2-chloro-3,6-dimethylpyridine (0.060 g, 0.42 mmol, 1 eq) in place of 2,3-dichloro-5-methylpyridine. The product was isolated as a light brown film (52.6 mg, 39%). $^1$H NMR (500 MHz, CD$_3$OD) δ ppm 1.28 (s, 6H), 1.50-1.60 (m, 2H), 1.75-1.82 (m, 2H), 2.11 (m, 5H), 2.25 (s, 3H), 2.36 (s, 3H), 2.79-2.85 (m, 2H), 3.66-3.76 (m, 1H), 4.30 (s, 2H), 6.64-6.69 (m, 1H), 7.29-7.34 (m, 1H); ESI-MS [M+H]$^+$ calc'd for C$_{18}$H$_{29}$N$_3$O$_2$, 320.23; found, 320.45.

Example 84: 3-((3,5-dimethylpyridin-2-yl)oxy)-2,2-dimethyl-N-(1-methylpiperidin-4-yl)propanamide

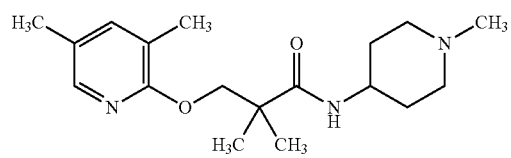

The title compound was prepared in a manner similar to EXAMPLE 82, using 2-chloro-3,5-dimethylpyridine (0.060 g, 0.42 mmol, 1 eq) in place of 2,3-dichloro-5-methylpyridine. The product was isolated as a light brown film (4.9 mg, 3.6%). $^1$H NMR (500 MHz, CD$_3$OD) δ ppm 1.30 (s, 6H), 1.51-1.64 (m, 2H), 1.75-1.85 (m, 2H), 2.08-2.19 (m, 2H), 2.28 (s, 3H), 2.82-2.91 (m, 2H), 3.62-3.80 (m, 1H), 4.30 (s, 2H), 6.83-6.90 (m, 1H), 7.46-7.50 (m, 1H), 7.89-7.98 (m, 1H); ESI-MS [M+H]$^+$ calc'd for C$_{18}$H$_{29}$N$_3$O$_2$, 320.23; found, 320.3.

Example 85: 3-((3-ethylpyridin-2-yl)oxy)-2,2-dimethyl-N-(1-methylpiperidin-4-yl)propanamide

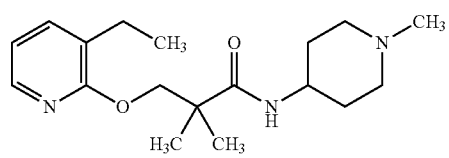 [SMILES: CCc1cccnc1OCC(C)(C)C(=O)NC1CCN(C)CC1]

The title compound was prepared in a manner similar to EXAMPLE 82, using 2-chloro-3-ethylpyridine (0.060 g, 0.42 mmol, 1 eq) in place of 2,3-dichloro-5-methylpyridine. The product was isolated as a light brown semisolid (18.4 mg, 14%). $^1$H NMR (500 MHz, CD$_3$OD) δ ppm 1.15-1.19 (m, 3H), 1.30 (s, 6H), 1.49-1.63 (m, 2H), 1.73-1.84 (m, 2H), 2.08-2.18 (m, 2H), 2.28 (s, 3H), 2.58 (d, J=7.3 Hz, 2H), 2.81-2.90 (m, 2H), 3.65-3.76 (m, 1H), 4.30 (s, 2H), 6.82-6.91 (m, 1H), 7.43-7.51 (m, 1H), 7.88-7.97 (m, 1H); ESI-MS [M+H]$^+$ calc'd for $C_{18}H_{29}N_3O_2$, 320.23; found, 320.26.

Example 86: (R)-3-((3-ethylpyridin-2-yl)oxy)-2,2-dimethyl-N-(1-methylpyrrolidin-3-yl)propanamide

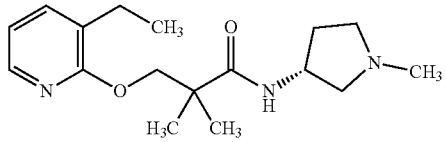

The title compound was prepared in a manner similar to EXAMPLE 82, using (R)-3-hydroxy-2,2-dimethyl-N-(1-methylpyrrolidin-3-yl)propanamide (0.085 g, 0.42 mmol) in place of 3-hydroxy-2,2-dimethyl-N-(1-methylpiperidin-4-yl)propanamide, and 2-chloro-3-ethylpyridine (0.060 g, 0.42 mmol) in place of 2,3-dichloro-5-methylpyridine. The product was isolated as a brown film (17.3 mg, 13%). $^1$H NMR (500 MHz, CD$_3$OD) δ ppm 1.17 (t, J=7.6 Hz, 3H), 1.30 (app d, J=1.0 Hz, 6H), 1.62-1.75 (m, 1H), 2.20-2.31 (m, 1H), 2.35 (s, 3H), 2.46 (dd, J=10.2, 4.4 Hz, 2H), 2.58 (q, J=7.8 Hz, 2H), 2.72 (dd, J=10.2, 7.3 Hz, 2H), 4.30 (s, 2H), 4.36-4.44 (m, 1H), 6.84-6.90 (m, 1H), 7.49 (d, J=2.0 Hz, 1H) 7.92 (dd, J=5.4, 2.0 Hz, 1H); ESI-MS [M+H]$^+$ calc'd for $C_{17}H_{27}N_3O_2$, 306.21; found, 306.26.

Example 87: 3-((3-ethylpyrazin-2-yl)oxy)-2,2-dimethyl-N-(1-methylpiperidin-4-yl)propanamide

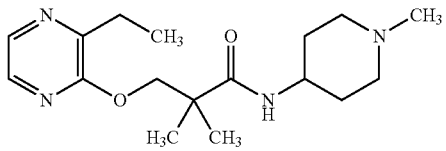

The title compound was prepared in a manner similar to EXAMPLE 82, using 2-chloro-3-ethylpyrazine (0.060 g, 0.42 mmol, 1 eq) in place of 2,3-dichloro-5-methylpyridine. The product was isolated as a brown film (78.4 mg, 58%). $^1$H NMR (500 MHz, CD$_3$OD) δ ppm 1.23 (t, J=7.6 Hz, 3H), 1.31 (s, 6H), 1.51-1.64 (m, 2H), 1.74-1.83 (m, 2H), 2.02-2.14 (m, 2H), 2.26 (s, 3H), 2.79 (d, J=7.3 Hz, 2H), 2.82-2.89 (m, 2H), 3.65-3.75 (m, 1H), 4.37 (s, 2H), 7.98 (d, J=2.4 Hz, 2H); ESI-MS [M+H]$^+$ calc'd for $C_{17}H_{28}N_4O_2$, 321.22; found, 321.29.

Example 88: 3-((3,4-dimethylpyridin-2-yl)oxy)-2,2-dimethyl-N-(1-methylpiperidin-4-yl)propanamide

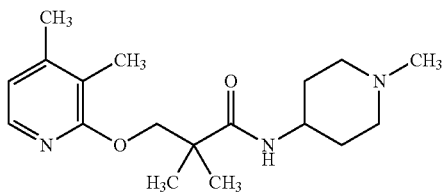 [SMILES: Cc1ccnc(OCC(C)(C)C(=O)NC2CCN(C)CC2)c1C]

The title compound was prepared in a manner similar to EXAMPLE 82, using 2-chloro-3,4-dimethylpyridine (0.050 g, 0.35 mmol. 1 eq) in place of 2,3-dichloro-5-methylpyridine. The product was isolated as a brown film (29.3 mg, 26%). $^1$H NMR (500 MHz, CD$_3$OD) δ ppm 1.29 (s, 6H), 1.50-1.62 (m, 2H), 1.75-1.83 (m, 2H), 2.11 (m, 5H), 2.26 (s, 6H), 2.79-2.88 (m, 2H), 3.65-3.75 (m, 1H), 4.26 (s, 2H), 6.72-6.79 (m, 1H), 7.71-7.81 (m, 1H); ESI-MS [M+H]$^+$ calc'd for $C_{18}H_{29}N_3O_2$, 320.23; found, 320.26.

Example 89: 1-(((3-cyclopropylpyridin-2-yl)oxy)methyl)-N-(1-methylpiperidin-4-yl)cyclobutane-1-carboxamide

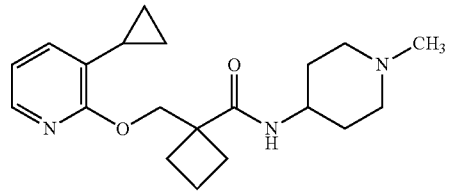 [SMILES: CN1CCC(NC(=O)C2(COc3ncccc3C3CC3)CCC2)CC1]

The title compound was prepared in a manner similar to EXAMPLE 82, using 1-(hydroxymethyl)-N-(1-methylpiperidin-4-yl)cyclobutane-1-carboxamide (0.099 g, 0.39 mmol) in place of 3-hydroxy-2,2-dimethyl-N-(1-methylpiperidin-4-yl)propanamide, and 2-chloro-3-cyclopropylpyridine (0.060 g, 0.39 mmol) in place of 2,3-dichloro-5-methylpyridine. The product was isolated as a colorless film (38.9 mg, 29%). $^1$H NMR (500 MHz, CD$_3$OD) δ ppm 0.65 (dd, J=5.4, 2.0 Hz, 2H), 0.92 (dd, J=8.3, 2.0 Hz, 2H), 1.48-1.58 (m, 2H), 1.76-1.92 (m, 3H), 2.08 (m, 6H), 2.25 (s, 3H), 2.40-2.49 (m, 2H), 2.79-2.87 (m, 2H), 3.66-3.75 (m, 1H), 4.55 (s, 2H), 6.84 (dd, J=7.3, 4.9 Hz, 1H), 7.16-7.22 (m, 1H), 7.84-7.91 (m, 1H); ESI-MS [M+H]$^+$ calc'd for $C_{20}H_{29}N_3O_2$, 344.23; found, 344.3.

Example 90: 3-((3-(difluoromethyl)pyridin-2-yl)oxy)-2,2-dimethyl-N-(1-methylpiperidin-4-yl)propanamide

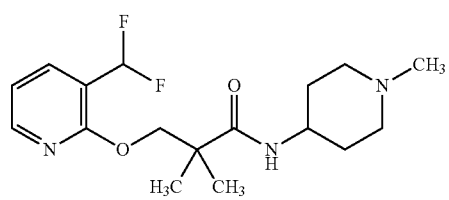 [SMILES: CN1CCC(NC(=O)C(C)(C)COc2ncccc2C(F)F)CC1]

The title compound was prepared in a manner similar to EXAMPLE 82, using 2-chloro-3-(difluoromethyl)pyridine (0.070 g, 0.43 mmol, 1 eq) in place of 2,3-dichloro-5-methylpyridine. The product was isolated as a brown semi-solid (103.7 mg, 71%). $^1$H NMR (500 MHz, CD$_3$OD) δ ppm 1.29 (s, 6H), 1.51-1.63 (m, 2H), 1.74-1.84 (m, 2H), 2.03-2.15 (m, 2H), 2.25 (s, 3H), 2.76-2.94 (m, 2H), 3.63-3.77 (m, 1H), 4.39 (s, 2H), 6.68-6.97 (m, 1H), 7.01-7.12 (m, 1H), 7.83-7.92 (m, 1H), 8.15-8.29 (m, 1H); ESI-MS [M+H]$^+$ calc'd for $C_{17}H_{25}F_2N_3O_2$, 342.19; found, 342.5.

Example 91: 2,2-dimethyl-3-((3-methyl-5-(trifluoromethyl)pyridin-2-yl)oxy)-N-(1-methylpiperidin-4-yl)propanamide

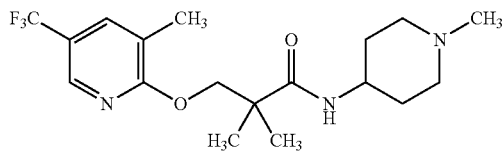 [SMILES: Cc1cc(C(F)(F)F)cnc1OCC(C)(C)C(=O)NC1CCN(C)CC1]

The title compound was prepared in a manner similar to EXAMPLE 82, using 2-chloro-3-methyl-5-(trifluoromethyl)pyridine (0.070 g, 0.36 mmol, 1 eq) in place of 2,3-dichloro-5-methylpyridine. The product was isolated as a white solid (42.7 mg, 32%). $^1$H NMR (500 MHz, CD$_3$OD) δ ppm 1.30 (s, 6H), 1.57 (br s, 2H), 1.77 (d, J=2.0 Hz, 2H), 2.09 (d, J=2.0 Hz, 2H), 2.22 (s, 3H), 2.26 (s, 3H), 2.80-2.89 (m, 2H), 3.65-3.76 (m, 1H), 4.40 (s, 2H), 7.70-7.75 (m, 1H), 8.21-8.29 (m, 1H); ESI-MS [M+H]$^+$ calc'd for C$_{18}$H$_{26}$F$_3$N$_3$O$_2$, 374.20; found, 374.4.

Example 92: 2,2-dimethyl-N-(1-methylpiperidin-4-yl)-3-((3-(trifluoromethoxy)pyridin-2-yl)oxy)propanamide

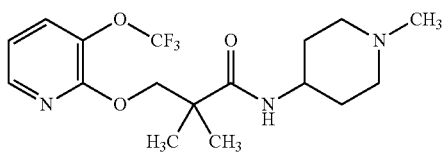

The title compound was prepared in a manner similar to EXAMPLE 82, using 2-chloro-3-(trifluoromethoxy)pyridine (0.070 g, 0.35 mmol, 1 eq) in place of 2,3-dichloro-5-methylpyridine. The product was isolated as a brown solid (38.2 mg, 0.102 mmol). $^1$H NMR (500 MHz, CD$_3$OD) δ ppm 1.29 (s, 6H), 1.52-1.62 (m, 2H), 1.75-1.84 (m, 2H), 2.03-2.14 (m, 2H), 2.26 (s, 3H), 2.72-2.93 (m, 2H), 3.65-3.75 (m, 1H), 4.39 (s, 2H), 6.95-7.05 (m, 1H), 7.58-7.72 (m, 1H), 8.05-8.14 (m, 1H); ESI-MS [M+H]$^+$ calc'd for C$_{17}$H$_{24}$F$_3$N$_3$O$_3$, 376.18; found, 376.4.

Example 93: trans-N-(4-(4-chlorophenyl)-1-methylpyrrolidin-3-yl)-3-((3,5-dimethylpyridin-2-yl)oxy)-2,2-dimethylpropanamide

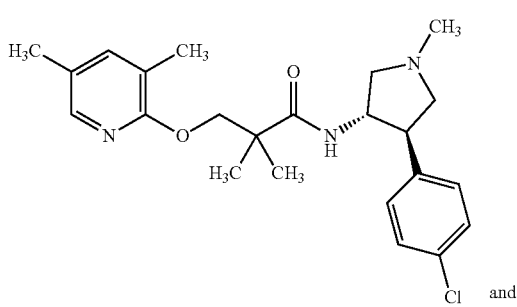

and

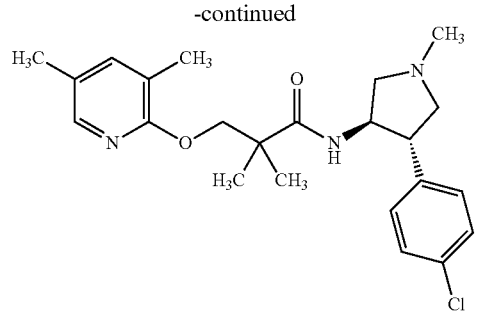

The title compound was prepared in a manner similar to EXAMPLE 82, using trans-N-(4-(4-chlorophenyl)-1-methylpyrrolidin-3-yl)-2,2-dimethyl-3-((3-methylpyridin-2-yl)oxy)propanamide (0.157 g, 0.353 mmol) in place of 3-hydroxy-2,2-dimethyl-N-(1-methylpiperidin-4-yl)propanamide, and 2-chloro-3,5-dimethylpyridine (0.050 g, 0.35 mmol) in place of 2,3-dichloro-5-methylpyridine. The product was isolated as a brown solid (10.5 mg, 7.2%). $^1$H NMR (500 MHz, CD$_3$OD) δ ppm 1.26 (app d, J=4.9 Hz, 6H), 1.96 (s, 3H), 2.20 (s, 3H), 2.40 (s, 3H), 2.52-2.59 (m, 1H), 2.62-2.69 (m, 1H), 2.88-2.96 (m, 1H), 3.11-3.19 (m, 1H), 3.25-3.29 (m, 1H), 4.21 (d, J=8.8 Hz, 2H), 4.43-4.51 (m, 1H), 7.18 (d, J=4.9 Hz, 4H), 7.27-7.32 (m, 1H), 7.68-7.72 (m, 1H); ESI-MS [M+H]$^+$ calc'd for C$_{23}$H$_{30}$ClN$_3$O$_2$, 416.20; found, 416.4.

Example 94: trans-N-(4-(4-chlorophenyl)-1-methylpyrrolidin-3-yl)-3-((3-cyclopropylpyridin-2-yl)oxy)-2,2-dimethylpropanamide

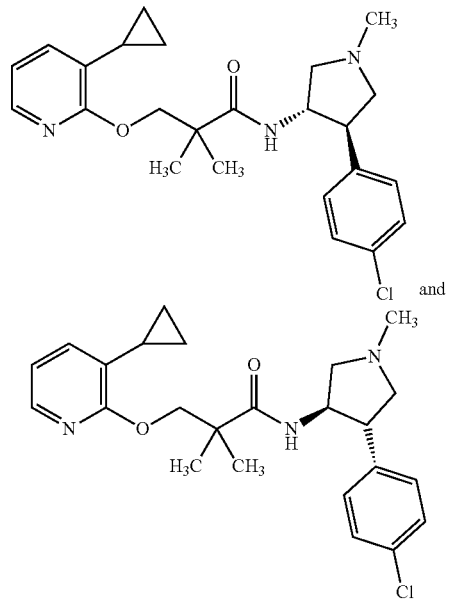

The title compound was prepared in a manner similar to EXAMPLE 82, using trans-N-(4-(4-chlorophenyl)-1-methylpyrrolidin-3-yl)-2,2-dimethyl-3-((3-methylpyridin-2-yl)oxy)propanamide (0.145 g, 0.326 mmol) in place of 3-hydroxy-2,2-dimethyl-N-(1-methylpiperidin-4-yl)propanamide, and 2-chloro-3-cyclopropylpyridine (0.050 g, 0.33 mmol) in place of 2,3-dichloro-5-methylpyridine. The product was isolated as a brown solid (15.8 mg, 11%). ¹H NMR (500 MHz, CD₃OD) δ ppm 0.52-0.60 (m, 2H), 0.75-0.82 (m, 2H), 1.29 (app d, J=4.9 Hz, 6H), 1.80-1.89 (m, 1H), 2.40 (s, 3H), 2.52-2.60 (m, 1H), 2.63-2.71 (m, 1H), 2.92 (s, 1H), 3.11-3.19 (m, 1H), 3.25-3.29 (m, 1H), 4.22-4.33 (m, 2H), 4.39-4.52 (m, 1H), 6.80-6.87 (m, 1H), 7.14-7.25 (m, 5H), 7.83-7.89 (m, 1H); ESI-MS [M+H]⁺ calc'd for C₂₄H₃₀ClN₃O₂, 428.20; found, 428.4.

Example 95: trans-N-(4-ethoxy-1-methylpyrrolidin-3-yl)-3-(2-ethylphenoxy)-2,2-dimethylpropanamide

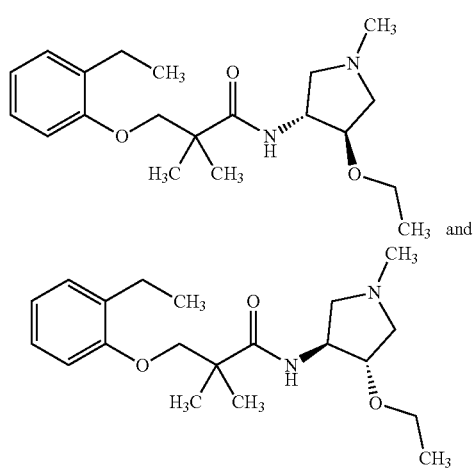

In a 20 mL vial, 3-(2-ethylphenoxy)-2,2-dimethylpropanoic acid (0.050 g, 0.225 mmol) was taken up in DMF (3 mL), which was followed by the addition of trans-4-ethoxy-1-methylpyrrolidin-3-amine (0.032 g, 0.225 mmol), HATU (0.103 g, 0.270 mmol) and DIPEA (0.073 g, 0.562 mmol). The reaction mixture was allowed to stir at room temperature overnight and was then filtered through a hydrophilic PTFE 0.45 m filter (Millipore® Millex-LCR) which was rinsed with methanol. The filtrate was purified by preparative HPLC (Method C) eluting with a gradient of 20-40% ACN in water. The product-containing fractions were evaporated to give a TFA salt of the title compound as a clear semi-solid (16 mg, 15%). ¹H NMR (500 MHz, CD₃OD) δ ppm 1.16 (td, J=7.3, 3.4 Hz, 6H), 1.34 (s, 6H), 2.60 (q, J=7.8 Hz, 2H), 2.95 (s, 3H), 3.43-3.65 (m, 3H), 3.97-4.01 (m, 2H), 4.08-4.13 (m, 1H), 4.31 (br s, 1H), 6.81-6.91 (m, 2H), 7.08-7.16 (m, 2H); ESI-MS [M+H]⁺ calc'd for C₂₀H₃₂N₂O₃, 349.24; found, 349.2.

Example 96: trans-3-(2-ethylphenoxy)-N-(4-methoxy-1-methylpyrrolidin-3-yl)-2,2-dimethylpropanamide

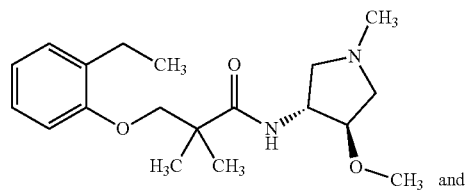

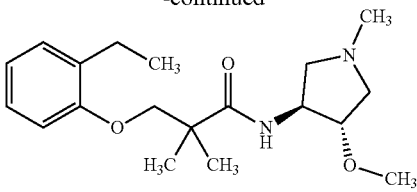

A TFA salt of the title compound was prepared in a manner similar to EXAMPLE 95, using trans-4-methoxy-1-methylpyrrolidin-3-amine (0.029 g, 0.225 mmol) in place of trans-4-ethoxy-1-methylpyrrolidin-3-amine. The product was isolated as an off-white oil (4 mg, 4%). ¹H NMR (500 MHz, CD₃OD) δ ppm 1.13-1.18 (m, 3H), 1.33 (d, J=1.5 Hz, 6H), 2.48 (s, 3H), 2.57-2.66 (m, 3H), 2.78 (dd, J=10.7, 2.9 Hz, 1H), 3.04-3.16 (m, 2H), 3.31 (s, 3H) 3.80 (dt, J=5.9, 2.9 Hz, 1H), 3.98 (s, 2H), 4.28 (ddd, J=7.3, 5.4, 2.0 Hz, 1H), 6.82-6.90 (m, 2H), 7.08-7.15 (m, 2H); ESI-MS [M+H]⁺ calc'd for C₁₉H₃₀N₂O₃, 335.23; found, 335.2.

Example 97: 3-(2-ethylphenoxy)-2,2-dimethyl-N-(1-methyl-4-phenylpyrrolidin-3-yl)propanamide

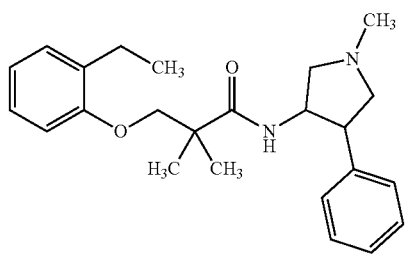 [SMILES: CCc1ccccc1OCC(C)(C)C(=O)NC1CN(C)CC1c1ccccc1]

A TFA salt of the title compound was prepared in a manner similar to EXAMPLE 95, using 1-methyl-4-phenylpyrrolidin-3-amine (0.016 g, 0.090 mmol, 1 eq) in place of trans-4-ethoxy-1-methylpyrrolidin-3-amine. The product was isolated as an off-white oil (28 mg, 63%). ¹H NMR (400 MHz, CD₃OD) δ ppm 0.85-1.17 (m, 7H), 1.24-1.40 (m, 3H), 1.92-2.05 (m, 1H), 2.52 (q, J=7.4 Hz, 2H), 2.98-3.16 (m, 3H), 3.59-3.79 (m, 3H), 3.86-4.17 (m, 3H), 6.73-6.90 (m, 2H), 7.06-7.15 (m, 2H), 7.21-7.35 (m, 5H); ESI-MS [M+H]⁺ calc'd for C₂₄H₃₂N₂O₂, 381.25; found, 381.2.

Example 98: 3-((6-chloro-4-(trifluoromethyl)pyridazin-3-yl)oxy)-2,2-dimethyl-N-(1-methylpiperidin-4-yl)propanamide

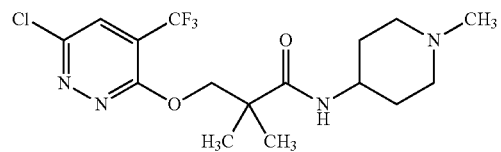 [SMILES: CN1CCC(NC(=O)C(C)(C)COc2nnc(Cl)cc2C(F)(F)F)CC1]

To a solution of 3-hydroxy-2,2-dimethyl-N-(1-methylpiperidin-4-yl)propanamide (0.033 g, 0.152 mmol) in DMF (3 mL) at 0° C. was added NaH (4.98 mg, 0.207 mmol). The mixture was allowed to stir at 0° C. for 30 minutes, then 3,6-dichloro-4-(trifluoromethyl)pyridazine (0.030 g, 0.138 mmol) was added, and the reaction mixture was allowed to stir at 80° C. overnight. The mixture was then slowly diluted with water (20 mL) and extracted with EtOAc. The combined organics were dried over MgSO$_4$, filtered, and concentrated under reduced pressure. The crude residue was taken up in MeOH and filtered through a hydrophilic PTFE 0.45 m filter (Millipore® Millex-LCR) which was rinsed with methanol. The filtrate was purified by preparative HPLC (Method B) to give the title compound as a white solid (8.0 mg, 15%). $^1$H NMR (400 MHz, CD$_3$CN) δ ppm 1.28-1.31 (m, 6H), 1.77-1.85 (m, 2H), 1.85-1.94 (m, 2H), 2.62 (s, 3H), 2.70-2.84 (m, 3H), 3.27 (br d, J=12.1 Hz, 2H), 3.82-3.93 (m, 1H), 4.57 (s, 2H), 6.42 (br d, J=6.8 Hz, 1H), 7.89 (d, J=1.0 Hz, 1H); ESI-MS [M+H]$^+$ calc'd for C$_{16}$H$_{22}$ClF$_3$N$_2$O$_2$, 395.15; found, 395.4.

Example 99: 3-(furo[3,2-c]pyridin-4-yloxy)-2,2-dimethyl-N-(1-methylpiperidin-4-yl)propanamide

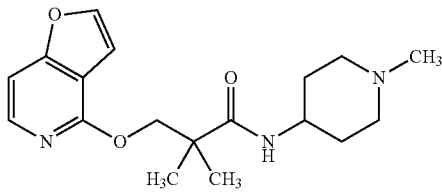 [SMILES: CN1CCC(NC(=O)C(C)(C)COc2nccc3occc23)CC1]

The title compound was prepared in a manner similar to EXAMPLE 98, using 4-chlorofuro[3,2-c]pyridine (0.030 g, 0.20 mmol, 1 eq) in place of 3,6-dichloro-4-(trifluoromethyl)pyridazine. The product was isolated as a white solid (0.015 g, 23%). $^1$H NMR (400 MHz, CD$_3$CN) δ ppm 1.29 (s, 6H), 1.51-1.63 (m, 2H), 1.74-1.84 (m, 2H), 2.24 (td, J=11.8, 2.3 Hz, 2H), 2.31 (s, 3H), 2.88 (br d, J=12.1 Hz, 2H), 3.66-3.76 (m, 1H), 4.43 (s, 2H), 6.37 (br d, J=5.6 Hz, 1H), 6.90 (dd, J=2.2, 0.9 Hz, 1H), 7.20 (dd, J=5.8, 1.0 Hz, 1H), 7.75 (d, J=2.0 Hz, 1H), 7.99 (d, J=6.1 Hz, 1H); ESI-MS [M+H]$^+$ calc'd for C$_{18}$H$_{25}$N$_3$O$_3$, 332.2; found, 332.4.

Example 100: 3-((5-bromo-3-(trifluoromethyl)pyridin-2-yl)oxy)-2,2-dimethyl-N-(1-methylpiperidin-4-yl)propanamide

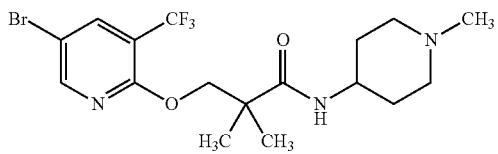

To a solution of 3-hydroxy-2,2-dimethyl-N-(1-methylpiperidin-4-yl)propanamide (0.181 g, 0.845 mmol) in THF (5 mL) at 0° C. was added NaH (60 wt %, 0.037 g, 0.92 mmol). The reaction mixture was stirred at 0° C. for 30 minutes, then 5-bromo-2-chloro-3-(trifluoromethyl)pyridine (0.200 g, 0.768 mmol) was added, and the reaction mixture was stirred at 50° C. overnight. Water (20 mL) was added and the reaction mixture was extracted with EtOAc. The combined organics were dried over MgSO$_4$, concentrated, and the residue was purified by automated flash silica column chromatography to give the title compound as a white solid (0.145 g, 43%). $^1$H NMR (400 MHz, DMSO-d$_6$) δ ppm 1.13-1.28 (m, 6H), 1.45 (qd, J=11.8, 3.6 Hz, 2H), 1.57 (br d, J=11.8 Hz, 2H), 1.79-1.92 (m, 2H), 2.12 (s, 3H), 2.69 (br d, J=11.7 Hz, 2H), 3.44-3.57 (m, 1H), 4.35 (s, 2H), 7.27 (br d, J=7.6 Hz, 1H), 8.31 (d, J=2.3 Hz, 1H), 8.58 (d, J=2.3 Hz, 1H); ESI-MS [M+H]$^+$ calc'd for C$_{17}$H$_{23}$BrF$_3$N$_3$O$_2$, 438.1; found, 438.4.

Example 101: 2,2-dimethyl-3-((5-methyl-3-(trifluoromethyl)pyridin-2-yl)oxy)-N-(1-methylpiperidin-4-yl)propanamide

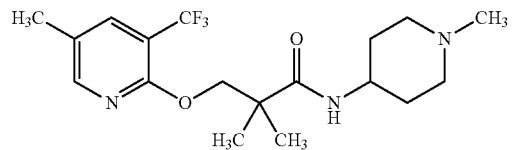

A mixture of 3-((5-bromo-3-(trifluoromethyl)pyridin-2-yl)oxy)-2,2-dimethyl-N-(1-methylpiperidin-4-yl)propanamide (0.070 g, 0.16 mmol), methylboronic acid (0.019 g, 0.319 mmol), 2 M aqueous potassium carbonate (0.160 mL, 0.319 mmol) and Pd-Amphos (0.011 g, 0.016 mmol) in dioxane (2 mL) was heated at 120° C. for 30 minutes under microwave irradiation. The crude reaction mixture was diluted with water and then extracted with EtOAc. The combined organics were dried over MgSO$_4$ and concentrated under reduced pressure. The crude residue was purified by automated flash silica column chromatography, eluting with a gradient of 0-10% MeOH in DCM to give the title compound as a white solid (0.030 g, 50%). $^1$H NMR (400 MHz, CD$_3$CN) δ ppm 1.21-1.29 (m, 6H), 1.31-1.50 (m, 2H), 1.66-1.80 (m, 2H), 1.93-1.95 (m, 1H), 1.98-2.01 (m, 1H), 2.17 (s, 3H), 2.27 (br s, 1H), 2.30 (s, 3H), 2.72 (br d, J=11.9 Hz, 2H), 3.55-3.67 (m, 1H), 4.30-4.40 (m, 2H), 6.20 (br s, 1H), 7.83 (s, 1H), 8.19 (s, 1H); ESI-MS [M+H]$^+$ calc'd for C$_{18}$H$_{26}$F$_3$N$_3$O$_2$, 374.21; found, 374.4.

Example 102: 2,2-dimethyl-N-(1-methylpiperidin-4-yl)-3-(2-(trifluoromethoxy)phenoxy)propanamide

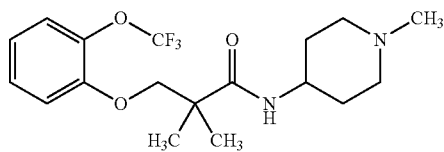

To a mixture of 2-(trifluoromethoxy)phenol (0.038 mL, 0.28 mmol), 3-hydroxy-2,2-dimethyl-N-(1-methylpiperidin-4-yl)propanamide (0.090 g, 0.42 mmol) and triphenylphosphine (0.088 g, 0.34 mmol) in toluene (3 mL) was added DIAD (0.065 mL, 0.34 mmol). The reaction mixture was heated at 80° C. overnight. Aqueous 1 M NaOH (10 mL) was added and the mixture was filtered. The filtrate was extracted with EtOAc and the combined organics were dried over MgSO$_4$, filtered, and concentrated under reduced pressure. The crude residue was taken up in MeOH and filtered through a hydrophilic PTFE 0.45 m filter (Millipore® Millex-LCR) which was rinsed methanol. The filtrate was purified by preparative HPLC (Method A) to give a TFA salt of the title compound as a clear oil (0.010 g, 7.3%). $^1$H NMR (400 MHz, CD$_3$CN) δ ppm 1.16-1.28 (m, 6H), 1.28-1.33 (m, 1H), 1.76-1.94 (m, 2H), 1.99-2.07 (m, 1H), 2.68-2.80 (m, 3H), 2.94 (br t, J=12.0 Hz, 2H), 3.37-3.55 (m, 2H), 3.84-3.99 (m, 1H), 3.99-4.12 (m, 2H), 6.38-6.60 (m, 1H), 7.02 (td, J=7.8, 1.4 Hz, 1H), 7.10-7.21 (m, 1H), 7.24-7.42 (m, 2H); ESI-MS [M+H]$^+$ calc'd for $C_{18}H_{25}F_3N_2O_3$, 375.19; found, 375.4.

Example 103: trans-N-(1-(cyanomethyl)-4-(6-methylpyridin-3-yl)pyrrolidin-3-yl)-2,2-dimethyl-3-((3-(trifluoromethyl)pyridin-2-yl)oxy)propanamide

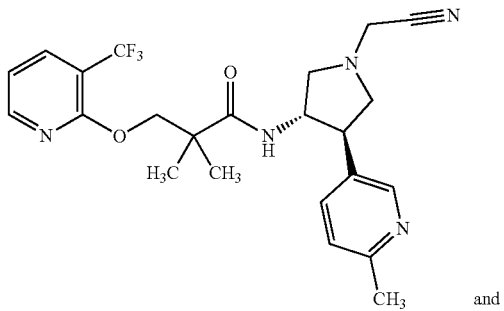

and

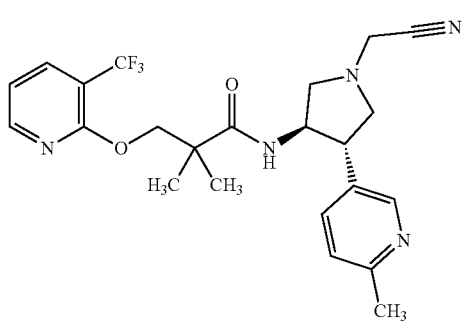

In a 125 mL round-bottomed flask, were combined trans-2,2-dimethyl-N-(4-(6-methylpyridin-3-yl)pyrrolidin-3-yl)-3-((3-(trifluoromethyl)pyridin-2-yl)oxy)propanamide (0.102 g, 0.241 mmol), 2-bromoacetonitrile (0.043 g, 0.36 mmol), and potassium carbonate (0.100 g, 0.724 mmol) in DMF (2 mL) to give a white suspension. The reaction mixture was stirred at 50° C. for 2 hours and was then filtered through a hydrophilic PTFE 0.45 m filter (Millipore® Millex-LCR) which was rinsed with methanol. The filtrate was purified by preparative HPLC (Method B) and the product-containing fractions were evaporated to give the title compound as a brown film (45.2 mg, 41%). $^1$H NMR (500 MHz, CD$_3$OD) δ ppm 1.27 (app d, J=10.7 Hz, 6H), 2.48 (s, 3H), 2.70-2.75 (m, 1H), 2.80 (s, 1H), 3.18 (s, 1H), 3.23 (s, 1H), 3.33-3.39 (m, 1H), 3.81 (d, J=6.4 Hz, 2H), 4.40 (d, J=5.4 Hz, 2H), 4.42-4.51 (m, 1H), 7.02-7.11 (m, 1H), 7.22 (s, 1H), 7.66-7.75 (m, 1H), 7.91-7.98 (m, 1H), 8.25-8.30 (m, 1H), 8.30-8.36 (m, 1H); ESI-MS [M+H]$^+$ calc'd for $C_{23}H_{26}F_3N_5O_2$, 462.20; found, 462.5.

Example 104: N-(1-(2-(4-chlorophenyl)-2-oxoethyl)piperidin-4-yl)-3-(2-ethylphenoxy)-2,2-dimethylpropanamide

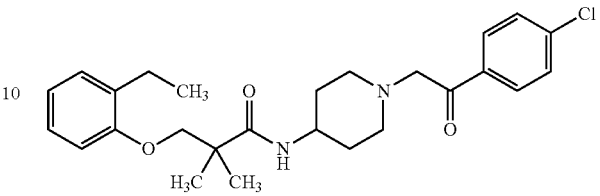

In a 20 mL vial, 3-(2-ethylphenoxy)-2,2-dimethylpropanoic acid (48 mg, 0.22 mmol) and 2-chloro-1-methylpyridin-1-ium iodide (166 mg, 0.648 mmol) were combined in DMF (2 mL). The reaction mixture was stirred for 30 minutes. Triethylamine (150 µL, 1.08 mmol) and 2-(4-aminopiperidin-1-yl)-1-(4-chlorophenyl)ethan-1-one (54.6 mg, 0.216 mmol) were then added. The reaction mixture was stirred at room temperature overnight and was then filtered through a hydrophilic PTFE 0.45 m Millipore® filter, which was rinsed with MeOH. The filtrate was purified by preparative HPLC (Method B) and the product-containing fractions were evaporated to give the title compound as a yellow oil (1 mg, 1%). $^1$H NMR (400 MHz, CD$_3$OD) δ ppm 1.12-1.27 (m, 3H), 1.30-1.44 (m, 6H), 1.66-1.83 (m, 2H), 1.88 (d, J=9.6 Hz, 2H), 2.33-2.42 (m, 1H), 2.59-2.71 (m, 2H), 3.08 (d, J=12.1 Hz, 2H), 3.76-3.87 (m, 1H), 3.96-4.08 (m, 3H), 6.87-6.96 (m, 2H), 7.11-7.20 (m, 2H), 7.44 (d, J=8.6 Hz, 1H), 7.52-7.63 (m, 2H), 7.97-8.10 (m, 2H).

Example 105: N-((3S,4S)-1,3-dimethylpiperidin-4-yl)-2,2-dimethyl-3-((3-(trifluoromethyl)pyridin-2-yl)oxy)propanamide

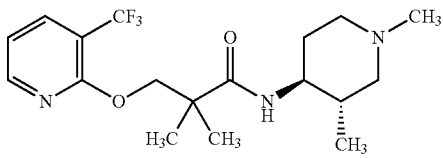 [SMILES: C[C@H]1CN(C)CC[C@@H]1NC(=O)C(C)(C)COc1ncccc1C(F)(F)F]

Racemic trans-N-(1,3-dimethylpiperidin-4-yl)-2,2-dimethyl-3-((3-(trifluoromethyl)pyridin-2-yl)oxy)propanamide (4.31 g, 11.54 mmol) was resolved by preparative SFC (Method A) eluting with 30% EtOH (containing 0.1% ammonium hydroxide) to give the title compound (2.10 g, 49%, second eluting peak) along with its enantiomer (EXAMPLE 106). The product was dissolved in ethyl acetate (10 mL) and HCl (4 M in dioxane, 1.34 mL, 5.36 mmol) was added. The mixture was concentrated and the residue was re-crystallized from heptane/isopropanol to give the HCl salt of the title compound as a white solid (1.97 g, 90%). $^1$H NMR (500 MHz, CD$_3$OD) δ ppm 0.83 (d, J=5.9 Hz, 3H), 1.31 (app d, J=3.9 Hz, 6H), 1.48-1.60 (m, 1H), 1.71-1.80 (m, 3H), 2.00-2.11 (m, 1H), 2.26 (s, 3H), 2.80-2.94 (m, 2H), 3.38-3.47 (m, 1H), 4.45 (d, J=7.3 Hz, 2H), 7.04-7.11 (m, 1H), 7.92-8.02 (m, 1H), 8.30-8.38 (m, 1H); ESI-MS [M+H]$^+$ calc'd for $C_{18}H_{26}F_3N_3O_2$, 374.20; found, 374.4.

Example 106: N-((3R,4R)-1,3-dimethylpiperidin-4-yl)-2,2-dimethyl-3-((3-(trifluoromethyl)pyridin-2-yl)oxy)propanamide

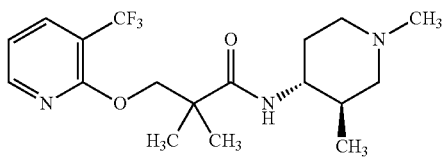 [SMILES: C[C@@H]1CN(C)CC[C@H]1NC(=O)C(C)(C)COc1ncccc1C(F)(F)F]

Racemic trans-N-(1,3-dimethylpiperidin-4-yl)-2,2-dimethyl-3-((3-(trifluoromethyl)pyridin-2-yl)oxy)propanamide (4.31 g, 11.54 mmol) was resolved by preparative SFC (Method A) eluting with 30% EtOH (containing 0.1% ammonium hydroxide) to give the title compound (2.07 g, 48%, first eluting peak) along with its enantiomer (EXAMPLE 105). $^1$H NMR (500 MHz, CD$_3$OD) δ ppm 0.83 (d, J=5.9 Hz, 3H), 1.31 (app d, J=3.9 Hz, 6H), 1.48-1.60 (m, 1H), 1.71-1.80 (m, 3H), 2.00-2.11 (m, 1H), 2.26 (s, 3H), 2.80-2.94 (m, 2H), 3.38-3.47 (m, 1H), 4.45 (d, J=7.3 Hz, 2H), 7.04-7.11 (m, 1H), 7.92-8.02 (m, 1H), 8.30-8.38 (m, 1H); ESI-MS [M+H]$^+$ calc'd for C$_{18}$H$_{26}$F$_3$N$_3$O$_2$, 374.20; found, 374.4.

Example 107: N-((3S,4S)-1,3-dimethylpiperidin-4-yl)-2,2-dimethyl-3-((3-(trifluoromethoxy)pyridin-2-yl)oxy)propanamide

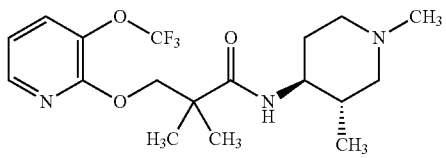 [SMILES: C[C@H]1CN(C)CC[C@@H]1NC(=O)C(C)(C)COc1ncccc1OC(F)(F)F]

Step A: tert-butyl trans-4-(2,2-dimethyl-3-((3-(trifluoromethoxy)pyridin-2-yl)oxy)propanamido)-3-methylpiperidine-1-carboxylate

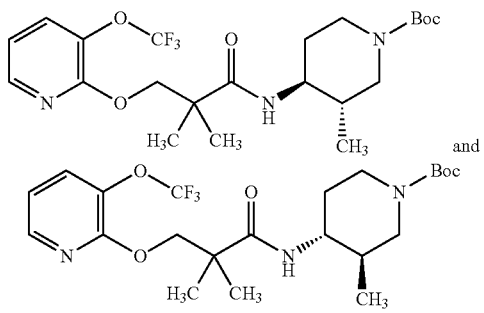

A solution of 2,2-dimethyl-3-((3-(trifluoromethoxy)pyridin-2-yl)oxy)propanoic acid (3.34 g, 12.0 mmol), tert-butyl trans-4-amino-3-methyl-1-piperidinecarboxylate, HCl (3.00 g, 12.0 mmol), HATU (5.00 g, 13.16 mmol) and DIPEA (6.25 mL, 35.9 mmol) in DMF (30 mL) was stirred at room temperature overnight. The reaction mixture was treated with water and extracted with EtOAc. The organic phase was washed with brine, dried over MgSO$_4$, filtered, and concentrated. The residue was purified by automated flash silica column chromatography (120 g column) eluting with a gradient of 20-50% EtOAc in heptanes. The product-containing fractions were evaporated to give the title compound (5.69 g, assumed quantitative). ESI-MS [M+H]$^+$ calc'd for C$_{22}$H$_{32}$F$_3$N$_3$O$_5$, 476.24; found, 476.4.

Step B: 2,2-dimethyl-N-(trans-3-methylpiperidin-4-yl)-3-((3-(trifluoromethoxy)pyridin-2-yl)oxy)propanamide

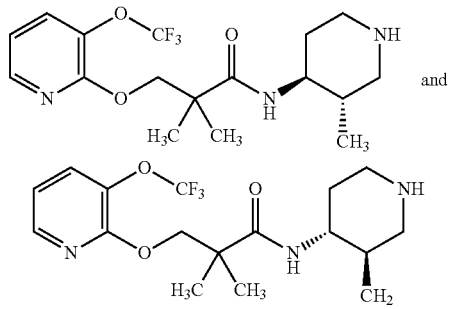

A solution of tert-butyl trans-4-(2,2-dimethyl-3-((3-(trifluoromethoxy)pyridin-2-yl)oxy)propanamido)-3-methylpiperidine-1-carboxylate (5.69 g, 12.0 mmol) in dioxane (25 mL) was treated with HCl (4 M in dioxane, 11.96 mL, 47.8 mmol). The reaction mixture was stirred at 50° C. for 1 hour and was then concentrated under reduced pressure to give an HCl salt of the title compound as a tan syrup (4.49 g, assumed quantitative) which was used without further purification. ESI-MS [M+H]$^+$ calc'd for C$_{17}$H$_{24}$F$_3$N$_3$O$_3$, 376.18; found, 376.3.

Step C: trans-N-(1,3-dimethylpiperidin-4-yl)-2,2-dimethyl-3-((3-(trifluoromethoxy)pyridin-2-yl)oxy)propanamide

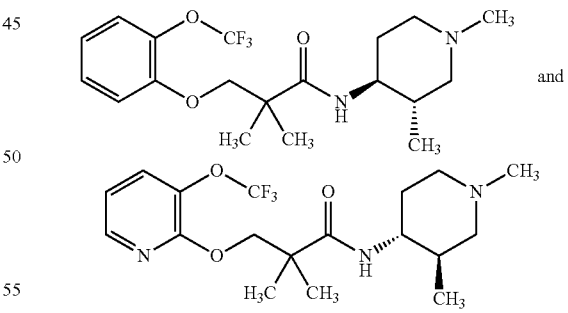

To a tan solution of 2,2-dimethyl-N-(trans-3-methylpiperidin-4-yl)-3-((3-(trifluoromethoxy)pyridin-2-yl)oxy)propanamide, HCl (4.49 g, 11.96 mmol) and formaldehyde (1.83 mL, 23.7 mmol) in methanol (35 mL) was added sodium cyanotrihydroborate (1.488 g, 23.68 mmol). The reaction mixture was stirred at room temperature overnight. Extra formaldehyde (1.83 mL, 23.7 mmol) and sodium cyanotrihydroborate (1.488 g, 23.68 mmol) were added. The mixture was stirred at room temperature for an additional 3 hours and was then filtered. The filtrate was purified by preparative HPLC (Method B) and the product-containing fractions were evaporated to give the title compound (2.53 g, 54%).

Step D: N-((3S,4S)-1,3-dimethylpiperidin-4-yl)-2,2-dimethyl-3-((3-(trifluoromethoxy)pyridin-2-yl)oxy) propanamide Racemic trans-N-(1,3-dimethylpiperidin-4-yl)-2,2-dimethyl-3-((3-(trifluoromethoxy)pyridin-2-yl)oxy)propanamide (5.52 g, 14.2 mmol) was resolved by preparative SFC (Method A) eluting with 20% EtOH (containing 0.1% ammonium hydroxide) to give the title compound (2.68 g, 48%, first eluting peak) along with its enantiomer (EXAMPLE 108). The product (2.58 g, 6.63 mmol) was dissolved in EtOAc (10 mL) and HCl (4 M in dioxane, 1.66 mL, 6.63 mmol) was added. The mixture was concentrated and the residue was re-crystallized from heptane/isopropanol to give an HCl salt of the title compound as a white solid (2.21 g, 78%). $^1$H NMR (500 MHz, CD$_3$OD) δ ppm 0.84 (d, J=6.4 Hz, 3H), 1.31 (app d, J=2.4 Hz, 6H), 1.51-1.62 (m, 1H), 1.68-1.80 (m, 3H), 2.02-2.11 (m, 1H), 2.26 (s, 3H), 2.82-2.92 (m, 2H), 3.38-3.49 (m, 1H), 4.41 (d, J=2.0 Hz, 2H), 6.99-7.06 (m, 1H), 7.61-7.68 (m, 1H), 8.05-8.14 (m, 1H); ESI-MS [M+H]$^+$ calc'd for C$_{18}$H$_{26}$F$_3$N$_3$O$_3$, 390.19; found 390.4.

Example 108: N-((3R,4R)-1,3-dimethylpiperidin-4-yl)-2,2-dimethyl-3-((3-(trifluoromethoxy)pyridin-2-yl)oxy)propanamide

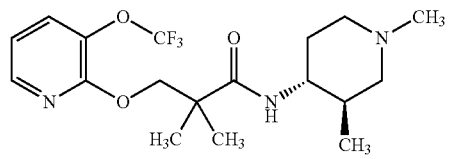 [SMILES: C[C@@H]1CN(C)CC[C@H]1NC(=O)C(C)(C)COc1ncccc1OC(F)(F)F]

Racemic trans-N-(1,3-dimethylpiperidin-4-yl)-2,2-dimethyl-3-((3-(trifluoromethoxy)pyridin-2-yl)oxy)propanamide (300 mg, 0.77 mmol) was resolved by preparative SFC (Method A) to give the title compound (second eluting peak) along with its enantiomer (EXAMPLE 107). $^1$H NMR (500 MHz, CD$_3$OD) δ ppm 0.84 (d, J=6.4 Hz, 3H), 1.31 (app d, J=2.4 Hz, 6H), 1.51-1.62 (m, 1H), 1.68-1.80 (m, 3H), 2.02-2.11 (m, 1H), 2.26 (s, 3H), 2.82-2.92 (m, 2H), 3.38-3.49 (m, 1H), 4.41 (d, J=2.0 Hz, 2H), 6.99-7.06 (m, 1H), 7.61-7.68 (m, 1H), 8.05-8.14 (m, 1H); ESI-MS [M+H]$^+$ calc'd for C$_{18}$H$_{26}$F$_3$N$_3$O$_3$, 390.19; found, 390.4.

Example 109: trans-N-(1,3-dimethylpiperidin-4-yl)-2,2-dimethyl-3-((3-(trifluoromethyl)pyridin-2-yl) oxy)propanamide

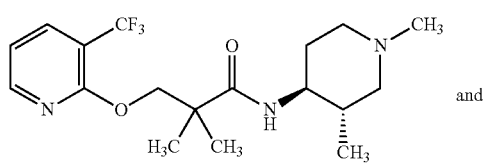

and

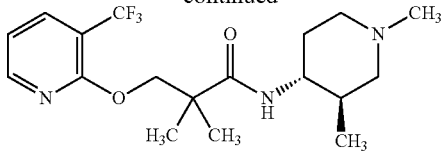

Step A: tert-butyl trans-4-(2,2-dimethyl-3-((3-(trifluoromethyl)pyridin-2-yl)oxy)propanamido)-3-methylpiperidine-1-carboxylate

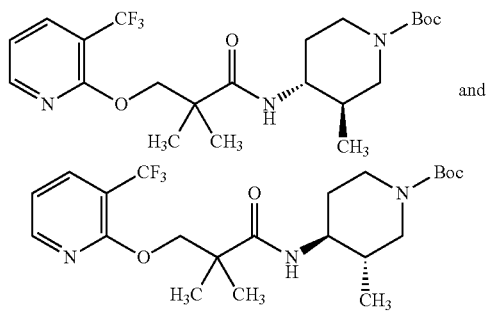

and

In a 200 mL round-bottomed flask, 2,2-dimethyl-3-((3-(trifluoromethyl)pyridin-2-yl)oxy)propanoic acid (4.00 g, 15.2 mmol), tert-butyl trans-4-amino-3-methylpiperidine-1-carboxylate, HCl (3.81 g, 15.2 mmol), HATU (5.78 g, 15.2 mmol) and DIPEA (7.94 mL, 45.6 mmol) were combined in DMF (38.0 mL) to give a yellow solution. The reaction mixture was stirred at room temperature overnight and was then treated with water and extracted with EtOAc. The organic phase was washed with brine, dried over MgSO$_4$, filtered, and concentrated under reduced pressure. The residue was purified by automated flash silica column chromatography (120 g column) eluting with a gradient of 20-50% EtOAc in heptanes. Fractions containing the desired product were evaporated to give the title compound (6.98 g, assumed quantitative). ESI-MS [M+H]$^+$ calc'd for C$_{22}$H$_{32}$F$_3$N$_3$O$_4$, 460.23; found, 460.55.

Step B: 2,2-dimethyl-N-(trans-3-methylpiperidin-4-yl)-3-((3-(trifluoromethyl)pyridin-2-yl)oxy)propanamide

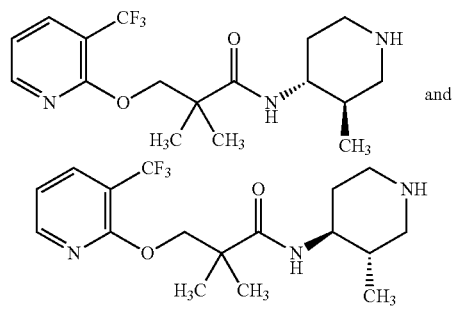

and

To a solution of tert-butyl trans-4-(2,2-dimethyl-3-((3-(trifluoromethyl)pyridin-2-yl)oxy)propanamido)-3-methylpiperidine-1-carboxylate (6.98 g, 15.2 mmol) in dioxane (30 mL) was added HCl (4 M in dioxane, 15.20 mL, 60.8 mmol). The mixture was heated at 50° C. for 3 hours. The mixture was concentrated to dryness to give the title compound as a light syrup (5.46 g, assumed quantitative) which was carried forward without purification. ESI-MS [M+H]+ calc'd for $C_{17}H_{24}F_3N_3O_2$, 360.19; found, 360.5.

Step C: trans-N-(1,3-dimethylpiperidin-4-yl)-2,2-dimethyl-3-((3-(trifluoromethyl)pyridin-2-yl)oxy)propanamide To a solution of 2,2-dimethyl-N-(trans-3-methylpiperidin-4-yl)-3-((3-(trifluoromethyl)pyridin-2-yl)oxy)propanamide (5.46 g, 15.2 mmol) and formaldehyde (37%, 2.33 mL, 30.1 mmol) in MeOH (35 mL) was added sodium cyanotrihydroborate (1.89 g, 30.1 mmol). The reaction mixture was stirred at room temperature overnight. The reaction mixture was purified by preparative HPLC (Method B) and the fractions which contain product were evaporated to give the title compound (4.31 g, 76%).

Example 110: trans-N-(3-ethyl-1-methylpiperidin-4-yl)-2,2-dimethyl-3-((3-(trifluoromethyl)pyridin-2-yl)oxy)propanamide

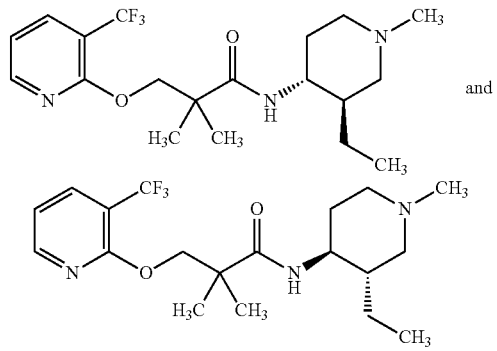

Example 111: cis-N-(3-ethyl-1-methylpiperidin-4-yl)-2,2-dimethyl-3-((3-(trifluoromethyl)pyridin-2-yl)oxy)propanamide

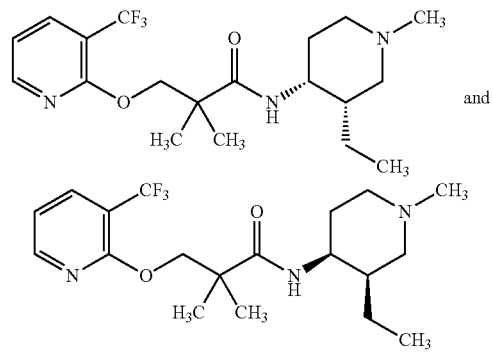

The title trans- and cis-stereoisomers were prepared in a manner similar to EXAMPLE 109, using tert-butyl 4-amino-3-ethylpiperidine-1-carboxylate (0.104 g, 0.456 mmol, 1 eq) in place of tert-butyl trans-4-amino-3-methylpiperidine-1-carboxylate, HCl. Following N-Boc deprotection of tert-butyl 4-(2,2-dimethyl-3-((3-(trifluoromethyl)pyridin-2-yl)oxy)propanamido)-3-ethylpiperidine-1-carboxylate, reductive methylation of N-(3-ethylpiperidin-4-yl)-2,2-dimethyl-3-((3-(trifluoromethyl)pyridin-2-yl)oxy)propanamide (170 mg, 0.456 mmol, 1 eq) gave a mixture of the title compounds, which was purified by preparative HPLC (Method B) to afford the trans-stereoisomer (first eluting peak) as a light brown film (29.3 mg, 17%) and the cis-stereoisomer (second eluting peak) as a light brown film (42.4 mg, 24%). Peak 1: $^1$H NMR (500 MHz, CD$_3$OD) δ ppm 0.77-0.86 (m, 3H), 0.99-1.08 (m, 1H), 1.31 (app d, J=3.9 Hz, 6H), 1.47-1.62 (m, 3H), 1.74 (br s, 2H), 2.00-2.11 (m, 1H), 2.28 (s, 3H), 2.83-2.91 (m, 1H), 2.94-3.03 (m, 1H), 3.46-3.58 (m, 1H), 4.45 (d, J=13.2 Hz, 2H), 7.03-7.14 (m, 1H), 7.94-8.03 (m, 1H), 8.29-8.39 (m, 1H); ESI-MS [M+H]+ calc'd for $C_{19}H_{28}F_3N_3O_2$, 388.21; found, 388.5. Peak 2: $^1$H NMR (500 MHz, CD$_3$OD) δ ppm 0.85 (t, J=7.6 Hz, 3H), 1.04-1.46 (m, 9H), 1.77 (dd, J=8.0, 3.7 Hz, 3H), 2.25 (s, 6H), 4.04-4.13 (m, 1H), 4.37-4.55 (m, 2H), 7.05-7.14 (m, 1H), 7.94-8.03 (m, 1H), 8.31-8.40 (m, 1H). ESI-MS [M+H]+ calc'd for $C_{19}H_{28}F_3N_3O_2$, 388.2; found, 388.5.

Example 112: 2,2-dimethyl-3-((3-(trifluoromethyl)pyridin-2-yl)oxy)-N-(1,3,3-trimethylpiperidin-4-yl)propanamide

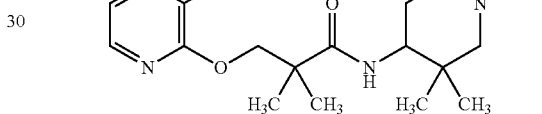

The title compound was prepared in a manner similar to EXAMPLE 109, using tert-butyl 4-amino-3,3-dimethylpiperidine-1-carboxylate (0.100 g, 0.438 mmol, 1 eq) in place of tert-butyl trans-4-amino-3-methylpiperidine-1-carboxylate, HCl. Following N-Boc deprotection of tert-butyl 4-(2,2-dimethyl-3-((3-(trifluoromethyl)pyridin-2-yl)oxy)propanamido)-3,3-dimethylpiperidine-1-carboxylate, reductive methylation of N-(3,3-dimethylpiperidin-4-yl)-2,2-dimethyl-3-((3-(trifluoromethyl)pyridin-2-yl)oxy)propanamide (164 mg, 0.438 mmol, 1 eq) gave the title compound as a light brown film (53.9 mg, 32%). $^1$H NMR (500 MHz, CD$_3$OD) δ ppm 0.81 (s, 3H), 0.96 (s, 3H), 1.32 (s, 6H), 1.47-1.54 (m, 1H), 1.72-1.83 (m, 1H) 1.87 (d, J=11.7 Hz, 1H), 1.93-2.05 (m, 1H), 2.21 (s, 3H), 2.50 (d, J=11.7 Hz, 1H), 2.77-2.90 (m, 1H), 3.65-3.74 (m, 1H), 4.46 (s, 2H), 7.05-7.14 (m, 1H), 7.95-8.03 (m, 1H), 8.29-8.40 (m, 1H); ESI-MS [M+H]+ calc'd for $C_{19}H_{28}F_3N_3O_2$, 388.21; found, 388.4.

Example 113: N-(3-fluoro-1-methylpiperidin-4-yl)-2,2-dimethyl-3-((3-(trifluoromethyl)pyridin-2-yl)oxy)propanamide

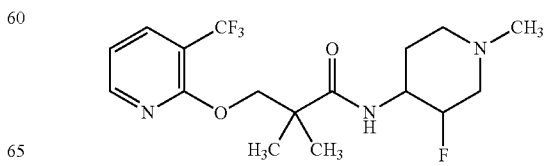

The title compound was prepared in a manner similar to EXAMPLE 109, using tert-butyl 4-amino-3-fluoropiperidine-1-carboxylate (0.104 g, 0.456 mmol, 1 eq) in place of tert-butyl trans-4-amino-3-methylpiperidine-1-carboxylate, HCl. Following N-Boc deprotection of tert-butyl 4-(2,2-dimethyl-3-((3-(trifluoromethyl)pyridin-2-yl)oxy)propanamido)-3-fluoropiperidine-1-carboxylate, reductive methylation of N-(3-fluoropiperidin-4-yl)-2,2-dimethyl-3-((3-(trifluoromethyl)pyridin-2-yl)oxy)propanamide (166 mg, 0.456 mmol, 1 eq) gave the title compound as a light brown film (56.6 mg, 33%). $^1$H NMR (500 MHz, CD$_3$OD) δ ppm 1.32 (app d, J=2.9 Hz, 6H), 1.59-1.71 (m, 1H), 1.97 (dd, J=12.7, 3.9 Hz, 1H), 2.15 (s, 1H), 2.27 (m, 4H), 2.85-2.94 (m, 1H), 3.08-3.21 (m, 1H), 3.82-3.97 (m, 1H), 4.37-4.50 (m, 2H), 4.57-4.73 (m, 1H), 7.04-7.13 (m, 1H), 7.93-8.03 (m, 1H), 8.29-8.40 (m, 1H); ESI-MS [M+H]$^+$ calc'd for C$_{17}$H$_{23}$F$_4$N$_3$O$_2$, 378.17; found, 378.4.

Example 114: 2,2-dimethyl-N-(5-methyl-5-azaspiro[2.5]octan-8-yl)-3-((3-(trifluoromethyl)pyridin-2-yl)oxy)propanamide

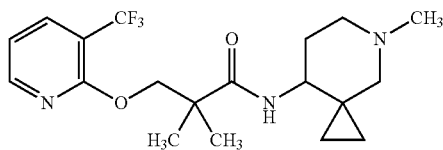 [SMILES: CN1CCC(NC(=O)C(C)(C)COc2ncccc2C(F)(F)F)C2(CC2)C1]

The title compound was prepared in a manner similar to EXAMPLE 109, using tert-butyl 8-amino-5-azaspiro[2.5]octane-5-carboxylate (0.198 g, 0.874 mmol, 1 eq) in place of tert-butyl trans-4-amino-3-methylpiperidine-1-carboxylate, HCl. Following N-Boc deprotection of tert-butyl 8-(2,2-dimethyl-3-((3-(trifluoromethyl)pyridin-2-yl)oxy)propanamido)-5-azaspiro[2.5]octane-5-carboxylate, reductive methylation of 2,2-dimethyl-N-(5-azaspiro[2.5]octan-8-yl)-3-((3-(trifluoromethyl)pyridin-2-yl)oxy)propanamide (169 mg, 0.456 mmol, 1 eq) gave the title compound as a light brown film (115.6 mg, 34%). $^1$H NMR (500 MHz, CD$_3$OD) δ ppm 0.20-0.32 (m, 2H), 0.34-0.41 (m, 1H), 0.48-0.56 (m, 1H), 1.29 (app d, J=5.9 Hz, 6H), 1.70-1.76 (m, 1H), 1.83 (s, 1H), 2.24 (s, 4H), 2.33 (br s, 2H), 2.67-2.84 (m, 1H), 3.81-3.98 (m, 1H), 4.35-4.52 (m, 2H), 7.04-7.13 (m, 1H), 7.94-8.03 (m, 1H), 8.30-8.40 (m, 1H); ESI-MS [M+H]$^+$ calc'd for C$_{19}$H$_{26}$F$_3$N$_3$O$_2$, 386.20; found, 386.4.

Example 115: N-(trans-3-ethyl-1-methylpiperidin-4-yl)-2,2-dimethyl-3-((3-(trifluoromethoxy)pyridin-2-yl)oxy)propanamide

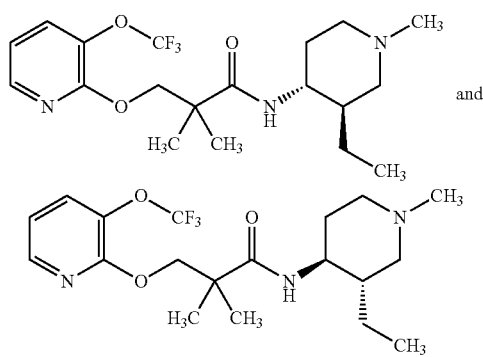

Example 116: N-(cis-3-ethyl-1-methylpiperidin-4-yl)-2,2-dimethyl-3-((3-(trifluoromethoxy)pyridin-2-yl)oxy)propanamide

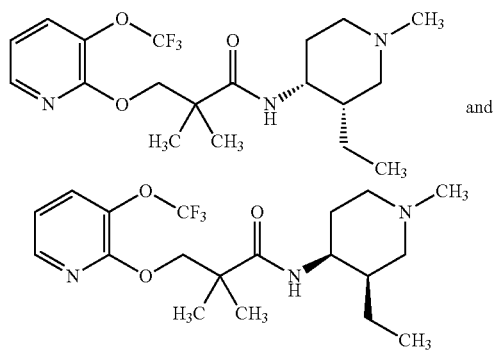

The title trans- and cis-stereoisomers were prepared in a manner similar to EXAMPLE 109, using 2,2-dimethyl-3-((3-(trifluoromethoxy)pyridin-2-yl)oxy)propanoic acid (0.122 g, 0.438 mmol) and tert-butyl 4-amino-3-ethylpiperidine-1-carboxylate (0.100 g, 0.438 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. Following N-Boc deprotection of tert-butyl 4-(2,2-dimethyl-3-((3-(trifluoromethoxy)pyridin-2-yl)oxy)propanamido)-3-ethylpiperidine-1-carboxylate, reductive methylation of N-(3-ethylpiperidin-4-yl)-2,2-dimethyl-3-((3-(trifluoromethoxy)pyridin-2-yl)oxy)propanamide (171 mg, 0.438 mmol, 1 eq) gave a mixture of the title compounds, which was purified by preparative HPLC (Method B) to afford the trans-stereoisomer (first eluting peak) as a colorless film (24.1 mg, 14%) and the cis-stereoisomer (second eluting peak) as a colorless film (12.5 mg, 7.1%). Peak 1: $^1$H NMR (500 MHz, CD$_3$OD) δ ppm 0.77-0.86 (m, 3H), 0.99-1.11 (m, 1H), 1.30 (app d, J=2.7 Hz, 6H), 1.49-1.62 (m, 3H), 1.74 (s, 2H), 2.01-2.11 (m, 1H), 2.28 (s, 3H), 2.83-2.90 (m, 1H), 2.95-3.00 (m, 1H), 3.48-3.56 (m, 1H), 4.40 (d, J=1.7 Hz, 2H), 6.99-7.05 (m, 1H), 7.61-7.69 (m, 1H), 8.06-8.14 (m, 1H); ESI-MS [M+H]$^+$ calc'd for C$_{19}$H$_{28}$F$_3$N$_3$O$_3$, 404.21; found, 404.4. Peak 2: $^1$H NMR (500 MHz, CD$_3$OD) δ ppm 0.85 (t, J=7.4 Hz, 3H), 1.32 (m, 9H), 1.65-1.82 (m, 3H), 2.24 (m, 4H), 2.41-2.59 (m, 2H), 4.05-4.14 (m, 1H), 4.42 (s, 2H), 7.02-7.09 (m, 1H), 7.66-7.74 (m, 1H), 8.11-8.15 (m, 1H); ESI-MS [M+H]$^+$ calc'd for C$_{19}$H$_{28}$F$_3$N$_3$O$_3$, 404.21; found, 404.4.

Example 117: N-((3S,4S)-3-fluoro-1-methylpiperidin-4-yl)-2,2-dimethyl-3-((3-(trifluoromethyl)pyridin-2-yl)oxy)propanamide

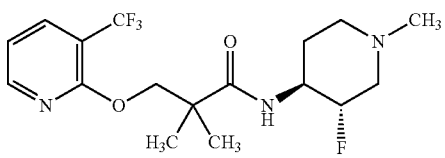 [SMILES: CN1CC[C@H](NC(=O)C(C)(C)COc2ncccc2C(F)(F)F)[C@@H](F)C1]

The title compound was prepared in a manner similar to EXAMPLE 109, using (3S,4S)-tert-butyl 4-amino-3-fluoropiperidine-1-carboxylate (0.058 g, 0.27 mmol, 1 eq) in place of tert-butyl trans-4-amino-3-methylpiperidine-1-carboxylate, HCl. Following N-Boc deprotection of (3S,4S)-tert-butyl 4-(2,2-dimethyl-3-((3-(trifluoromethyl)pyridin-2-yl)oxy)propanamido)-3-fluoropiperidine-1-carboxylate, reductive methylation of N-((3S,4S)-3-fluoropiperidin-4-yl)-2,2-dimethyl-3-((3-(trifluoromethyl)pyridin-2-yl)oxy)propanamide (97 mg, 0.266 mmol, 1 eq) gave the title compound as a light grey film (62.3 mg, 62%). $^1$H NMR (500 MHz, CD$_3$OD) δ ppm 1.32 (app d, J=18.1 Hz, 6H), 1.49-1.63 (m, 1H), 1.82-1.92 (m, 1H), 2.05-2.15 (m, 2H), 2.32 (s, 3H), 2.72-2.79 (m, 1H), 3.12 (br dd, J=6.0, 4.8 Hz, 1H), 3.83-3.93 (m, 1H), 4.39 (d, J=10.5 Hz, 1H), 4.42-4.60 (m, 2H), 7.01-7.12 (m, 1H), 7.93-8.01 (m, 1H), 8.27-8.38 (m, 1H); ESI-MS [M+H]$^+$ calc'd for C$_{17}$H$_{23}$F$_4$N$_3$O$_2$, 378.17; found, 378.3.

Example 118: N-(3,3-difluoro-1-methylpiperidin-4-yl)-2,2-dimethyl-3-((3-(trifluoromethyl)pyridin-2-yl)oxy)propanamide

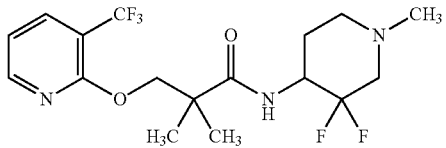 [SMILES: CN1CCC(NC(=O)C(C)(C)COc2ncccc2C(F)(F)F)C(F)(F)C1]

The title compound was prepared in a manner similar to EXAMPLE 109, using tert-butyl 4-amino-3,3-difluoropiperidine-1-carboxylate (0.090 g, 0.38 mmol, 1 eq) in place of tert-butyl trans-4-amino-3-methylpiperidine-1-carboxylate, HCl. Following N-Boc deprotection of tert-butyl 4-(2,2-dimethyl-3-((3-(trifluoromethyl)pyridin-2-yl)oxy)propanamido)-3,3-difluoropiperidine-1-carboxylate, reductive methylation of N-(3,3-difluoropiperidin-4-yl)-2,2-dimethyl-3-((3-(trifluoromethyl)pyridin-2-yl)oxy)propanamide (145 mg, 0.38 mmol, 1 eq) gave the title compound as a colorless film (88.5 mg, 59%). $^1$H NMR (500 MHz, CD$_3$OD) δ ppm 1.33 (app d, J=13.9 Hz, 6H), 1.75-1.91 (m, 2H), 2.16-2.24 (m, 1H), 2.33 (m, 4H), 2.83-2.91 (m, 1H), 3.05-3.14 (m, 1H), 4.19-4.33 (m, 1H), 4.41-4.53 (m, 2H), 7.06-7.13 (m, 1H), 7.95-8.01 (m, 1H), 8.31-8.37 (m, 1H); ESI-MS [M+H]$^+$ calc'd for C$_{17}$H$_{22}$F$_5$N$_3$O$_2$, 396.16; found, 396.3.

Example 119: 2,2-dimethyl-N-(5-methyl-5-azaspiro[2.5]octan-8-yl)-3-((3-(trifluoromethoxy)pyridin-2-yl)oxy)propanamide

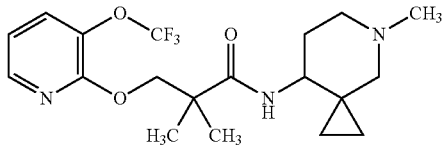 [SMILES: CN1CCC(NC(=O)C(C)(C)COc2ncccc2OC(F)(F)F)C2(CC2)C1]

The title compound was prepared in a manner similar to EXAMPLE 109, using 2,2-dimethyl-3-((3-(trifluoromethoxy)pyridin-2-yl)oxy)propanoic acid (0.123 g, 0.442 mmol) and tert-butyl 8-amino-5-azaspiro[2.5]octane-5-carboxylate (0.100 g, 0.442 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. Following N-Boc deprotection of tert-butyl 8-(2,2-dimethyl-3-((3-(trifluoromethoxy)pyridin-2-yl)oxy)propanamido)-5-azaspiro[2.5]octane-5-carboxylate, reductive methylation of 2,2-dimethyl-N-(5-azaspiro[2.5]octan-8-yl)-3-((3-(trifluoromethoxy)pyridin-2-yl)oxy)propanamide (171 mg, 0.442 mmol, 1 eq) gave the title compound as a colorless film (32.9 mg, 19%). $^1$H NMR (500 MHz, CD$_3$OD) δ ppm 0.20-0.32 (m, 2H), 0.41 (br d, J=4.6 Hz, 1H), 0.51 (s, 1H), 1.28 (app d, J=1.0 Hz, 6H), 1.75 (br d, J=4.4 Hz, 1H), 1.79-1.89 (m, 1H), 2.24 (m, 4H), 2.33 (br d, J=8.3 Hz, 2H), 2.68-2.81 (m, 1H), 3.81-3.95 (m, 1H), 4.39 (s, 2H), 6.98-7.08 (m, 1H), 7.64-7.71 (m, 1H), 8.08-8.15 (m, 1H); ESI-MS [M+H]$^+$ calc'd for C$_{19}$H$_{26}$F$_3$N$_3$O$_3$, 402.19; found, 402.3.

Example 120: N-(3-chloro-1-methylpiperidin-4-yl)-2,2-dimethyl-3-((3-(trifluoromethyl)pyridin-2-yl)oxy)propanamide

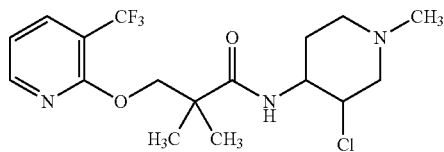

The title compound was prepared in a manner similar to EXAMPLE 109, using tert-butyl 4-amino-3-chloropiperidine-1-carboxylate (0.169 g, 0.490 mmol, 1 eq) in place of tert-butyl trans-4-amino-3-methylpiperidine-1-carboxylate, HCl. Following N-Boc deprotection of tert-butyl 3-chloro-4-(2,2-dimethyl-3-((3-(trifluoromethyl)pyridin-2-yl)oxy)propanamido)piperidine-1-carboxylate, reductive methylation of N-(3-chloropiperidin-4-yl)-2,2-dimethyl-3-((3-(trifluoromethyl)pyridin-2-yl)oxy)propanamide (186 mg, 0.49 mmol, 1 eq) gave the title compound as a colorless film (6.4 mg, 3.3%). $^1$H NMR (500 MHz, CD$_3$OD) δ ppm 1.32 (app d, J=8.5 Hz, 6H), 1.52-1.63 (m, 1H), 2.01-2.13 (m, 1H), 2.14-2.23 (m, 1H), 2.29 (s, 3H), 2.52-2.62 (m, 1H), 2.85-2.96 (m, 1H), 3.04-3.15 (m, 1H), 3.95-4.05 (m, 1H), 4.36-4.52 (m, 3H), 7.05-7.12 (m, 1H), 7.93-8.02 (m, 1H), 8.34 (s, 1H); ESI-MS [M+H]$^+$ calc'd for C$_{17}$H$_{23}$ClF$_3$N$_3$O$_2$, 394.14; found, 394.3.

Example 121: N-((3S,4S)-3-fluoro-1-methylpiperidin-4-yl)-2,2-dimethyl-3-((3-methylpyridin-2-yl)oxy)propanamide

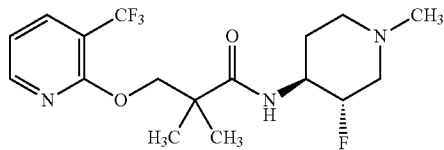 [SMILES: CN1CC[C@H](NC(=O)C(C)(C)COc2ncccc2C(F)(F)F)[C@@H](F)C1]

The title compound was prepared in a manner similar to EXAMPLE 109, using 2,2-dimethyl-3-((3-methylpyridin-2-yl)oxy)propanoic acid (0.061 g, 0.29 mmol) (3S,4S)-tert-butyl 4-amino-3-fluoropiperidine-1-carboxylate (0.058 g, 0.27 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. Following N-Boc deprotection of (3S,4S)-tert-butyl 4-(2,2-dimethyl-3-((3-methylpyridin-2-yl)oxy)propanamido)-3-fluoropiperidine-1-carboxylate, reductive methylation of N-((3S,4S)-3-fluoropiperidin-4-yl)-2,2-dimethyl-3-((3-methylpyridin-2-yl)oxy)propanamide (82 mg, 0.266 mmol, 1 eq) gave the title compound as a colorless film (71.0 mg, 83%). $^1$H NMR (500 MHz, CD$_3$OD) δ ppm 1.31 (s, 6H), 1.50-1.62 (m, 1H), 1.80-1.90 (m, 1H), 2.04-2.13 (m, 2H), 2.15 (s, 3H), 2.31 (s, 3H), 2.71-2.79 (m, 1H), 3.07-3.16 (m, 1H), 3.83-3.95 (m, 1H), 4.30 (d, J=1.7 Hz, 2H), 4.41-4.60 (m, 1H), 6.83 (dd, J=7.1, 5.1 Hz, 1H), 7.45 (s, 1H), 7.83-7.93 (m, 1H); ESI-MS [M+H]$^+$ calc'd for C$_{17}$H$_{26}$FN$_3$O$_2$, 324.20; found, 324.4.

Example 122: 3-((3,5-dimethylpyridin-2-yl)oxy)-N-((3S,4S)-3-fluoro-1-methylpiperidin-4-yl)-2,2-dimethylpropanamide

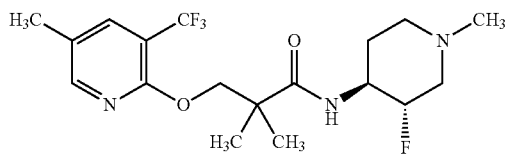

The title compound was prepared in a manner similar to EXAMPLE 109, using 3-((3,5-dimethylpyridin-2-yl)oxy)-2,2-dimethylpropanoic acid (0.065 g, 0.29 mmol) and (3S,4S)-tert-butyl 4-amino-3-fluoropiperidine-1-carboxylate (0.058 g, 0.27 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. Following N-Boc deprotection of (3S,4S)-tert-butyl 4-(3-((3,5-dimethylpyridin-2-yl)oxy)-2,2-dimethylpropanamido)-3-fluoropiperidine-1-carboxylate, reductive methylation of 3-((3,5-dimethylpyridin-2-yl)oxy)-N-((3S,4S)-3-fluoropiperidin-4-yl)-2,2-dimethylpropanamide (86 mg, 0.266 mmol, 1 eq) gave the title compound as a colorless film (35.2 mg, 39%). $^1$H NMR (500 MHz, CD$_3$OD) δ ppm 1.30 (app d, J=1.5 Hz, 6H), 1.49-1.61 (m, 1H), 1.81-1.90 (m, 1H), 2.05-2.14 (m, 5H), 2.19 (s, 3H), 2.31 (s, 3H), 2.72-2.80 (m, 1H), 3.06-3.16 (m, 1H), 3.83-3.94 (m, 1H), 4.26 (d, J=1.2 Hz, 2H), 4.41-4.58 (m, 1H), 7.29-7.33 (m, 1H), 7.68-7.74 (m, 1H); ESI-MS [M+H]$^+$ calc'd for C$_{18}$H$_{28}$FN$_3$O$_2$, 338.22; found, 338.3.

Example 123: 3-((3-cyclopropylpyridin-2-yl)oxy)-N-((3S,4S)-3-fluoro-1-methylpiperidin-4-yl)-2,2-dimethylpropanamide

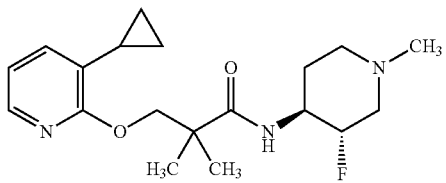 [SMILES: CN1CC[C@H](NC(=O)C(C)(C)COc2ncccc2C2CC2)[C@@H](F)C1]

The title compound was prepared in a manner similar to EXAMPLE 109, using 3-((3-cyclopropylpyridin-2-yl)oxy)-2,2-dimethylpropanoic acid (73 mg, 0.29 mmol) and (3S,4S)-tert-butyl 4-amino-3-fluoropiperidine-1-carboxylate (0.058 g, 0.27 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. Following N-Boc deprotection of (3S,4S)-tert-butyl 4-(3-((3-cyclopropylpyridin-2-yl)oxy)-2,2-dimethylpropanamido)-3-fluoropiperidine-1-carboxylate, reductive methylation of 3-((3-cyclopropylpyridin-2-yl)oxy)-N-((3S,4S)-3-fluoropiperidin-4-yl)-2,2-dimethylpropanamide (89 mg, 0.266 mmol, 1 eq) gave crude product, which was purified by preparative HPLC (Method A) to afford a TFA salt of the title compound as a colorless film (5.7 mg, 4.6%). $^1$H NMR (500 MHz, CD$_3$OD) δ ppm 0.65 (br d, J=3.9 Hz, 2H), 0.91 (br d, J=7.6 Hz, 2H), 1.35 (s, 6H), 1.80-2.03 (m, 2H), 2.07-2.37 (m, 1H), 2.82-2.97 (m, 3H), 3.10-3.25 (m, 2H), 3.37-3.54 (m, 1H), 3.58-3.88 (m, 1H), 4.11-4.22 (m, 1H), 4.35 (br s, 2H), 4.85 (s, 1H), 6.86 (br s, 1H), 7.25 (br s, 1H), 7.82-7.93 (m, 1H); ESI-MS [M+H]$^+$ calc'd for C$_{19}$H$_{28}$FN$_3$O$_2$, 350.22; found, 350.3.

Example 124: N-((3S,4S)-3-fluoro-1-methylpiperidin-4-yl)-2,2-dimethyl-3-((3-(trifluoromethoxy)pyridin-2-yl)oxy)propanamide

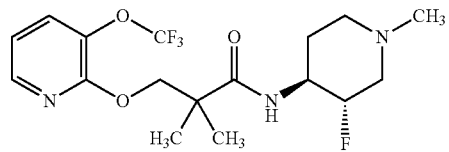 [SMILES: CN1CC[C@H](NC(=O)C(C)(C)COc2ncccc2OC(F)(F)F)[C@@H](F)C1]

The title compound was prepared in a manner similar to EXAMPLE 109, using 2,2-dimethyl-3-((3-(trifluoromethoxy)pyridin-2-yl)oxy)propanoic acid (0.082 g, 0.29 mmol) and (3S,4S)-tert-butyl 4-amino-3-fluoropiperidine-1-carboxylate (0.058 g, 0.27 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. Following N-Boc deprotection of (3S,4S)-tert-butyl 4-(2,2-dimethyl-3-((3-(trifluoromethoxy)pyridin-2-yl)oxy)propanamido)-3-fluoropiperidine-1-carboxylate, reductive methylation of N-((3S,4S)-3-fluoropiperidin-4-yl)-2,2-dimethyl-3-((3-(trifluoromethoxy)pyridin-2-yl)oxy)propanamide (101 mg, 0.266 mmol, 1 eq) gave the title compound as a pale beige solid (74.4 mg, 71%). $^1$H NMR (500 MHz, CD$_3$OD) δ ppm 1.31 (app d, J=14.6 Hz, 6H), 1.50-1.62 (m, 1H), 1.80-1.93 (m, 1H), 2.05-2.16 (m, 2H), 2.32 (s, 3H), 2.69-2.80 (m, 1H), 3.06-3.17 (m, 1H), 3.82-3.95 (m, 1H), 4.35-4.60 (m, 3H), 6.96-7.05 (m, 1H), 7.59-7.70 (m, 1H), 8.07-8.14 (m, 1H), 8.37-8.39 (m, 1H); ESI-MS [M+H]$^+$ calc'd for C$_{17}$H$_{23}$F$_4$N$_3$O$_3$, 394.17; found, 394.3.

Example 125: trans-N-(3-(1-(difluoromethyl)-1H-pyrazol-4-yl)-1-methylpiperidin-4-yl)-2,2-dimethyl-3-((3-(trifluoromethyl)pyridin-2-yl)oxy)propanamide

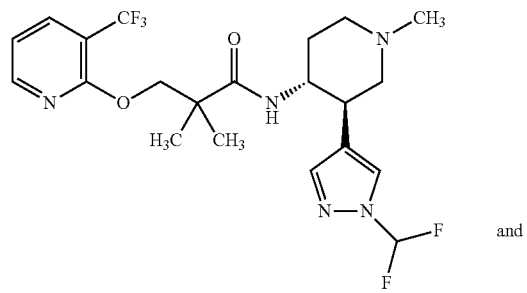

and

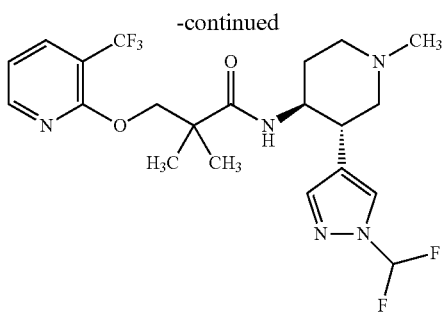

The title compound was prepared in a manner similar to EXAMPLE 109, using trans-tert-butyl 4-amino-3-(1-(difluoromethyl)-1H-pyrazol-4-yl)piperidine-1-carboxylate (0.120 g, 0.380 mmol, 1 eq) in place of tert-butyl trans-4-amino-3-methylpiperidine-1-carboxylate, HCl. Following N-Boc deprotection of trans-tert-butyl 3-(1-(difluoromethyl)-1H-pyrazol-4-yl)-4-(2,2-dimethyl-3-((3-(trifluoromethyl)pyridin-2-yl)oxy)propanamido)piperidine-1-carboxylate, reductive methylation of N-(3-(1-(difluoromethyl)-1H-pyrazol-4-yl)piperidin-4-yl)-2,2-dimethyl-3-((3-(trifluoromethyl)pyridin-2-yl)oxy)propanamide (175 mg, 0.38 mmol, 1 eq) gave crude product, which was purified by preparative HPLC (Method A) to afford a TFA salt of the title compound as a colorless film (3.7 mg, 1.7%). $^1$H NMR (500 MHz, CD$_3$OD) δ ppm 1.05 (s, 3H), 1.14-1.18 (m, 3H), 2.08-2.14 (m, 1H), 2.90 (s, 3H), 3.21-3.27 (m, 1H), 3.58-3.65 (m, 2H), 4.05-4.14 (m, 3H), 4.19-4.25 (m, 2H), 4.36-4.44 (m, 1H), 7.02-7.13 (m, 1H), 7.27-7.70 (m, 2H), 7.97 (s, 2H), 8.29-8.37 (m, 1H); ESI-MS [M+H]$^+$ calc'd for C$_{21}$H$_{26}$F$_5$N$_5$O$_2$, 476.20; found, 476.3.

Example 126: trans-N-(3-(1-(difluoromethyl)-1H-pyrazol-4-yl)-1-methylpiperidin-4-yl)-2,2-dimethyl-3-((3-(trifluoromethoxy)pyridin-2-yl)oxy)propanamide

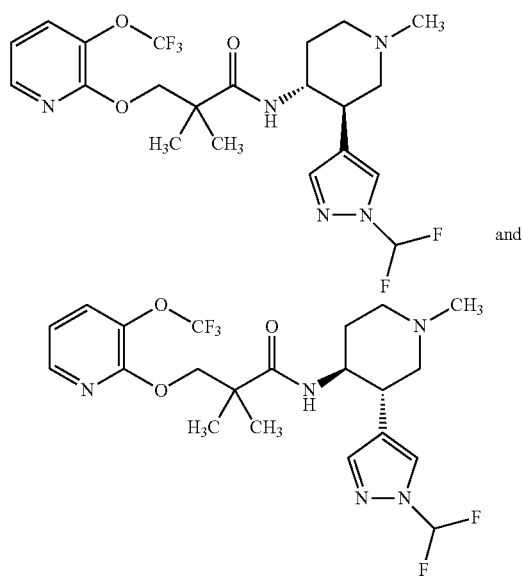

The title compound was prepared in a manner similar to EXAMPLE 109, using 2,2-dimethyl-3-((3-(trifluoromethoxy)pyridin-2-yl)oxy)propanoic acid (0.120 g, 0.430 mmol) and trans-tert-butyl 4-amino-3-(1-(difluoromethyl)-1H-pyrazol-4-yl)piperidine-1-carboxylate (0.136 g, 0.430 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. Following N-Boc deprotection of trans-tert-butyl 3-(1-(difluoromethyl)-1H-pyrazol-4-yl)-4-(2,2-dimethyl-3-((3-(trifluoromethoxy)pyridin-2-yl)oxy)propanamido)piperidine-1-carboxylate, reductive methylation of trans-N-(3-(1-(difluoromethyl)-1H-pyrazol-4-yl)piperidin-4-yl)-2,2-dimethyl-3-((3-(trifluoromethoxy)pyridin-2-yl)oxy)propanamide (205 mg, 0.43 mmol, 1 eq) gave crude product, which was purified by preparative HPLC (Method A) to afford a TFA salt of the title compound as a white solid (9.0 mg, 3.5%). $^1$H NMR (500 MHz, CD$_3$OD) δ ppm 1.05 (s, 3H), 1.17 (s, 3H), 1.92-2.03 (m, 1H), 2.06-2.15 (m, 1H), 2.90 (s, 3H), 3.18-3.28 (m, 2H), 3.33-3.37 (m, 1H), 3.56-3.67 (m, 2H), 4.18-4.27 (m, 2H), 4.32-4.40 (m, 1H), 7.02 (ddd, J=7.8, 5.0, 0.8 Hz, 1H), 7.66 (s, 3H), 7.95-7.99 (m, 1H), 8.06-8.11 (m, 1H); ESI-MS [M+H]$^+$ calc'd for C$_{21}$H$_{26}$F$_5$N$_5$O$_3$, 492.20; found, 492.4.

Example 127: trans-N-(3-ethyl-1-methylpiperidin-4-yl)-2,2-dimethyl-3-((3-methylpyridin-2-yl)oxy)propanamide

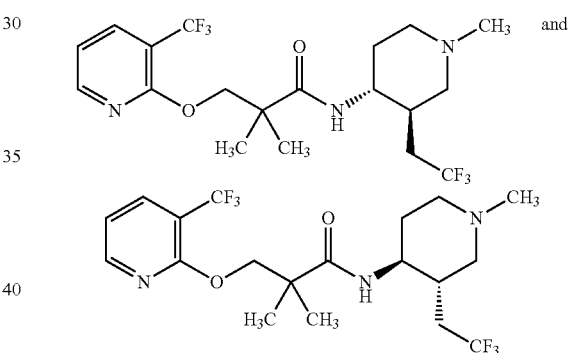

The title compound was prepared in a manner similar to EXAMPLE 109, using 2,2-dimethyl-3-((3-methylpyridin-2-yl)oxy)propanoic acid (0.070 g, 0.34 mmol) and tert-butyl trans-4-amino-3-ethylpiperidine-1-carboxylate (0.076 g, 0.34 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. Following N-Boc deprotection of tert-butyl trans-4-(2,2-dimethyl-3-((3-methylpyridin-2-yl)oxy)propanamido)-3-ethylpiperidine-1-carboxylate, reductive methylation of trans-N-(3-ethylpiperidin-4-yl)-2,2-dimethyl-3-((3-methylpyridin-2-yl)oxy)propanamide (107 mg, 0.335 mmol, 1 eq) gave the title compound as a light brown film (23.5 mg, 21%). $^1$H NMR (500 MHz, CD$_3$OD) δ ppm 0.79 (t, J=7.6 Hz, 3H), 0.97-1.08 (m, 1H), 1.31 (s, 6H), 1.56 (br s, 3H), 1.74 (t, J=11.4 Hz, 2H), 2.00-2.09 (m, 1H), 2.82-3.00 (m, 2H), 3.48-3.58 (m, 1H), 4.31 (d, J=9.3 Hz, 2H), 6.81-6.87 (m, 1H), 7.45-7.50 (m, 1H), 7.89-7.94 (m, 1H); ESI-MS [M+H]$^+$ calc'd for C$_{19}$H$_{31}$N$_3$O$_2$, 334.24; found, 334.3.

Example 128: trans-3-((3,5-dimethylpyridin-2-yl)oxy)-N-(3-ethyl-1-methylpiperidin-4-yl)-2,2-dimethylpropanamide

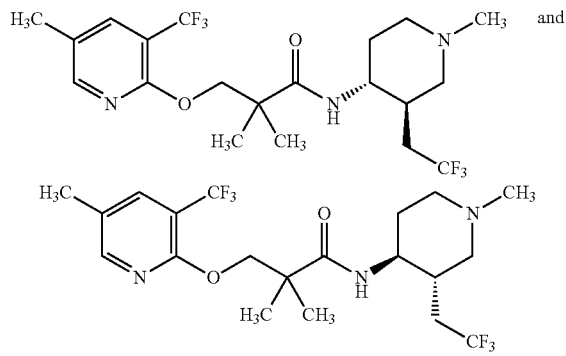

The title compound was prepared in a manner similar to EXAMPLE 109, using 3-((3,5-dimethylpyridin-2-yl)oxy)-2,2-dimethylpropanoic acid (0.070 g, 0.31 mmol) and tert-butyl trans-4-amino-3-ethylpiperidine-1-carboxylate (0.072 g, 0.31 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. Following N-Boc deprotection of tert-butyl trans-4-(3-((3,5-dimethylpyridin-2-yl)oxy)-2,2-dimethylpropanamido)-3-ethylpiperidine-1-carboxylate, reductive methylation of trans-3-((3,5-dimethylpyridin-2-yl)oxy)-N-(3-ethylpiperidin-4-yl)-2,2-dimethylpropanamide (105 mg, 0.314 mmol, 1 eq) gave the title compound as a colorless film (19.8 mg, 18%). $^1$H NMR (500 MHz, CD$_3$OD) δ ppm 0.79 (s, 3H), 0.97-1.07 (m, 1H), 1.30 (s, 6H), 1.47-1.59 (m, 3H), 1.74 (s, 2H), 2.02-2.09 (m, 1H), 2.13 (s, 3H), 2.20 (s, 3H), 2.28 (s, 3H), 2.83-3.00 (m, 2H), 3.47-3.56 (m, 1H), 4.22-4.32 (m, 2H), 7.30-7.34 (m, 1H), 7.70-7.74 (m, 1H); ESI-MS [M+H]$^+$ calc'd for C$_{20}$H$_{33}$N$_3$O$_2$, 348.26; found, 348.3.

Example 129: cis-N-(1,2-dimethylpiperidin-4-yl)-2,2-dimethyl-3-((3-(trifluoromethyl)pyridin-2-yl)oxy)propanamide

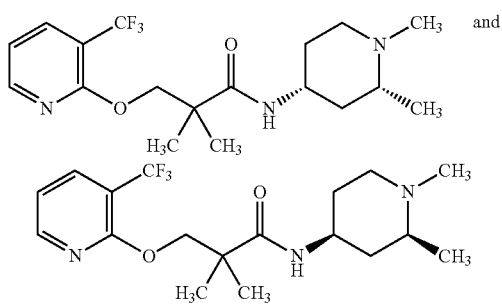

The title compound was prepared in a manner similar to EXAMPLE 109, using cis-tert-butyl 4-amino-2-methylpiperidine-1-carboxylate (0.081 g, 0.38 mmol, 1 eq) in place of tert-butyl trans-4-amino-3-methylpiperidine-1-carboxylate, HCl. Following N-Boc deprotection of tert-butyl cis-4-(2,2-dimethyl-3-((3-(trifluoromethyl)pyridin-2-yl)oxy)propanamido)-2-methylpiperidine-1-carboxylate, reductive methylation of cis-2,2-dimethyl-N-(2-methylpiperidin-4-yl)-3-((3-(trifluoromethyl)pyridin-2-yl)oxy)propanamide (137 mg, 0.38 mmol, 1 eq) gave the title compound as a light brown film (92.7 mg, 65%). $^1$H NMR (400 MHz, CD$_3$OD) δ ppm 1.11 (d, J=6.3 Hz, 3H), 1.29 (m, 7H), 1.50-1.65 (m, 1H), 1.73-1.85 (m, 2H), 2.03-2.14 (m, 1H), 2.17-2.26 (m, 1H), 2.28 (s, 3H), 2.86-2.96 (m, 1H), 3.70-3.87 (m, 1H), 4.43 (s, 2H), 7.03-7.13 (m, 1H), 7.89-8.03 (m, 1H), 8.29-8.39 (m, 1H); ESI-MS [M+H]$^+$ calc'd for C$_{18}$H$_{26}$F$_3$N$_3$O$_2$, 374.20; found, 374.3.

Example 130: trans-N-(4-fluoropyrrolidin-3-yl)-2,2-dimethyl-3-((3-(trifluoromethyl)pyridin-2-yl)oxy)propanamide

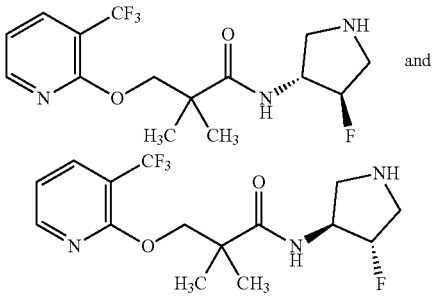

The title compound was prepared in a manner similar to EXAMPLE 109, (STEPS A and B) using trans-tert-butyl 3-amino-4-fluoropyrrolidine-1-carboxylate (0.078 g, 0.38 mmol) in place of tert-butyl trans-4-amino-3-methylpiperidine-1-carboxylate, HCl. N-Boc deprotection of tert-butyl trans-3-(2,2-dimethyl-3-((3-(trifluoromethyl)pyridin-2-yl)oxy)propanamido)-4-fluoropyrrolidine-1-carboxylate (0.157 g, 0.349 mmol, 1 eq) gave crude product, which was purified by preparative HPLC (Method A) to give a TFA salt of the title compound as a colorless film (9.6 mg, 6%). $^1$H NMR (400 MHz, CD$_3$OD) δ ppm 1.32 (app d, J=2.3 Hz, 6H), 3.40-3.49 (m, 1H), 3.57-3.81 (m, 3H), 4.42 (m, 3H), 5.15-5.34 (m, 1H), 7.04-7.14 (m, 1H), 7.94-8.03 (m, 1H), 8.29-8.39 (m, 1H); ESI-MS [M+H]$^+$ calc'd for C$_{15}$H$_{19}$F$_4$N$_3$O$_2$, 350.14; found, 350.3.

Example 131: N-(4,4-difluoropyrrolidin-3-yl)-2,2-dimethyl-3-((3-(trifluoromethyl)pyridin-2-yl)oxy)propanamide

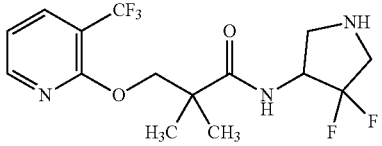 [SMILES: CC(C)(COc1ncccc1C(F)(F)F)C(=O)NC1CNCC1(F)F]

The title compound was prepared in a manner similar to EXAMPLE 109 (STEPS A and B) using tert-butyl 4-amino-3,3-difluoropyrrolidine-1-carboxylate (0.100 g, 0.450 mmol, 1 eq) in place of tert-butyl trans-4-amino-3-methylpiperidine-1-carboxylate, HCl. N-Boc deprotection of tert-butyl 4-(2,2-dimethyl-3-((3-(trifluoromethyl)pyridin-2-yl)oxy)propanamido)-3,3-difluoropyrrolidine-1-carboxylate (210 mg, 0.45 mmol, 1 eq) gave crude product, which was purified by preparative HPLC (Method B) to give the title compound as an off-white solid (122.3 mg, 74%). $^1$H NMR (400 MHz, CD$_3$OD) δ ppm 1.34 (app d, J=10.6 Hz, 6H), 2.78-2.92 (m, 1H), 3.01-3.16 (m, 1H), 3.23-3.28 (m, 1H), 3.33-3.40 (m, 1H), 4.39-4.62 (m, 3H), 7.02-7.15 (m, 1H), 7.91-8.05 (m, 1H), 8.25-8.41 (m, 1H); ESI-MS [M+H]$^+$ calc'd for C$_{15}$H$_{18}$F$_5$N$_3$O$_2$, 368.13; found, 368.3.

Example 132: 2,2-dimethyl-3-((3-(trifluoromethyl)pyridin-2-yl)oxy)-N-(1,2,2-trimethylpiperidin-4-yl)propanamide

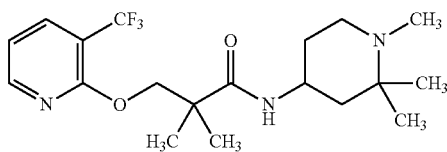 [SMILES: CN1CCC(NC(=O)C(C)(C)COc2ncccc2C(F)(F)F)CC1(C)C]

The title compound was prepared in a manner similar to EXAMPLE 109, using tert-butyl 4-amino-2,2-dimethylpiperidine-1-carboxylate (0.108 g, 0.304 mmol, 1 eq) in place of tert-butyl trans-4-amino-3-methylpiperidine-1-carboxylate, HCl. Following N-Boc deprotection of tert-butyl 4-(2,2-dimethyl-3-((3-(trifluoromethyl)pyridin-2-yl)oxy)propanamido)-2,2-dimethylpiperidine-1-carboxylate, reductive methylation of N-(2,2-dimethylpiperidin-4-yl)-2,2-dimethyl-3-((3-(trifluoromethyl)pyridin-2-yl)oxy)propanamide (114 mg, 0.304 mmol, 1 eq) gave the title compound as a yellowish-green film (31.8 mg, 27%). $^1$H NMR (400 MHz, CD$_3$OD) δ ppm 1.02 (s, 3H), 1.14 (s, 3H), 1.28 (s, 6H), 1.38 (s, 1H), 1.48-1.54 (m, 1H), 1.58-1.65 (m, 1H), 1.72-1.84 (m, 1H), 2.23 (s, 3H), 2.50-2.71 (m, 2H), 3.86-4.03 (m, 1H), 4.42 (s, 2H), 7.03-7.13 (m, 1H), 7.92-8.03 (m, 1H), 8.24-8.40 (m, 1H); ESI-MS [M+H]$^+$ calc'd for C$_{19}$H$_{28}$F$_3$N$_3$O$_2$, 388.21; found, 388.4.

Example 133: trans-N-(1,5-dimethylpyrrolidin-3-yl)-2,2-dimethyl-3-((3-(trifluoromethyl)pyridin-2-yl)oxy)propanamide

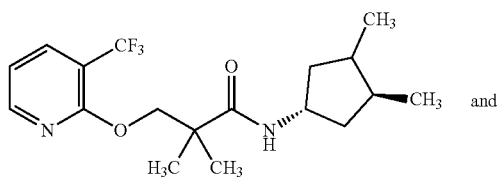

The title compound was prepared in a manner similar to EXAMPLE 109, using tert-butyl trans-4-amino-2-methylpyrrolidine-1-carboxylate (0.061 g, 0.30 mmol) in place of tert-butyl trans-4-amino-3-methylpiperidine-1-carboxylate, HCl. Following N-Boc deprotection of tert-butyl trans-4-(2,2-dimethyl-3-((3-(trifluoromethyl)pyridin-2-yl)oxy)propanamido)-2-methylpyrrolidine-1-carboxylate, reductive methylation of trans-2,2-dimethyl-N-(5-methylpyrrolidin-3-yl)-3-((3-(trifluoromethyl)pyridin-2-yl)oxy)propanamide (105 mg, 0.304 mmol, 1 eq) gave the title compound as a brown film (69.5 mg, 64%). $^1$H NMR (400 MHz, CD$_3$OD) δ ppm 1.10 (d, J=6.1 Hz, 3H), 1.29 (s, 6H), 1.75-1.93 (m, 2H), 2.16 (dd, J=9.8, 8.2 Hz, 1H), 2.29 (s, 3H), 2.40-2.54 (m, 1H), 3.33-3.39 (m, 1H), 4.24-4.35 (m, 1H), 4.42 (s, 2H), 7.03-7.13 (m, 1H), 7.93-8.02 (m, 1H), 8.29-8.39 (m, 1H); ESI-MS [M+H]$^+$ calc'd for C$_{17}$H$_{24}$F$_3$N$_3$O$_2$, 360.19; found, 360.3.

Example 134: cis-N-(1,5-dimethylpyrrolidin-3-yl)-2,2-dimethyl-3-((3-(trifluoromethyl)pyridin-2-yl)oxy)propanamide

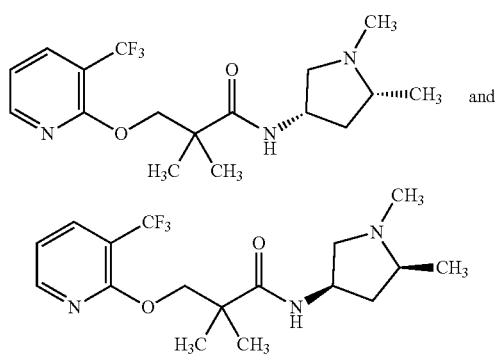

The title compound was prepared in a manner similar to EXAMPLE 109, using tert-butyl cis-4-amino-2-methylpyrrolidine-1-carboxylate (0.061 g, 0.30 mmol) in place of tert-butyl trans-4-amino-3-methylpiperidine-1-carboxylate, HCl. Following N-Boc deprotection of tert-butyl cis-4-(2,2-dimethyl-3-((3-(trifluoromethyl)pyridin-2-yl)oxy)propanamido)-2-methylpyrrolidine-1-carboxylate, reductive methylation of cis-2,2-dimethyl-N-(5-methylpyrrolidin-3-yl)-3-((3-(trifluoromethyl)pyridin-2-yl)oxy)propanamide (106 mg, 0.308 mmol, 1 eq) gave the title compound as a pale yellow film (76.4 mg, 69%). $^1$H NMR (400 MHz, CD$_3$OD) δ ppm 1.15 (d, J=6.1 Hz, 3H), 1.29 (app d, J=1.6 Hz, 6H), 1.30-1.36 (m, 1H), 2.15-2.25 (m, 1H), 2.29 (s, 3H), 2.39-2.53 (m, 2H), 2.82-2.93 (m, 1H), 4.21-4.33 (m, 1H), 4.41 (d, J=0.8 Hz, 2H), 7.08 (dd, J=7.2, 5.1 Hz, 1H), 7.90-8.04 (m, 1H), 8.27-8.38 (m, 1H); ESI-MS [M+H]$^+$ calc'd for C$_{17}$H$_{24}$F$_3$N$_3$O$_2$, 360.19; found, 360.3.

Example 135: trans-N-(1,2-dimethylpiperidin-4-yl)-2,2-dimethyl-3-((3-(trifluoromethoxy)pyridin-2-yl)oxy)propanamide

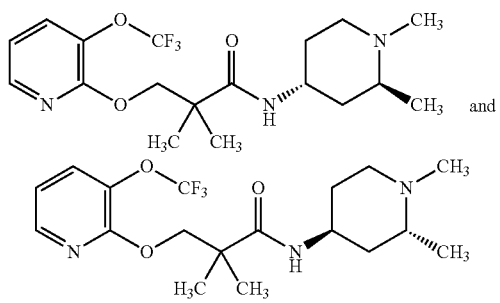

The title compound was prepared in a manner similar to EXAMPLE 109, using 2,2-dimethyl-3-((3-(trifluoromethoxy)pyridin-2-yl)oxy)propanoic acid (0.100 g, 0.358 mmol) and tert-butyl trans-4-amino-2-methylpiperidine-1-carboxylate (0.077 g, 0.36 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. Following N-Boc deprotection of tert-butyl trans-4-(2,2-dimethyl-3-((3-(trifluoromethoxy)pyridin-2-yl)oxy)propanamido)-2-methylpiperidine-1-carboxylate, reductive methylation of trans-2,2-dimethyl-N-(2-methylpiperidin-4-yl)-3-((3-(trifluoromethoxy)pyridin-2-yl)oxy)propanamide (134 mg, 0.358 mmol, 1 eq) gave crude product, which was purified by preparative HPLC (Method A) to afford a TFA salt of the title compound as a colorless film (15.9 mg, 8.8%). $^1$H NMR (400 MHz, CD$_3$OD) δ ppm 1.32 (app d, J=15.4 Hz, 6H), 1.40 (br s, 3H), 1.73-1.87 (m, 1H), 1.98 (br s, 3H), 2.77-2.94 (m, 3H), 3.10-3.23 (m, 1H), 3.35-3.50 (m, 1H), 3.71-3.82 (m, 1H), 4.13 (br d, J=1.9 Hz, 1H), 4.42 (br d, J=16.0 Hz, 2H), 6.98-7.10 (m, 1H), 7.61-7.73 (m, 1H), 8.12 (br s, 1H); ESI-MS [M+H]$^+$ calc'd for C$_{18}$H$_{26}$F$_3$N$_3$O$_3$, 390.19; found, 390.4.

Example 136: cis-N-(1,2-dimethylpiperidin-4-yl)-2,2-dimethyl-3-((3-(trifluoromethoxy)pyridin-2-yl)oxy)propanamide

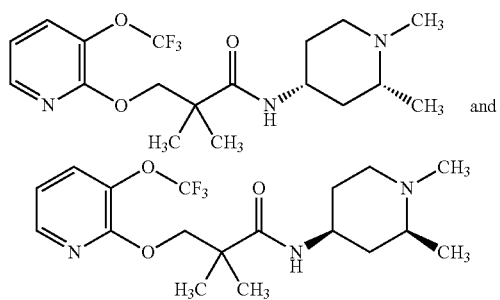 and

The title compound was prepared in a manner similar to EXAMPLE 109, using 2,2-dimethyl-3-((3-(trifluoromethoxy)pyridin-2-yl)oxy)propanoic acid (0.100 g, 0.358 mmol) and tert-butyl cis-4-amino-2-methylpiperidine-1-carboxylate (0.077 g, 0.36 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. Following N-Boc deprotection of tert-butyl cis-4-(2,2-dimethyl-3-((3-(trifluoromethoxy)pyridin-2-yl)oxy)propanamido)-2-methylpiperidine-1-carboxylate, reductive methylation of cis-2,2-dimethyl-N-(2-methylpiperidin-4-yl)-3-((3-(trifluoromethoxy)pyridin-2-yl)oxy)propanamide (134 mg, 0.358 mmol, 1 eq) gave crude product, which was purified by preparative HPLC (Method) to afford a TFA salt of the title compound as a colorless film (27.4 mg, 15%). $^1$H NMR (400 MHz, CD$_3$OD) δ ppm 1.30 (br s, 6H), 1.38 (br d, J=5.7 Hz, 3H), 1.56-1.94 (m, 2H), 2.01-2.21 (m, 2H), 2.87 (br s, 3H), 3.08-3.26 (m, 2H), 3.51-3.63 (m, 1H), 3.93-4.09 (m, 1H), 4.40 (s, 2H), 6.95-7.09 (m, 1H), 7.63-7.74 (m, 1H), 8.04-8.16 (m, 1H); ESI-MS [M+H]$^+$ calc'd for C$_{18}$H$_{26}$F$_3$N$_3$O$_3$, 390.19; found, 390.4.

Example 137: N-(2-ethyl-1-methylpiperidin-4-yl)-2,2-dimethyl-3-((3-(trifluoromethyl)pyridin-2-yl)oxy)propanamide

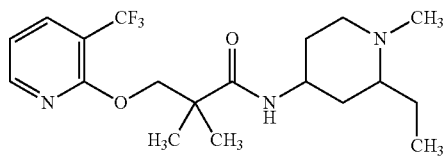 [SMILES: CCC1CC(NC(=O)C(C)(C)COc2ncccc2C(F)(F)F)CCN1C]

The title compound was prepared in a manner similar to EXAMPLE 109, using tert-butyl 4-amino-2-ethylpiperidine-1-carboxylate (0.110 g, 0.376 mmol, 1.1) in place of tert-butyl trans-4-amino-3-methylpiperidine-1-carboxylate, HCl. Following N-Boc deprotection of tert-butyl 4-(2,2-dimethyl-3-((3-(trifluoromethyl)pyridin-2-yl)oxy)propanamido)-2-ethylpiperidine-1-carboxylate, reductive methylation of N-(2-ethylpiperidin-4-yl)-2,2-dimethyl-3-((3-(trifluoromethyl)pyridin-2-yl)oxy)propanamide (128 mg, 0.342 mmol, 1 eq) gave the title compound as a red film (29.6 mg, 22%). $^1$H NMR (400 MHz, CD$_3$OD) δ ppm 1.20 (d, J=12.2 Hz, 1H), 1.28-1.32 (m, 6H), 1.33-1.42 (m, 1H), 1.50-1.63 (m, 1H), 1.67-1.81 (m, 2H), 1.81-1.98 (m, 2H), 2.15-2.31 (m, 4H), 2.85-2.95 (m, 1H), 3.65-3.83 (m, 1H), 4.43 (s, 2H), 7.01-7.17 (m, 1H), 7.91-8.04 (m, 1H), 8.27-8.40 (m, 1H); ESI-MS [M+H]$^+$ calc'd for C$_{19}$H$_{28}$F$_3$N$_3$O$_2$, 388.21; found, 388.4.

Example 138: 2,2-dimethyl-N-(5-methyl-5-azaspiro[2.4]heptan-7-yl)-3-((3-(trifluoromethyl)pyridin-2-yl)oxy)propanamide

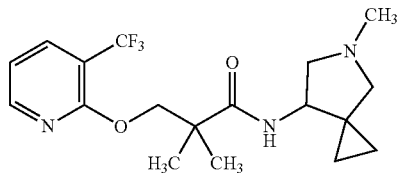 [SMILES: CN1CC(NC(=O)C(C)(C)COc2ncccc2C(F)(F)F)C2(CC2)C1]

The title compound was prepared in a manner similar to EXAMPLE 109, using tert-butyl 7-amino-5-azaspiro[2.4]heptane-5-carboxylate (0.073 g, 0.34 mmol, 1 eq) in place of tert-butyl trans-4-amino-3-methylpiperidine-1-carboxylate, HCl. Following N-Boc deprotection of tert-butyl 7-(2,2-dimethyl-3-((3-(trifluoromethyl)pyridin-2-yl)oxy)propanamido)-5-azaspiro[2.4]heptane-5-carboxylate, reductive methylation of 2,2-dimethyl-N-(5-azaspiro[2.4]heptan-7-yl)-3-((3-(trifluoromethyl)pyridin-2-yl)oxy)propanamide (122 mg, 0.342 mmol, 1 eq) gave the title compound as a light brown film (103.7 mg, 82%). $^1$H NMR (400 MHz, CD$_3$OD) δ ppm 0.44-0.55 (m, 1H), 0.64 (s, 2H), 0.69-0.80 (m, 1H), 1.31 (s, 6H), 2.37 (s, 3H), 2.44 (d, J=9.3 Hz, 1H), 2.55-2.64 (m, 1H), 2.73 (d, J=9.3 Hz, 1H), 2.92-3.02 (m, 1H), 4.20-4.29 (m, 1H), 4.42 (s, 2H), 7.01-7.13 (m, 1H), 7.85-8.03 (m, 1H), 8.27-8.40 (m, 1H); ESI-MS [M+H]$^+$ calc'd for C$_{18}$H$_{24}$F$_3$N$_3$O$_2$, 372.18; found, 372.5.

Example 139: trans-N-(1,2-dimethylpiperidin-4-yl)-2,2-dimethyl-3-((3-(trifluoromethyl)pyridin-2-yl)oxy)propanamide

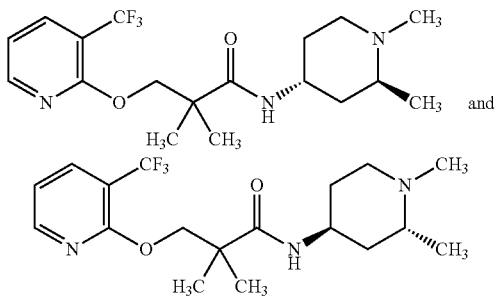

The title compound was prepared in a manner similar to EXAMPLE 109, using tert-butyl trans-4-amino-2-methylpiperidine-1-carboxylate (0.081 g, 0.380 mmol, 1 eq) in place of tert-butyl trans-4-amino-3-methylpiperidine-1-carboxylate, HCl. Following N-Boc deprotection of tert-butyl trans-4-(2,2-dimethyl-3-(2-(trifluoromethyl)phenoxy)propanamido)-2-methylpiperidine-1-carboxylate, reductive methylation of trans-2,2-dimethyl-N-(2-methylpiperidin-4-yl)-3-((3-(trifluoromethyl)pyridin-2-yl)oxy)propanamide (137 mg, 0.38 mmol, 1 eq) gave the title compound as a light brown film (98.5 mg, 69%). $^1$H NMR (400 MHz, CD$_3$OD) δ ppm 1.06 (d, J=6.51 Hz, 3H), 1.31 (s, 6H), 1.51-1.62 (m, 1H), 1.64-1.84 (m, 3H), 2.25 (s, 3H), 2.37 (s, 1H), 2.46-2.57 (m, 1H), 2.59-2.70 (m, 1H), 3.92-4.04 (m, 1H), 4.46 (d, J=1.0 Hz, 2H), 7.03-7.14 (m, 1H), 7.91-8.05 (m, 1H), 8.29-8.41 (m, 1H); ESI-MS [M+H]$^+$ calc'd for C$_{18}$H$_{26}$F$_3$N$_3$O$_2$, 374.20; found, 374.4.

Example 140: N-((3R,4R)-1,3-dimethylpiperidin-4-yl)-3-((3,5-dimethylpyridin-2-yl)oxy)-2,2-dimethylpropanamide

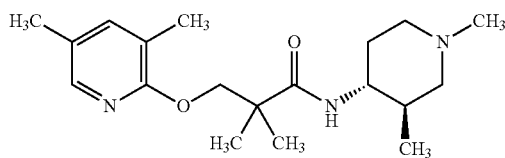

Example 141: N-((3S,4S)-1,3-dimethylpiperidin-4-yl)-3-((3,5-dimethylpyridin-2-yl)oxy)-2,2-dimethylpropanamide

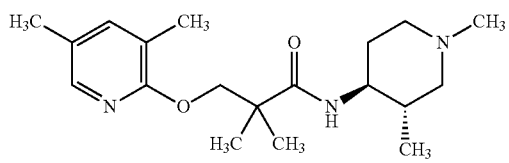

The title compounds were prepared in a manner similar to EXAMPLE 109, using 3-((3,5-dimethylpyridin-2-yl)oxy)-2,2-dimethylpropanoic acid (0.150 g, 0.672 mmol, 1 eq) in place of 2,2-dimethyl-3-((3-(trifluoromethyl)pyridin-2-yl)oxy)propanoic acid. Following N-Boc deprotection of tert-butyl trans-4-(3-((3,5-dimethylpyridin-2-yl)oxy)-2,2-dimethylpropanamido)-3-methylpiperidine-1-carboxylate, reductive methylation of 3-((3,5-dimethylpyridin-2-yl)oxy)-2,2-dimethyl-N-(trans-3-methylpiperidin-4-yl)propanamide (215 mg, 0.672 mmol, 1 eq) gave racemic N-(trans-1,3-dimethylpiperidin-4-yl)-3-((3,5-dimethylpyridin-2-yl)oxy)-2,2-dimethylpropanamide. The racemate was resolved by preparative chiral SFC to give a first eluting peak, which was assigned (3R,4R)-stereo configuration (24.6 mg, 11%), and a second eluting peak, which was assigned (3S,4S)-stereo configuration (22.1 mg, 9.8%). The title compounds were obtained (without recrystallization) as colorless films. Peak 1: $^1$H NMR (500 MHz, CD$_3$OD) δ ppm 0.82 (d, J=6.1 Hz, 3H), 1.30 (s, 6H), 1.48-1.59 (m, 1H), 1.66-1.80 (m, 3H), 1.99-2.09 (m, 1H), 2.13 (s, 3H), 2.19 (s, 3H), 2.26 (s, 3H), 2.81-2.90 (m, 2H), 3.39-3.47 (m, 1H), 4.27 (s, 2H), 7.28-7.34 (m, 1H), 7.68-7.75 (m, 1H); ESI-MS [M+H]$^+$ calc'd for C$_{19}$H$_{31}$N$_3$O$_2$, 334.24; found, 334.4. Peak 2: $^1$H NMR (500 MHz, CD$_3$OD) δ ppm 0.82 (d, J=6.1 Hz, 3H), 1.30 (s, 6H), 1.48-1.59 (m, 1H), 1.66-1.80 (m, 3H), 1.99-2.09 (m, 1H), 2.13 (s, 3H), 2.19 (s, 3H), 2.26 (s, 3H), 2.81-2.90 (m, 2H), 3.39-3.47 (m, 1H), 4.27 (s, 2H), 7.28-7.34 (m, 1H), 7.68-7.75 (m, 1H). ESI-MS [M+H]$^+$ calc'd for C$_{19}$H$_{31}$N$_3$O$_2$, 334.24; found, 334.4.

Example 142: N-((3R,4R)-1,3-dimethylpiperidin-4-yl)-2,2-dimethyl-3-((3-methylpyridin-2-yl)oxy)propanamide

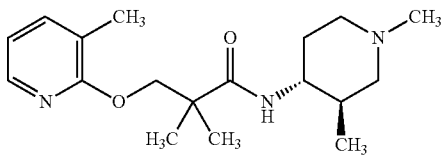

Example 143: N-((3S,4S)-1,3-dimethylpiperidin-4-yl)-2,2-dimethyl-3-((3-methylpyridin-2-yl)oxy)propanamide

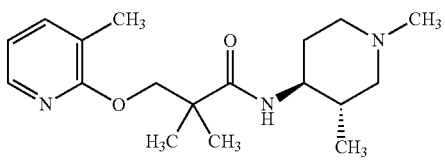

The title compounds were prepared in a manner similar to EXAMPLE 109, using 2,2-dimethyl-3-((3-methylpyridin-2-yl)oxy)propanoic acid (0.500 g, 2.39 mmol, 1 eq) in place of 2,2-dimethyl-3-((3-(trifluoromethyl)pyridin-2-yl)oxy)propanoic acid. Following N-Boc deprotection of tert-butyl trans-4-(2,2-dimethyl-3-((3-methylpyridin-2-yl)oxy)propanamido)-3-methylpiperidine-1-carboxylate, reductive methylation of trans-2,2-dimethyl-N-(3-methylpiperidin-4-yl)-3-((3-methylpyridin-2-yl)oxy)propanamide (0.730 g, 2.39 mmol, 1 eq) gave racemic trans-N-(1,3-dimethylpiperidin-4-yl)-2,2-dimethyl-3-((3-methylpyridin-2-yl)oxy)propanamide. The racemate was resolved by preparative chiral SFC to give a first eluting peak, which was assigned (3R,4R)-stereo configuration (151.3 mg, 18%), and a second eluting peak, which was assigned (3S,4S)-stereo configuration (179.4 mg, 21%). The separated enantiomers were treated with 4 M HCl in dioxane and recrystallized to give an HCl salt of the title compounds as white solids. Peak 1: $^1$H NMR (500 MHz, CD$_3$OD) δ ppm 0.82 (d, J=6.4 Hz, 3H), 1.31 (s, 6H), 1.49-1.59 (m, 1H), 1.68-1.79 (m, 3H), 2.00-2.10 (m, 1H), 2.16 (s, 3H), 2.26 (s, 3H), 2.80-2.91 (m, 2H), 3.38-3.47 (m, 1H), 4.32 (s, 2H), 6.84 (dd, J=7.1, 5.1 Hz, 1H), 7.42-7.50 (m, 1H), 7.88-7.94 (m, 1H); ESI-MS [M+H]$^+$ calc'd for C$_{18}$H$_{29}$N$_3$O$_2$, 320.23; found, 320.4. Peak 2: $^1$H NMR (500 MHz, CD$_3$OD) δ ppm 0.82 (d, J=6.4 Hz, 3H), 1.31 (s, 6H), 1.49-1.59 (m, 1H), 1.68-1.79 (m, 3H), 2.00-2.10 (m, 1H), 2.16 (s, 3H), 2.26 (s, 3H), 2.80-2.91 (m, 2H), 3.38-3.47 (m, 1H), 4.32 (s, 2H), 6.84 (dd, J=7.1, 5.1 Hz, 1H), 7.42-7.50 (m, 1H), 7.88-7.94 (m, 1H); ESI-MS [M+H]$^+$ calc'd for C$_{18}$H$_{29}$N$_3$O$_2$, 320.23; found, 320.4.

Example 144: N-((3R,4R)-3-ethyl-1-methylpiperidin-4-yl)-2,2-dimethyl-3-((3-(trifluoromethyl)pyridin-2-yl)oxy)propanamide

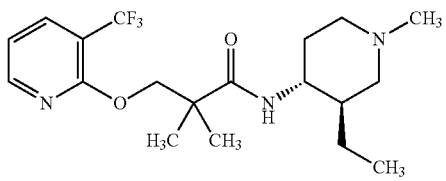 [SMILES: CC[C@@H]1CN(C)CC[C@H]1NC(=O)C(C)(C)COc1ncccc1C(F)(F)F]

Example 145: N-((3S,4S)-3-ethyl-1-methylpiperidin-4-yl)-2,2-dimethyl-3-((3-(trifluoromethyl)pyridin-2-yl)oxy)propanamide

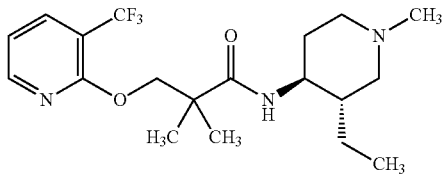 [SMILES: CC[C@H]1CN(C)CC[C@@H]1NC(=O)C(C)(C)COc1ncccc1C(F)(F)F]

The title compounds were prepared in a manner similar to EXAMPLE 109, using 2,2-dimethyl-3-((3-(trifluoromethyl)pyridin-2-yl)oxy)propanoic acid (0.200 g, 0.760 mmol) and tert-butyl trans-4-amino-3-ethylpiperidine-1-carboxylate (0.173 g, 0.760 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. Following N-Boc deprotection of tert-butyl trans-4-(2,2-dimethyl-3-((3-(trifluoromethyl)pyridin-2-yl)oxy)propanamido)-3-ethylpiperidine-1-carboxylate, reductive methylation of trans-N-(3-ethylpiperidin-4-yl)-2,2-dimethyl-3-((3-(trifluoromethyl)pyridin-2-yl)oxy)propanamide (284 mg, 0.76 mmol, 1 eq) gave racemic trans-N-(3-ethyl-1-methylpiperidin-4-yl)-2,2-dimethyl-3-((3-(trifluoromethyl)pyridin-2-yl)oxy)propanamide. The racemate was resolved by preparative chiral SFC to give a first eluting peak, which was assigned (3R,4R)-stereo configuration (17.8 mg, 6.1%), and a second eluting peak, which was assigned (3S,4S)-stereo configuration (24.0 mg, 8.2%). The title compounds were obtained as colorless films. Peak 1: $^1$H NMR (500 MHz, CD$_3$OD) δ ppm 0.77-0.86 (m, 3H), 0.99-1.08 (m, 1H), 1.31 (app d, J=3.9 Hz, 6H), 1.47-1.62 (m, 3H), 1.74 (br s, 2H), 2.00-2.11 (m, 1H), 2.28 (s, 3H), 2.83-2.91 (m, 1H), 2.94-3.03 (m, 1H), 3.46-3.58 (m, 1H), 4.45 (d, J=13.2 Hz, 2H), 7.03-7.14 (m, 1H), 7.94-8.03 (m, 1H), 8.29-8.39 (m, 1H); ESI-MS [M+H]$^+$ calc'd for C$_{19}$H$_{28}$F$_3$N$_3$O$_2$, 388.21; found, 388.5. Peak 2: $^1$H NMR (500 MHz, CD$_3$OD) δ ppm 0.77-0.86 (m, 3H), 0.99-1.08 (m, 1H), 1.31 (app d, J=3.9 Hz, 6H), 1.47-1.62 (m, 3H), 1.74 (br s, 2H), 2.00-2.11 (m, 1H), 2.28 (s, 3H), 2.83-2.91 (m, 1H), 2.94-3.03 (m, 1H), 3.46-3.58 (m, 1H), 4.45 (d, J=13.2 Hz, 2H), 7.03-7.14 (m, 1H), 7.94-8.03 (m, 1H), 8.29-8.39 (m, 1H); ESI-MS [M+H]$^+$ calc'd for C$_{19}$H$_{28}$F$_3$N$_3$O$_2$, 388.21; found, 388.5.

Example 146: N-(2-ethyl-1-methylpiperidin-4-yl)-2,2-dimethyl-3-((3-(trifluoromethoxy)pyridin-2-yl)oxy)propanamide

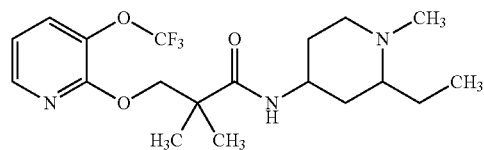 [SMILES: CCC1CC(NC(=O)C(C)(C)COc2ncccc2OC(F)(F)F)CCN1C]

The title compound was prepared in a manner similar to EXAMPLE 109, using 2,2-dimethyl-3-((3-(trifluoromethoxy)pyridin-2-yl)oxy)propanoic acid (0.090 g, 0.32 mmol) and tert-butyl 4-amino-2-ethylpiperidine-1-carboxylate (0.123 g, 0.419 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. After N-Boc deprotection of tert-butyl 4-(2,2-dimethyl-3-((3-(trifluoromethoxy)pyridin-2-yl)oxy)propanamido)-2-ethylpiperidine-1-carboxylate, reductive methylation of N-(2-ethylpiperidin-4-yl)-2,2-dimethyl-3-((3-(trifluoromethoxy)pyridin-2-yl)oxy)propanamide (125 mg, 0.322 mmol, 1 eq) gave the title compound as a light yellow film (44.7 mg, 34%). $^1$H NMR (400 MHz, CD$_3$OD) δ ppm 0.99 (s, 3H), 1.31 (app d, J=2.5 Hz, 6H), 1.54-1.69 (m, 1H), 1.74-1.88 (m, 2H), 1.92-2.24 (m, 3H), 2.88 (s, 3H), 3.08-3.24 (m, 2H), 3.45-3.60 (m, 1H), 3.90-4.07 (m, 1H), 4.40 (s, 2H), 6.99-7.09 (m, 1H), 7.63-7.75 (m, 1H), 8.07-8.16 (m, 1H); ESI-MS [M+H]$^+$ calc'd for C$_{19}$H$_{28}$F$_3$N$_3$O$_3$, 404.22; found, 404.4.

Example 147: 3-((3-cyclopropylpyridin-2-yl)oxy)-N-((2R,4R)-1,2-dimethylpiperidin-4-yl)-2,2-dimethylpropanamide

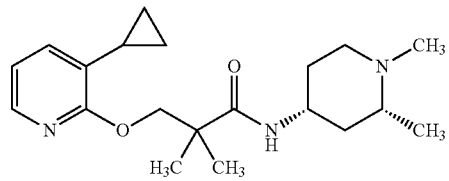 [SMILES: C[C@@H]1C[C@H](NC(=O)C(C)(C)COc2ncccc2C2CC2)CCN1C]

The title compound was prepared in a manner similar to EXAMPLE 109, using 3-((3-cyclopropylpyridin-2-yl)oxy)-2,2-dimethylpropanoic acid (0.090 g, 0.34 mmol) and tert-butyl (2R,4R)-4-amino-2-methylpiperidine-1-carboxylate (0.074 g, 0.34 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. After N-Boc deprotection of tert-butyl (2R,4R)-4-(3-((3-cyclopropylpyridin-2-yl)oxy)-2,2-dimethylpropanamido)-2-methylpiperidine-1-carboxylate, reductive methylation of 3-((3-cyclopropylpyridin-2-yl)oxy)-2,2-dimethyl-N-((2R,4R)-2-methylpiperidin-4-yl)propanamide (114 mg, 0.344 mmol, 1 eq) gave the title compound as a colorless film (38.4 mg, 32%). $^1$H NMR (400 MHz, CD$_3$OD) δ ppm 0.66 (dd, J=5.3, 1.9 Hz, 2H), 0.92 (dd, J=8.5, 2.0 Hz, 2H), 1.09 (d, J=6.2 Hz, 3H), 1.16-1.27 (m, 1H), 1.30 (s, 6H), 1.49-1.62 (m, 1H), 1.71-1.87 (m, 2H), 1.96-2.10 (m, 2H), 2.13-2.22 (m, 1H), 2.26 (s, 3H), 2.82-2.96 (m, 1H), 3.69-3.85 (m, 1H), 4.32 (s, 2H), 6.76-6.90 (m, 1H), 7.13-7.26 (m, 1H), 7.77-7.94 (m, 1H); ESI-MS [M+H]$^+$ calc'd for C$_{20}$H$_{31}$N$_3$O$_2$, 346.25; found, 346.3.

Example 148: (R)-2,2-dimethyl-N-(5-methyl-5-azaspiro[2.4]heptan-7-yl)-3-((3-(trifluoromethyl)pyridin-2-yl)oxy)propanamide

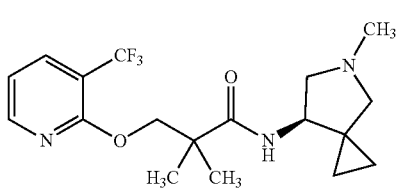 [SMILES: CN1C[C@H](NC(=O)C(C)(C)COc2ncccc2C(F)(F)F)C2(CC2)C1]

The title compound was prepared in a manner similar to EXAMPLE 109, using tert-butyl (R)-7-amino-5-azaspiro[2.4]heptane-5-carboxylate (0.065 g, 0.30 mmol, 1 eq) in place of tert-butyl trans-4-amino-3-methylpiperidine-1-carboxylate, HCl. After N-Boc deprotection of tert-butyl (R)-7-(2,2-dimethyl-3-((3-(trifluoromethyl)pyridin-2-yl)oxy)propanamido)-5-azaspiro[2.4]heptane-5-carboxylate, reductive methylation of (R)-2,2-dimethyl-N-(5-azaspiro[2.4]heptan-7-yl)-3-((3-(trifluoromethyl)pyridin-2-yl)oxy)propanamide (109 mg, 0.304 mmol, 1 eq) gave the title compound as a light brown film (85.2 mg, 75%). $^1$H NMR (400 MHz, CD$_3$OD) δ ppm 0.43-0.53 (m, 1H), 0.57-0.68 (m, 2H), 0.70-0.80 (m, 1H), 1.30 (s, 6H), 2.37 (s, 3H), 2.42-2.52 (m, 1H), 2.57-2.64 (m, 1H), 2.69-2.79 (m, 1H), 2.91-3.06 (m, 1H), 4.18-4.28 (m, 1H), 4.42 (s, 2H), 7.01-7.15 (m, 1H), 7.90-8.03 (m, 1H), 8.24-8.43 (m, 1H); ESI-MS [M+H]$^+$ calc'd for C$_{18}$H$_{24}$F$_3$N$_3$O$_2$, 372.19; found, 372.5.

Example 149: trans-N-(2-ethyl-1-methylpyrrolidin-3-yl)-2,2-dimethyl-3-((3-(trifluoromethyl)pyridin-2-yl)oxy)propanamide

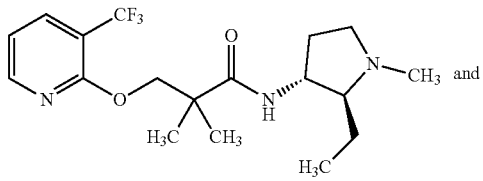
and

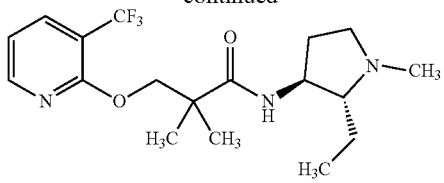

The title compound was prepared in a manner similar to EXAMPLE 109, using tert-butyl trans-3-amino-2-ethylpyrrolidine-1-carboxylate (0.065 g, 0.30 mmol, 1 eq) in place of tert-butyl trans-4-amino-3-methylpiperidine-1-carboxylate, HCl. After N-Boc deprotection of tert-butyl trans-3-(2,2-dimethyl-3-((3-(trifluoromethyl)pyridin-2-yl)oxy)propanamido)-2-ethylpyrrolidine-1-carboxylate, reductive methylation of trans-N-(2-ethylpyrrolidin-3-yl)-2,2-dimethyl-3-((3-(trifluoromethyl)pyridin-2-yl)oxy)propanamide (0.109 g, 0.304 mmol, 1 eq) gave the title compound as a light brown solid (84.2 mg, 74%). $^1$H NMR (400 MHz, CD$_3$OD) δ ppm 0.90 (t, J=7.5 Hz, 3H), 1.30 (app d, J=5.5 Hz, 6H), 1.34-1.46 (m, 1H), 1.48-1.58 (m, 1H), 1.63-1.77 (m, 1H), 2.05-2.19 (m, 2H), 2.31 (s, 3H), 2.38-2.53 (m, 1H), 2.90-3.01 (m, 1H), 4.10-4.24 (m, 1H), 4.44 (d, J=8.2 Hz, 2H), 7.02-7.15 (m, 1H), 7.91-8.01 (m, 1H), 8.26-8.41 (m, 1H); ESI-MS [M+H]$^+$ calc'd for C$_{18}$H$_{26}$F$_3$N$_3$O$_2$, 374.21; found, 374.4.

Example 150: (R)-2,2-dimethyl-N-(5-methyl-5-azaspiro[2.4]heptan-7-yl)-3-((3-(trifluoromethoxy)pyridin-2-yl)oxy)propanamide

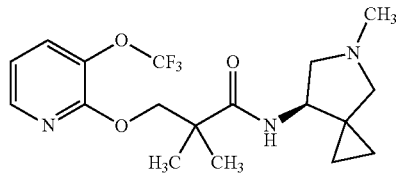 [SMILES: CN1C[C@H](NC(=O)C(C)(C)COc2ncccc2OC(F)(F)F)C2(CC2)C1]

The title compound was prepared in a manner similar to EXAMPLE 109, using 2,2-dimethyl-3-((3-(trifluoromethoxy)pyridin-2-yl)oxy)propanoic acid (0.080 g, 0.29 mmol) and tert-butyl (R)-7-amino-5-azaspiro[2.4]heptane-5-carboxylate (0.061 g, 0.29 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. After N-Boc deprotection of tert-butyl (R)-7-(2,2-dimethyl-3-((3-(trifluoromethoxy)pyridin-2-yl)oxy)propanamido)-5-azaspiro[2.4]heptane-5-carboxylate and reductive methylation of (R)-2,2-dimethyl-N-(5-azaspiro[2.4]heptan-7-yl)-3-((3-(trifluoromethoxy)pyridin-2-yl)oxy)propanamide (107 mg, 0.287 mmol, 1 eq), the product was purified by preparative HPLC (Method A) to give a TFA salt of the title compound as a light yellow film (53.3 mg, 37%). $^1$H NMR (400 MHz, CD$_3$OD) δ ppm 0.36-0.52 (m, 1H), 0.59-0.76 (m, 3H), 1.16 (d, J=5.9 Hz, 3H), 1.30 (d, J=5.9 Hz, 3H), 2.35 (d, J=8.0 Hz, 3H), 2.44 (s, 1H), 2.52-2.75 (m, 2H), 2.90-3.01 (m, 1H), 3.45 (d, J=0.8 Hz, 1H), 4.15-4.28 (m, 1H), 4.38 (d, J=9.3 Hz, 1H), 4.50 (s, 1H), 7.06 (s, 1H), 7.33-7.38 (m, 1H), 7.61-7.71 (m, 1H), 8.07-8.14 (m, 1H); ESI-MS [M+H]$^+$ calc'd for C$_{18}$H$_{24}$F$_3$N$_3$O$_3$, 388.18; found, 388.4.

Example 151: 2,2-dimethyl-N-(5-methyl-5-azaspiro[3.4]octan-8-yl)-3-((3-(trifluoromethyl)pyridin-2-yl)oxy)propanamide

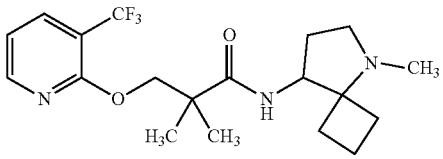 [SMILES: CN1CCC(NC(=O)C(C)(C)COc2ncccc2C(F)(F)F)C12CCC2]

The title compound was prepared in a manner similar to EXAMPLE 109, using tert-butyl 8-amino-5-azaspiro[3.4]octane-5-carboxylate (0.069 g, 0.30 mmol, 1 eq) in place of tert-butyl trans-4-amino-3-methylpiperidine-1-carboxylate, HCl. After N-Boc deprotection of tert-butyl 8-(2,2-dimethyl-3-((3-(trifluoromethyl)pyridin-2-yl)oxy)propanamido)-5-azaspiro[3.4]octane-5-carboxylate and reductive methylation of 2,2-dimethyl-N-(5-azaspiro[3.4]octan-8-yl)-3-((3-(trifluoromethyl)pyridin-2-yl)oxy)propanamide (113 mg, 0.304 mmol, 1 eq), the product was purified by preparative HPLC (Method A) to give a TFA salt of the title compound as a light yellow film (93.3 mg, 61%). $^1$H NMR (400 MHz, CD$_3$OD) δ ppm 1.35 (s, 6H), 1.92 (br d, J=5.9 Hz, 4H), 2.08-2.20 (m, 1H), 2.38 (br d, J=12.8 Hz, 1H), 2.49-2.63 (m, 2H), 2.94 (s, 3H), 2.96-3.07 (m, 1H), 3.66-3.81 (m, 1H), 4.42-4.49 (m, 2H), 4.50-4.60 (m, 1H), 7.10 (ddd, J=7.5, 5.0, 0.6 Hz, 1H), 7.89-8.01 (m, 1H), 8.31-8.43 (m, 1H); ESI-MS [M+H]$^+$ calc'd for C$_{19}$H$_{26}$F$_3$N$_3$O$_2$, 386.21; found, 386.5.

Example 152: N-((2S,4S)-1,2-dimethylpiperidin-4-yl)-2,2-dimethyl-3-((3-(trifluoromethoxy)pyridin-2-yl)oxy)propanamide

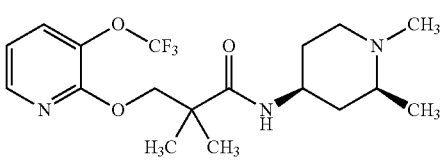 [SMILES: C[C@H]1C[C@@H](NC(=O)C(C)(C)COc2ncccc2OC(F)(F)F)CCN1C]

The title compound was prepared in a manner similar to EXAMPLE 109, using 2,2-dimethyl-3-((3-(trifluoromethoxy)pyridin-2-yl)oxy)propanoic acid (0.100 g, 0.358 mmol) and tert-butyl (2S,4S)-4-amino-2-methylpiperidine-1-carboxylate (0.077 g, 0.36 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. After N-Boc deprotection of tert-butyl (2S,4S)-4-(2,2-dimethyl-3-((3-(trifluoromethoxy)pyridin-2-yl)oxy)propanamido)-2-methylpiperidine-1-carboxylate and reductive methylation of 2,2-dimethyl-N-((2S,4S)-2-methylpiperidin-4-yl)-3-((3-(trifluoromethoxy)pyridin-2-yl)oxy)propanamide (134 mg, 0.358 mmol, 1 eq), the product was purified by preparative HPLC (Method A) to give a TFA salt of the title compound as a white solid (46.3 mg, 26%). $^1$H NMR (400 MHz, CD$_3$OD) δ ppm 1.30 (s, 6H), 1.38 (d, J=6.4 Hz, 3H), 1.53-1.67 (m, 1H), 1.75-1.89 (m, 1H), 2.02-2.16 (m, 2H), 2.87 (s, 3H), 3.08-3.20 (m, 1H), 3.21-3.27 (m, 1H), 3.49-3.61 (m, 1H), 3.89-4.09 (m, 1H), 4.40 (s, 2H), 6.97-7.09 (m, 1H), 7.62-7.70 (m, 1H), 8.00-8.15 (m, 1H); ESI-MS [M+H]$^+$ calc'd for C$_{18}$H$_{26}$F$_3$N$_3$O$_3$, 390.20; found, 390.3.

Example 153: (R)-2,2-dimethyl-N-(5-methyl-5-azaspiro[2.4]heptan-7-yl)-3-((3-methylpyridin-2-yl)oxy)propanamide

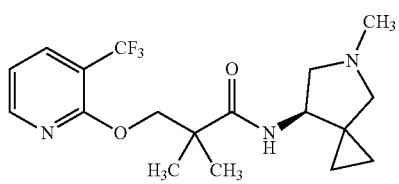 [SMILES: CN1C[C@H](NC(=O)C(C)(C)COc2ncccc2C(F)(F)F)C2(CC2)C1]

The title compound was prepared in a manner similar to EXAMPLE 109, using 2,2-dimethyl-3-((3-methylpyridin-2-yl)oxy)propanoic acid (0.080 g, 0.38 mmol) and tert-butyl (R)-7-amino-5-azaspiro[2.4]heptane-5-carboxylate (0.081 g, 0.38 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. After N-Boc deprotection of tert-butyl (R)-7-(2,2-dimethyl-3-((3-methylpyridin-2-yl)oxy)propanamido)-5-azaspiro[2.4]heptane-5-carboxylate, reductive methylation of (R)-2,2-dimethyl-3-((3-methylpyridin-2-yl)oxy)-N-(5-azaspiro[2.4]heptan-7-yl)propanamide (116 mg, 0.382 mmol, 1 eq) gave the title compound as a light brown film (88.6 mg, 73%). $^1$H NMR (400 MHz, CD$_3$OD) δ ppm 0.41-0.48 (m, 1H), 0.63 (s, 2H), 0.70-0.79 (m, 1H), 1.30 (app d, J=5.1 Hz, 6H), 2.18 (s, 3H), 2.35 (s, 3H), 2.43 (d, J=9.2 Hz, 1H), 2.56-2.63 (m, 1H), 2.68-2.73 (m, 1H), 2.91-2.99 (m, 1H), 4.24-4.34 (m, 3H), 6.80-6.88 (m, 1H), 7.44-7.50 (m, 1H), 7.87-7.95 (m, 1H); ESI-MS [M+H]$^+$ calc'd for C$_{18}$H$_{27}$N$_3$O$_2$, 318.22; found, 318.5.

Example 154: (R)-3-((3,5-dimethylpyridin-2-yl)oxy)-2,2-dimethyl-N-(5-methyl-5-azaspiro[2.4]heptan-7-yl)propanamide

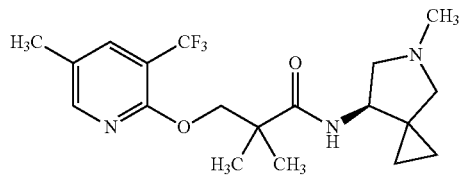 [SMILES: Cc1cnc(OCC(C)(C)C(=O)N[C@H]2CN(C)CC23CC3)c(C(F)(F)F)c1]

The title compound was prepared in a manner similar to EXAMPLE 109, using 3-((3,5-dimethylpyridin-2-yl)oxy)-2,2-dimethylpropanoic acid (0.080 g, 0.36 mmol) and tert-butyl (R)-7-amino-5-azaspiro[2.4]heptane-5-carboxylate (0.076 g, 0.36 mmol) in place of 2,2-dimethyl-3-((3-(trifluoromethyl)pyridin-2-yl)oxy)propanoic acid and tert-butyl trans-4-amino-3-methylpiperidine-1-carboxylate, HCl. After N-Boc deprotection of tert-butyl (R)-7-(3-((3,5-dimethylpyridin-2-yl)oxy)-2,2-dimethylpropanamido)-5-azaspiro[2.4]heptane-5-carboxylate and reductive methylation of (R)-3-((3,5-dimethylpyridin-2-yl)oxy)-2,2-dimethyl-N-(5-azaspiro[2.4]heptan-7-yl)propanamide (114 mg, 0.358 mmol, 1 eq), the product was purified by preparative HPLC (Method A) to give a TFA salt of the title compound as a colorless film (92.6 mg, 58%). ¹H NMR (400 MHz, CD₃OD) δ ppm 0.61-0.70 (m, 1H), 0.74-0.89 (m, 3H), 1.32 (app d, J=6.4 Hz, 6H), 2.15 (s, 3H), 2.21 (s, 3H), 2.97 (s, 3H), 3.27 (brd, J=11.2 Hz, 2H), 3.56-3.76 (m, 2H), 4.29 (s, 3H), 7.38 (dd, J=1.5, 0.6 Hz, 1H), 7.73-7.77 (m, 1H); ESI-MS [M+H]⁺ calc'd for C₁₉H₂₉N₃O₂, 332.23; found, 332.5.

Example 155: N,2,2-trimethyl-N-(trans-3-(o-tolyl) piperidin-4-yl)-3-((3-(trifluoromethyl)pyridin-2-yl) oxy)propanamide

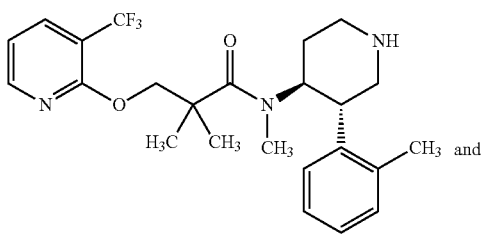

Example 156: N,2,2-trimethyl-N-(cis-3-(o-tolyl) piperidin-4-yl)-3-((3-(trifluoromethyl)pyridin-2-yl) oxy)propanamide

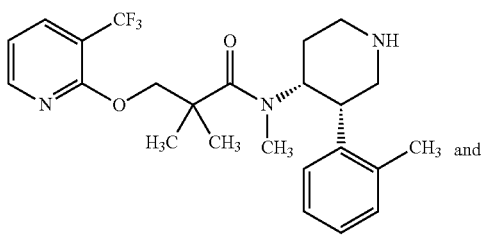

A solution of tert-butyl 3-(o-tolyl)-4-(N,2,2-trimethyl-3-((3-(trifluoromethyl)pyridin-2-yl)oxy)propanamido)piperidine-1-carboxylate TFA salt (17 mg, 0.026 mmol) in DCM (1.5 mL) and TFA (0.8 mL) was stirred at room temperature for 1.5 hours. The mixture was purified by preparative HPLC (Method A) to give the title trans- and cis-stereoisomers as TFA salts. The major peak was assigned to be the trans-stereoisomer and the minor peak was assigned to be the cis-stereoisomer based on the steric selectivity in the reaction. Major peak: ¹H NMR (500 MHz, CD₃OD) δ ppm 1.06 (br s, 3H), 1.11-1.24 (m, 3H), 1.95-2.15 (m, 2H), 2.34-2.48 (m, 3H), 2.80-2.96 (m, 3H), 3.05 (t, J=12.4 Hz, 1H), 3.37-3.52 (m, 2H), 3.56 (d, J=12.2 Hz, 1H), 4.31-4.43 (m, 2H), 6.44 (t, J=6.6 Hz, 1H), 7.09 (dd, J=7.3, 4.9 Hz, 1H), 7.16 (d, J=6.4 Hz, 3H), 7.21 (br s, 1H), 7.63-7.67 (m, 1H), 7.94-8.00 (m, 1H), 8.33 (d, J=3.4 Hz, 1H); ESI-MS [M+H]⁺ calc'd for C₂₄H₃₀F₃N₃O₂, 450.2; found, 450.1. Minor peak: ¹H NMR (500 MHz, CD₃OD) δ ppm 1.15 (d, J=9.3 Hz, 1H), 1.21 (m, 5H), 2.21-2.37 (m, 2H), 2.41 (m, 4H), 2.64 (s, 3H), 3.75-3.84 (m, 2H), 4.01-4.09 (m, 1H), 4.20 (br s, 1H), 4.39 (s, 2H), 7.09 (dd, J=7.6, 5.1 Hz, 1H), 7.18-7.24 (m, 4H), 7.99 (d, J=7.3 Hz, 1H), 8.35 (d, J=4.9 Hz, 1H); ESI-MS [M+H]⁺ calc'd for C₂₄H₃₀F₃N₃O₂, 450.2; found, 450.1.

Example 157: 2,2-dimethyl-N-(trans-3-(o-tolyl)piperidin-4-yl)-3-((3-(trifluoromethyl)pyridin-2-yl)oxy) propanamide

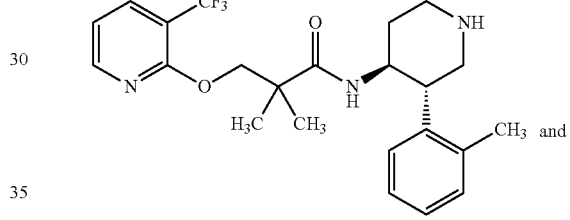

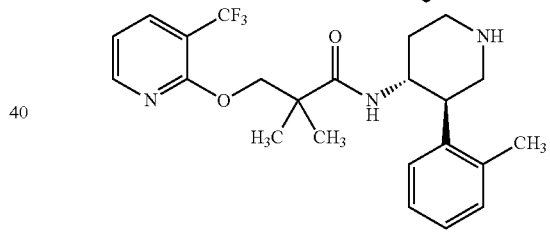

The title compound was prepared in a manner similar to EXAMPLES 155 and 156 using trans-tert-butyl 4-(2,2-dimethyl-3-((3-(trifluoromethyl)pyridin-2-yl)oxy)propanamido)-3-(o-tolyl)piperidine-1-carboxylate (34 mg, 0.063 mmol, 1 eq) in place of tert-butyl 3-(o-tolyl)-4-(N,2,2-trimethyl-3-((3-(trifluoromethyl)pyridin-2-yl)oxy)propanamido)piperidine-1-carboxylate. The product was purified by preparative HPLC (Method A) to give a TFA salt of the title compound as a colorless oil (35 mg, quantitative). ¹H NMR (500 MHz, CD₃OD) δ ppm 0.90 (s, 3H), 0.98-1.06 (m, 3H), 1.22 (s, 1H), 1.96-2.07 (m, 1H), 2.11-2.18 (m, 1H), 2.37-2.41 (m, 3H), 3.06 (t, J=12.4 Hz, 1H), 3.21-3.28 (m, 1H), 3.34-3.43 (m, 1H), 3.49-3.58 (m, 2H), 3.60-3.66 (m, 1H), 4.09 (d, J=10.7 Hz, 1H), 4.22 (d, J=10.7 Hz, 1H), 4.30 (d, J=10.2 Hz, 1H), 4.48 (d, J=11.7 Hz, 1H), 4.63 (dd, J=8.3, 3.4 Hz, 1H), 7.03-7.18 (m, 4H), 7.23-7.29 (m, 1H), 7.45 (d, J=8.8 Hz, 1H), 7.93-7.99 (m, 1H), 8.25-8.36 (m, 1H); ESI-MS [M+H]⁺ calc'd for C₂₃H₂₈F₃N₃O₂, 436.2; found, 436.1.

Example 158: N-((3S,4S)-3-fluoropiperidin-4-yl)-2,2-dimethyl-3-((3-(trifluoromethyl)pyridin-2-yl)oxy)propanamide

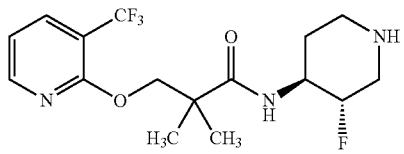

Step A: tert-butyl (3S,4S)-4-(2,2-dimethyl-3-((3-(trifluoromethyl)pyridin-2-yl)oxy)propanamido)-3-fluoropiperidine-1-carboxylate

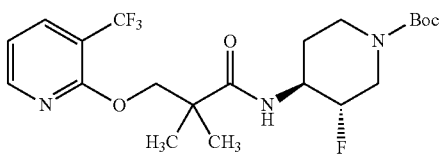 [SMILES: CC(C)(C)OC(=O)N1CC[C@H](NC(=O)C(C)(C)COc2ncccc2C(F)(F)F)[C@@H](F)C1]

The title compound was prepared in a manner similar to PREPARATION 75, using tert-butyl (3S,4S)-4-amino-3-fluoropiperidine-1-carboxylate (100 mg, 0.458 mmol, 1.2 eq) in place of tert-butyl 4-amino-3-phenylpiperidine-1-carboxylate. The product was purified by column chromatography to give the title compound as a white solid (160 mg, 90%). ESI-MS [M+H]$^+$ calc'd for $C_{21}H_{29}F_4N_3O_4$, 464.21; found, 464.2.

Step B: N-((3S,4S)-3-fluoropiperidin-4-yl)-2,2-dimethyl-3-((3-(trifluoromethyl)pyridin-2-yl)oxy)propanamide The title compound was prepared in a manner similar to EXAMPLES 155 and 156, using tert-butyl (3S,4S)-4-(2,2-dimethyl-3-((3-(trifluoromethyl)pyridin-2-yl)oxy)propanamido)-3-fluoropiperidine-1-carboxylate (32 mg, 0.069 mmol, 1 eq) in place of tert-butyl 3-(o-tolyl)-4-(N,2,2-trimethyl-3-((3-(trifluoromethyl)pyridin-2-yl)oxy)propanamido)piperidine-1-carboxylate. The product was purified by preparative HPLC (Method A) to give a TFA salt of the title compound as a colorless oil (6.1 mg, 19%). $^1$H NMR (500 MHz, CD$_3$OD) δ ppm 1.33 (app d, J=7.8 Hz, 6H), 1.80-1.92 (m, 1H), 2.13-2.27 (m, 1H), 3.16 (ddd, J=13.1, 9.5, 3.5 Hz, 1H), 3.22-3.28 (m, 1H), 3.34-3.41 (m, 1H), 3.55 (ddd, J=16.6, 12.9, 3.9 Hz, 1H), 4.11-4.28 (m, 1H), 4.37-4.51 (m, 2H), 4.74-4.85 (m, 1H), 7.10 (dd, J=7.6, 5.1 Hz, 1H), 7.76 (br d, J=6.8 Hz, 1H), 7.98 (d, J=7.6 Hz, 1H), 8.30-8.40 (m, 1H); ESI-MS [M+H]$^+$ calc'd for $C_{16}H_{21}F_4N_3O_2$, 364.16; found, 364.1.

Example 159: N-(3,3-difluoropiperidin-4-yl)-2,2-dimethyl-3-((3-(trifluoromethyl)pyridin-2-yl)oxy)propanamide

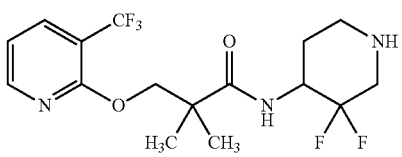 [SMILES: CC(C)(COc1ncccc1C(F)(F)F)C(=O)NC1CCNCC1(F)F]

Step A: tert-butyl 4-(benzylamino)-3,3-difluoropiperidine-1-carboxylate

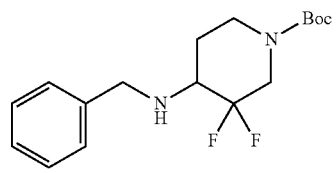 [SMILES: CC(C)(C)OC(=O)N1CCC(NCc2ccccc2)C(F)(F)C1]

A mixture of tert-butyl 3,3-difluoro-4-oxopiperidine-1-carboxylate (125 mg, 0.531 mmol), phenylmethanamine (56.9 mg, 0.531 mmol) and sodium triacetoxyborohydride (450 mg, 2.13 mmol) in DCM (5.3 mL) was stirred at room temperature for 24 hours. The crude product was purified by automated flash silica column chromatography (NH column) eluting with a gradient of 0-15% methanol in DCM. The title compound was isolated as a colorless oil (68 mg, 39%). ESI-MS [M+H]$^+$ calc'd for $C_{17}H_{24}F_2N_2O_2$, 327.18; found, 327.1.

Step B: tert-butyl 4-amino-3,3-difluoropiperidine-1-carboxylate

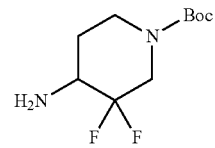

A mixture of tert-butyl 4-(benzylamino)-3,3-difluoropiperidine-1-carboxylate (68 mg, 0.208 mmol) and palladium on carbon (10%, 2.2 mg, 0.021 mmol) in methanol (2.0 mL) was stirred at room temperature under hydrogen atmosphere (H$_2$ balloon) for 8 hours. The reaction mixture was filtered and concentrated to give the title compound (49 mg, quantitative) which was used without further purification. ESI-MS [M+Na]$^+$ calc'd for $C_{10}H_{18}F_2N_2O_2$, 259.12; found, 259.1.

Step C: tert-butyl 4-(2,2-dimethyl-3-((3-(trifluoromethyl)pyridin-2-yl)oxy)propanamido)-3,3-difluoropiperidine-1-carboxylate

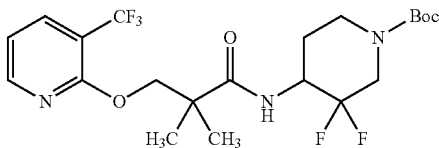 [SMILES: CC(C)(C)OC(=O)N1CCC(NC(=O)C(C)(C)COc2ncccc2C(F)(F)F)C(F)(F)C1]

The title compound was prepared in a manner similar to PREPARATION 75, using tert-butyl 4-amino-3,3-difluoropiperidine-1-carboxylate (22 mg, 0.093 mmol, 1 eq) in place of tert-butyl 4-amino-3-phenylpiperidine-1-carboxylate. The product was purified by preparative HPLC (Method A) to give a TFA salt of the title compound (15 mg, 34%). ESI-MS [M+H]$^+$ calc'd for $C_{21}H_{28}F_5N_3O_4$, 482.20; found, 482.1.

Step D: N-(3,3-difluoropiperidin-4-yl)-2,2-dimethyl-3-((3-(trifluoromethyl)pyridin-2-yl)oxy)propanamide The title compound was prepared in a manner similar to EXAMPLE 155 and 156, using tert-butyl 4-(2,2-dimethyl-3-((3-(trifluoromethyl)pyridin-2-yl)oxy)propanamido)-3,3-difluoropiperidine-1-carboxylate (15 mg, 0.031 mmol, 1 eq) in place of tert-butyl 3-(o-tolyl)-4-(N,2,2-trimethyl-3-((3-(trifluoromethyl)pyridin-2-yl)oxy)propanamido)piperidine-1-carboxylate. The product was purified by preparative HPLC (Method A) to give a TFA salt of the title compound as a colorless film (5.5 mg, 36%). $^1$H NMR (500 MHz, CD$_3$OD) δ ppm 1.36 (app d, J=8.8 Hz, 6H), 2.02-2.23 (m, 2H), 3.12-3.26 (m, 1H), 3.42-3.65 (m, 2H), 3.74-3.88, (m, 1H), 4.50 (q, J=10.6 Hz, 2H), 4.59-4.73 (m, 1H), 7.12 (dd, J=7.3, 5.1 Hz, 1H), 7.60-7.79 (m, 1H), 8.00 (d, J=7.6 Hz, 1H), 8.31-8.47 (m, 1H); ESI-MS [M+H]$^+$ calc'd for $C_{16}H_{20}F_5N_3O_2$, 382.15; found, 382.0.

Example 160: N-((3S,4S)-3-fluoropiperidin-4-yl)-N,2,2-trimethyl-3-((3-(trifluoromethyl)pyridin-2-yl)oxy)propanamide

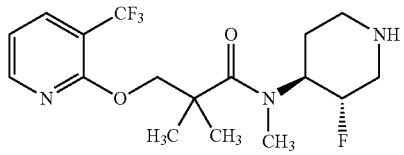 [SMILES: CN(C(=O)C(C)(C)COc1ncccc1C(F)(F)F)[C@H]1CCNC[C@@H]1F]

Step A: tert-butyl (3S,4S)-3-fluoro-4-(N,2,2-trimethyl-3-((3-(trifluoromethyl)pyridin-2-yl)oxy)propanamido)piperidine-1-carboxylate

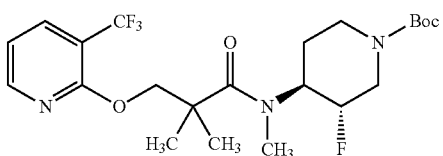

To a solution of tert-butyl (3S,4S)-4-(2,2-dimethyl-3-((3-(trifluoromethyl)pyridin-2-yl)oxy)propanamido)-3-fluoropiperidine-1-carboxylate (40 mg, 0.086 mmol) in DMF (0.86 mL) at 0° C. was added sodium hydride (60 wt %, 6.90 mg, 0.173 mmol) followed by methyl iodide (5.4 μL, 0.086 mmol) in DMF (0.1 mL). The resulting mixture was stirred at 0° C. for 3 hours. Another aliquot of methyl iodide (5.4 μL, 0.086 mmol) in DMF (0.1 mL) was added and the reaction mixture was stirred at room temperature for 10 hours. The resulting crude product was purified by preparative HPLC (Method A) to give the title compound as a colorless oil (8 mg, 19%). ESI-MS [M+H]$^+$ calc'd for $C_{22}H_{31}F_4N_3O_4$, 478.23; found, 478.1.

Step B: N-((3S,4S)-3-fluoropiperidin-4-yl)-N,2,2-trimethyl-3-((3-(trifluoromethyl)pyridin-2-yl)oxy)propanamide The title compound was prepared in a manner similar to EXAMPLES 155 and 156, using tert-butyl (3S,4S)-3-fluoro-4-(N,2,2-trimethyl-3-((3-(trifluoromethyl)pyridin-2-yl)oxy)propanamido)piperidine-1-carboxylate (7 mg, 0.015 mmol, 1 eq) in place of tert-butyl 3-(o-tolyl)-4-(N,2,2-trimethyl-3-((3-(trifluoromethyl)pyridin-2-yl)oxy)propanamido)piperidine-1-carboxylate. The product was purified by preparative HPLC (Method A) to give a TFA salt of the title compound as a colorless oil (7 mg, quantitative). $^1$H NMR (500 MHz, CD$_3$OD) δ ppm 1.47 (app d, J=4.8 Hz, 6H), 1.92-2.06 (m, 1H), 2.11-2.29 (m, 1H), 3.16 (m, 5H), 3.40-3.51 (m, 1H), 3.70-3.80 (m, 1H), 4.34-4.49 (m, 1H), 4.50-4.63 (m, 2H), 4.98-5.24 (m, 1H), 7.10 (dd, J=7.5, 5.1 Hz, 1H), 7.96-8.07 (m, 1H), 8.29-8.41 (m, 1H); ESI-MS [M+H]$^+$ calc'd for $C_{17}H_{23}F_4N_3O_2$, 378.17; found, 378.1.

Example 161: 2,2-dimethyl-N-(trans-1-methyl-3-(o-tolyl)piperidin-4-yl)-3-((3-(trifluoromethyl)pyridin-2-yl)oxy)propanamide

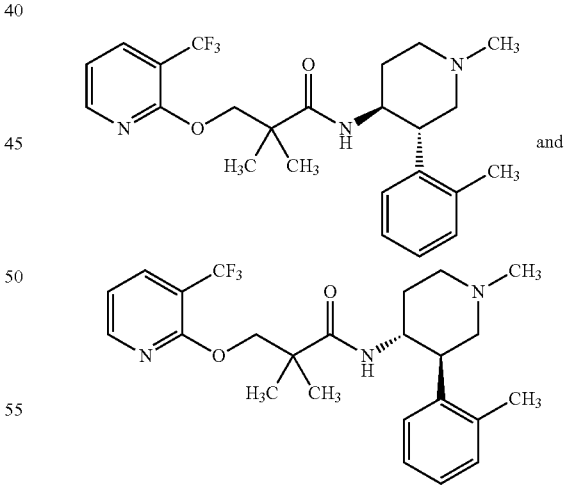

To a solution of 2,2-dimethyl-N-(trans-3-(o-tolyl)piperidin-4-yl)-3-((3-(trifluoromethyl)pyridin-2-yl)oxy)propanamide TFA salt (32 mg, 0.058 mmol) in DCM (582 μL) were added formaldehyde (4.8 μL, 0.18 mmol), sodium triacetoxyhydroborohydride (37.0 mg, 0.175 mmol) and DIPEA (11.2 μL, 0.064 mmol). The resulting mixture was stirred at room temperature for 3 days and then purified by preparative HPLC (Method A) to give a TFA salt of the title compound as a white solid (7.2 mg, 22%). $^1$H NMR (500 MHz, CD$_3$OD) δ ppm 0.90 (s, 3H), 1.03 (s, 3H), 2.03-2.21 (m, 2H), 2.39 (s, 3H), 2.89 (s, 3H), 3.15 (t, J=12.7 Hz, 1H), 3.26 (d, J=3.9 Hz, 1H), 3.49 (d, J=12.7 Hz, 1H), 3.55-3.69 (m, 2H), 4.10 (d, J=10.2 Hz, 1H), 4.30 (d, J=10.2 Hz, 1H), 4.39-4.54 (m, 1H), 7.03-7.20 (m, 4H), 7.24-7.30 (m, 1H), 7.45 (d, J=8.3 Hz, 1H), 7.91-8.02 (m, 1H), 8.24-8.36 (m, 1H); ESI-MS [M+H]$^+$ calc'd for C$_{24}$H$_{30}$F$_3$N$_3$O$_2$, 450.2; found, 450.1.

Example 162: trans-N,2,2-trimethyl-N-(3-phenylpiperidin-4-yl)-3-((3-(trifluoromethyl)pyridin-2-yl)oxy)propanamide

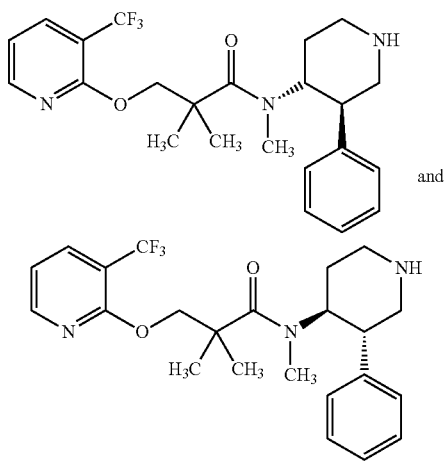

and

To a mixture of trans-tert-butyl 3-phenyl-4-(N,2,2-trimethyl-3-((3-(trifluoromethyl)pyridin-2-yl)oxy)propanamido)piperidine-1-carboxylate (35 mg, 65 μmol) in DCM (2 mL) was added TFA (1 mL) at 25° C. under nitrogen. The mixture was stirred at 25° C. for 1 hour and then concentrated. The residue was partitioned between EtOAc and saturated aq NaHCO$_3$. The organic phase was dried, filtered, and concentrated. The crude product was purified by preparative HPLC (Phenomenex Gemini 10 μm, 25 mm ID×150 mm column) eluting with a gradient of 46-76% ACN in water (containing 0.05% ammonium hydroxide) to give the title compound as a light yellow oil (15 mg, 52%). $^1$H NMR (400 MHz, CD$_3$OD) δ ppm 1.00 (br s, 3H), 1.15 (s, 3H), 1.63-1.93 (m, 2H), 2.61-3.08 (m, 6H), 3.08-3.28 (m, 2H), 4.33 (s, 2H), 4.90-5.01 (m, 1H), 7.07 (dd, J=7.5, 5.3 Hz, 1H), 7.12-7.35 (m, 5H), 7.96 (br d, J=6.4 Hz, 1H), 8.32 (br d, J=5.1 Hz, 1H); ESI-MS [M+H]$^+$ calc'd for C$_{23}$H$_{28}$F$_3$N$_3$O$_2$, 436.22; found, 436.2.

Example 163: 2,2-dimethyl-N-(cis-1-methyl-3-phenylpiperidin-4-yl)-3-((3-(trifluoromethyl)pyridin-2-yl)oxy)propanamide

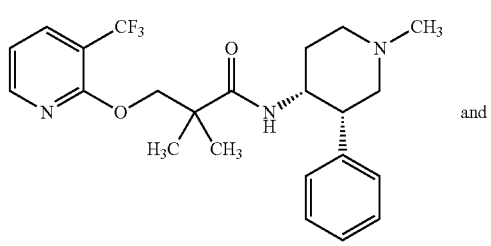

and

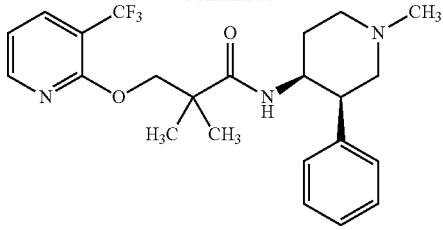

Example 164: 2,2-dimethyl-N-(trans-1-methyl-3-phenylpiperidin-4-yl)-3-((3-(trifluoromethyl)pyridin-2-yl)oxy)propanamide

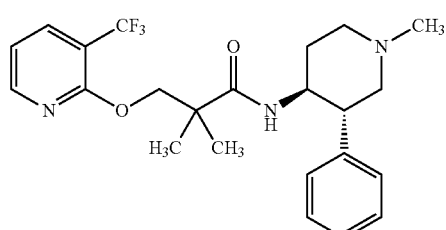

and

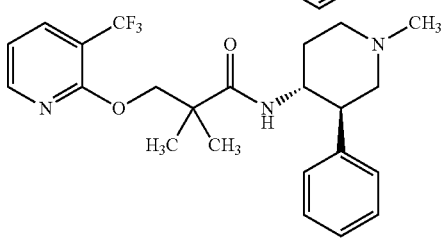

To a solution of 2,2-dimethyl-N-(3-phenylpiperidin-4-yl)-3-((3-(trifluoromethyl)pyridin-2-yl)oxy)propanamide TFA salt (87 mg, 0.162 mmol) and paraformaldehyde (13.4 μL, 0.487 mmol) in DCM (1.6 mL) were added sodium triacetoxyborohydride (103 mg, 0.487 mmol) and DIPEA (85 μL, 0.487 mmol). The resulting mixture was stirred at room temperature for 16 hours at which time EtOAc (30 mL) and saturated aq NaHCO$_3$(10 mL) were added. The reaction mixture was stirred vigorously for 1 hour. The organic layer was separated and washed with brine. The solvent was removed and the residue was purified by preparative HPLC and chiral SFC to give the title compounds as their TFA salts. The major peak was arbitrarily assigned to be the cis-stereoisomer (17 mg, 24%) and the minor peak to be the trans-stereoisomer (4.4 mg, 6.2%). Major peak: $^1$H NMR (400 MHz, CD$_3$OD) δ ppm 0.91 (s, 3H), 0.99 (s, 3H), 1.61 (qd, J=12.4, 3.7 Hz, 1H), 1.93-2.03 (m, 1H), 2.10-2.24 (m, 2H), 2.29 (s, 3H), 2.72-2.85 (m, 1H), 2.93 (br t, J=14.6 Hz, 2H), 3.97 (d, J=10.5 Hz, 1H), 4.02-4.13 (m, 1H), 4.25 (d, J=10.5 Hz, 1H), 6.78 (br d, J=8.8 Hz, 1H), 6.92-7.05 (m, 1H), 7.08-7.35 (m, 5H), 7.88 (br d, J=7.3 Hz, 1H), 8.25 (br d, J=4.4 Hz, 1H); ESI-MS [M+H]$^+$ calc'd for C$_{23}$H$_{28}$F$_3$N$_3$O$_2$, 436.21; found, 436.1. Minor peak: $^1$H NMR (500 MHz, CD$_3$OD) δ ppm 1.05 (s, 3H), 1.10 (s, 3H), 1.77-1.93 (m, 2H), 2.31 (s, 4H), 2.50-2.66 (m, 2H), 2.74-2.85 (m, 1H), 3.14-3.21 (m, 1H), 4.12 (d, J=10.7 Hz, 1H), 4.21-4.30 (m, 2H), 6.06-6.18 (m, 1H), 7.05 (dd, J=7.3, 5.1 Hz, 1H), 7.08-7.14 (m, 1H), 7.18 (t, J=7.6 Hz, 2H), 7.23-

7.37 (m, 2H), 7.90 (d, J=7.6 Hz, 1H), 8.26-8.36 (m, 1H); ESI-MS [M+H]+ calc'd for $C_{23}H_{28}F_3N_3O_2$, 436.21; found, 436.1.

Example 165: N-(trans-1,4-dimethylpyrrolidin-3-yl)-2,2-dimethyl-3-((3-(trifluoromethyl)pyridin-2-yl)oxy)propanamide

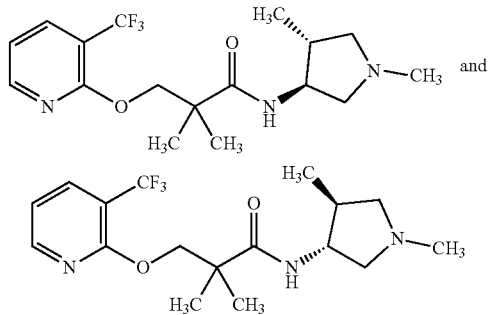

Step A: tert-butyl trans-3-(2,2-dimethyl-3-((3-(trifluoromethyl)pyridin-2-yl)oxy)propanamido)-4-methylpyrrolidine-1-carboxylate

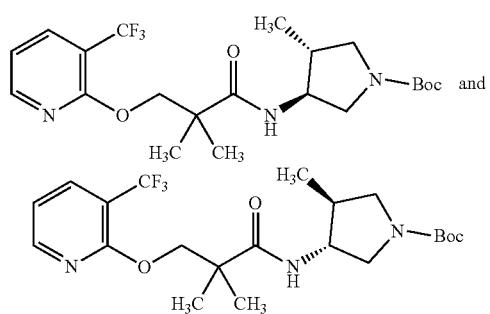

The title compound was prepared in a manner similar to PREPARATION 75, using tert-butyl trans-3-amino-4-methylpyrrolidine-1-carboxylate (60 mg, 0.300 mmol, 1 eq) in place of tert-butyl 4-amino-3-phenylpiperidine-1-carboxylate. The product was purified by preparative HPLC (Method A) to give a colorless oil (70 mg, 53%). ESI-MS [M+H]+ calc'd for $C_{21}H_{30}F_3N_3O_4$, 446.22; found, 446.1.

Step B: 2,2-dimethyl-N-(trans-4-methylpyrrolidin-3-yl)-3-((3-(trifluoromethyl)pyridin-2-yl)oxy)propanamide

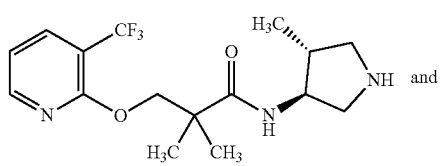

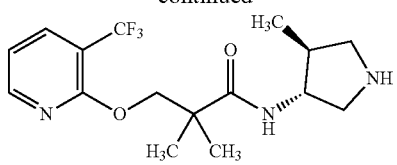

The title compound was prepared in a manner similar to EXAMPLES 155 and 156; using 2,2-dimethyl-N-(trans-4-methylpyrrolidin-3-yl)-3-((3-(trifluoromethyl)pyridin-2-yl)oxy)propanamide (70 mg, 0.157 mmol, 1 eq) in place of tert-butyl 3-(o-tolyl)-4-(N,2,2-trimethyl-3-((3-(trifluoromethyl)pyridin-2-yl)oxy)propanamido)piperidine-1-carboxylate. The solvent was removed to give a TFA salt of the title compound as a colorless oil (72 mg, quantitative) which was used without further purification. ESI-MS [M+H]+ calc'd for $C_{16}H_{21}F_4N_3O_2$, 346.16; found, 346.1.

Step C: N-(trans-1,4-dimethylpyrrolidin-3-yl)-2,2-dimethyl-3-((3-(trifluoromethyl)pyridin-2-yl)oxy)propanamide The title compound was prepared in a manner similar to EXAMPLES 163 and 164, using 2,2-dimethyl-N-(trans-4-methylpyrrolidin-3-yl)-3-((3-(trifluoromethyl)pyridin-2-yl)oxy)propanamide (72 mg, 0.157 mmol, 1 eq) in place of 2,2-dimethyl-N-(3-phenylpiperidin-4-yl)-3-((3-(trifluoromethyl)pyridin-2-yl)oxy)propanamide. The product was purified by preparative HPLC (Method A) to give a TFA salt of the title compound as a colorless oil (37 mg, 50%). ESI-MS [M+H]+ calc'd for $C_{17}H_{24}F_3N_3O_2$, 360.18; found, 360.1.

Example 166: 2,2-dimethyl-N-(cis-1-methyl-3-phenylpiperidin-4-yl)-3-((3-(trifluoromethoxy)pyridin-2-yl)oxy)propanamide

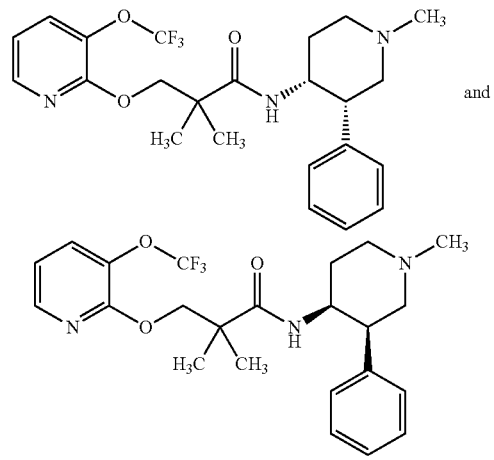

Step A: 2,2-dimethyl-N-(cis-3-phenylpiperidin-4-yl)-3-((3-(trifluoromethoxy)pyridin-2-yl)oxy)propanamide

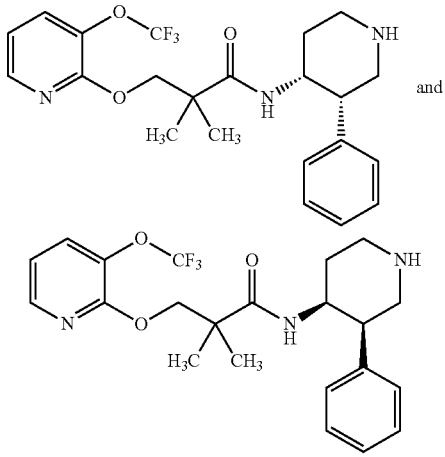
and

The title compound was prepared in a manner similar to EXAMPLE 162, using tert-butyl cis-4-(2,2-dimethyl-3-((3-(trifluoromethoxy)pyridin-2-yl)oxy)propanamido)-3-phenylpiperidine-1-carboxylate (52 mg, 0.097 mmol, 1 eq) in place of trans-tert-butyl 3-phenyl-4-(N,2,2-trimethyl-3-((3-(trifluoromethyl)pyridin-2-yl)oxy)propanamido)piperidine-1-carboxylate. The solvent was removed to give a TFA salt of the title compound (55 mg, quantitative) which was used without further purification.

Step B: 2,2-dimethyl-N-(cis-1-methyl-3-phenylpiperidin-4-yl)-3-((3-(trifluoromethoxy)pyridin-2-yl)oxy)propanamide The title compound was prepared in a manner similar to EXAMPLES 163 and 164, using 2,2-dimethyl-N-(cis-3-phenylpiperidin-4-yl)-3-((3-(trifluoromethoxy)pyridin-2-yl)oxy)propanamide (45 mg, 0.082 mmol, 1 eq) in place of 2,2-dimethyl-N-(3-phenylpiperidin-4-yl)-3-((3-(trifluoromethyl)pyridin-2-yl)oxy)propanamide. The product was purified by preparative HPLC (Method A) to give the title compound as a TFA salt (30 mg, 65%). ESI-MS [M+H]+ calc'd for $C_{23}H_{28}F_3N_3O_3$, 452.20; found, 452.1.

Example 167: 2,2-dimethyl-N-(trans-1-methyl-3-phenylpiperidin-4-yl)-3-((3-(trifluoromethoxy)pyridin-2-yl)oxy)propanamide

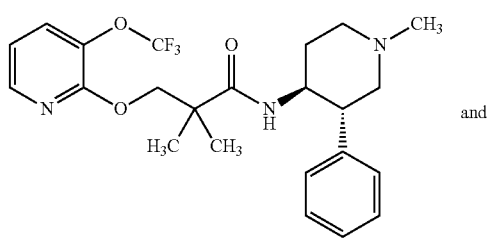
and

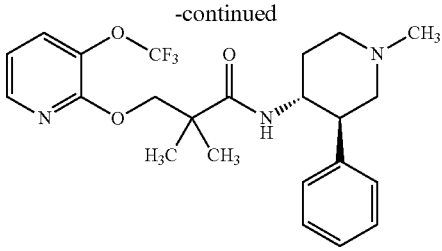

Step A: 2,2-dimethyl-N-(trans-3-phenylpiperidin-4-yl)-3-((3-(trifluoromethoxy)pyridin-2-yl)oxy)propanamide

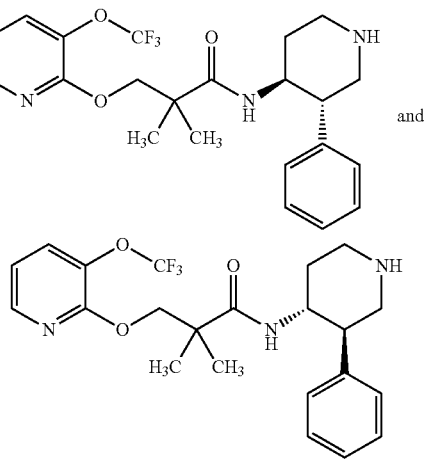

The title compound was prepared in a manner similar to EXAMPLE 162, using tert-butyl trans-4-(2,2-dimethyl-3-((3-(trifluoromethoxy)pyridin-2-yl)oxy)propanamido)-3-phenylpiperidine-1-carboxylate (44 mg, 0.082 mmol, 1 eq) in place of trans-tert-butyl 3-phenyl-4-(N,2,2-trimethyl-3-((3-(trifluoromethyl)pyridin-2-yl)oxy)propanamido)piperidine-1-carboxylate. The solvent was removed to give a TFA salt of the title compound (47 mg, quantitative) which was used without further purification.

Step B: 2,2-dimethyl-N-(trans-1-methyl-3-phenylpiperidin-4-yl)-3-((3-(trifluoromethoxy)pyridin-2-yl)oxy)propanamide The title compound was prepared in a manner similar to EXAMPLES 163 and 164, using 2,2-dimethyl-N-(trans-3-phenylpiperidin-4-yl)-3-((3-(trifluoromethoxy)pyridin-2-yl)oxy)propanamide (53 mg, 0.096 mmol, 1 eq) in place of 2,2-dimethyl-N-(3-phenylpiperidin-4-yl)-3-((3-(trifluoromethyl)pyridin-2-yl)oxy)propanamide. The product was purified by preparative HPLC (Method A) to give the title compound as a TFA salt (9.2 mg, 17%). ESI-MS [M+H]+ calc'd for $C_{23}H_{28}F_3N_3O_3$, 452.20; found, 452.1.

Example 168: trans-3-(o-tolyl)piperidin-4-yl 2,2-dimethyl-3-((3-(trifluoromethyl)pyridin-2-yl)oxy)propanoate

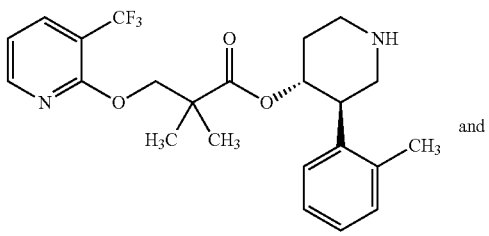
and

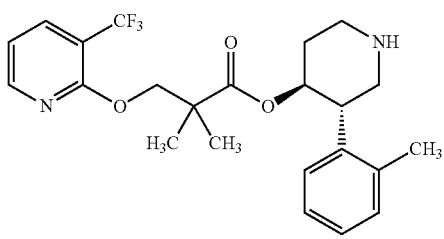

Step A: tert-butyl 4-oxo-3-(o-tolyl)piperidine-1-carboxylate

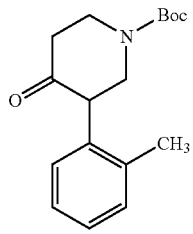

To a solution of Pd(OAc)₂ (281.7 mg, 1.25 mmol) and tri-tert-butylphosphine (10% in toluene, 5.08 g, 2.51 mmol) in THF (50 mL) were added tert-butyl 4-oxopiperidine-1-carboxylate (5.00 g, 25.1 mmol), 1-bromo-2-methyl-benzene (4.51 g, 26.4 mmol) and sodium tert-butoxide (3.62 g, 37.6 mmol) at 20° C. The reaction mixture was allowed to stir at 50° C. for 6 hours and was then poured into saturated aq NaHCO₃ (50 mL) and extracted with EtOAc (3×50 mL). The organic layers were combined, dried over anhydrous Na₂SO₄, filtered, and concentrated under reduced pressure. The crude product was purified by flash silica column chromatography, eluting with petroleum ether and EtOAc to give the title compound as a yellow solid (2.6 g, 36%). ESI-MS [M+H]⁺ calc'd for C₁₇H₂₃NO₃, 290.18; found [M-t-Bu], 234.1.

Step B: trans-tert-butyl 4-hydroxy-3-(o-tolyl)piperidine-1-carboxylate

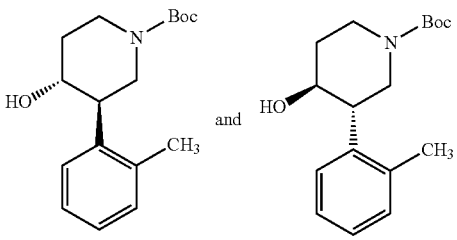 [SMILES: Cc1ccccc1[C@@H]1CN(C(=O)OC(C)(C)C)CC[C@H]1O ; Cc1ccccc1[C@H]1CN(C(=O)OC(C)(C)C)CC[C@@H]1O]
and

To a solution of tert-butyl 3-(o-tolyl)-4-oxo-piperidine-1-carboxylate (1.00 g, 3.46 mmol) in methanol (15 mL) was added NaBH₄ (261 mg, 6.91 mmol) at 0° C. The reaction mixture was stirred at 15° C. for 2 hours, and was then quenched with water and extracted with EtOAc. The organic phase was dried over anhydrous Na₂SO₄, filtered, and concentrated under reduced pressure. The crude product was purified by flash silica column chromatography, eluting with petroleum ether and EtOAc to give the title compound as a yellow gum (0.6 g, 60%). ESI-MS [M+Na]⁺ calc'd for C₁₇H₂₅NO₃, 314.2; found, 314.1.

Step C: trans-tert-butyl 4-((2,2-dimethyl-3-((3-(trifluoromethyl)pyridin-2-yl)oxy)propanoyl)oxy)-3-(o-tolyl)piperidine-1-carboxylate

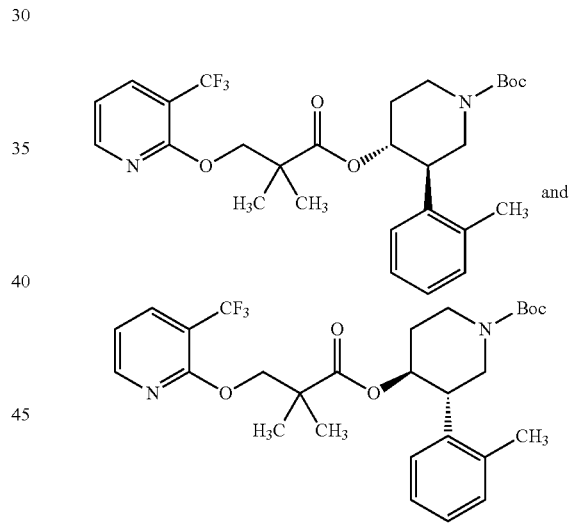

A mixture of 2,2-dimethyl-3-((3-(trifluoromethyl)pyridin-2-yl)oxy)propanoic acid (162.6 mg, 0.618 mmol), trans-tert-butyl 4-hydroxy-3-(o-tolyl)piperidine-1-carboxylate (150 mg, 0.515 mmol), DMAP (31.4 mg, 0.257 mmol) and DCC (150 mg, 0.727 mmol) in DCM (3 mL) was stirred at room temperature overnight. The mixture was then diluted with EtOAc (30 mL) and filtered. The filtrate was concentrated under reduced pressure and purified by preparative TLC, eluting with 2:1 petroleum ether/EtOAc to give the title compound as a colorless gum (110 mg, 39%). ESI-MS [M+H]⁺ calc'd for C₂₈H₃₅F₃N₂O₅, 537.26; found [M-t-Bu], 481.2.

Step D: trans-3-(o-tolyl)piperidin-4-yl 2,2-dimethyl-3-((3-(trifluoromethyl)pyridin-2-yl)oxy)propanoate To a mixture of trans-tert-butyl 4-(2,2-dimethyl-3-((3-(trifluoromethyl)-2-pyridyl)oxy)propanoyl)oxy-3-(o-tolyl)

piperidine-1-carboxylate (80 mg, 0.15 mmol) in DCM (3 mL) was added TFA (1.16 g, 10.1 mmol). The reaction mixture was stirred at 25° C. for 10 minutes and then concentrated under reduced pressure. The residue was dissolved in water and adjusted to pH 8-9 by addition of saturated aq NaHCO$_3$ solution. The mixture was extracted with DCM. The combined organic layers were dried, filtered, and concentrated under reduced pressure. The crude product was purified by flash silica column chromatography, eluting with methanol in DCM to give the title compound as a colorless gum (53 mg, 81%). $^1$H NMR (400 MHz, CDCl$_3$) δ ppm 0.95 (s, 3H), 1.02 (s, 3H), 1.43-1.55 (m, 1H), 2.17 (br d, J=8.0 Hz, 1H), 2.38 (s, 3H), 2.73 (t, J=12.8 Hz, 1H), 2.79-2.88 (m, 1H), 3.07-3.16 (m, 2H), 3.20 (br d, J=11.5 Hz, 1H), 4.13-4.22 (m, 2H), 5.10 (td, J=10.8, 4.5 Hz, 1H), 6.93-7.01 (m, 2H), 7.02-7.09 (m, 2H), 7.12-7.17 (m, 1H), 7.83 (d, J=7.5 Hz, 1H), 8.28 (d, J=3.5 Hz, 1H). ESI-MS [M+H]$^+$ calc'd for C$_{23}$H$_{27}$F$_3$N$_2$O$_3$, 437.20; found, 437.2.

Example 169: 2,2-dimethyl-N-(trans-1-methyl-4-(1-methyl-1H-pyrazol-4-yl)piperidin-3-yl)-3-((3-(trifluoromethyl)pyridin-2-yl)oxy)propanamide

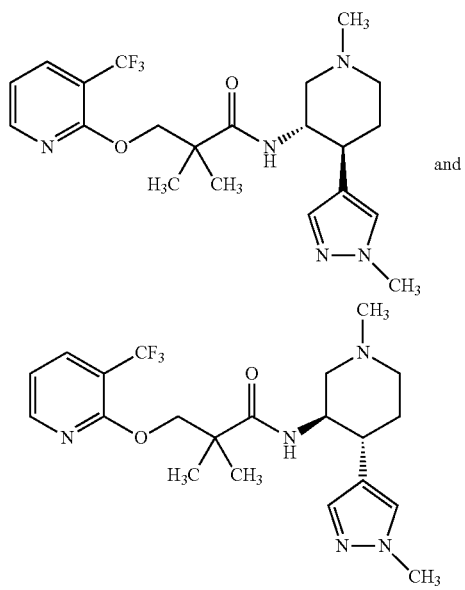

The title compound was prepared in a manner similar to PREPARATION 75, using trans-1-methyl-4-(1-methyl-1H-pyrazol-4-yl)piperidin-3-amine (15 mg, 0.077 mmol, 1 eq) in place of tert-butyl 4-amino-3-phenylpiperidine-1-carboxylate. The product was purified by preparative HPLC (Method A) to give a TFA salt of the title compound as a white solid (12 mg, 28%). ESI-MS [M+H]$^+$ calc'd for C$_{21}$H$_{28}$F$_3$N$_5$O$_2$, 440.22; found, 440.1.

Example 170: trans-3-(2-methylpyridin-3-yl)piperidin-4-yl 2,2-dimethyl-3-((3-(trifluoromethyl)pyridin-2-yl)oxy)propanoate

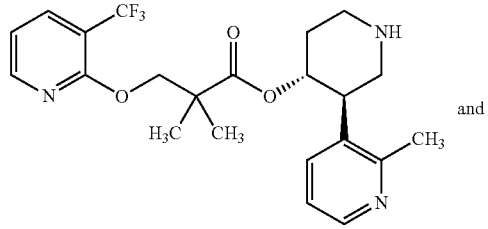

and

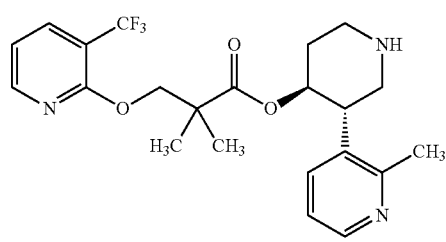

Step A: tert-butyl 3-(2-methylpyridin-3-yl)-4-oxopiperidine-1-carboxylate

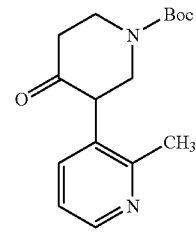

A mixture of t-BuONa (5.79 g, 60.2 mmol) and Pd(OAc)$_2$ (901 mg, 4.02 mmol) in THF (80 mL) was stirred at 15° C. for 15 minutes. Tri-tert-butylphosphine (10% in toluene, 16.25 g, 8.03 mmol), 3-bromo-2-methyl-pyridine (7.60 g, 44.2 mmol) and tert-butyl 4-oxopiperidine-1-carboxylate (8.00 g, 40.2 mmol) were added. The reaction mixture was stirred at 45° C. overnight under argon atmosphere. The reaction mixture was subsequently diluted with EtOAc and washed with water. The organic layer was dried over Na$_2$SO$_4$, filtered, and concentrated under reduced pressure to give crude product. The crude product was purified by automated flash silica column chromatography (60 g column) eluting with a gradient of 0-50% EtOAc in petroleum ether to give the title compound as a yellow oil (4.3 g, 37%). ESI-MS [M+H]$^+$ calc'd for C$_{16}$H$_{22}$N$_2$O$_3$, 291.17; found, 291.2.

Step B: trans-tert-butyl 4-hydroxy-3-(2-methylpyridin-3-yl)piperidine-1-carboxylate

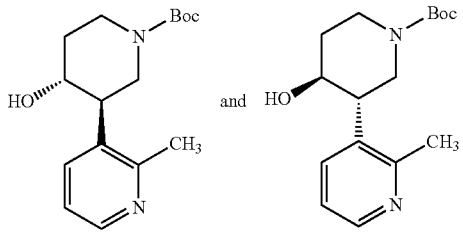 [SMILES: Cc1ncccc1[C@@H]1CN(C(=O)OC(C)(C)C)CC[C@H]1O ; Cc1ncccc1[C@H]1CN(C(=O)OC(C)(C)C)CC[C@@H]1O]

To a solution of tert-butyl 3-(2-methylpyridin-3-yl)-4-oxopiperidine-1-carboxylate (100 mg, 0.344 mmol) in MeOH (2 mL) was added NaBH$_4$ (39.1 mg, 1.03 mmol) at 20° C. The reaction mixture was allowed to stir at room temperature overnight and was then treated with water (100 mL) and extracted with EtOAc (3×50 mL). The organic layers were combined, dried over Na$_2$SO$_4$, filtered, and concentrated under reduced pressure to give crude product. The crude product was purified by preparative TLC, eluting with DCM/methanol (15:1) to give the title compound (58 mg, 49%) as a white solid (85% purity). ESI-MS [M+H]$^+$ calc'd for C$_{16}$H$_{24}$N$_2$O$_3$, 293.19; found, 293.0.

Step C: trans-tert-butyl 4-((2,2-dimethyl-3-((3-(trifluoromethyl)pyridin-2-yl)oxy)propanoyl)oxy)-3-(2-methylpyridin-3-yl)piperidine-1-carboxylate

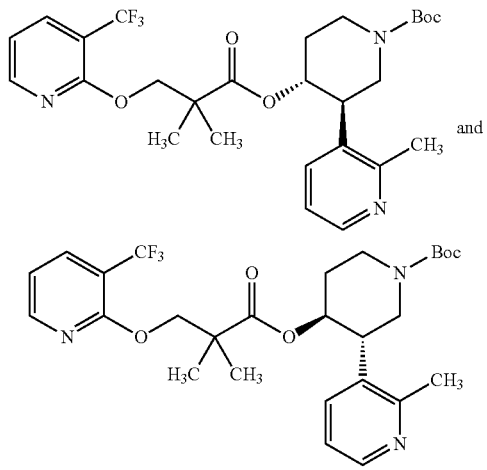

A mixture of trans-tert-butyl 4-hydroxy-3-(2-methylpyridin-3-yl)piperidine-1-carboxylate (50.0 mg, 0.171 mmol), 2,2-dimethyl-3-((3-(trifluoromethyl)pyridin-2-yl)oxy)propanoic acid (49.5 mg, 0.188 mmol), DMAP (10.4 mg, 0.085 μmol) and DCC (52.9 mg, 0.257 mmol) in DCM (1 mL) was stirred at room temperature overnight. The mixture was filtered and the filtrate was purified by preparative TLC, eluting with EtOAc/petroleum ether (1:1) to give the title compound (65 mg, 66%) as a white solid (93% purity). ESI-MS [M+H]$^+$ calc'd for C$_{27}$H$_{34}$F$_3$N$_3$O$_5$, 538.25; found, 538.6.

Step D: trans-3-(2-methylpyridin-3-yl)piperidin-4-yl 2,2-dimethyl-3-((3-(trifluoromethyl)pyridin-2-yl)oxy)propanoate To a solution of trans-tert-butyl 4-(2,2-dimethyl-3-((3-(trifluoromethyl)-2-pyridyl)oxy)propanoyl)oxy-3-(2-methyl-3-pyridyl)piperidine-1-carboxylate (65.0 mg, 0.121 mmol) in DCM (0.5 mL) was added TFA (275.7 mg, 2.42 mmol) at 20° C. The reaction mixture was stirred at room temperature for 1 hour and then aq Na$_2$CO$_3$ was added to raise the pH to 10. The organic layer was separated, concentrated under reduced pressure, and purified by preparative HPLC (Phenomenex Gemini 10 μm, 25 mm ID×150 mm column) eluting with a gradient of 30-60% ACN in water (containing 0.05% ammonium hydroxide) to give the title compound as a colorless oil (17.4 mg, 33%). $^1$H NMR (400 MHz, CDCl$_3$) δ ppm 0.99 (s, 3H), 1.04 (s, 3H), 1.53-1.57 (m, 1H), 2.08-2.20 (m, 1H), 2.58-2.72 (m, 4H), 2.81 (td, J=12.7, 2.4 Hz, 1H), 3.05-3.26 (m, 3H), 4.19 (s, 2H), 5.00-5.14 (m, 1H), 6.98 (td, J=8.1, 5.2 Hz, 2H), 7.45 (br d, J=7.9 Hz, 1H), 7.82 (br d, J=7.5 Hz, 1H), 8.15-8.32 (m, 2H); ESI-MS [M+H]$^+$ calc'd for C$_{22}$H$_{26}$F$_3$N$_3$O$_3$, 438.20; found, 438.4.

Example 171: trans-3-phenylpiperidin-4-yl 2,2-dimethyl-3-((3-(trifluoromethyl)pyridin-2-yl)oxy)propanoate

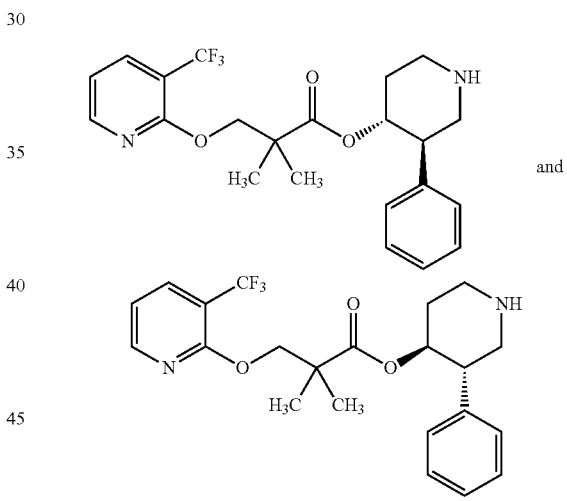

Step A: tert-butyl 4-oxo-3-phenylpiperidine-1-carboxylate

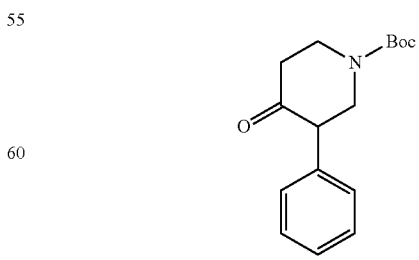

To a solution of t-BuONa (7.24 g, 75.3 mmol) in THF (100 mL) was added Pd(OAc)$_2$ (1.13 g, 5.02 mmol) under nitrogen at 25° C. The reaction mixture was stirred for 15 minutes. Next tert-butyl 4-oxopiperidine-1-carboxylate (10.0 g, 50.2 mmol), bromobenzene (8.67 g, 55.2 mmol) and tri-tert-butylphosphine (10% in toluene, 20.31 g, 10.04 mmol) were added. The reaction mixture was warmed to 45° C. and stirred at 45° C. overnight. The reaction mixture was partitioned between EtOAc and saturated aq NaHCO$_3$. The organic phase was separated, washed with brine, dried over anhydrous Na$_2$SO$_4$, filtered, and concentrated under reduced pressure. The resulting crude product was purified by flash silica column chromatography, eluting with petroleum ether and EtOAc to give the title compound (2.8 g, 18%) as a yellow solid (90% purity). ESI-MS [M+H]$^+$ calc'd for C$_{16}$H$_{21}$NO$_3$, 276.15; found [M-t-Bu], 220.1.

Step B: trans-tert-butyl 4-hydroxy-3-phenylpiperidine-1-carboxylate

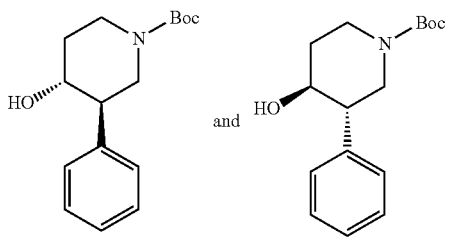 [SMILES: CC(C)(C)OC(=O)N1CC[C@@H](O)[C@H](c2ccccc2)C1 ; CC(C)(C)OC(=O)N1CC[C@H](O)[C@@H](c2ccccc2)C1]

To a mixture of tert-butyl 4-oxo-3-phenylpiperidine-1-carboxylate (200 mg, 0.726 mmol) in methanol (5 mL) was added NaBH$_4$ (55.0 mg, 1.45 mmol) at 0° C. under nitrogen. The reaction mixture was stirred at 0° C. for 1 hour and was then quenched by the addition of water at 0° C. and extracted with EtOAc. The organic layers were combined, washed with brine, dried over Na$_2$SO$_4$, filtered, and concentrated under reduced pressure. The resulting crude product was purified by preparative TLC, eluting with petroleum ether/EtOAc (3:1) to give the title compound (120 mg, 57%) as a white solid (96% purity). ESI-MS [M+H]$^+$ calc'd for C$_{16}$H$_{23}$NO$_3$, 278.17; found [M-t-Bu], 222.1.

Step C: trans-tert-butyl 4-((2,2-dimethyl-3-((3-(trifluoromethyl)pyridin-2-yl)oxy)propanoyl) oxy)-3-phenylpiperidine-1-carboxylate To a mixture of 2,2-dimethyl-3-((3-(trifluoromethyl)pyridin-2-yl)oxy)propanoic acid (136.7 mg, 0.519 mmol) and trans-tert-butyl 4-hydroxy-3-phenyl-piperidine-1-carboxylate (120 mg, 0.433 mmol) in DCM (10 mL) were added DMAP (26.4 mg, 0.216 mmol) and DCC (133.9 mg, 0.649 mmol) at 25° C. under nitrogen. The reaction mixture was allowed to stir at room temperature overnight and was then concentrated under reduced pressure. The resulting crude product was purified by flash silica column chromatography, eluting with petroleum ether and EtOAc to give the title compound (100 mg, 41%) as a colorless oil (92% purity). ESI-MS [M+Na]$^+$ calc'd for C$_{27}$H$_{33}$F$_3$N$_2$O$_5$, 545.22; found, 545.1.

Step D: trans-3-phenylpiperidin-4-yl 2,2-dimethyl-3-((3-(trifluoromethyl)pyridin-2-yl)oxy)propanoate To a solution of trans-tert-butyl 4-(2,2-dimethyl-3-((3-(trifluoromethyl)-2-pyridyl)oxy)propanoyl)oxy-3-phenyl-piperidine-1-carboxylate (100 mg, 0.176 mmol) in DCM (15 mL) was added TFA (10.04 g, 88.03 mmol) drop wise at 0° C. The reaction mixture was allowed to stir at room temperature for 2 hours and then concentrated under reduced pressure. The residue was diluted with aq NaHCO$_3$ and extracted with EtOAc. The organic layers were combined, washed with brine, dried, filtered, and concentrated under reduced pressure. The resulting crude product was purified by preparative HPLC (Phenomenex Gemini 10 μm, 25 mm IDx150 mm column) eluting with a gradient of 54-84% ACN in water (containing 0.05% ammonium hydroxide) to give the title compound (27.9 mg, 36%) as a colorless oil (97% purity). $^1$H NMR (400 MHz, CD$_3$OD) δ ppm 0.94 (s, 3H), 1.02 (s, 3H), 1.43-1.55 (m, 1H), 2.02-2.12 (m, 1H), 2.71-2.88 (m, 3H), 3.02-3.18 (m, 2H), 4.08-4.25 (m, 2H), 5.08 (td, J=10.7, 4.6 Hz, 1H), 7.04-7.12 (m, 2H), 7.14-7.23 (m, 4H), 7.95 (dd, J=7.5, 1.1 Hz, 1H), 8.31 (dd, J=4.8, 1.1 Hz, 1H); ESI-MS [M+H]$^+$ calc'd for C$_{22}$H$_{25}$F$_3$N$_2$O$_3$, 423.19; found, 423.2.

Example 172: N,2,2-trimethyl-N-(trans-3-(2-methylpyridin-3-yl)piperidin-4-yl)-3-((3-(trifluoromethyl)pyridin-2-yl)oxy)propanamide

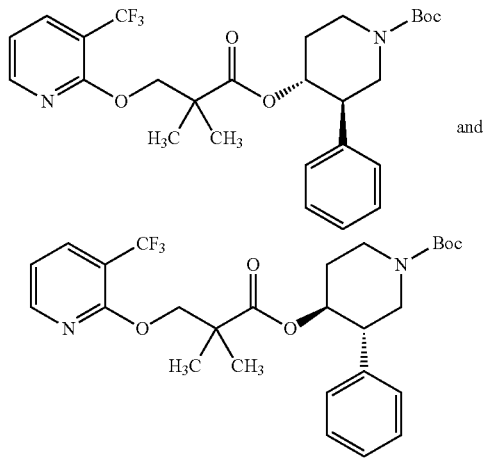

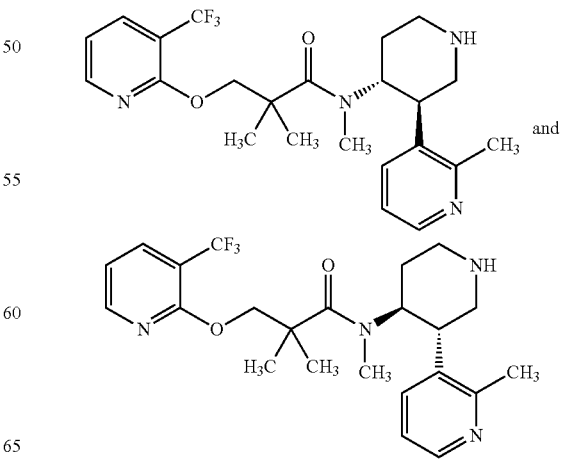

Step A: (E)-tert-butyl 4-(hydroxyimino)-3-(2-methylpyridin-3-yl)piperidine-1-carboxylate

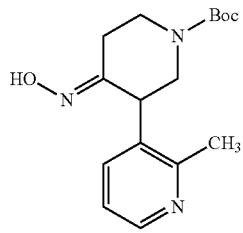 [SMILES: Cc1ncccc1C1CN(C(=O)OC(C)(C)C)CC/C1=N\O]

To a solution of tert-butyl 3-(2-methyl-3-pyridyl)-4-oxo-piperidine-1-carboxylate (3.00 g, 10.3 mmol) in EtOH (30 mL) were added NH$_2$OH·HCl (1.08 g, 15.5 mmol) and NaOAc (1.70 g, 20.7 mmol). The reaction mixture was allowed to stir at room temperature overnight, and was then diluted with water and extracted with EtOAc. The organic layer was dried over anhydrous Na$_2$SO$_4$, filtered, and concentrated under reduced pressure to give the title compound (3.5 g, 99%) which was used without further purification (90% purity). ESI-MS [M+H]$^+$ calc'd for C$_{16}$H$_{23}$N$_3$O$_3$, 306.18; found, 306.0.

Step B: tert-butyl trans-4-amino-3-(2-methylpyridin-3-yl)piperidine-1-carboxylate

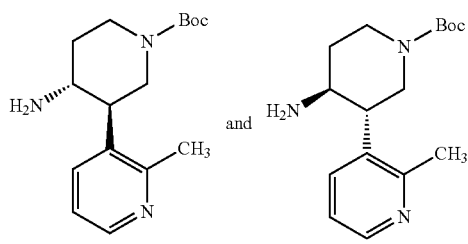 [SMILES: Cc1ncccc1[C@@H]1CN(C(=O)OC(C)(C)C)CC[C@H]1N ; Cc1ncccc1[C@H]1CN(C(=O)OC(C)(C)C)CC[C@@H]1N]

To a solution of (E)-tert-butyl 4-(hydroxyimino)-3-(2-methylpyridin-3-yl)piperidine-1-carboxylate (1.30 g, 4.26 mmol) in EtOH (10 mL) was added Raney-Ni (186 mg) at 20° C. The suspension was degassed under vacuum and purged three times with H$_2$. The reaction mixture was allowed to stir at room temperature overnight under H$_2$ (50 psi) atmosphere. The suspension was filtered and the filtrate was concentrated under reduced pressure. The resulting crude product was purified by automated flash silica column chromatography (10 g column) eluting with a gradient of 0-8% methanol in DCM to give the title compound as a white solid (208 mg, 17%). ESI-MS [M+H]$^+$ calc'd for C$_{16}$H$_{25}$N$_3$O$_2$, 292.20; found, 292.0.

Step C: tert-butyl trans-4-(2,2-dimethyl-3-((3-(trifluoromethyl)pyridin-2-yl)oxy)propanamido)-3-(2-methylpyridin-3-yl)piperidine-1-carboxylate

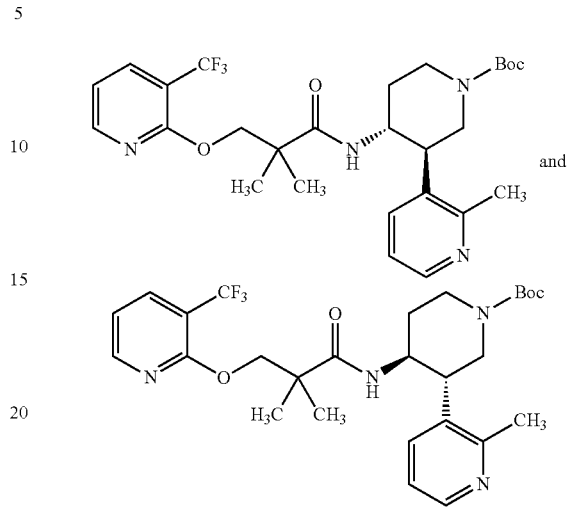

A mixture of tert-butyl trans-4-amino-3-(2-methylpyridin-3-yl)piperidine-1-carboxylate (100 mg, 0.343 mmol), 2,2-dimethyl-3-((3-(trifluoromethyl)pyridin-2-yl)oxy)propanoic acid (99.4 mg, 0.377 mmol), HATU (156.6 mg, 0.412 mmol) and DIPEA (133.1 mg, 1.03 mmol) in DMF (1 mL) was stirred at room temperature overnight. The reaction mixture was diluted with EtOAc and washed with water. The organic layer was dried over anhydrous Na$_2$SO$_4$, filtered, and concentrated under reduced pressure. The resulting crude product was purified by preparative TLC, eluting with petroleum ether/EtOAc (1:1) to give the title compound (70 mg, 33%) as a white solid (87% purity). ESI-MS [M+H]$^+$ calc'd for C$_{27}$H$_{35}$F$_3$N$_4$O$_4$, 537.27; found, 537.6.

Step D: tert-butyl trans-3-(2-methylpyridin-3-yl)-4-(N,2,2-trimethyl-3-((3-(trifluoromethyl)pyridin-2-yl)oxy)propanamido)piperidine-1-carboxylate

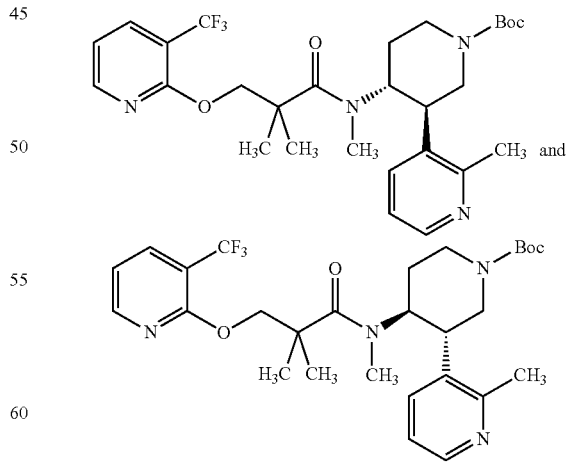

To a solution of tert-butyl trans-4-(2,2-dimethyl-3-((3-(trifluoromethyl)pyridin-2-yl)oxy) propanamido)-3-(2-methylpyridin-3-yl)piperidine-1-carboxylate (30.0 mg, 55.9 µmol) in THF (1 mL) was added NaH (60 wt %, 22.4 mg, 559 µmol) at 0° C. After stirring at 0° C. for 15 minutes, MeI (79.4 mg, 559 µmol) was added, and the reaction mixture was allowed to stir at room temperature overnight. The reaction was subsequently quenched with water and the reaction mixture extracted with EtOAc. The organic layer was dried over Na$_2$SO$_4$, filtered, and concentrated under reduced pressure. The resulting crude product was purified by preparative TLC, eluting with petroleum ether/EtOAc (1:1) to give the title compound (35 mg, 85%) as a light yellow solid (75% purity). ESI-MS [M+H]$^+$ calc'd for C$_{28}$H$_{37}$F$_3$N$_4$O$_4$, 551.28; found, 551.1.

Step E: N,2,2-trimethyl-N-(trans-3-(2-methylpyridin-3-yl)piperidin-4-yl)-3-((3-(trifluoromethyl)pyridin-2-yl)oxy)propanamide To a solution of tert-butyl trans-3-(2-methylpyridin-3-yl)-4-(N,2,2-trimethyl-3-((3-(trifluoromethyl)pyridin-2-yl)oxy)propanamido)piperidine-1-carboxylate (35 mg, 48 µmol, 75% purity) in DCM (1 mL) was added TFA (72.5 mg, 635 µmol) at 20° C. The reaction mixture was allowed to stir at room temperature for 1 hour and was then concentrated under reduced pressure. The resulting crude product was purified by preparative HPLC (Phenomenex Gemini 10 µm, 25 mm ID×150 mm column) eluting with a gradient of 30-50% ACN in water (containing 0.05% ammonia hydroxide) to give the title compound as a light yellow solid (5.4 mg, 19%). $^1$H NMR (400 MHz, CD$_3$OD) δ ppm 1.02-1.12 (m, 3H), 1.15-1.25 (m, 3H), 1.65-1.89 (m, 2H), 2.42-2.56 (m, 1H), 2.62 (s, 3H), 2.75-2.95 (m, 4H), 3.05-3.27 (m, 3H), 4.29-4.43 (m, 2H), 4.96-5.10 (m, 1H), 7.03-7.10 (m, 1H), 7.16 (dd, J=7.5, 5.1 Hz, 1H), 7.53-7.63 (m, 1H), 7.91-8.01 (m, 1H), 8.21 (dd, J=5.1, 1.5 Hz, 1H), 8.31 (dd, J=5.2, 1.0 Hz, 1H); ESI-MS [M+H]$^+$ calc'd for C$_{23}$H$_{29}$F$_3$N$_4$O$_2$, 451.23; found, 451.2.

Example 173: (S)-2,2-dimethyl-N-(5-methyl-5-azaspiro[2.4]heptan-7-yl)-3-((3-(trifluoromethyl)pyridin-2-yl)oxy)propanamide

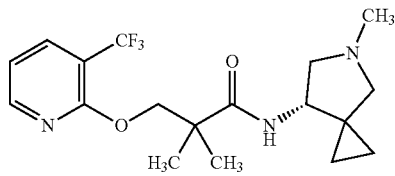 [SMILES: CN1C[C@@H](NC(=O)C(C)(C)COc2ncccc2C(F)(F)F)C2(CC2)C1]

Step A: (S)—N-(5-benzyl-5-azaspiro[2.4]heptan-7-yl)-2,2-dimethyl-3-((3-(trifluoromethyl)pyridin-2-yl)oxy)propanamide

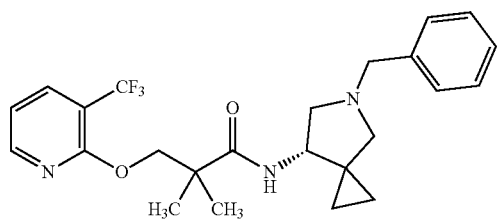 [SMILES: CC(C)(COc1ncccc1C(F)(F)F)C(=O)N[C@@H]1CN(Cc2ccccc2)CC12CC2]

A mixture of 2,2-dimethyl-3-((3-(trifluoromethyl)pyridin-2-yl)oxy)propanoic acid (0.080 g, 0.30 mmol), (S)-5-benzyl-5-azaspiro[2.4]heptan-7-amine (0.061 g, 0.30 mmol), HATU (0.116 g, 0.304 mmol), and DIPEA (0.159 mL, 0.912 mL) in DMF (3 mL) was stirred at room temperature overnight. The reaction mixture was treated with water and extracted with EtOAc. The organic phase was washed with brine, dried over MgSO$_4$, filtered, and concentrated to give the title compound as a yellow oil (0.136 g, assumed quantitative) which was used without further purification. ESI-MS [M+H]$^+$ calc'd for C$_{24}$H$_{28}$F$_3$N$_3$O$_2$, 448.22; found, 448.4.

Step B: (S)-2,2-dimethyl-N-(5-azaspiro[2.4]heptan-7-yl)-3-((3-(trifluoromethyl)pyridin-2-yl)oxy)propanamide

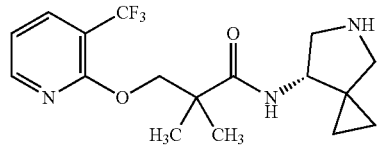 [SMILES: CC(C)(COc1ncccc1C(F)(F)F)C(=O)N[C@@H]1CNCC12CC2]

A vessel containing a mixture of (S)—N-(5-benzyl-5-azaspiro[2.4]heptan-7-yl)-2,2-dimethyl-3-((3-(trifluoromethyl)pyridin-2-yl)oxy)propanamide (0.136 g, 0.304 mmol) and dihydroxypalladium on carbon (20 wt %, 0.021 g, 0.030 mmol) in THF (20 mL) and ethanol (20 mL) was evacuated and back-filled with hydrogen gas three times. The reaction mixture was stirred at room temperature under hydrogen atmosphere (balloon) for 64 hours. The reaction mixture was filtered and the filtrate was concentrated to give the title compound as a tan film (0.109 g, assumed quantitative) which was used without further purification. ESI-MS [M+H]$^+$ calc'd for C$_{17}$H$_{22}$F$_3$N$_3$O$_2$, 358.17; found, 358.3.

Step C: (S)-2,2-dimethyl-N-(5-methyl-5-azaspiro[2.4]heptan-7-yl)-3-((3-(trifluoromethyl)pyridin-2-yl)oxy)propanamide A tan solution of (S)-2,2-dimethyl-N-(5-azaspiro[2.4]heptan-7-yl)-3-((3-(trifluoromethyl)pyridin-2-yl)oxy)propanamide (0.109 g, 0.304 mmol) and formaldehyde (37%, 0.047 mL, 0.60 mmol) in methanol (3 mL) was treated with sodium cyanoborohydride (37.8 mg, 0.602 mmol). The reaction mixture was stirred at room temperature overnight. The product was purified by preparative HPLC (Method A) to give a TFA salt of the title compound as a colorless film (74.9 mg, 51%). $^1$H NMR (400 MHz, CD$_3$OD) δ ppm 0.60-0.93 (m, 4H), 1.32 (app d, J=5.0 Hz, 6H), 2.98 (s, 3H), 3.19-3.30 (m, 2H), 3.57-3.78 (m, 2H), 4.20 (br d, J=7.8 Hz, 1H), 4.43 (s, 2H), 7.10 (s, 1H), 7.93-8.05 (m, 1H), 8.26-8.40 (m, 1H); ESI-MS [M+H]$^+$ calc'd for C$_{18}$H$_{24}$F$_3$N$_3$O$_2$, 372.18; found, 372.3.

Example 174: 2,2-dimethyl-N-(4-methyl-4-azaspiro[2.5]octan-7-yl)-3-((3-(trifluoromethoxy)pyridin-2-yl)oxy)propanamide

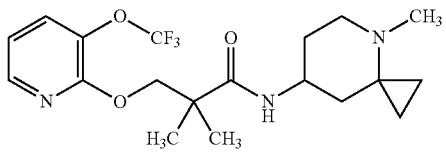 [SMILES: CN1CCC(NC(=O)C(C)(C)COc2ncccc2OC(F)(F)F)CC12CC2]

The title compound was prepared in a manner similar to EXAMPLE 173, using 2,2-dimethyl-3-((3-(trifluoromethoxy)pyridin-2-yl)oxy)propanoic acid (0.097 g, 0.35 mmol) and 4-benzyl-4-azaspiro[2.5]octan-7-amine (0.075 g, 0.35 mmol) in place of 2,2-dimethyl-3-((3-(trifluoromethyl)pyridin-2-yl)oxy)propanoic acid and (S)-5-benzyl-5-azaspiro[2.4]heptan-7-amine. Following N-benzyl deprotection of N-(4-benzyl-4-azaspiro[2.5]octan-7-yl)-2,2-dimethyl-3-((3-(trifluoromethoxy)pyridin-2-yl)oxy)propanamide, reductive methylation of 2,2-dimethyl-N-(4-azaspiro[2.5]octan-7-yl)-3-((3-(trifluoromethoxy)pyridin-2-yl)oxy)propanamide (134 mg, 0.347 mmol, 1 eq) gave a TFA salt of the title compound as a colorless film (28.8 mg, 16%). $^1$H NMR (400 MHz, CD$_3$OD) δ ppm 0.81-0.91 (m, 1H), 0.94-1.02 (m, 1H), 1.17 (s, 6H), 1.31 (d, J=0.8 Hz, 3H), 1.93-2.10 (m, 2H), 2.84-2.89 (m, 1H), 2.92-3.05 (m, 2H), 3.46 (s, 3H), 4.03-4.18 (m, 1H), 4.38-4.54 (m, 2H), 7.01-7.10 (m, 1H), 7.27-7.39 (m, 1H), 7.61-7.70 (m, 1H), 8.07-8.15 (m, 1H); ESI-MS [M+H]$^+$ calc'd for C$_{19}$H$_{26}$F$_3$N$_3$O$_3$, 402.19; found, 402.4.

Example 175: 2,2-dimethyl-N-(4-methyl-4-azaspiro[2.5]octan-7-yl)-3-((3-(trifluoromethyl)pyridin-2-yl)oxy)propanamide

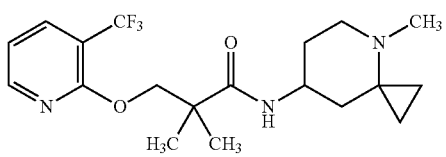 [SMILES: CN1CCC(NC(=O)C(C)(C)COc2ncccc2C(F)(F)F)CC12CC2]

The title compound was prepared in a manner similar to EXAMPLE 173, using 4-benzyl-4-azaspiro[2.5]octan-7-amine (0.075 g, 0.35 mmol) in place of (S)-5-benzyl-5-azaspiro[2.4]heptan-7-amine. Following N-benzyl deprotection of N-(4-benzyl-4-azaspiro[2.5]octan-7-yl)-2,2-dimethyl-3-((3-(trifluoromethyl)pyridin-2-yl)oxy)propanamide, reductive methylation of 2,2-dimethyl-N-(4-azaspiro[2.5]octan-7-yl)-3-((3-(trifluoromethyl)pyridin-2-yl)oxy)propanamide (129 mg, 0.347 mmol, 1 eq) gave a TFA salt of the title compound as a colorless film (37.9 mg, 22%). $^1$H NMR (400 MHz, CD$_3$OD) δ ppm 0.75-1.43 (m, 1H), 1.31 (app d, J=2.7 Hz, 6H), 1.95-2.12 (m, 2H), 2.29-2.46 (m, 1H), 3.00 (br s, 3H), 3.28-3.33 (m, 1H), 4.04-4.19 (m, 1H), 4.43 (s, 2H), 7.02-7.14 (m, 1H), 7.92-8.03 (m, 1H), 8.29-8.41 (m, 1H); ESI-MS [M+H]$^+$ calc'd for C$_{19}$H$_{26}$F$_3$N$_3$O$_2$, 386.20; found, 386.4.

Example 176: N-((2R,4R)-1,2-dimethylpiperidin-4-yl)-2,2-dimethyl-3-((3-(trifluoromethyl)pyridin-2-yl)oxy)propanamide

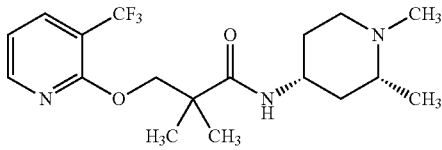 [SMILES: C[C@@H]1C[C@H](NC(=O)C(C)(C)COc2ncccc2C(F)(F)F)CCN1C]

Step A: tert-butyl (2R,4R)-4-(2,2-dimethyl-3-((3-(trifluoromethyl)pyridin-2-yl)oxy)propanamido)-2-methylpiperidine-1-carboxylate

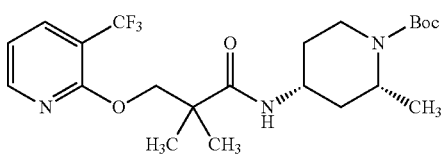 [SMILES: C[C@@H]1C[C@H](NC(=O)C(C)(C)COc2ncccc2C(F)(F)F)CCN1C(=O)OC(C)(C)C]

To a suspension of 2,2-dimethyl-3-((3-(trifluoromethyl)pyridin-2-yl)oxy)propanoic acid (1.00 g, 3.80 mmol) in DCM (38.0 mmol) were added DIPEA (1.99 mL, 11.4 mmol) and 2-chloro-1-methylpyridinium iodide (1.94 g, 7.60 mmol). The orange reaction mixture was stirred at room temperature for 10 minutes and tert-butyl (2R,4R)-4-amino-2-methylpiperidine-1-carboxylate (0.977 g, 4.56 mmol) was added. The reaction mixture was stirred at room temperature for 30 minutes and then washed with water (2×30 mL) and brine. The organic phase was collected, dried over sodium sulfate, and concentrated to afford an orange oil. The oil was purified by automated flash silica column chromatography (120 g column) eluting with a gradient of 0-70% EtOAc in DCM. The product-containing fractions were evaporated to give the title compound as a thick colorless oil (1.56 g, 89%). ESI-MS [M+H]$^+$ calc'd for C$_{22}$H$_{32}$F$_3$N$_3$O$_4$, 460.24; found, 460.5.

Step B: 2,2-dimethyl-N-((2R,4R)-2-methylpiperidin-4-yl)-3-((3-(trifluoromethyl)pyridin-2-yl)oxy)propanamide

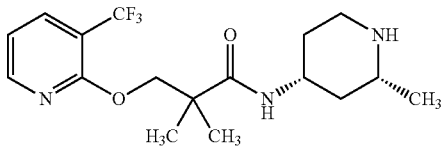 [SMILES: C[C@@H]1C[C@H](NC(=O)C(C)(C)COc2ncccc2C(F)(F)F)CCN1]

To a solution of tert-butyl (2R,4R)-4-(2,2-dimethyl-3-((3-(trifluoromethyl)pyridin-2-yl)oxy)propanamido)-2-methylpiperidine-1-carboxylate (1.56 g, 3.39 mmol) in DCM (5 mL) was added HCl (4 M in dioxane, 5.09 mL, 20.4 mmol). The reaction mixture was stirred at ambient temperature for 2 hours and then concentrated to dryness to give an HCl salt of the title compound as a white solid (1.34 g, quantitative). ESI-MS [M+H]$^+$ calc'd for C$_{17}$H$_{24}$F$_3$N$_3$O$_2$, 360.19; found, 360.3.

Step C: N-((2R,4R)-1,2-dimethylpiperidin-4-yl)-2,2-dimethyl-3-((3-(trifluoromethyl)pyridin-2-yl)oxy)propanamide In a 250 mL round-bottomed flask, a clear solution of 2,2-dimethyl-N-((2R,4R)-2-methylpiperidin-4-yl)-3-((3-(trifluoromethyl)pyridin-2-yl)oxy)propanamide hydrochloride (1.34 g, 3.39 mmol) and formaldehyde (37%, 1.308 mL, 16.93 mmol) in methanol (30 mL) was stirred at room temperature for 20 minutes. Sodium cyanoborohydride (0.425 g, 6.77 mmol) was added portion wise over 10 minutes. The reaction mixture was stirred at room temperature for 90 minutes and was then concentrated. The resulting residue was purified by automated flash silica column chromatography (80 g) eluting with a gradient of 10-40% methanol in a 3:2 mixture of EtOAc and DCM. The product-containing fractions were evaporated to give the title compound as a clear oil (0.892 g, 71%). $^1$H NMR (500 MHz, CD$_3$OD) δ ppm 1.07-1.13 (m, 3H), 1.20-1.33 (m, 7H), 1.49-1.62 (m, 1H), 1.75-1.84 (m, 2H), 2.00-2.13 (m, 1H), 2.20 (td, J=12.4, 2.5 Hz, 1H), 2.25-2.30 (m, 3H), 2.85-2.96 (m, 1H), 3.67-3.83 (m, 1H), 4.42 (s, 2H), 6.97-7.18 (m, 1H), 7.98 (ddd, J=7.5, 1.9, 0.8 Hz, 1H), 8.26-8.41 (m, 1H); ESI-MS [M+H]$^+$ calc'd for C$_{18}$H$_{26}$F$_3$N$_3$O$_2$, 374.21; found, 374.4.

Example 177: N-((2R,4S)-1,2-dimethylpiperidin-4-yl)-2,2-dimethyl-3-((3-(trifluoromethyl)pyridin-2-yl)oxy)propanamide

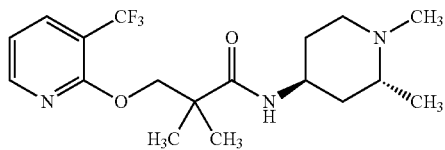 [SMILES: C[C@@H]1C[C@@H](NC(=O)C(C)(C)COc2ncccc2C(F)(F)F)CCN1C]

The title compound was prepared in a manner similar to EXAMPLE 176, using tert-butyl (2R,4S)-4-amino-2-methylpiperidine-1-carboxylate (0.977 g, 4.56 mmol, 1.2 eq) in place of tert-butyl (2R,4R)-4-amino-2-methylpiperidine-1-carboxylate. After N-Boc deprotection of tert-butyl (2R,4S)-4-(2,2-dimethyl-3-((3-(trifluoromethyl)pyridin-2-yl)oxy)propanamido)-2-methylpiperidine-1-carboxylate, reductive methylation of 2,2-dimethyl-N-((2R,4S)-2-methylpiperidin-4-yl)-3-((3-(trifluoromethyl)pyridin-2-yl)oxy)propanamide hydrochloride (1.29 g, 3.26 mmol, 1 eq) gave the title compound as a clear oil (0.541 g, 44.5%). $^1$H NMR (400 MHz, DMSO-d$_6$) δ ppm 0.90 (d, J=6.4 Hz, 3H), 1.21 (s, 6H), 1.32-1.42 (m, 1H), 1.47-1.65 (m, 3H), 2.12 (s, 3H), 2.23 (ddd, J=11.0, 8.0, 3.8 Hz, 1H), 2.36-2.48 (m, 2H), 3.74-3.88 (m, 1H), 4.32-4.45 (m, 2H), 6.99 (br d, J=6.7 Hz, 1H), 7.16 (dd, J=7.4, 5.0 Hz, 1H), 7.98-8.15 (m, 1H), 8.42 (d, J=3.9 Hz, 1H); ESI-MS [M+H]$^+$ calc'd for C$_{18}$H$_{26}$F$_3$N$_3$O$_2$, 374.21; found, 374.4.

Example 178: N-((2S,4S)-1,2-dimethylpiperidin-4-yl)-2,2-dimethyl-3-((3-(trifluoromethyl)pyridin-2-yl)oxy)propanamide

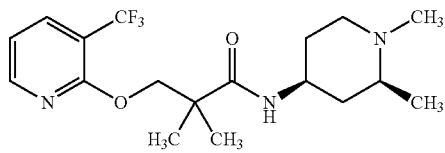 [SMILES: C[C@H]1C[C@@H](NC(=O)C(C)(C)COc2ncccc2C(F)(F)F)CCN1C]

The title compound was prepared in a manner similar to EXAMPLE 176, using tert-butyl (2S,4S)-4-amino-2-methylpiperidine-1-carboxylate (0.977 g, 4.56 mmol, 1.2 eq). After N-Boc deprotection of tert-butyl (2S,4S)-4-(2,2-dimethyl-3-((3-(trifluoromethyl)pyridin-2-yl)oxy)propanamido)-2-methylpiperidine-1-carboxylate, reductive methylation of 2,2-dimethyl-N-((2S,4S)-2-methylpiperidin-4-yl)-3-((3-(trifluoromethyl)pyridin-2-yl)oxy)propanamide hydrochloride (1.68 g, 4.24 mmol, 1 eq) gave the title compound as a clear oil (0.839 g, 52.9%). $^1$H NMR (400 MHz, DMSO-d$_6$) δ ppm 0.96 (d, J=6.1 Hz, 3H), 1.08-1.24 (m, 7H), 1.37-1.51 (m, 1H), 1.53-1.62 (m, 2H), 1.81 (ddd, J=11.0, 6.0, 2.1 Hz, 1H), 1.94 (td, J=12.1, 2.0 Hz, 1H), 2.11 (s, 3H), 2.67-2.80 (m, 1H), 3.57 (dtd, J=11.8, 7.8, 4.1 Hz, 1H), 4.35 (s, 2H), 7.15 (dd, J=7.4, 5.2 Hz, 1H), 7.24 (br d, J=7.9 Hz, 1H), 8.00-8.14 (m, 1H), 8.42 (d, J=4.8 Hz, 1H); ESI-MS [M+H]$^+$ calc'd for C$_{18}$H$_{26}$F$_3$N$_3$O$_2$, 374.21; found, 374.4.

Example 179: N-((2R,4R)-1,2-dimethylpiperidin-4-yl)-2,2-dimethyl-3-((3-(trifluoromethoxy)pyridin-2-yl)oxy)propanamide

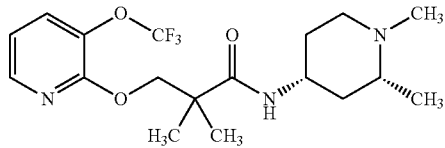 [SMILES: C[C@@H]1C[C@H](NC(=O)C(C)(C)COc2ncccc2OC(F)(F)F)CCN1C]

Step A: tert-butyl (2R,4R)-4-(2,2-dimethyl-3-((3-(trifluoromethoxy)pyridin-2-yl)oxy)propanamido)-2-methylpiperidine-1-carboxylate

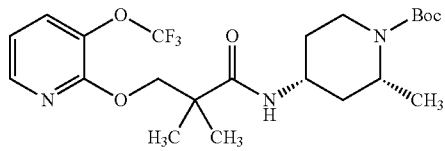 [SMILES: C[C@@H]1C[C@H](NC(=O)C(C)(C)COc2ncccc2OC(F)(F)F)CCN1C(=O)OC(C)(C)C]

A yellow solution of 2,2-dimethyl-3-((3-(trifluoromethoxy)pyridin-2-yl)oxy)propanoic acid (1.00 g, 3.58 mmol), tert-butyl (2R,4R)-4-amino-2-methylpiperidine-1-carboxylate (0.768 g, 3.58 mmol), HATU (1.362 g, 3.58 mmol), and DIPEA (1.87 mL, 10.7 mmol) in DMF (12 mL) was stirred at room temperature for 64 hours. The reaction mixture was treated with water and extracted with EtOAc. The organic extracts were washed with brine, dried over MgSO₄, filtered, and concentrated under reduced pressure to give the title compound as a colorless oil (1.70 g, assumed quantitative) which was used without further purification. ESI-MS [M+H]⁺ calc'd for C₂₂H₃₂F₃N₃O₅, 476.24; found, 476.5.

Step B: 2,2-dimethyl-N-((2R,4R)-2-methylpiperidin-4-yl)-3-((3-(trifluoromethoxy)pyridin-2-yl)oxy)propanamide

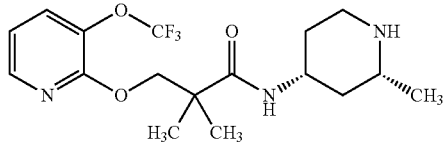 [SMILES: C[C@@H]1C[C@H](NC(=O)C(C)(C)COc2ncccc2OC(F)(F)F)CCN1]

A solution of tert-butyl (2R,4R)-4-(2,2-dimethyl-3-((3-(trifluoromethoxy)pyridin-2-yl)oxy)propanamido)-2-methylpiperidine-1-carboxylate (1.70 g, 3.58 mmol) in dioxane (6 mL) was treated with HCl (4 M in dioxane, 3.58 mL, 14.3 mmol). The reaction mixture was stirred at 50° C. for 3 hours and was then concentrated to dryness to give an HCl salt of the title compound as a light brown syrup (1.47 g, assumed quantitative) which was used without further purification. ESI-MS [M+H]⁺ calc'd for C₁₇H₂₄F₃N₃O₃, 376.18; found, 376.3.

Step C: N-((2R,4R)-1,2-dimethylpiperidin-4-yl)-2,2-dimethyl-3-((3-(trifluoromethoxy)pyridin-2-yl)oxy)propanamide A brown solution of 2,2-dimethyl-N-((2R,4R)-2-methylpiperidin-4-yl)-3-((3-(trifluoromethoxy)pyridin-2-yl)oxy)propanamide (1.47 g, 3.58 mmol) and formaldehyde (37%, 0.548 mL, 7.09 mmol) in methanol (3 mL) was treated with sodium cyanoborohydride (1 M, 7.09 mL, 7.09 mmol). The reaction mixture was stirred at room temperature overnight. The product was purified by preparative HPLC (Method B) to give the title compound as a light brown film (78.7 mg, 5.6%). ¹H NMR (400 MHz, CD₃OD) δ ppm 1.10 (d, J=6.3 Hz, 3H), 1.28 (m, 7H), 1.47-1.64 (m, 1H), 1.70-1.85 (m, 2H), 2.00-2.12 (m, 1H), 2.14-2.22 (m, 1H), 2.27 (s, 3H), 2.82-2.97 (m, 1H), 3.68-3.86 (m, 1H), 4.39 (s, 2H), 7.02 (dd, J=7.8, 5.0 Hz, 1H), 7.57-7.71 (m, 1H), 7.99-8.15 (m, 1H); ESI-MS [M+H]⁺ calc'd for C₁₈H₂₆F₃N₃O₃, 390.20; found, 390.5.

Example 180: N-(trans-1,4-dimethylpyrrolidin-3-yl)-2,2-dimethyl-3-((3-(trifluoromethoxy)pyridin-2-yl)oxy)propanamide

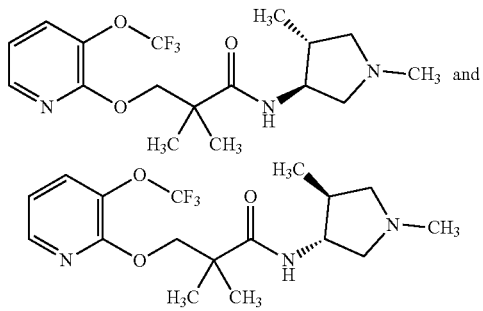

Step A: tert-butyl trans-3-(2,2-dimethyl-3-((3-(trifluoromethoxy)pyridin-2-yl)oxy)propanamido)-4-methylpyrrolidine-1-carboxylate

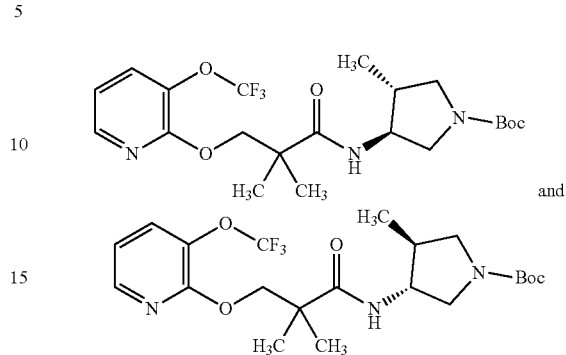

To a solution of 2,2-dimethyl-3-((3-(trifluoromethoxy)pyridin-2-yl)oxy)propanoic acid (84 mg, 0.300 mmol) and HATU (114 mg, 0.300 mmol) in DMF (1498 µL) was added DIPEA (157 µL, 0.899 mmol). The solution was stirred at room temperature for 5 minutes and then tert-butyl trans-3-amino-4-methylpyrrolidine-1-carboxylate (60 mg, 0.300 mmol) was added. The reaction mixture was allowed to stir at room temperature for 12 hours. The product was purified by preparative HPLC (Method A) to give the title compound as a colorless oil (90 mg, 65%).

Step B: trans-2,2-dimethyl-N-(4-methylpyrrolidin-3-yl)-3-((3-(trifluoromethoxy)pyridin-2-yl)oxy)propanamide

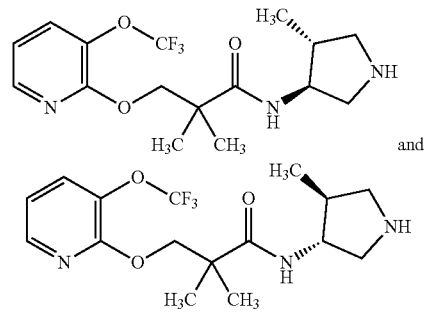

A solution of tert-butyl trans-3-(2,2-dimethyl-3-((3-(trifluoromethoxy)pyridin-2-yl)oxy)propanamido)-4-methylpyrrolidine-1-carboxylate (90 mg, 0.195 mmol) in DCM (2 mL) and TFA (1 mL) was stirred at room temperature for 1.5 hours. The solvent was removed to give a pale oil, which was dried under high vacuum to give a TFA salt of the title compound (93 mg, 0.196 mmol).

Step C: trans-N-(1,4-dimethylpyrrolidin-3-yl)-2,2-dimethyl-3-((3-(trifluoromethoxy)pyridin-2-yl)oxy)propanamide A mixture of trans-2,2-dimethyl-N-(4-methylpyrrolidin-3-yl)-3-((3-(trifluoromethoxy)pyridin-2-yl)oxy)propanamide TFA salt (93 mg, 0.196 mmol), paraformaldehyde (17.62 mg, 0.587 mmol), sodium triacetoxyborohydride (166 mg, 0.783 mmol) and DIPEA (137 µL, 0.783 mmol) in DCM (1956 µL) was stirred at room temperature for 3 days.

The reaction mixture was diluted with EtOAc (10 mL) and saturated aq NaHCO₃ 10 (mL) and stirred vigorously for 1 hour. The organic phase was separated, washed with brine, and purified by preparative HPLC (Method A) to give a TFA salt of the title compound as a colorless oil (26 mg, 27%). ¹H NMR (400 MHz, CD₃OD) δ ppm 1.16 (d, J=6.8 Hz, 3H), 1.34 (s, 6H), 2.55 (dq, J=10.8, 7.1 Hz, 1H), 2.94 (s, 3H), 3.42-3.63 (m, 2H), 3.65-3.83 (m, 1H), 3.89-4.05 (m, 1H), 4.36-4.48 (m, 2H), 7.06 (dd, J=7.8, 5.0 Hz, 1H), 7.65-7.75 (m, 1H), 8.13 (dd, J=4.9, 1.6 Hz, 1H); ESI-MS [M+H]⁺ calc'd for C₁₇H₂₄F₃N₃O₃, 376.18; found, 376.1.

Example 181: 3-((3-cyclopropylpyridin-2-yl)oxy)-N-(trans-1,4-dimethylpyrrolidin-3-yl)-2,2-dimethyl-propanamide

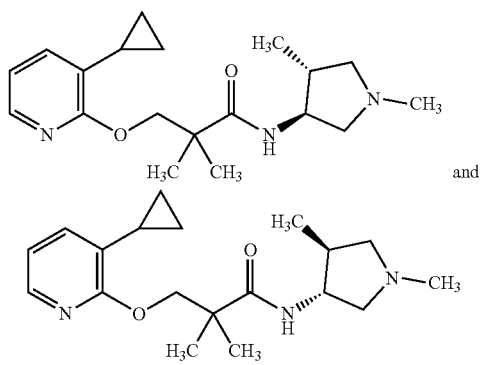

The title compound was prepared in a manner similar to EXAMPLE 180, using 3-((3-cyclopropylpyridin-2-yl)oxy)-2,2-dimethylpropanoic acid (0.070 g, 0.30 mmol, 1 eq) in place of 2,2-dimethyl-3-((3-(trifluoromethoxy)pyridin-2-yl)oxy)propanoic acid. After N-Boc deprotection of tert-butyl trans-3-(3-((3-cyclopropylpyridin-2-yl)oxy)-2,2-dimethyl-propanamido)-4-methylpyrrolidine-1-carboxylate and reductive methylation of trans-3-((3-cyclopropylpyridin-2-yl)oxy)-2,2-dimethyl-N-(4-methylpyrrolidin-3-yl)propanamide TFA salt (46.5 mg, 0.108 mmol, 1 eq), the product was purified by preparative HPLC (Method A) to give a TFA salt of the title compound as a colorless oil (19 mg, 40%). ¹H NMR (400 MHz, CD₃OD) δ ppm 0.62-0.75 (m, 2H), 0.90-1.01 (m, 2H), 1.12 (d, J=6.8 Hz, 3H), 1.36 (app d, J=0.8 Hz, 6H), 2.03 (tt, J=8.5, 5.3 Hz, 1H), 2.46-2.58 (m, 1H), 2.92 (s, 4H), 3.39-3.61 (m, 2H), 3.65-3.80 (m, 1H), 3.92-4.02 (m, 1H), 4.35 (d, J=1.4 Hz, 2H), 6.87 (dd, J=7.5, 5.2 Hz, 1H), 7.23-7.30 (m, 1H), 7.91 (dd, J=5.0, 1.8 Hz, 1H); ESI-MS [M+H]⁺ calc'd for C₁₉H₂₉N₃O₂, 332.23; found, 332.1.

Example 182: N-(trans-1,4-dimethylpyrrolidin-3-yl)-2,2-dimethyl-3-((3-methylpyridin-2-yl)oxy)propanamide

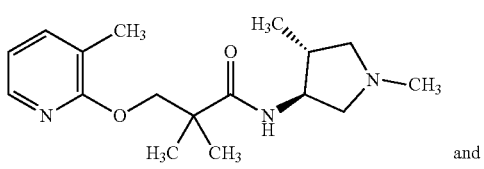

and

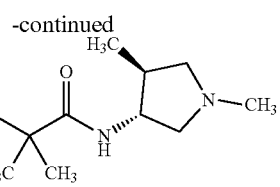

The title compound was prepared in a manner similar to EXAMPLE 180, using 2,2-dimethyl-3-((3-methylpyridin-2-yl)oxy)propanoic acid (0.063 g, 0.30 mmol, 1 eq) in place of 2,2-dimethyl-3-((3-(trifluoromethoxy)pyridin-2-yl)oxy)propanoic acid. After N-Boc deprotection of tert-butyl trans-3-(2,2-dimethyl-3-((3-methylpyridin-2-yl)oxy)propanamido)-4-methylpyrrolidine-1-carboxylate and reductive methylation of trans-2,2-dimethyl-3-((3-methylpyridin-2-yl)oxy)-N-(4-methylpyrrolidin-3-yl)propanamide TFA salt (93 mg, 0.229 mmol, 1 eq), the product was purified by preparative HPLC (Method A) to give a TFA salt of the title compound as a colorless oil (22 mg, 23%). ¹H NMR (400 MHz, CD₃OD) δ ppm 1.13 (d, J=6.8 Hz, 3H), 1.34 (s, 6H), 2.19 (s, 3H), 2.52 (dq, J=10.6, 7.3 Hz, 1H), 2.92 (m, 4H), 3.41-3.63 (m, 2H), 3.64-3.79 (m, 1H), 3.90-4.05 (m, 1H), 4.28-4.40 (m, 2H), 6.88 (dd, J=7.2, 5.0 Hz, 1H), 7.45-7.54 (m, 1H), 7.95 (ddd, J=5.1, 1.9, 0.6 Hz, 1H); ESI-MS [M+H]⁺ calc'd for C₁₇H₂₇N₃O₂, 306.22; found, 306.1.

Example 183: 3-((3,5-dimethylpyridin-2-yl)oxy)-N-(trans-1,4-dimethylpyrrolidin-3-yl)-2,2-dimethylpropanamide

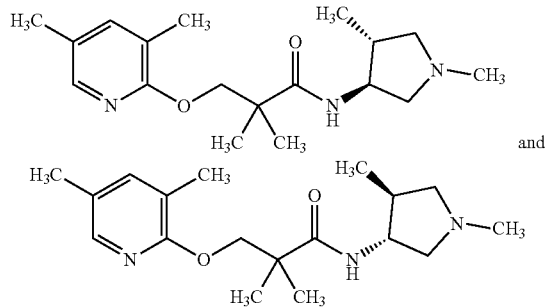

The title compound was prepared in a manner similar to EXAMPLE 180, using 3-((3,5-dimethylpyridin-2-yl)oxy)-2,2-dimethylpropanoic acid (0.067 g, 0.30 mmol, 1 eq) in place of 2,2-dimethyl-3-((3-(trifluoromethoxy)pyridin-2-yl)oxy)propanoic acid. After N-Boc deprotection of tert-butyl trans-3-(3-((3,5-dimethylpyridin-2-yl)oxy)-2,2-dimethyl-propanamido)-4-methylpyrrolidine-1-carboxylate and reductive methylation of trans-3-((3,5-dimethylpyridin-2-yl)oxy)-2,2-dimethyl-N-(4-methylpyrrolidin-3-yl)propanamide TFA salt (98 mg, 0.234 mmol, 1 eq), the product was purified by preparative HPLC (Method A) to give a TFA salt of the title compound as a colorless oil (45 mg, 44%). ¹H NMR (400 MHz, CD₃OD) δ ppm 1.13 (d, J=6.8 Hz, 3H), 1.33 (s, 6H), 2.12-2.26 (m, 6H), 2.51 (dq, J=10.7, 7.1 Hz, 1H), 2.91 (m, 4H), 3.40-3.59 (m, 2H), 3.60-3.78 (m, 1H), 3.91-4.02 (m, 1H), 4.23-4.34 (m, 2H), 7.36 (dd, J=1.5, 0.6 Hz, 1H), 7.75 (dd, J=1.6, 0.8 Hz, 1H); ESI-MS [M+H]⁺ calc'd for C₁₈H₂₉N₃O₂, 320.23; found, 320.2.

Example 184: trans-N-(1-(cyanomethyl)-3-methylpiperidin-4-yl)-2,2-dimethyl-3-((3-(trifluoromethoxy)pyridin-2-yl)oxy)propanamide

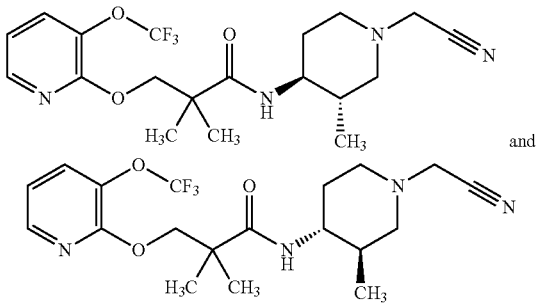

To a 500 mL flask charged with 2,2-dimethyl-N-(3-methylpiperidin-4-yl)-3-((3-(trifluoromethoxy)pyridin-2-yl)oxy)propanamide hydrochloride (13.4 g, 25.5 mmol) in MeOH (100 mL) was added formaldehyde (37 wt %, 3.97 mL, 50.9 mmol) at room temperature. Next, sodium cyanoborohydride (3.20 g, 50.9 mmol) was added portion-wise over a 7 minute period at room temperature. The mixture was stirred for 3 days at 23° C. and then concentrated in a rotary evaporator to provide crude product (20.5 g) as a thick white suspension. The crude material was diluted with saturated NaHCO$_3$ (100 mL) and extracted with EtOAc (100 mL). Water (50 mL) was added to help dissolve salts. The layers were separated and the aqueous phase was washed with EtOAc (100 mL). The organic layers were combined, washed with brine (100 mL), dried over Na$_2$SO$_4$, filtered, rinsed with EtOAc, and concentrated in a rotary evaporator. The crude product was dissolved in EtOAc (12 mL) and purified by automated flash silica column chromatography (220 g column) eluting with a gradient of 0-20% methanol in EtOAc. The early fractions were combined, concentrated, and dried under reduced pressure to give the title compound as a white solid (481.9 mg, 4.6%) along with a larger quantity of trans-N-(1,3-dimethylpiperidin-4-yl)-2,2-dimethyl-3-((3-(trifluoromethoxy)pyridin-2-yl)oxy)propanamide (Example 13). $^1$H NMR (400 MHz, CD$_3$OD) δ ppm 0.87 (d, J=6.5 Hz, 3H), 1.31 (app d, J=1.2 Hz, 6H), 1.59 (qd, J=12.3, 4.1 Hz, 1H), 1.71-1.89 (m, 2H), 1.97-2.11 (m, 1H), 2.34 (td, J=12.0, 2.8 Hz, 1H), 2.80-2.94 (m, 2H), 3.38-3.52 (m, 1H), 3.63 (s, 2H), 4.41 (d, J=1.3 Hz, 2H), 7.02 (dd, J=7.9, 4.9 Hz, 1H), 7.31 (br d, J=8.8 Hz, 1H), 7.65 (dquin, J=7.9, 1.4 Hz, 1H), 8.10 (dd, J=5.0, 1.8 Hz, 1H); ESI-MS [M+H]$^+$ calc'd for C$_{19}$H$_{25}$F$_3$N$_4$O$_3$, 415.20; found, 415.1.

Example 185: 3-((3-(chlorodifluoromethoxy)pyridin-2-yl)oxy)-N-((3S,4S)-1,3-dimethylpiperidin-4-yl)-2,2-dimethylpropanamide

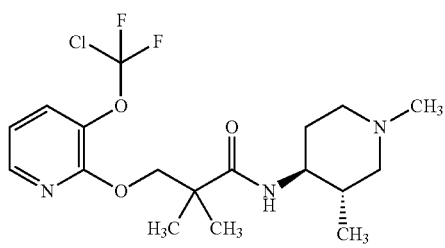 [SMILES: C[C@H]1CN(C)CC[C@@H]1NC(=O)C(C)(C)COc1ncccc1OC(F)(F)Cl]

The title compound was isolated during the purification of N-((3S,4S)-1,3-dimethylpiperidin-4-yl)-2,2-dimethyl-3-((3-(trifluoromethoxy)pyridin-2-yl)oxy)propanamide (EXAMPLE 107) by preparative HPLC (Method B) as a minor impurity. The later-eluting fractions were combined, concentrated, and dried under reduced pressure to give the title compound as an off-white solid (3.9 mg). The origin of the 3-(chlorodifluoromethoxy)pyridin-2-yl group was an impure commercial reagent, 2-chloro-3-(trifluoromethoxy)pyridine, used as a starting material for preparing the compound of EXAMPLE 107. $^1$H NMR (400 MHz, CDCl$_3$) δ ppm 0.87 (d, J=6.8 Hz, 3H), 1.33 (app d, J=4.8 Hz, 6H), 1.39-1.51 (m, 1H), 1.58-1.67 (m, 1H), 1.74-1.80 (m, 1H), 1.86-1.96 (m, 1H), 1.98-2.10 (m, 1H), 2.28 (s, 3H), 2.78-2.93 (m, 2H), 3.47-3.60 (m, 1H), 4.38 (s, 2H), 5.94 (br d, J=8.5 Hz, 1H), 6.95 (dd, J=7.8, 5.0 Hz, 1H), 7.56 (dq, J=7.8, 1.5 Hz, 1H), 8.10 (dd, J=4.9, 1.6 Hz, 1H); ESI-MS [M+H]$^+$ calc'd for C$_{18}$H$_{26}$ClF$_2$N$_3$O$_3$, 406.17; found, 406.1.

Example 186: trans-3-(2-chlorophenoxy)-N-(1,3-dimethylpiperidin-4-yl)-2,2-dimethylpropanamide

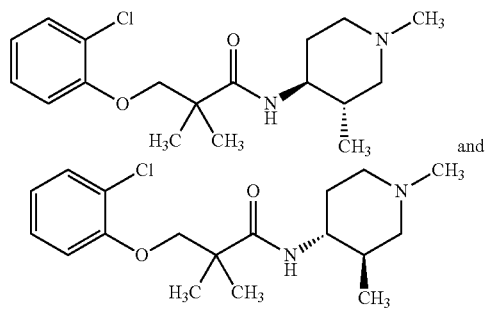

A solution of 3-(2-chlorophenoxy)-2,2-dimethylpropanoic acid (59 mg, 0.26 mmol), 1,3-dimethylpiperidin-4-amine (45.3 mg, 0.335 mmol), HATU (130 mg, 0.335 mmol) and Et$_3$N (144 µL, 1.03 mmol) in THF (1.29 mL) was stirred at room temperature for 12 hours. The reaction mixture was filtered through a hydrophilic PTFE 0.45 m filter (Millipore® Millex-LCR) which was rinsed with methanol. The filtrate was purified by preparative HPLC (Method A) to give a TFA salt of the title compound as a pale yellow solid (89 mg, 76%). $^1$H NMR (400 MHz, CDCl$_3$) δ ppm 0.96 (d, J=6.5 Hz, 3H), 1.35 (app d, J=5.5 Hz, 6H), 1.91-2.05 (m, 1H), 2.06-2.14 (m, 1H), 2.14-2.24 (m, 1H), 2.42-2.52 (m, 1H), 2.70-2.85 (m, 4H), 3.48-3.56 (m, 1H), 3.57-3.65 (m, 1H), 3.75-3.86 (m, 1H), 3.93-4.00 (m, 2H), 6.58 (br d, J=8.8 Hz, 1H), 6.93 (qd, J=8.0, 1.2 Hz, 2H), 7.22 (td, J=7.8, 1.6 Hz, 1H), 7.39 (dd, J=7.8, 1.5 Hz, 1H); ESI-MS [M+H]$^+$ calc'd for C$_{18}$H$_{27}$ClN$_2$O$_2$, 339.18; found, 339.4.

Example 187: 3-(2-chlorophenoxy)-N-((3S,4S)-3-fluoropiperidin-4-yl)-2,2-dimethylpropanamide

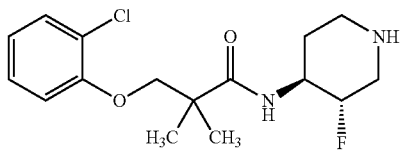 [SMILES: CC(C)(COc1ccccc1Cl)C(=O)N[C@H]1CCNC[C@@H]1F]

To a solution of tert-butyl (3S,4S)-4-(3-(2-chlorophenoxy)-2,2-dimethylpropanamido)-3-fluoropiperidine-1-carboxylate (95 mg, 0.22 mmol) in DCM (0.89 mL) was added HCl (4M in dioxane, 332 μL, 1.33 mmol) at room temperature. The reaction mixture was stirred for 12 hours and then filtered through a hydrophilic PTFE 0.45 m filter (Millipore® Millex-LCR) which was rinsed with methanol. The filtrate was purified by preparative HPLC (Method A) to give a TFA salt of the title compound as a colorless oil (69 mg, 70%). $^1$H NMR (400 MHz, CDCl$_3$) δ ppm 1.36 (app d, J=6.5 Hz, 6H), 1.78-1.93 (m, 1H), 2.30-2.42 (m, 1H), 3.01-3.20 (m, 2H), 3.24-3.38 (m, 1H), 3.48-3.60 (m, 1H), 3.91-4.04 (m, 2H), 4.21-4.33 (m, 1H), 4.75-4.96 (m, 1H), 6.87 (d, J=7.0 Hz, 1H), 6.91-6.99 (m, 2H), 7.25 (td, J=7.8, 1.6 Hz, 1H), 7.39 (dd, J=7.9, 1.6 Hz, 1H); ESI-MS [M+H]$^+$ calc'd for C$_{16}$H$_{22}$ClFN$_2$O$_2$, 329.14; found, 329.3.

The title compound was prepared in a manner similar to EXAMPLE 1, using 2,2-difluoro-3-((3-(trifluoromethyl)pyridin-2-yl)oxy)propanoic acid (67.8 mg, 0.250 mmol) in place of 2,2-dimethyl-3-((3-methylpyridin-2-yl)oxy)propanoic acid and trans-1,3-dimethylpiperidin-4-amine (32.1 mg, 0.250 mmol) in place of 1-methylpiperidin-4-amine. The product was purified by preparative HPLC (Method A) to give a TFA salt of the title compound as a colorless film (17 mg, 14%). $^1$H NMR (400 MHz, CD$_3$OD) δ ppm 0.98 (d, J=6.6 Hz, 3H), 1.82-1.98 (m, 1H), 2.02-2.17 (m, 2H), 2.87 (m, 4H), 3.04-3.16 (m, 1H), 3.47-3.61 (m, 2H), 3.67-3.83 (m, 1H), 4.88-5.04 (m, 2H), 7.11-7.25 (m, 1H), 7.98-8.07 (m, 1H), 8.30-8.47 (m, 1H), 8.91-9.01 (m, 1H); ESI-MS [M+H]$^+$ calc'd for C$_{16}$H$_{20}$F$_5$N$_3$O$_2$, 382.16; found, 382.3.

Example 188: 3-(2-chlorophenoxy)-N-((3S,4S)-3-fluoro-1-methylpiperidin-4-yl)-2,2-dimethylpropanamide

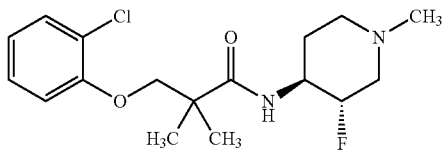 [SMILES: CN1CC[C@H](NC(=O)C(C)(C)COc2ccccc2Cl)[C@@H](F)C1]

Example 190: 3-(2-chlorophenoxy)-2,2-dimethyl-N-((3S,4S)-3-methylpiperidin-4-yl)propanamide

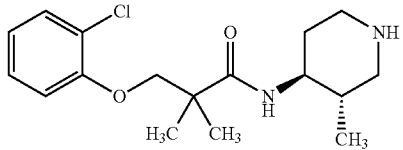 [SMILES: C[C@H]1CNCC[C@@H]1NC(=O)C(C)(C)COc1ccccc1Cl]

To a solution of 3-(2-chlorophenoxy)-N-((3S,4S)-3-fluoropiperidin-4-yl)-2,2-dimethylpropanamide TFA salt (28 mg, 0.063 mmol) in DCM (422 μL) was added Et$_3$N (26 μL, 0.19 mmol) and formaldehyde (24 μL, 0.32 mmol) at room temperature, and the solution was stirred for 30 minutes. Sodium triacetoxyborohydride (69.1 mg, 0.316 mmol) was then added in one portion and stirring was continued at room temperature for 12 hours. The reaction mixture was filtered through a hydrophilic PTFE 0.45 m filter (Millipore® Millex-LCR) which was rinsed with methanol. The filtrate was purified by preparative HPLC (Method A) to give a TFA salt of the title compound as a white solid (21 mg, 73%). $^1$H NMR (400 MHz, CDCl$_3$) δ ppm 1.36 (app d, J=8.3 Hz, 6H), 1.86-2.07 (m, 1H), 2.21-2.45 (m, 1H), 2.76-2.93 (m, 4H), 3.06-3.41 (m, 1H), 3.50-3.63 (m, 1H), 3.75-3.90 (m, 1H), 3.93-4.04 (m, 2H), 4.21-4.37 (m, 1H), 4.78-5.01 (m, 1H), 6.88-7.02 (m, 3H), 7.24 (td, J=5.0, 2.4 Hz, 1H), 7.36-7.45 (m, 1H); ESI-MS [M+H]$^+$ calc'd for C$_{17}$H$_{24}$ClFN$_2$O$_2$, 343.16; found, 343.3.

To a solution of tert-butyl (3S,4S)-4-(3-(2-chlorophenoxy)-2,2-dimethylpropanamido)-3-methylpiperidine-1-carboxylate (150 mg, 0.353 mmol) in DCM (706 μL) was added HCl (4M in dioxane, 529 μL, 2.12 mmol) at room temperature. The resulting reaction mixture was stirred for 12 hours and then filtered through a hydrophilic PTFE 0.45 m filter (Millipore® Millex-LCR) which was rinsed with methanol. The filtrate was purified by preparative HPLC (Method A) to give a TFA salt of the title compound as a white solid (139 mg, 90%). $^1$H NMR (400 MHz, CDCl$_3$) δ ppm 0.97 (d, J=6.3 Hz, 3H), 1.36 (app d, J=5.0 Hz, 6H), 1.72-1.86 (m, 1H), 1.92-2.07 (m, 1H), 2.13 (br d, J=13.8 Hz, 1H), 2.30-2.48 (m, 1H), 2.57-2.72 (m, 1H), 2.88-3.01 (m, 1H), 3.34-3.50 (m, 2H), 3.76-3.88 (m, 1H), 3.92-4.01 (m, 2H), 6.52 (br d, J=8.3 Hz, 1H), 6.90-6.98 (m, 2H), 7.23 (td, J=7.8, 1.6 Hz, 1H), 7.39 (dd, J=7.9, 1.6 Hz, 1H); ESI-MS [M+H]$^+$ calc'd for C$_{17}$H$_{25}$ClN$_2$O$_2$, 325.17; found, 325.4.

Example 189: trans-N-(1,3-dimethylpiperidin-4-yl)-2,2-difluoro-3-((3-(trifluoromethyl)pyridin-2-yl)oxy)propanamide

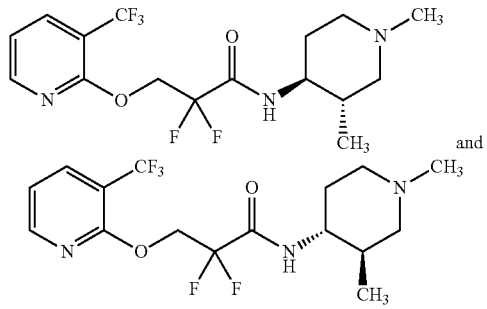

Example 191: cis-N-(1,2-dimethylpiperidin-4-yl)-2,2-difluoro-3-((3-(trifluoromethyl)pyridin-2-yl)oxy)propanamide

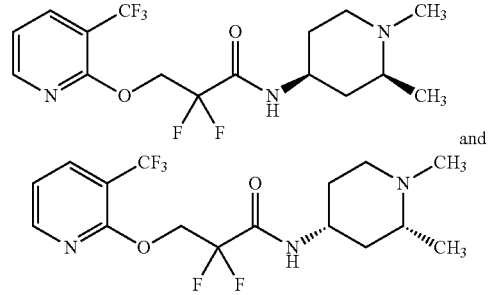

Step A: tert-butyl cis-4-(2,2-difluoro-3-((3-(trifluoromethyl)pyridin-2-yl)oxy)propanamido)-2-methylpiperidine-1-carboxylate

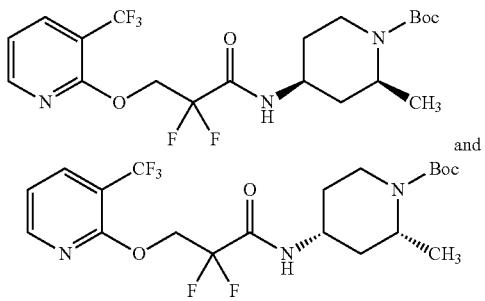

and

A solution of 2,2-difluoro-3-((3-(trifluoromethyl)pyridin-2-yl)oxy)propanoic acid (81 mg, 0.30 mmol), tert-butyl cis-4-amino-2-methylpiperidine-1-carboxylate (64 mg, 0.30 mmol), HATU (114 mg, 0.300 mmol), and DIPEA (157 µL, 0.900 mmol) in DMF (3 mL) was stirred at room temperature overnight. The reaction mixture was diluted with water and extracted with EtOAc. The organic phase was washed with brine, dried over $MgSO_4$, filtered, and concentrated to give crude title compound as a tan syrup (140 mg, assumed quantitative) which was used without further purification. ESI-MS $[M+H]^+$ calc'd for $C_{20}H_{26}F_5N_3O_4$, 468.19; found, 468.3.

Step B: 2,2-difluoro-N-(cis-2-methylpiperidin-4-yl)-3-((3-(trifluoromethyl)pyridin-2-yl)oxy)propanamide

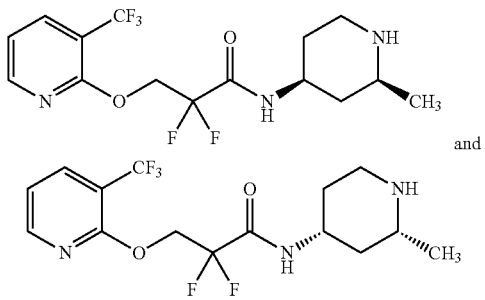

and

A solution of tert-butyl cis-4-(2,2-difluoro-3-((3-(trifluoromethyl)pyridin-2-yl)oxy)propanamido)-2-methylpiperidine-1-carboxylate (0.140 g, 0.30 mmol) and HCl (4M in dioxane, 0.300 mL, 1.20 mmol) in dioxane (3 mL) was stirred at 50° C. overnight. The reaction mixture was concentrated to dryness to give crude title compound as a brown film (110 mg, assumed quantitative) which was used without further purification. ESI-MS $[M+H]^+$ calc'd for $C_{15}H_{18}F_5N_3O_2$, 368.14; found, 368.3.

Step C: cis-N-(1,2-dimethylpiperidin-4-yl)-2,2-difluoro-3-((3-(trifluoromethyl)pyridin-2-yl)oxy)propanamide To a solution of 2,2-difluoro-N-(cis-2-methylpiperidin-4-yl)-3-((3-(trifluoromethyl)pyridin-2-yl)oxy)propanamide (110 mg, 0.30 mmol) and formaldehyde (37 wt %, 47 µL, 0.60 mmol) in MeOH (3 mL) was added $NaBH_3CN$ (37.7 mg, 0.600 mmol). The reaction mixture was stirred at room temperature for 5 hours and was purified by preparative HPLC (Method B) to give the title compound as a white solid (17.2 mg, 15%). $^1$H NMR (400 MHz, $CD_3OD$) δ ppm 1.12 (d, J=6.3 Hz, 3H), 1.26-1.43 (m, 1H), 1.56-1.70 (m, 1H), 1.75-1.88 (m, 2H), 2.00-2.14 (m, 1H), 2.16-2.25 (m, 1H), 2.28 (s, 3H), 2.87-2.98 (m, 1H), 3.62-3.88 (m, 1H), 4.90 (s, 2H), 7.10-7.23 (m, 1H), 7.95-8.10 (m, 1H), 8.30-8.43 (m, 1H); ESI-MS $[M+H]^+$ calc'd for $C_{16}H_{20}F_5N_3O_2$, 382.16; found, 382.4.

Example 192: trans-3-((3-cyclopropylpyridin-2-yl)oxy)-N-(1,3-dimethylpiperidin-4-yl)-2,2-difluoropropanamide

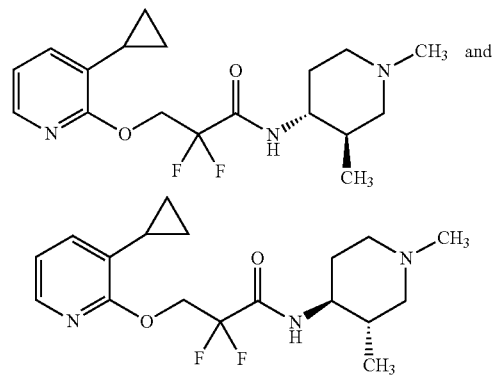

The title compound was prepared in a manner similar to EXAMPLE 1, using 3-((3-cyclopropylpyridin-2-yl)oxy)-2,2-difluoropropanoic acid (60.8 mg, 0.250 mmol) in place of 2,2-dimethyl-3-((3-methylpyridin-2-yl)oxy)propanoic acid and trans-1,3-dimethylpiperidin-4-amine (32.1 mg, 0.250 mmol) in place of 1-methylpiperidin-4-amine. The product was purified by preparative HPLC (Method A) to give a TFA salt of the title compound as a colorless film (12.7 mg, 11%). $^1$H NMR (400 MHz, $CD_3OD$) δ ppm 0.69 (dd, J=5.3, 1.9 Hz, 2H), 0.89-0.99 (m, 5H), 1.83-1.96 (m, 1H), 2.00-2.15 (m, 3H), 2.86 (m, 4H), 3.02-3.15 (m, 1H), 3.45-3.60 (m, 2H), 3.69-3.82 (m, 1H), 4.80-4.88 (m, 2H), 6.85-6.95 (m, 1H), 7.18-7.28 (m, 1H), 7.86-7.94 (m, 1H); ESI-MS $[M+H]^+$ calc'd for $C_{18}H_{25}F_2N_3O_2$, 354.20; found, 354.4.

Example 193: 3-(2-chlorophenoxy)-N-((3S,4S)-1,3-dimethylpiperidin-4-yl)-2,2-dimethylpropanamide

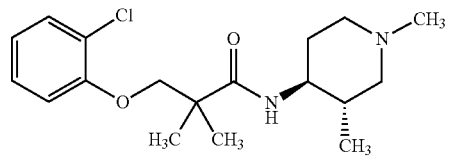

To a solution of 3-(2-chlorophenoxy)-2,2-dimethyl-N-((3S,4S)-3-methylpiperidin-4-yl)propanamide TFA salt (108 mg, 0.246 mmol) in DCM (1.23 mL) were added $Et_3N$ (103 µL, 0.738 mmol) and formaldehyde (55.0 µL, 0.738 mmol) at room temperature, and the solution was stirred for 30 minutes. Sodium triacetoxyborohydride (161 mg, 0.738 mmol) was added in one portion and stirring was continued at room temperature for 12 hours. The reaction mixture was then filtered through a hydrophilic PTFE 0.45 m filter (Millipore® Millex-LCR) which was rinsed with methanol. The filtrate was purified by preparative HPLC (Method A) to give a TFA salt of the title compound as a white solid (89 mg, 80%). $^1$H NMR (400 MHz, CDCl$_3$) δ ppm 0.96 (d, J=6.8 Hz, 3H), 1.35 (app d, J=5.8 Hz, 6H), 1.91-2.05 (m, 1H), 2.06-2.24 (m, 2H), 2.41-2.53 (m, 1H), 2.71-2.85 (m, 4H), 3.54 (br d, J=11.8 Hz, 1H),) 3.59-3.66 (m, 1H), 3.76-3.87 (m, 1H), 3.90-4.01 (m, 2H), 6.60 (br d, J=9.0 Hz, 1H), 6.88-6.98 (m, 2H), 7.19-7.25 (m, 1H), 7.39 (dd, J=7.9, 1.6 Hz, 1H); ESI-MS [M+H]$^+$ calc'd for C$_{18}$H$_{27}$ClN$_2$O$_2$, 339.18; found, 339.4.

Example 194: 3-((3-cyclopropylpyridin-2-yl)oxy)-N-((2R,4R)-1,2-dimethylpiperidin-4-yl)-2,2-difluoropropanamide

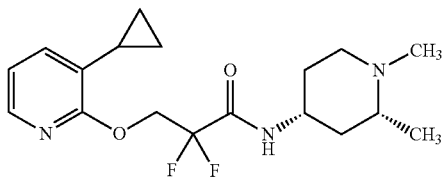 [SMILES: C[C@@H]1C[C@H](NC(=O)C(F)(F)COc2ncccc2C2CC2)CCN1C]

Step A: tert-butyl (2R,4R)-4-(3-((3-cyclopropylpyridin-2-yl)oxy)-2,2-difluoropropanamido)-2-methylpiperidine-1-carboxylate

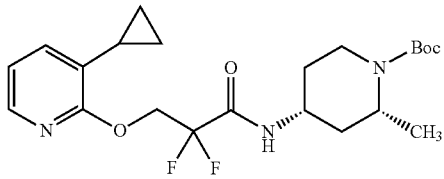 [SMILES: C[C@@H]1C[C@H](NC(=O)C(F)(F)COc2ncccc2C2CC2)CCN1C(=O)OC(C)(C)C]

A solution of 3-((3-cyclopropylpyridin-2-yl)oxy)-2,2-difluoropropanoic acid (73 mg, 0.30 mmol), tert-butyl (2R,4R)-4-amino-2-methylpiperidine-1-carboxylate (64 mg, 0.30 mmol), HATU (0.137 g, 0.360 mmol), and DIPEA (157 µL, 0.900 mmol) in DMF (3 mL) was stirred at room temperature overnight. The mixture was then diluted with water and extracted with EtOAc. The organic phase was dried over MgSO$_4$, filtered, and concentrated to give crude title compound as a brown syrup (132 mg, assumed quantitative) which was used without further purification. ESI-MS [M+H]$^+$ calc'd for C$_{22}$H$_{31}$F$_2$N$_3$O$_4$, 440.24; found, 440.39.

Step B: 3-((3-cyclopropylpyridin-2-yl)oxy)-2,2-difluoro-N-((2R,4R)-2-methylpiperidin-4-yl)propanamide

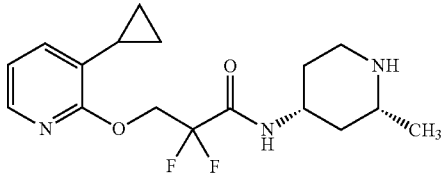 [SMILES: C[C@@H]1C[C@H](NC(=O)C(F)(F)COc2ncccc2C2CC2)CCN1]

A solution of tert-butyl (2R,4R)-4-(3-((3-cyclopropylpyridin-2-yl)oxy)-2,2-difluoropropanamido)-2-methylpiperidine-1-carboxylate (132 mg, 0.300 mmol) and HCl (4M in dioxane, 0.300 mL, 1.20 mmol) in dioxane (3 mL) was stirred at 50° C. for 4 hours. The mixture was concentrated to dryness to give an HCl salt of the title compound (crude) as a brown solid (113 mg, assumed quantitative) which was used without further purification. ESI-MS [M+H]$^+$ calc'd for C$_{17}$H$_{23}$F$_2$N$_3$O$_2$, 340.18; found, 340.3.

Step C: 3-((3-cyclopropylpyridin-2-yl)oxy)-N-((2R,4R)-1,2-dimethylpiperidin-4-yl)-2,2-difluoropropanamide To a solution of 3-((3-cyclopropylpyridin-2-yl)oxy)-2,2-difluoro-N-((2R,4R)-2-methylpiperidin-4-yl)propanamide HCl salt (113 mg, 0.300 mmol) and formaldehyde (47 µL, 0.60 mmol) in MeOH (3 mL) was added sodium cyanotrihydroborate (37.7 mg, 0.600 mmol). The reaction mixture was stirred at room temperature overnight and then filtered through a hydrophilic PTFE 0.45 m filter (Millipore® Millex-LCR) which was rinsed with methanol. The filtrate was purified by preparative HPLC (Method A) to give a TFA salt of the title compound as a colorless film (3.5 mg, 2.5%). $^1$H NMR (400 MHz, CD$_3$OD) δ ppm 0.65-0.73 (m, 2H), 0.89-0.98 (m, 2H), 1.39 (d, J=6.4 Hz, 3H), 1.58-1.70 (m, 1H), 1.77-1.92 (m, 1H), 1.99-2.19 (m, 3H), 2.88 (s, 3H), 3.10-3.29 (m, 2H), 3.53-3.61 (m, 1H), 3.99-4.12 (m, 1H), 4.80-4.88 (m, 2H), 6.85-6.95 (m, 1H), 7.20-7.33 (m, 1H), 7.86-7.97 (m, 1H); ESI-MS [M+H]$^+$ calc'd for C$_{18}$H$_{25}$F$_2$N$_3$O$_2$, 354.20; found, 354.3.

Example 195: 3-(2-fluorophenoxy)-2,2-dimethyl-N-(1-methylpiperidin-4-yl)propanamide

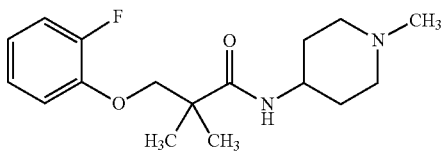 [SMILES: CN1CCC(NC(=O)C(C)(C)COc2ccccc2F)CC1]

To a solution of 3-(2-fluorophenoxy)-2,2-dimethylpropanoic acid (40.0 mg, 0.188 mmol), 1-methylpiperidin-4-amine (23.7 mg, 0.207 mmol), and HATU (89.0 mg, 0.226 mmol) in DMF (628 µL) was added DIPEA (99 µL, 0.56 mmol). The reaction mixture was stirred at room temperature overnight and then filtered through a hydrophilic PTFE 0.45 m filter (Millipore® Millex-LCR) which was rinsed with methanol. The filtrate was purified by preparative HPLC (Method B) to give the title compound as a clear oil (24 mg, 41%). ¹H NMR (400 MHz, CDCl₃) δ ppm 1.33 (s, 6H), 1.46-1.67 (m, 2H), 1.86-1.98 (m, 2H), 2.07-2.18 (m, 2H), 2.29 (s, 3H), 2.68-2.81 (m, 2H), 3.75-3.87 (m, 1H), 3.97 (s, 2H), 6.31-6.43 (m, 1H), 6.90-7.03 (m, 2H), 7.05-7.14 (m, 2H); ESI-MS [M+H]⁺ calc'd for $C_{17}H_{25}FN_2O_2$, 309.19; found, 309.3.

Example 196: 3-(2-fluorophenoxy)-2,2-dimethyl-N-((3S,4S)-3-methylpiperidin-4-yl)propanamide

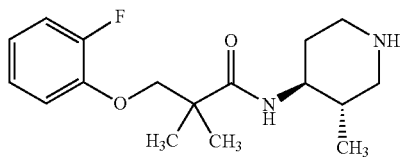 [SMILES: C[C@H]1CNCC[C@@H]1NC(=O)C(C)(C)COc1ccccc1F]

To a solution of 3-(2-fluorophenoxy)-2,2-dimethylpropanoic acid (100 mg, 0.471 mmol), tert-butyl (3S,4S)-4-amino-3-methylpiperidine-1-carboxylate (121 mg, 0.565 mmol), and HATU (222 mg, 0.565 mmol) in DMF (1.57 mL) was added DIPEA (247 μL, 1.41 mmol). The reaction mixture was stirred at room temperature overnight and then filtered through a hydrophilic PTFE 0.45 m filter (Millipore® Millex-LCR) which was rinsed with methanol. The filtrate was purified by preparative HPLC (Method B) to give the title compound as a clear oil (111 mg, 76%). ¹H NMR (400 MHz, CDCl₃) δ ppm 1.00 (m, 3H), 1.34 (m, 6H), 1.47-1.84 (m, 2H), 1.90-2.02 (m, 1H), 2.11-2.23 (m, 1H), 2.54-2.73 (m, 1H), 2.83-3.04 (m, 1H), 3.27-3.49 (m, 2H), 3.73-3.88 (m, 1H), 3.99 (d, J=10.7 Hz, 2H), 6.30-6.47 (m, 1H), 6.90-7.05 (m, 2H), 7.05-7.17 (m, 2H); ESI-MS [M+H]⁺ calc'd for $C_{17}H_{25}FN_2O_2$, 309.19; found, 309.3.

Example 197: 2,2-difluoro-N-((3S,4S)-3-fluoropiperidin-4-yl)-3-((3-(trifluoromethyl)pyridin-2-yl)oxy)propanamide

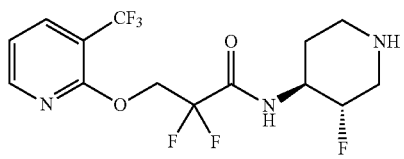

The title compound was prepared in a manner similar to EXAMPLE 194 (STEP A and STEP B only) using 2,2-difluoro-3-((3-(trifluoromethyl)pyridin-2-yl)oxy)propanoic acid (87 mg, 0.32 mmol) in place of 3-((3-cyclopropylpyridin-2-yl)oxy)-2,2-difluoropropanoic acid and tert-butyl (3S,4S)-4-amino-3-fluoropiperidine-1-carboxylate (0.140 g, 0.642 mmol) in place of tert-butyl (2R,4R)-4-amino-2-methylpiperidine-1-carboxylate. After N-Boc deprotection, the product was purified by preparative HPLC (Method B) to give the title compound as a white solid (20.5 mg, 17%). ¹H NMR (400 MHz, CD₃OD) δ ppm 1.48-1.64 (m, 1H), 1.83-1.98 (m, 1H), 2.50-2.65 (m, 2H), 2.89-3.03 (m, 1H), 3.20-3.29 (m, 1H), 3.89-4.04 (m, 1H), 4.24-4.54 (m, 1H), 4.91 (d, J=10.9 Hz, 2H), 7.09-7.23 (m, 1H), 7.92-8.10 (m, 1H), 8.31-8.41 (m, 1H); ESI-MS [M+H]⁺ calc'd for $C_{14}H_{15}F_6N_3O_2$, 372.12; found, 372.2.

Example 198: 3-((3-cyclopropylpyridin-2-yl)oxy)-2,2-difluoro-N-((3S,4S)-3-fluoropiperidin-4-yl)propanamide

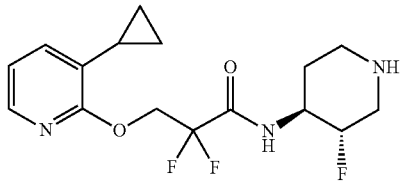 [SMILES: O=C(N[C@H]1CCNC[C@@H]1F)C(F)(F)COc1ncccc1C1CC1]

The title compound was prepared in a manner similar to EXAMPLE 194 (STEP A and STEP B only) using tert-butyl (3S,4S)-4-amino-3-fluoropiperidine-1-carboxylate (0.116 g, 0.533 mmol) in place of tert-butyl (2R,4R)-4-amino-2-methylpiperidine-1-carboxylate. After N-Boc deprotection, the product was purified by preparative HPLC (Method B) to give the title compound as a white solid (7.9 mg, 8.6%). ¹H NMR (400 MHz, CD₃OD) δ ppm 0.66 (dd, J=5.3, 1.9 Hz, 2H), 0.91 (dd, J=8.6, 2.1 Hz, 2H), 1.45-1.63 (m, 1H), 1.83-1.95 (m, 1H), 1.98-2.09 (m, 1H), 2.49-2.63 (m, 2H), 2.88-2.99 (m, 1H), 3.25-3.29 (m, 1H), 3.88-4.07 (m, 1H), 4.30-4.54 (m, 1H), 4.73-4.77 (m, 1H), 4.80-4.85 (m, 1H), 6.82-6.95 (m, 1H), 7.16-7.29 (m, 1H), 7.78-7.99 (m, 1H); ESI-MS [M+H]⁺ calc'd for $C_{16}H_{20}F_3N_3O_2$, 344.16; found, 344.3.

Example 199: N-(trans-1,3-dimethylpiperidin-4-yl)-2,2-difluoro-3-((3-methylpyridin-2-yl)oxy)propanamide

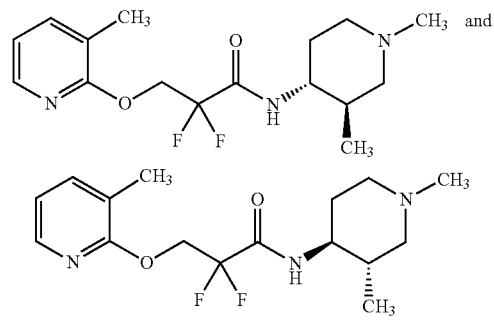

The title compound was prepared in a manner similar to EXAMPLE 1, using 2,2-difluoro-3-((3-methylpyridin-2-yl)oxy)propanoic acid (57 mg, 0.26 mmol) in place of 2,2-dimethyl-3-((3-methylpyridin-2-yl)oxy)propanoic acid and trans-1,3-dimethylpiperidin-4-amine (34 mg, 0.26 mmol) in place of 1-methylpiperidin-4-amine. The product was purified by preparative HPLC (Method B) to give the title compound as a white solid (20.8 mg, 24%). ¹H NMR (400 MHz, CD₃OD) δ ppm 0.86 (d, J=6.0 Hz, 3H), 1.56-1.70 (m, 1H), 1.72-1.85 (m, 3H), 2.02-2.11 (m, 1H), 2.17 (s, 3H), 2.27 (s, 3H), 2.81-2.93 (m, 2H), 3.38-3.58 (m, 1H), 4.73-4.79 (m, 2H), 6.84-6.95 (m, 1H), 7.40-7.61 (m, 1H), 7.88-8.01 (m, 1H); ESI-MS [M+H]⁺ calc'd for $C_{16}H_{23}F_2N_3O_2$, 328.18; found, 328.3.

Example 200: N-(trans-1,3-dimethylpiperidin-4-yl)-2,2-difluoro-3-((3-(trifluoromethoxy)pyridin-2-yl)oxy)propanamide

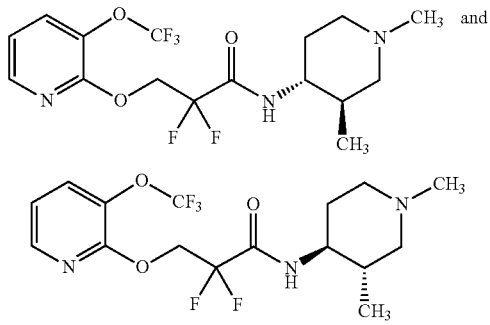

The title compound was prepared in a manner similar to EXAMPLE 1, using 2,2-difluoro-3-((3-(trifluoromethoxy)pyridin-2-yl)oxy)propanoic acid (94 mg, 0.25 mmol) in place of 2,2-dimethyl-3-((3-methylpyridin-2-yl)oxy)propanoic acid and trans-1,3-dimethylpiperidin-4-amine (32 mg, 0.25 mmol) in place of 1-methylpiperidin-4-amine. The product was purified by preparative HPLC (Method B) to give the title compound as a white solid (18.2 mg, 18%). $^1$H NMR (400 MHz, CD$_3$OD) δ ppm 0.87 (d, J=6.0 Hz, 3H), 1.58-1.86 (m, 4H), 1.95-2.14 (m, 1H), 2.28 (s, 3H) 2.79-2.95 (m, 2H), 3.36-3.49 (m, 1H), 4.83-4.97 (m, 2H), 7.11 (dd, J=7.8, 5.0 Hz, 1H), 7.62-7.77 (m, 1H), 8.03-8.23 (m, 1H); ESI-MS [M+H]$^+$ calc'd for C$_{16}$H$_{20}$F$_5$N$_3$O$_3$, 398.15; found, 398.4.

Example 201: 2,2-difluoro-N-((3S,4S)-3-fluoropiperidin-4-yl)-3-((3-methylpyridin-2-yl)oxy)propanamide

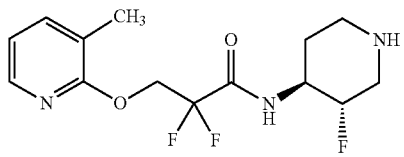 [SMILES: Cc1cccnc1OCC(F)(F)C(=O)N[C@H]1CCNC[C@@H]1F]

The title compound was prepared in a manner similar to EXAMPLE 194 (STEP A and STEP B only) using 2,2-difluoro-3-((3-methylpyridin-2-yl)oxy)propanoic acid (57 mg, 0.26 mmol) in place of 3-((3-cyclopropylpyridin-2-yl)oxy)-2,2-difluoropropanoic acid and tert-butyl (3S,4S)-4-amino-3-fluoropiperidine-1-carboxylate (0.115 g, 0.525 mmol) in place of tert-butyl (2R,4R)-4-amino-2-methylpiperidine-1-carboxylate. After N-Boc deprotection, the product was purified by preparative HPLC (Method B) to give the title compound as a white solid (23.5 mg, 28%). $^1$H NMR (400 MHz, CD$_3$OD) δ ppm 1.45-1.63 (m, 1H), 1.81-1.98 (m, 1H), 2.17 (s, 3H), 2.48-2.64 (m, 2H), 2.89-3.04 (m, 1H), 3.26-3.30 (m, 1H), 3.85-4.09 (m, 1H), 4.32-4.56 (m, 1H), 4.74 (s, 1H), 4.79-4.81 (m, 1H), 6.81-6.96 (m, 1H), 7.42-7.54 (m, 1H), 7.81-8.01 (m, 1H); ESI-MS [M+H]$^+$ calc'd for C$_{14}$H$_{18}$F$_3$N$_3$O$_2$, 318.14; found, 318.3.

Example 202: N-((3S,4S)-1,3-dimethylpiperidin-4-yl)-3-(2-fluorophenoxy)-2,2-dimethylpropanamide

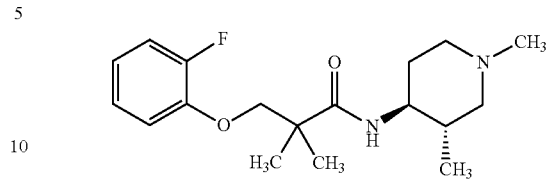

To a solution of 3-(2-fluorophenoxy)-2,2-dimethyl-N-((3S,4S)-3-methylpiperidin-4-yl)propanamide (111 mg, 0.360 mmol) in THF (1.20 mL) was added DIPEA (189 µL, 1.08 mmol) and formaldehyde (80 µL, 1.1 mmol) and the solution was stirred at room temperature for 30 minutes. Sodium triacetoxyborohydride (236 mg, 1.08 mmol) was added in one portion. The reaction mixture was stirred at room temperature overnight and then filtered through a hydrophilic PTFE 0.45 m filter (Millipore® Millex-LCR) which was rinsed with methanol. The filtrate was purified by preparative (Method B) to give the title compound as a pale-yellow oil (46 mg, 40%). $^1$H NMR (400 MHz, CDCl$_3$) δ ppm 0.90 (d, J=6.5 Hz, 3H), 1.34 (app d, J=6.3 Hz, 6H), 1.38-1.70 (m, 2H), 1.71-1.81 (m, 1H), 1.88-1.97 (m, 1H), 1.99-2.10 (m, 1H), 2.28 (s, 3H), 2.75-2.90 (m, 2H), 3.43-3.60 (m, 1H), 3.99 (d, J=6.0 Hz, 2H), 6.18-6.32 (m, 1H), 6.90-7.03 (m, 2H), 7.05-7.14 (m, 2H); ESI-MS [M+H]$^+$ calc'd for C$_{18}$H$_{27}$FN$_2$O$_2$, 323.21; found, 323.3.

Example 203: 3-(3-fluorophenoxy)-2,2-dimethyl-N-(1-methylpiperidin-4-yl)propanamide

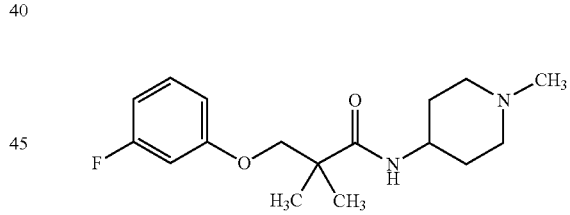

To a solution of 3-(3-fluorophenoxy)-2,2-dimethylpropanoic acid (40.0 mg, 0.188 mmol), 1-methylpiperidin-4-amine (23.7 mg, 0.207 mmol), and HATU (89.0 mg, 0.226 mmol) in DMF (628 µL) was added DIPEA (99 µL, 0.56 mmol). The reaction mixture was stirred at room temperature overnight and then filtered through a hydrophilic PTFE 0.45 µm filter (Millipore® Millex-LCR) which was rinsed with methanol. The filtrate was purified by preparative HPLC (Method B) to give the title compound as a pale-yellow oil (46 mg, 40%). $^1$H NMR (400 MHz, CDCl$_3$) δ ppm 1.31 (s, 6H), 1.39-1.54 (m, 2H), 1.88-1.99 (m, 2H), 2.08-2.19 (m, 2H), 2.29 (s, 3H), 2.65-2.77 (m, 2H), 3.74-3.88 (m, 1H), 3.92 (s, 2H), 5.94-6.08 (m, 1H), 6.59-6.66 (m, 1H), 6.67-6.73 (m, 2H), 7.20-7.27 (m, 1H); ESI-MS [M+H]$^+$ calc'd for C$_{17}$H$_{25}$FN$_2$O$_2$, 309.19; found, 309.3.

Example 204: 3-(4-fluorophenoxy)-2,2-dimethyl-N-(1-methylpiperidin-4-yl)propanamide

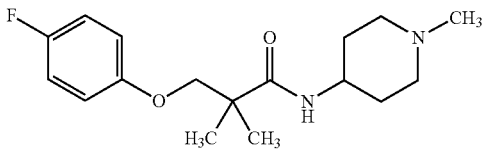 [SMILES: CN1CCC(NC(=O)C(C)(C)COc2ccc(F)cc2)CC1]

To a solution of 3-(4-fluorophenoxy)-2,2-dimethylpropanoic acid (40.0 mg, 0.188 mmol), 1-methylpiperidin-4-amine (23.7 mg, 0.207 mmol), and HATU (89.0 mg, 0.226 mmol) in DMF (628 μL) was added DIPEA (99 μL, 0.56 mmol). The reaction mixture was stirred at room temperature overnight and then filtered through a hydrophilic PTFE 0.45 m filter (Millipore® Millex-LCR) which was rinsed with methanol. The filtrate was purified by preparative HPLC (Method B) give the title compound as a pale-yellow oil (37.5 mg, 64%). $^1$H NMR (400 MHz, CDCl$_3$) δ ppm 1.31 (s, 6H), 1.40-1.53 (m, 2H), 1.87-1.99 (m, 2H), 2.08-2.20 (m, 2H), 2.28 (s, 3H), 2.66-2.79 (m, 2H), 3.70-3.88 (m, 1H), 3.89 (s, 2H), 6.02-6.20 (m, 1H), 6.78-6.93 (m, 1H), 6.89-6.90 (m, 1H), 6.98 (d, J=8.2 Hz, 2H); ESI-MS [M+H]$^+$ calc'd for C$_{17}$H$_{25}$FN$_2$O$_2$, 309.19; found, 309.3.

Example 205: N-((2R,4R)-1,2-dimethylpiperidin-4-yl)-2,2-difluoro-3-((3-methylpyridin-2-yl)oxy)propanamide

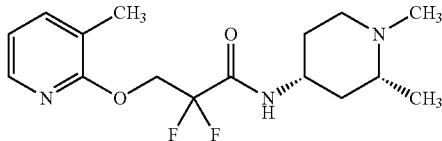 [SMILES: Cc1cccnc1OCC(F)(F)C(=O)N[C@@H]1CCN(C)[C@H](C)C1]

The title compound was prepared in a manner similar to EXAMPLE 194, using 2,2-difluoro-3-((3-methylpyridin-2-yl)oxy)propanoic acid (57 mg, 0.26 mmol) in place of 3-((3-cyclopropylpyridin-2-yl)oxy)-2,2-difluoropropanoic acid. The final reaction mixture was purified by preparative HPLC (Method B) to give the title compound as a white solid (20.5 mg, 24%). $^1$H NMR (400 MHz, CD$_3$OD) δ ppm 1.11 (d, J=6.3 Hz, 3H), 1.21-1.38 (m, 1H), 1.56-1.68 (m, 1H), 1.71-1.86 (m, 2H), 1.95-2.12 (m, 1H), 2.18 (m, 4H), 2.27 (s, 3H), 2.81-2.99 (m, 1H), 3.71-3.89 (m, 1H), 4.73-4.77 (m, 1H), 4.79-4.80 (m, 1H), 6.83-6.97 (m, 1H), 7.45-7.57 (m, 1H), 7.89-7.97 (m, 1H); ESI-MS [M+H]$^+$ calc'd for C$_{16}$H$_{23}$F$_2$N$_3$O$_2$, 328.18; found, 328.4.

Example 206: N-((2R,4R)-1,2-dimethylpiperidin-4-yl)-2,2-difluoro-3-((3-(trifluoromethoxy)pyridin-2-yl)oxy)propanamide

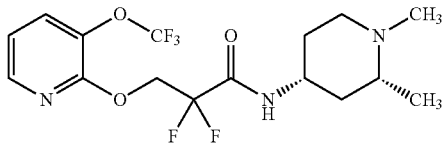 [SMILES: C[C@@H]1C[C@H](NC(=O)C(F)(F)COc2ncccc2OC(F)(F)F)CCN1C]

The title compound was prepared in a manner similar to EXAMPLE 194, using 2,2-difluoro-3-((3-(trifluoromethoxy)pyridin-2-yl)oxy)propanoic acid (94 mg, 0.25 mmol) in place of 3-((3-cyclopropylpyridin-2-yl)oxy)-2,2-difluoropropanoic acid. The final reaction mixture was purified by preparative HPLC (Method B) to give the title compound as a white solid (13.2 mg, 13%). $^1$H NMR (400 MHz, CD$_3$OD) δ ppm 1.12 (d, J=6.3 Hz, 3H), 1.26-1.43 (m, 1H), 1.52-1.71 (m, 1H), 1.75-1.86 (m, 2H), 2.00-2.13 (m, 1H), 2.15-2.25 (m, 1H), 2.28 (s, 3H), 2.84-2.98 (m, 1H), 3.63-3.88 (m, 1H), 4.86 (s, 2H), 7.00-7.19 (m, 1H), 7.65-7.79 (m, 1H), 8.04-8.20 (m, 1H); ESI-MS [M+H]$^+$ calc'd for C$_{16}$H$_{20}$F$_5$N$_3$O$_3$, 398.15; found, 398.4.

Example 207: 2,2-difluoro-N-((3S,4S)-3-fluoropiperidin-4-yl)-3-((3-(trifluoromethoxy)pyridin-2-yl)oxy)propanamide

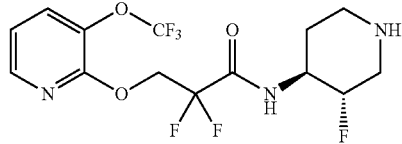 [SMILES: O=C(N[C@H]1CCNC[C@@H]1F)C(F)(F)COc1ncccc1OC(F)(F)F]

The title compound was prepared in a manner similar to EXAMPLE 194 (STEP A and STEP B only) using 2,2-difluoro-3-((3-(trifluoromethoxy)pyridin-2-yl)oxy)propanoic acid (94 mg, 0.25 mmol) in place of 3-((3-cyclopropylpyridin-2-yl)oxy)-2,2-difluoropropanoic acid and tert-butyl (3S,4S)-4-amino-3-fluoropiperidine-1-carboxylate (109 mg, 0.500 mmol) in place of tert-butyl (2R,4R)-4-amino-2-methylpiperidine-1-carboxylate. After N-Boc deprotection, the product was purified by preparative HPLC (Method B) to give the title compound as a white solid (17.1 mg, 18%). $^1$H NMR (400 MHz, CD$_3$OD) δ ppm 1.42-1.64 (m, 1H), 1.83-1.98 (m, 1H), 2.58 (br d, J=2.6 Hz, 2H), 2.87-3.04 (m, 1H), 3.25-3.29 (m, 1H), 3.90-4.07 (m, 1H), 4.26-4.56 (m, 1H), 4.83-4.95 (m, 2H), 7.03-7.15 (m, 1H), 7.66-7.75 (m, 1H), 8.13 (dd, J=4.9, 1.6 Hz, 1H); ESI-MS [M+H]$^+$ calc'd for C$_{14}$H$_{15}$F$_6$N$_3$O$_3$, 388.11; found, 388.3.

Example 208: 2,2-difluoro-N-((3S,4S)-3-methylpiperidin-4-yl)-3-((3-(trifluoromethyl)pyridin-2-yl)oxy)propanamide

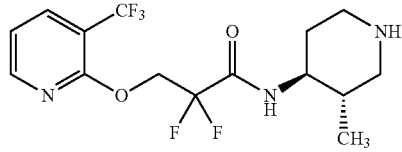 [SMILES: C[C@H]1CNCC[C@@H]1NC(=O)C(F)(F)COc1ncccc1C(F)(F)F]

The title compound was prepared in a manner similar to EXAMPLE 194 (STEP A and STEP B only) using 2,2-difluoro-3-((3-(trifluoromethyl)pyridin-2-yl)oxy)propanoic acid (87 mg, 0.32 mmol) in place of 3-((3-cyclopropylpyridin-2-yl)oxy)-2,2-difluoropropanoic acid and tert-butyl (3S,4S)-4-amino-3-methylpiperidine-1-carboxylate (68.8 mg, 0.321 mmol) in place of tert-butyl (2R,4R)-4-amino-2-methylpiperidine-1-carboxylate. After N-Boc deprotection, the product was purified by preparative HPLC (Method B) to give the title compound as a white solid (3.4 mg, 2.9%).

¹H NMR (400 MHz, CD₃OD) δ ppm 0.86 (d, J=6.6 Hz, 3H), 1.46-1.72 (m, 2H), 1.73-1.90 (m, 1H), 2.24-2.41 (m, 1H), 2.59-2.74 (m, 1H), 2.98-3.14 (m, 2H), 3.46-3.63 (m, 1H), 4.93 (s, 2H), 7.07-7.23 (m, 1H), 7.89-8.11 (m, 1H), 8.25-8.49 (m, 1H); ESI-MS [M+H]⁺ calc'd for C₁₅H₁₈F₅N₃O₂, 368.14; found, 368.3.

Example 209: 3-((3-cyclopropylpyridin-2-yl)oxy)-2,2-difluoro-N-((3S,4S)-3-methylpiperidin-4-yl)propanamide

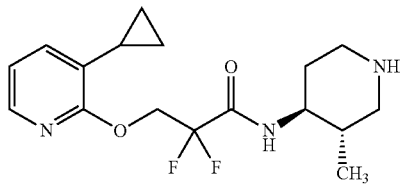

The title compound was prepared in a manner similar to EXAMPLE 194 (STEP A and STEP B only) using tert-butyl (3S,4S)-4-amino-3-methylpiperidine-1-carboxylate (57 mg, 0.27 mmol) in place of tert-butyl (2R,4R)-4-amino-2-methylpiperidine-1-carboxylate. After N-Boc deprotection, the product was purified by preparative HPLC (Method B) to give the title compound as a white solid (3.9 mg, 4.3%). ¹H NMR (400 MHz, CD₃OD) δ ppm 0.60-0.72 (m, 2H), 0.84 (d, J=6.5 Hz, 3H), 0.88-0.99 (m, 2H), 1.40-1.58 (m, 1H), 1.58-1.70 (m, 1H), 1.73-1.83 (m, 1H), 1.96-2.11 (m, 1H), 2.24-2.36 (m, 1H), 2.57-2.69 (m, 1H), 2.95-3.11 (m, 2H), 3.46-3.63 (m, 1H), 4.79 (br s, 2H), 6.80-6.96 (m, 1H), 7.13-7.30 (m, 1H), 7.75-8.01 (m, 1H); ESI-MS [M+H]⁺ calc'd for C₁₇H₂₃F₂N₃O₂, 340.18; found, 340.4.

Example 210: 2,2-difluoro-N-((3S,4S)-3-methylpiperidin-4-yl)-3-((3-(trifluoromethoxy)pyridin-2-yl)oxy)propanamide

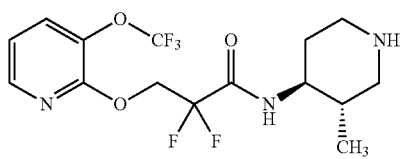 [SMILES: C[C@H]1CNCC[C@@H]1NC(=O)C(F)(F)COc1ncccc1OC(F)(F)F]

The title compound was prepared in a manner similar to EXAMPLE 194 (STEP A and STEP B only) using 2,2-difluoro-3-((3-(trifluoromethoxy)pyridin-2-yl)oxy)propanoic acid (71.8 mg, 0.250 mmol) in place of 3-((3-cyclopropylpyridin-2-yl)oxy)-2,2-difluoropropanoic acid and tert-butyl (3S,4S)-4-amino-3-methylpiperidine-1-carboxylate (53.6 mg, 0.250 mmol) in place of tert-butyl (2R,4R)-4-amino-2-methylpiperidine-1-carboxylate. After N-Boc deprotection, the product was purified by preparative HPLC (Method B) to give the title compound (8.3 mg, 8.7%). ¹H NMR (400 MHz, CD₃OD) δ ppm 0.86 (d, J=6.5 Hz, 3H), 1.47-1.59 (m, 1H), 1.61-1.72 (m, 1H), 1.75-1.90 (m, 1H), 2.22-2.43 (m, 1H), 2.59-2.73 (m, 1H), 2.99-3.11 (m, 2H), 3.49-3.60 (m, 1H), 4.82-4.97 (m, 2H), 7.05-7.16 (m, 1H), 7.66-7.76 (m, 1H), 8.07-8.20 (m, 1H); ESI-MS [M+H]⁺ calc'd for C₁₅H₁₈F₅N₃O₃, 384.14; found, 384.3.

Example 211: 3-((3-cyclopropylpyridin-2-yl)oxy)-2,2-difluoro-N-((2R,4R)-2-methylpiperidin-4-yl)propanamide

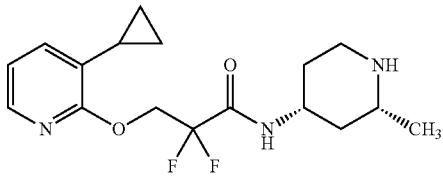 [SMILES: C[C@@H]1C[C@H](NC(=O)C(F)(F)COc2ncccc2C2CC2)CCN1]

The title compound was prepared in a manner similar to EXAMPLE 194 (STEP A and STEP B only). After N-Boc deprotection, the product was purified by preparative HPLC (Method B) to give the title compound as a colorless film (3.9 mg, 4.3%). ¹H NMR (400 MHz, CD₃OD) δ ppm 0.62-0.72 (m, 2H), 0.84 (d, J=6.5 Hz, 3H), 0.88-0.99 (m, 2H), 1.40-1.56 (m, 1H), 1.57-1.68 (m, 1H), 1.71-1.84 (m, 1H), 1.99-2.13 (m, 1H), 2.21-2.36 (m, 1H), 2.53-2.71 (m, 1H), 2.96-3.10 (m, 2H), 3.45-3.62 (m, 1H), 4.79-4.83 (m, 2H), 6.83-6.95 (m, 1H), 7.16-7.29 (m, 1H), 7.85-7.96 (m, 1H); ESI-MS [M+H]⁺ calc'd for C₁₇H₂₃F₂N₃O₂, 340.18; found, 340.4.

Example 212: 2,2-difluoro-N-((2R,4R)-2-methylpiperidin-4-yl)-3-((3-(trifluoromethoxy)pyridin-2-yl)oxy)propanamide

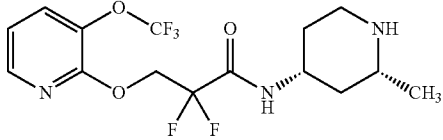 [SMILES: C[C@@H]1C[C@H](NC(=O)C(F)(F)COc2ncccc2OC(F)(F)F)CCN1]

The title compound was prepared in a manner similar to EXAMPLE 194 (STEP A and STEP B only) using 2,2-difluoro-3-((3-(trifluoromethoxy)pyridin-2-yl)oxy)propanoic acid (71.8 mg, 0.250 mmol) in place of 3-((3-cyclopropylpyridin-2-yl)oxy)-2,2-difluoropropanoic acid. After N-Boc deprotection, the product was purified by preparative HPLC (Method B) to give the title compound as a colorless film (8.3 mg, 8.7%). ¹H NMR (400 MHz, CD₃OD) δ ppm 0.86 (d, J=6.6 Hz, 3H), 1.48-1.73 (m, 2H), 1.75-1.86 (m, 1H), 2.26-2.39 (m, 1H), 2.57-2.72 (m, 1H), 3.00-3.12 (m, 2H), 3.50-3.61 (m, 1H), 4.83-4.96 (m, 2H), 7.06-7.14 (m, 1H), 7.61-7.77 (m, 1H), 8.09-8.20 (m, 1H), 8.69-8.76 (m, 1H); ESI-MS [M+H]⁺ calc'd for C₁₅H₁₈F₅N₃O₃, 384.14; found, 384.3.

Example 213: 3-(2-chlorophenoxy)-2,2-dimethyl-N-(piperidin-4-yl)propanamide

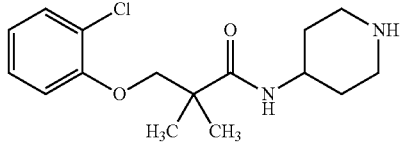 [SMILES: CC(C)(COc1ccccc1Cl)C(=O)NC1CCNCC1]

To a solution of tert-butyl 4-(3-(2-chlorophenoxy)-2,2-dimethylpropanamido)piperidine-1-carboxylate (577 mg, 1.40 mmol) in DCM (4.01 mL) was added HCl (4M in dioxane, 427 μL, 14.0 mmol) dropwise via syringe at room temperature. The reaction mixture was stirred for 12 hours and then filtered through a hydrophilic PTFE 0.45 m filter (Millipore® Millex-LCR) which was rinsed with methanol. The filtrate was purified by preparative HPLC (Method A) to give a TFA salt of the title compound as a white sticky solid (490 mg, 82%). $^1$H NMR (400 MHz, DMSO-$d_6$) δ ppm 1.23 (s, 6H), 1.56-1.69 (m, 2H), 1.84 (br dd, J=13.6, 2.8 Hz, 2H), 2.89-3.02 (m, 2H), 3.26 (br d, J=12.8 Hz, 2H), 3.81-3.92 (m, 1H), 4.03 (s, 2H), 6.94 (td, J=7.6, 1.2 Hz, 1H), 7.12 (dd, J=8.3, 1.2 Hz, 1H), 7.29 (ddd, J=8.2, 7.5, 1.6 Hz, 1H), 7.40 (dd, J=7.9, 1.6 Hz, 1H), 7.48 (d, J=7.5 Hz, 1H), 8.34 (br s, 1H); ESI-MS [M+H]$^+$ calc'd for $C_{16}H_{23}ClN_2O_2$, 311.14; found, 311.3.

Example 214: 3-((3,5-dimethylpyridin-2-yl)oxy)-N-((3R,4R)-3-fluoropiperidin-4-yl)-2,2-dimethylpropanamide

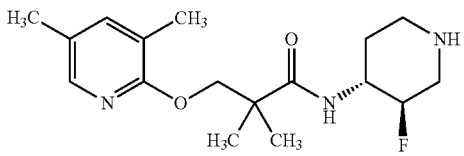 [SMILES: Cc1cnc(OCC(C)(C)C(=O)N[C@@H]2CCNC[C@H]2F)c(C)c1]

The title compound was prepared in a manner similar to EXAMPLE 194 (STEP A and STEP B only) using 3-((3,5-dimethylpyridin-2-yl)oxy)-2,2-dimethylpropanoic acid (55.8 mg, 0.25 mmol) in place of 3-((3-cyclopropylpyridin-2-yl)oxy)-2,2-difluoropropanoic acid and tert-butyl (3R,4R)-4-amino-3-fluoropiperidine-1-carboxylate (109 mg, 0.500 mmol) in place of tert-butyl (2R,4R)-4-amino-2-methylpiperidine-1-carboxylate. After N-Boc deprotection, the product was purified by preparative HPLC (Method B) to give the title compound as a colorless film (44.5 mg, 55%). $^1$H NMR (400 MHz, CD$_3$OD) δ ppm 1.32 (app d, J=1.0 Hz, 6H), 1.41-1.55 (m, 1H), 1.85-1.96 (m, 1H), 2.15 (s, 3H), 2.21 (s, 3H), 2.53-2.65 (m, 2H), 2.89-2.98 (m, 1H), 3.22-3.30 (m, 1H), 3.93-4.06 (m, 1H), 4.29 (d, J=1.1 Hz, 2H), 4.31-4.52 (m, 1H), 7.33 (dd, J=1.5, 0.8 Hz, 1H), 7.65-7.78 (m, 1H); ESI-MS [M+H]$^+$ calc'd for $C_{17}H_{26}FN_3O_2$, 324.21; found, 324.4.

Example 215: 3-(2-chlorophenoxy)-2,2-difluoro-N-(1-methylpiperidin-4-yl)propanamide

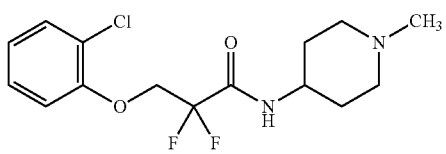 [SMILES: CN1CCC(NC(=O)C(F)(F)COc2ccccc2Cl)CC1]

To a mixture of 3-(2-chlorophenoxy)-2,2-difluoropropanoic acid (40.0 mg, 0.169 mmol) in DCE (1 mL) and DMF (3 drops) was added oxalyl chloride (30 μL, 0.34 mmol). The mixture was stirred for 1 hour at room temperature. A solution of 1-methylpiperidin-4-amine (21.2 mg, 0.186 mmol) in DCE (1 mL) and DIPEA (88 μL, 0.51 mmol) was added. The reaction mixture was heated to 70° C. for 1 hour, then cooled to room temperature and concentrated under reduced pressure. The reaction mixture was filtered through a hydrophilic PTFE 0.45 m filter (Millipore® Millex-LCR) which was rinsed with methanol. The filtrate was purified by preparative HPLC (Method B) to give the title compound as a white solid (3.0 mg, 5.3%). $^1$H NMR (400 MHz, CD$_3$OD) δ ppm 1.61-1.77 (m, 2H), 1.83-1.94 (m, 2H), 2.08-2.20 (m, 2H), 2.30 (s, 3H), 2.84-2.96 (m, 2H), 3.71-3.85 (m, 1H), 4.45-4.59 (m, 2H), 6.95-7.05 (m, 1H), 7.10-7.16 (m, 1H), 7.25-7.33 (m, 1H), 7.37-7.43 (m, 1H); ESI-MS [M+H]$^+$ calc'd for $C_{15}H_{19}ClF_2N_2O_2$, 333.11; found, 333.3.

Example 216: 3-(2-chlorophenoxy)-2,2-difluoro-N-((3S,4S)-3-methylpiperidin-4-yl)propanamide

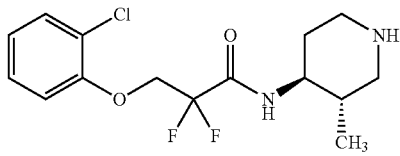 [SMILES: C[C@H]1CNCC[C@@H]1NC(=O)C(F)(F)COc1ccccc1Cl]

A solution of tert-butyl (3S,4S)-4-(3-(2-chlorophenoxy)-2,2-difluoropropanamido)-3-methylpiperidine-1-carboxylate (6.0 mg, 0.014 mmol) and 4M HCl in dioxane (35 μL, 0.14 mmol) in dichloromethane (69 μL) was stirred for 2 hours at room temperature. The solution was concentrated under reduced pressure to give an HCl salt of the title compound as a white solid (4.2 mg, 82%). $^1$H NMR (400 MHz, CD$_3$OD) δ ppm 0.86-0.96 (m, 3H), 1.73-1.88 (m, 1H), 1.92-2.05 (m, 2H), 2.58-2.78 (m, 1H), 2.93-3.08 (m, 1H), 3.61-3.76 (m, 2H), 4.30-4.53 (m, 2H), 6.86-6.93 (m, 1H), 7.00-7.06 (m, 1H), 7.14-7.22 (m, 1H), 7.26 (d, J=1.6 Hz, 1H); ESI-MS [M+H]$^+$ calc'd for $C_{15}H_{19}ClF_2N_2O_2$, 333.11; found, 333.3.

Example 217: 3-(4-chlorophenoxy)-2,2-dimethyl-N-(1-methylpiperidin-4-yl)propanamide

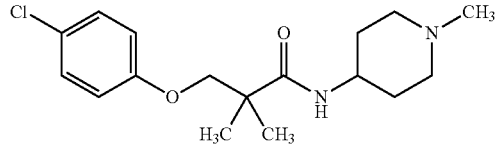 [SMILES: CN1CCC(NC(=O)C(C)(C)COc2ccc(Cl)cc2)CC1]

A solution of 3-(4-chlorophenoxy)-2,2-dimethylpropanoic acid (61.0 mg, 0.267 mmol), 1-methylpiperidin-4-amine (39.6 mg, 0.347 mmol), HATU (135 mg, 0.347 mmol) and Et$_3$N (149 μL, 1.07 mmol) in DMA (1.33 mL) was stirred at room temperature for 12 hours and then filtered through a hydrophilic PTFE 0.45 m filter (Millipore® Millex-LCR) which was rinsed with methanol. The filtrate was purified by preparative HPLC (Method A) to give a TFA salt of the title compound as a white solid (88 mg, 75%). $^1$H NMR (400 MHz, CDCl$_3$) δ ppm 1.30 (s, 6H), 1.99-2.14 (m, 4H), 2.29 (br s, 3H), 2.82 (s, 2H), 3.61 (br d, J=12.3 Hz, 2H), 3.89 (s, 2H), 4.00-4.12 (m, 1H), 6.11-6.26 (m, 1H), 6.79-6.85 (m, 2H), 7.22-7.26 (m, 2H); ESI-MS [M+H]$^+$ calc'd for $C_{17}H_{25}ClN_2O_2$, 325.17; found, 325.3.

Example 218: N-((2R,4R)-1,2-dimethylpiperidin-4-yl)-3-((3,5-dimethylpyridin-2-yl)oxy)-2,2-dimethyl-propanamide

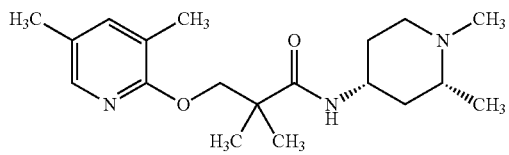

The title compound was prepared in a manner similar to EXAMPLE 194, using 3-((3,5-dimethylpyridin-2-yl)oxy)-2,2-dimethylpropanoic acid (56 mg, 0.25 mmol) in place of 3-((3-cyclopropylpyridin-2-yl)oxy)-2,2-difluoropropanoic acid. The final reaction mixture was purified by preparative HPLC (Method A) to give a TFA salt of the title compound as a colorless film (48.4 mg, 43%). $^1$H NMR (400 MHz, CD$_3$OD) δ ppm 1.25-1.33 (m, 6H), 1.38 (d, J=6.4 Hz, 3H), 1.57-1.71 (m, 1H), 1.76-1.90 (m, 1H), 1.99-2.11 (m, 2H), 2.15 (s, 3H), 2.22 (s, 3H), 2.87 (s, 3H), 3.07-3.27 (m, 2H), 3.49-3.59 (m, 1H), 3.93-4.08 (m, 1H), 4.30 (s, 2H), 7.35-7.44 (m, 1H), 7.67-7.79 (m, 1H); ESI-MS [M+H]$^+$ calc'd for C$_{19}$H$_{31}$N$_3$O$_2$, 334.25; found, 334.4.

Table 5 lists biological assay data (SSTR4 activity, SSTR4 binding, and SSTR1 binding) for some of the compounds shown in the examples, where larger pEC$_{50}$ and pIC$_{50}$ values represent higher activity or potency. All of the compounds shown in Table 5 were tested in accordance with a cell-based assay which measures the inhibition of forskolin stimulated cAMP in cells overexpressing SSTR4 (reported as pEC$_{50}$). Many of the compounds shown in Table 5 were also tested in accordance with membrane-based assays which measure competitive binding of the compounds to SSTR4 and SSTR1 (reported as pIC$_{50}$). These assays are described in the section entitled Biological Activity, above.

TABLE 5

Biological Assay Data

| EXAMPLE No. | SSTR4 Activity pEC$_{50}$ | SSTR4 Binding pIC$_{50}$ | SSTR1 Binding pIC$_{50}$ |
|---|---|---|---|
| 1 | 7.3 | 6.4 | <5.0 |
| 2 | 6.3 | — | — |
| 3 | 5.8 | — | — |
| 4 | 6.5 | — | — |
| 5 | 6.8 | — | — |
| 6 | 7.3 | — | — |
| 7 | 7.2 | — | — |
| 8 | 7.0 | — | — |
| 9 | 7.1 | — | — |
| 10 | 6.8 | — | — |
| 11 | 8.0 | 7.0 | 5.1 |
| 12 | 6.9 | 6.2 | <5.0 |
| 13 | 8.4 | 7.5 | 5.3 |
| 14 | 7.1 | 6.4 | <5.0 |
| 15 | 7.7 | 6.8 | 5.5 |
| 16 | 7.8 | 7.2 | 5.5 |
| 17 | 7.7 | 6.7 | 4.7 |
| 18 | 7.1 | 6.0 | 5.1 |
| 19 | 7.7 | 6.8 | 6.1 |
| 20 | 8.3 | 7.2 | 5.5 |
| 21 | 7.6 | 6.5 | <5.0 |
| 22 | 7.9 | 7.0 | 6.0 |
| 23 | 8.0 | 6.6 | 5.8 |
| 24 | 8.3 | 7.0 | 6.4 |
| 25 | 8.3 | 7.0 | 6.4 |
| 26 | 8.6 | 7.3 | 6.1 |
| 27 | 8.9 | 7.6 | 6.9 |
| 28 | 8.8 | 7.7 | 6.8 |
| 29 | 8.4 | 7.4 | 6.4 |
| 30 | 9.0 | 7.8 | 6.9 |
| 31 | 7.6 | 6.6 | 4.8 |
| 32 | 5.8 | — | — |
| 33 | 9.1 | — | — |
| 34 | 6.1 | — | — |
| 35 | 6.5 | — | — |
| 36 | 6.1 | — | — |
| 37 | 6.3 | — | — |
| 38 | 7.0 | — | — |
| 39 | 6.3 | — | — |
| 40 | 6.1 | — | — |
| 41 | 7.4 | 6.4 | 4.2 |
| 42 | 7.2 | — | — |
| 43 | 6.9 | — | — |
| 44 | 5.9 | — | — |
| 45 | 5.8 | — | — |
| 46 | 5.4 | — | — |
| 47 | 8.1 | 7.1 | 4.8 |
| 48 | 6.8 | — | — |
| 49 | 6.7 | 6.0 | <5.0 |
| 50 | 6.2 | — | — |
| 51 | 6.1 | — | — |
| 52 | 7.1 | — | — |
| 53 | 7.4 | 6.6 | 4.6 |
| 54 | 7.0 | — | — |
| 55 | 7.5 | — | — |
| 56 | 7.6 | — | — |
| 57 | 7.2 | — | — |
| 58 | 7.7 | 6.7 | 6.9 |
| 59 | 7.5 | — | — |
| 60 | 7.1 | — | — |
| 61 | 7.2 | — | — |
| 62 | 7.8 | 6.7 | 6.6 |
| 63 | 5.8 | — | — |
| 64 | 7.9 | 7.0 | 5.1 |
| 65 | 7.9 | 7.0 | 5.1 |
| 66 | 7.7 | 7.0 | 4.9 |
| 67 | 8.1 | 7.4 | 5.1 |
| 68 | 7.5 | 6.8 | 4.6 |
| 69 | 8.4 | 7.2 | 5.2 |
| 70 | 8.4 | 7.6 | 5.5 |
| 71 | 8.3 | 7.3 | 5.3 |
| 72 | 8.1 | 7.1 | 4.8 |
| 73 | 7.0 | — | — |
| 74 | 6.4 | — | — |
| 75 | 5.5 | — | — |
| 76 | 7.7 | 6.7 | 4.7 |
| 77 | 6.4 | — | — |
| 78 | 7.4 | 6.7 | <5.0 |
| 79 | 7.0 | — | — |
| 80 | 6.1 | — | — |
| 81 | 6.3 | — | — |
| 82 | 7.0 | — | — |
| 83 | 7.3 | — | — |
| 84 | 7.4 | 6.5 | <5.0 |
| 85 | 7.1 | — | — |
| 86 | 7.3 | — | — |
| 87 | 6.4 | — | — |
| 88 | 6.6 | — | — |
| 89 | 6.8 | — | — |
| 90 | 6.6 | — | — |
| 91 | 6.0 | — | — |
| 92 | 7.7 | 6.8 | 4.8 |
| 93 | 6.7 | — | — |
| 94 | 7.7 | — | — |
| 95 | 7.1 | — | — |
| 96 | 6.7 | — | — |
| 97 | 7.9 | — | — |
| 98 | 6.2 | — | — |
| 99 | 7.1 | — | — |
| 100 | 7.2 | — | — |
| 101 | 7.3 | — | — |

TABLE 5-continued

Biological Assay Data

| EXAMPLE No. | SSTR4 Activity pEC$_{50}$ | SSTR4 Binding pIC$_{50}$ | SSTR1 Binding pIC$_{50}$ |
|---|---|---|---|
| 102 | 8.7 | 7.8 | 5.6 |
| 103 | 6.2 | — | — |
| 104 | 9.2 | 8.0 | 4.8 |
| 105 | 8.1 | 7.2 | 5.2 |
| 106 | 6.0 | — | — |
| 107 | 8.7 | 7.7 | 5.4 |
| 108 | 6.8 | 6.1 | 4.7 |
| 109 | 8.0 | 7.0 | 5.1 |
| 110 | 9.0 | 7.8 | 5.7 |
| 111 | 7.7 | 6.7 | 4.7 |
| 112 | 6.1 | — | — |
| 113 | 5.9 | — | — |
| 114 | 8.0 | 6.9 | 4.6 |
| 115 | 9.2 | 8.3 | 5.8 |
| 116 | 7.5 | 6.2 | 4.5 |
| 117 | 7.6 | 6.7 | 4.5 |
| 118 | 6.2 | — | — |
| 119 | 9.0 | 7.3 | 5.0 |
| 120 | 5.9 | — | — |
| 121 | 6.9 | 6.6 | <5.0 |
| 122 | 6.6 | — | — |
| 123 | 7.8 | 7.2 | 4.9 |
| 124 | 7.6 | 7.4 | 5.1 |
| 125 | 8.8 | 7.3 | 6.1 |
| 126 | 8.8 | — | — |
| 127 | 7.9 | 7.1 | 5.1 |
| 128 | 7.8 | 7.2 | 5.5 |
| 129 | 7.7 | 6.8 | 4.9 |
| 130 | 6.6 | — | — |
| 131 | 6.1 | — | — |
| 132 | 7.1 | — | — |
| 133 | 6.2 | — | — |
| 134 | 5.7 | — | — |
| 135 | 7.6 | — | — |
| 136 | 8.1 | 7.1 | 4.8 |
| 137 | 6.7 | — | — |
| 138 | 8.0 | 7.2 | 5.7 |
| 139 | 7.9 | 7.2 | 5.2 |
| 140 | 6.2 | — | — |
| 141 | 7.4 | 6.8 | 5.0 |
| 142 | 6.1 | — | — |
| 143 | 7.9 | 6.9 | 4.8 |
| 144 | 8.7 | 8.0 | 5.8 |
| 145 | 6.2 | — | — |
| 146 | 6.7 | — | — |
| 147 | 8.6 | 7.5 | 5.3 |
| 148 | 8.1 | 7.4 | 5.8 |
| 149 | 6.9 | — | — |
| 150 | 8.2 | 7.3 | 5.6 |
| 151 | 6.8 | — | — |
| 152 | 7.0 | 6.6 | 4.6 |
| 153 | 8.1 | — | — |
| 154 | 7.4 | — | — |
| 155 | 8.0 | 7.2 | 5.4 |
| 156 | 7.2 | 6.4 | 4.6 |
| 157 | 9.9 | 8.8 | 7.0 |
| 158 | 8.2 | 8.1 | <5.0 |
| 159 | 6.7 | — | — |
| 160 | 6.4 | — | — |
| 161 | 9.1 | 7.7 | 6.5 |
| 162 | 6.9 | 5.8 | 4.3 |
| 163 | 7.3 | 6.1 | 5.2 |
| 164 | 6.6 | — | — |
| 165 | 7.5 | 6.8 | 5.3 |
| 166 | 8.5 | 7.4 | 6.2 |
| 167 | 6.8 | — | — |
| 168 | 7.6 | 6.8 | 4.8 |
| 169 | 6.6 | — | — |
| 170 | 7.4 | 6.7 | <5.0 |
| 171 | 6.5 | — | — |
| 172 | 7.9 | 5.7 | 4.4 |
| 173 | 6.3 | — | — |
| 174 | 7.0 | — | — |
| 175 | 6.2 | — | — |
| 176 | 7.7 | 7.1 | <4.30 |
| 177 | 6.9 | — | — |
| 178 | 7.2 | 6.5 | 4.5 |
| 179 | 8.1 | 7.4 | 4.8 |
| 180 | 7.6 | 6.5 | 5.4 |
| 181 | 7.8 | 6.4 | 5.5 |
| 182 | 7.5 | 6.1 | 4.9 |
| 183 | 6.6 | — | — |
| 184 | 7.6 | 6.0 | <4.3 |
| 185 | 8.5 | 7.6 | 5.7 |
| 186 | 8.1 | 7.4 | 5.5 |
| 187 | 8.8 | 8.4 | 4.8 |
| 188 | 8.2 | 7.6 | 5.0 |
| 189 | 6.8 | — | — |
| 190 | 9.8 | 7.6 | 5.3 |
| 191 | 7.1 | 6.7 | <4.3 |
| 192 | 7.9 | — | — |
| 193 | 8.9 | — | — |
| 194 | 8.4 | 7.7 | 4.4 |
| 195 | 6.5 | — | — |
| 196 | 8.5 | 7.5 | <4.3 |
| 197 | 7.7 | 7.0 | <4.3 |
| 198 | 8.2 | — | — |
| 199 | 6.8 | 6.1 | <4.3 |
| 200 | 7.5 | 6.9 | 4.4 |
| 201 | 7.5 | 6.7 | <4.3 |
| 202 | 7.1 | 7.0 | 5.0 |
| 203 | 7.1 | — | — |
| 204 | 6.4 | — | — |
| 205 | 6.9 | — | — |
| 206 | 7.7 | 6.7 | <4.3 |
| 207 | 8.1 | 7.6 | <4.3 |
| 208 | 8.6 | 7.1 | 4.4 |
| 209 | 9.2 | 7.6 | 4.9 |
| 210 | 9.1 | 7.6 | 4.5 |
| 211 | 8.9 | 7.2 | 4.8 |
| 212 | 8.6 | 7.4 | 4.5 |
| 213 | 8.7 | 7.6 | 4.6 |
| 214 | 8.2 | 6.8 | <4.3 |
| 215 | 6.7 | 6.0 | <4.3 |
| 216 | 9.4 | 7.7 | 4.8 |
| 217 | 5.8 | — | — |
| 218 | 7.5 | 6.2 | <4.3 |

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. The above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references cited in the disclosure, including patents, patent applications and publications, are herein incorporated by reference in their entirety and for all purposes.

What is claimed is:

1. A method of treating a disease, disorder or condition in a subject, the method comprising administering to the subject a compound of Formula 1,

1

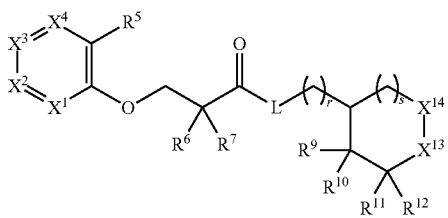

or a pharmaceutically acceptable salt thereof in which:
$X^1$ is selected from N and $CR^1$;
$X^2$ is selected from N and $CR^2$;
$X^3$ is selected from N and $CR^3$; and
$X^4$ is selected from N and $CR^4$, provided no more than two of $X^1$, $X^2$, $X^3$, and $X^4$ are N;
$X^{13}$ is $NR^{13}$ and $X^{14}$ is $CR^{15}R^{16}$ or $X^{13}$ is $CH_2$ and $X^{14}$ is $NR^{14}$;
L is selected from $NR^8$ and O;
r is selected from 0 and 1;
s is selected from 0 and 1;
$R^1$, $R^2$, and $R^3$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo;
$R^4$ is selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo;
$R^5$ is selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo, oxo, and phenyl which is substituted with 0 to 3 optional substituents independently selected from halo; or
$R^4$ and $R^5$, together with the carbon atoms to which they are attached, form a cyclopent-1-en-1,2-diyl or a furan-2,3-diyl;
$R^6$ and $R^7$ are each independently selected from halo and $C_{1-3}$ alkyl, or $R^6$ and $R^7$, together with the carbon atom to which they are attached, form a $C_{3-4}$ cycloalkan-1,1-diyl;
$R^8$ is selected from H and $C_{1-4}$ alkyl;
$R^9$ and $R^{10}$ are each independently selected from
  (a) hydrogen, halo, hydroxy, and cyano;
  (b) $C_{1-4}$ alkyl, $C_{3-6}$ cycloalkyl, and $C_{1-4}$ alkoxy, each substituted with 0 to 3 optional substituents independently selected from halo; and
  (c) phenyl and $C_{1-5}$ heteroaryl, each substituted with 0 to 3 optional substituents independently selected from halo, $C_{1-4}$ alkyl, and $C_{1-4}$ alkoxy, wherein the $C_{1-5}$ heteroaryl substituent is a monocyclic ring with 5 to 6 ring members in which 1 to 4 ring members are heteroatoms, each of the heteroatoms independently selected from N, O, and S, provided no more than one of the ring members is O or S, and wherein the $C_{1-4}$ alkyl and $C_{1-4}$ alkoxy optional substituents on phenyl and $C_{1-5}$ heteroaryl are each independently substituted with 0 to 3 optional substituents independently selected from halo; or
$R^9$ and $R^{10}$, together with the carbon atom to which they are attached, form a $C_{3-4}$ cycloalkan-1,1-diyl;

$R^{11}$ and $R^{12}$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo; or
$R^{11}$ and $R^{12}$, together with the carbon atom to which they are attached, form a $C_{3-4}$ cycloalkan-1,1-diyl;
$R^{13}$ and $R^{14}$ are each independently selected from
  (a) hydrogen; and
  (b) $C_{1-4}$ alkyl, which is unsubstituted or substituted with a substituent selected from cyano and oxo; and
$R^{15}$ and $R^{16}$ are each independently selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo; or
$R^{15}$ and $R^{16}$, together with the carbon atom to which they are attached, form a $C_{3-4}$ cycloalkan-1,1-diyl;
wherein the disease, disorder or condition is pain.

2. The method according to claim 1, wherein $X^1$ is $CR^1$, $X^2$ is $CR^2$, $X^3$ is $CR^3$, and $X^4$ is $CR^4$.

3. The method according to claim 2, wherein $R^1$, $R^2$, $R^3$, and $R^4$ are each independently selected from
  (a) hydrogen, halo, and cyano; and
  (b) $C_{1-4}$ alkyl, $C_{3-6}$ cycloalkyl, and $C_{1-4}$ alkoxy, each substituted with 0 to 3 optional substituents independently selected from halo.

4. The method according to claim 1, wherein $X^1$ is N, $X^2$ is $CR^2$, $X^3$ is $CR^3$, and $X^4$ is $CR^4$.

5. The method according to claim 4, wherein $R^2$, $R^3$, and $R^4$ are each independently selected from
  (a) hydrogen, halo, and cyano; and
  (b) $C_{1-4}$ alkyl, $C_{3-6}$ cycloalkyl, and $C_{1-4}$ alkoxy, each substituted with 0 to 3 optional substituents independently selected from halo.

6. The method according to claim 1, wherein $R^5$ is selected from
  (a) hydrogen, halo, hydroxy, and cyano; and
  (b) $C_{1-4}$ alkyl, $C_{3-6}$ cycloalkyl, and $C_{1-4}$ alkoxy, each substituted with 0 to 3 optional substituents independently selected from halo, oxo, and phenyl which is substituted with 0 to 3 optional substituents independently selected from halo.

7. The method according to claim 1, wherein $R^6$ and $R^7$ are each independently selected from fluoro and methyl or together with the carbon atom to which they are attached form a cyclopropan-1,1-diyl or a cyclobutan-1,1-diyl.

8. The method according to claim 1, wherein each of $R^6$ and $R^7$ is methyl.

9. The method according to claim 1, wherein L is $NR^8$.

10. The method according to claim 9, wherein $R^8$ is hydrogen.

11. The method according to claim 1, wherein $R^9$ and $R^{10}$ are each independently selected from
  (a) hydrogen, halo, hydroxy, and cyano;
  (b) $C_{1-4}$ alkyl, $C_{3-6}$ cycloalkyl, and $C_{1-4}$ alkoxy, each substituted with 0 to 3 optional substituents independently selected from halo; and
  (c) phenyl and $C_{1-5}$ heteroaryl, each substituted with 0 to 3 optional substituents independently selected from halo, $C_{1-4}$ alkyl, and $C_{1-4}$ alkoxy, wherein the $C_{1-5}$ heteroaryl substituent is a monocyclic ring with 5 to 6 ring members in which 1 to 4 ring members are heteroatoms, each of the heteroatoms independently selected from N, O, and S, provided no more than one of the ring members is O or S, and wherein the $C_{1-4}$ alkyl and $C_{1-4}$ alkoxy optional substituents on phenyl and C$_{1-5}$ heteroaryl are each independently substituted with 0 to 3 optional substituents independently selected from halo.

12. The method according to claim 1, wherein R$^{11}$ and R$^{12}$ are each independently selected from
   (a) hydrogen, halo, hydroxy, and cyano; and
   (b) C$_{1-4}$ alkyl, C$_{3-6}$ cycloalkyl, and C$_{1-4}$ alkoxy, each substituted with 0 to 3 optional substituents independently selected from halo.

13. The method according to claim 1, wherein X$^{13}$ is NR$^{13}$ and X$^{14}$ is CR$^{15}$R$^{16}$.

14. The method according to claim 13, wherein R$^{13}$ is selected from
   (a) hydrogen; and
   (b) C$_{1-4}$ alkyl, which is unsubstituted or substituted with a substituent selected from cyano and oxo.

15. The method according to claim 13, wherein R$^{15}$ and R$^{16}$ are each independently selected from
   (a) hydrogen, halo, hydroxy, and cyano; and
   (b) C$_{1-4}$ alkyl, C$_{3-6}$ cycloalkyl, and C$_{1-4}$ alkoxy, each substituted with 0 to 3 optional substituents independently selected from halo.

16. The method according to claim 1, wherein r is 0.

17. The method according to claim 1, wherein s is 0.

18. The method according to claim 1, in which the compound is selected from the following compounds:
   2,2-dimethyl-N-(1-methylpiperidin-4-yl)-3-((3-methylpyridin-2-yl)oxy)propanamide;
   2,2-dimethyl-3-((3-methylpyridin-2-yl)oxy)-N-(1-methylpyrrolidin-3-yl)propanamide;
   3-((3-cyanopyridin-2-yl)oxy)-2,2-dimethyl-N-(1-methylpiperidin-4-yl)propanamide;
   (R)-3-((5-cyclopropylpyrimidin-4-yl)oxy)-2,2-dimethyl-N-(1-methylpyrrolidin-3-yl)propanamide;
   3-((5-cyclopropylpyrimidin-4-yl)oxy)-2,2-dimethyl-N-(1-methylpiperidin-4-yl)propanamide;
   3-((3-cyclopropyl-5-methylpyridin-2-yl)oxy)-2,2-dimethyl-N-(1-methylpiperidin-4-yl)propanamide;
   (R)-3-((3-cyclopropyl-5-methylpyridin-2-yl)oxy)-2,2-dimethyl-N-(1-methylpyrrolidin-3-yl)propanamide;
   3-((5-cyclopropyl-3-methylpyridin-2-yl)oxy)-2,2-dimethyl-N-(1-methylpiperidin-4-yl)propanamide;
   3-((3-cyclopropyl-6-methylpyridin-2-yl)oxy)-2,2-dimethyl-N-(1-methylpiperidin-4-yl)propanamide;
   (R)-3-((3-cyclopropyl-6-methylpyridin-2-yl)oxy)-2,2-dimethyl-N-(1-methylpyrrolidin-3-yl)propanamide;
   trans-N-(1,3-dimethylpiperidin-4-yl)-2,2-dimethyl-3-((3-(trifluoromethyl)pyridin-2-yl)oxy)propanamide;
   cis-N-(1,3-dimethylpiperidin-4-yl)-2,2-dimethyl-3-((3-(trifluoromethyl)pyridin-2-yl)oxy)propanamide;
   trans-N-(1,3-dimethylpiperidin-4-yl)-2,2-dimethyl-3-((3-(trifluoromethoxy)pyridin-2-yl)oxy)propanamide;
   cis-N-(1,3-dimethylpiperidin-4-yl)-2,2-dimethyl-3-((3-(trifluoromethoxy)pyridin-2-yl)oxy)propanamide;
   trans-N-(4-isopropyl-1-methylpyrrolidin-3-yl)-2,2-dimethyl-3-((3-(trifluoromethyl)pyridin-2-yl)oxy)propanamide;
   trans-N-(4-isopropyl-1-methylpyrrolidin-3-yl)-2,2-dimethyl-3-((3-(trifluoromethoxy)pyridin-2-yl)oxy)propanamide;
   trans-N-(1,3-dimethylpiperidin-4-yl)-2,2-dimethyl-3-((3-methylpyridin-2-yl)oxy)propanamide;
   trans-2,2-dimethyl-N-(1-methyl-4-(1-methyl-1H-pyrazol-4-yl)pyrrolidin-3-yl)-3-((3-methylpyridin-2-yl)oxy)propanamide;
   trans-2,2-dimethyl-N-(1-methyl-4-(1-methyl-1H-pyrazol-4-yl)pyrrolidin-3-yl)-3-((3-(trifluoromethyl)pyridin-2-yl)oxy)propanamide;
   trans-3-((3-cyclopropylpyridin-2-yl)oxy)-N-(1,3-dimethylpiperidin-4-yl)-2,2-dimethylpropanamide;
   cis-3-((3-cyclopropylpyridin-2-yl)oxy)-N-(1,3-dimethylpiperidin-4-yl)-2,2-dimethylpropanamide;
   trans-3-((3-cyclopropylpyridin-2-yl)oxy)-2,2-dimethyl-N-(1-methyl-4-(1-methyl-1H-pyrazol-4-yl)pyrrolidin-3-yl)propanamide;
   trans-N-(4-(1,3-dimethyl-1H-pyrazol-4-yl)-1-methylpyrrolidin-3-yl)-2,2-dimethyl-3-((3-methylpyridin-2-yl)oxy)propanamide;
   trans-3-((3-cyclopropylpyridin-2-yl)oxy)-N-(4-(1,3-dimethyl-1H-pyrazol-4-yl)-1-methylpyrrolidin-3-yl)-2,2-dimethylpropanamide;
   trans-N-(4-(1,3-dimethyl-1H-pyrazol-4-yl)-1-methylpyrrolidin-3-yl)-2,2-dimethyl-3-((3-(trifluoromethyl)pyridin-2-yl)oxy)propanamide;
   trans-N-(4-(1,5-dimethyl-1H-pyrazol-4-yl)-1-methylpyrrolidin-3-yl)-2,2-dimethyl-3-((3-methylpyridin-2-yl)oxy)propanamide;
   trans-3-((3-cyclopropylpyridin-2-yl)oxy)-N-(4-(1,5-dimethyl-1H-pyrazol-4-yl)-1-methylpyrrolidin-3-yl)-2,2-dimethylpropanamide;
   trans-N-(4-(1,5-dimethyl-1H-pyrazol-4-yl)-1-methylpyrrolidin-3-yl)-2,2-dimethyl-3-((3-(trifluoromethyl)pyridin-2-yl)oxy)propanamide;
   trans-N-(4-(1,3-dimethyl-1H-pyrazol-4-yl)-1-methylpyrrolidin-3-yl)-2,2-dimethyl-3-((3-(trifluoromethoxy)pyridin-2-yl)oxy)propanamide;
   trans-N-(4-(1,5-dimethyl-1H-pyrazol-4-yl)-1-methylpyrrolidin-3-yl)-2,2-dimethyl-3-((3-(trifluoromethoxy)pyridin-2-yl)oxy)propanamide;
   trans-N-(1,3-dimethylpiperidin-4-yl)-3-((3,5-dimethylpyridin-2-yl)oxy)-2,2-dimethylpropanamide;
   cis-N-(1,3-dimethylpiperidin-4-yl)-3-((3,5-dimethylpyridin-2-yl)oxy)-2,2-dimethylpropanamide;
   trans-N-(3-isopropyl-1-methylpiperidin-4-yl)-2,2-dimethyl-3-((3-(trifluoromethyl)pyridin-2-yl)oxy)propanamide;
   cis-N-(3-isopropyl-1-methylpiperidin-4-yl)-2,2-dimethyl-3-((3-(trifluoromethyl)pyridin-2-yl)oxy)propanamide;
   2,2-dimethyl-3-((3-(trifluoromethyl)pyridin-2-yl)oxy)-N-(1,5,5-trimethylpyrrolidin-3-yl)propanamide;
   (R)-2,2-dimethyl-N-((1-methylpyrrolidin-3-yl)methyl)-3-((3-(trifluoromethyl)pyridin-2-yl)oxy)propanamide;
   (S)-2,2-dimethyl-N-((1-methylpyrrolidin-3-yl)methyl)-3-((3-(trifluoromethyl)pyridin-2-yl)oxy)propanamide;
   3-((3-chloropyridin-2-yl)oxy)-2,2-dimethyl-N-(1-methylpiperidin-4-yl)propanamide;
   3-((3-fluoropyridin-2-yl)oxy)-2,2-dimethyl-N-(1-methylpiperidin-4-yl)propanamide;
   3-((3,5-difluoropyridin-2-yl)oxy)-2,2-dimethyl-N-(1-methylpiperidin-4-yl)propanamide;
   2,2-dimethyl-N-(1-methylpiperidin-4-yl)-3-((3-(trifluoromethyl)pyridin-2-yl)oxy)propanamide;
   2,2-dimethyl-N-(1-methylpiperidin-4-yl)-3-((4-(trifluoromethyl)pyridin-3-yl)oxy)propanamide;
   2,2-dimethyl-N-(1-methylpiperidin-4-yl)-3-((3-(trifluoromethyl)pyridin-4-yl)oxy)propanamide;
   3-((4-chloro-3-fluoropyridin-2-yl)oxy)-2,2-dimethyl-N-(1-methylpiperidin-4-yl)propanamide;
   3-((3-chloro-5-fluoropyridin-2-yl)oxy)-2,2-dimethyl-N-(1-methylpiperidin-4-yl)propanamide;

3-((6-chloro-2-methylpyridin-3-yl)oxy)-2,2-dimethyl-N-(1-methylpiperidin-4-yl)propanamide;
3-((3-cyclopropylpyridin-2-yl)oxy)-2,2-dimethyl-N-(1-methylpiperidin-4-yl)propanamide;
3-((5-chloro-3-methylpyridin-2-yl)oxy)-2,2-dimethyl-N-(1-methylpiperidin-4-yl)propanamide;
3-((3-methoxypyridin-2-yl)oxy)-2,2-dimethyl-N-(1-methylpiperidin-4-yl)propanamide;
2,2-dimethyl-N-(1-methylpiperidin-4-yl)-3-((3-methylpyridin-4-yl)oxy)propanamide;
3-((5-cyano-3-methylpyridin-2-yl)oxy)-2,2-dimethyl-N-(1-methylpiperidin-4-yl)propanamide;
2,2-dimethyl-N-(1-methylpiperidin-4-yl)-3-((2-(trifluoromethyl)pyridin-3-yl)oxy)propanamide;
(R)-3-((3-cyclopropylpyridin-2-yl)oxy)-2,2-dimethyl-N-(1-methylpyrrolidin-3-yl)propanamide;
3-((3-ethoxypyridin-2-yl)oxy)-2,2-dimethyl-N-(1-methylpiperidin-4-yl)propanamide;
trans-N-(4-(4-chlorophenyl)-1-methylpyrrolidin-3-yl)-2,2-dimethyl-3-((3-methylpyridin-2-yl)oxy)propanamide;
trans-N-(4-(4-chlorophenyl)-1-methylpyrrolidin-3-yl)-2,2-dimethyl-3-((3-(trifluoromethyl)pyridin-2-yl)oxy)propanamide;
trans-2,2-dimethyl-N-(1-methyl-4-(6-(trifluoromethyl)pyridin-3-yl)pyrrolidin-3-yl)-3-((3-methylpyridin-2-yl)oxy)propanamide;
trans-3-((3-cyclopropylpyridin-2-yl)oxy)-2,2-dimethyl-N-(1-methyl-4-(6-(trifluoromethyl)pyridin-3-yl)pyrrolidin-3-yl)propanamide;
trans-2,2-dimethyl-N-(1-methyl-4-(6-(trifluoromethyl)pyridin-3-yl)pyrrolidin-3-yl)-3-((3-(trifluoromethyl)pyridin-2-yl)oxy)propanamide;
trans-2,2-dimethyl-N-(1-methyl-4-(6-methylpyridin-3-yl)pyrrolidin-3-yl)-3-((3-methylpyridin-2-yl)oxy)propanamide;
trans-3-((3-cyclopropylpyridin-2-yl)oxy)-2,2-dimethyl-N-(1-methyl-4-(6-methylpyridin-3-yl)pyrrolidin-3-yl)propanamide;
trans-2,2-dimethyl-N-(1-methyl-4-(6-methylpyridin-3-yl)pyrrolidin-3-yl)-3-((3-(trifluoromethyl)pyridin-2-yl)oxy)propanamide;
N-(1-methylpiperidin-4-yl)-1-(((3-methylpyridin-2-yl)oxy)methyl)cyclopropane-1-carboxamide;
2,2-dimethyl-N-(1-methylpiperidin-4-yl)-3-(2-(trifluoromethyl)phenoxy)propanamide;
(R)-2,2-dimethyl-N-(1-methylpyrrolidin-3-yl)-3-(2-(trifluoromethyl)phenoxy)propanamide;
3-(2-chlorophenoxy)-2,2-dimethyl-N-(1-methylpiperidin-4-yl)propanamide;
3-(2-bromophenoxy)-2,2-dimethyl-N-(1-methylpiperidin-4-yl)propanamide;
(R)-3-(2-chlorophenoxy)-2,2-dimethyl-N-(1-methylpyrrolidin-3-yl)propanamide;
(R)-3-(2-bromophenoxy)-2,2-dimethyl-N-(1-methylpyrrolidin-3-yl)propanamide;
3-(2-cyclopropylphenoxy)-2,2-dimethyl-N-(1-methylpiperidin-4-yl)propanamide;
(R)-3-(2-cyclopropylphenoxy)-2,2,-dimethyl-N-(1-methylpyrrolidin-3-yl)propanamide;
3-(2-ethylphenoxy)-2,2-dimethyl-N-(1-methylpiperidin-4-yl)propanamide;
3-(4-cyano-2-(trifluoromethyl)phenoxy)-2,2-dimethyl-N-(1-methylpiperidin-4-yl)propanamide;
2,2-dimethyl-N-(1-methylpiperidin-4-yl)-3-phenoxypropanamide;
3-(3-cyano-2-methylphenoxy)-2,2-dimethyl-N-(1-methylpiperidin-4-yl)propanamide;
2,2-dimethyl-N-(1-methylpiperidin-4-yl)-3-(o-tolyloxy)propanamide;
3-(2-cyano-6-methylphenoxy)-2,2-dimethyl-N-(1-methylpiperidin-4-yl)propanamide;
3-(2-ethoxyphenoxy)-2,2-dimethyl-N-(1-methylpiperidin-4-yl)propanamide;
3-((2,3-dihydro-1H-inden-4-yl)oxy)-2,2-dimethyl-N-(1-methylpiperidin-4-yl)propanamide;
3-((3-cyclopropylpyrazin-2-yl)oxy)-2,2-dimethyl-N-(1-methylpiperidin-4-yl)propanamide;
1-((2-chlorophenoxy)methyl)-N-(1-methylpiperidin-4-yl)cyclopropane-1-carboxamide;
3-((3-chloro-5-methylpyridin-2-yl)oxy)-2,2-dimethyl-N-(1-methylpiperidin-4-yl)propanamide;
3-((3,6-dimethylpyridin-2-yl)oxy)-2,2-dimethyl-N-(1-methylpiperidin-4-yl)propanamide;
3-((3,5-dimethylpyridin-2-yl)oxy)-2,2-dimethyl-N-(1-methylpiperidin-4-yl)propanamide;
3-((3-ethylpyridin-2-yl)oxy)-2,2-dimethyl-N-(1-methylpiperidin-4-yl)propanamide;
(R)-3-((3-ethylpyridin-2-yl)oxy)-2,2-dimethyl-N-(1-methylpyrrolidin-3-yl)propanamide;
3-((3-ethylpyrazin-2-yl)oxy)-2,2-dimethyl-N-(1-methylpiperidin-4-yl)propanamide;
3-((3,4-dimethylpyridin-2-yl)oxy)-2,2-dimethyl-N-(1-methylpiperidin-4-yl)propanamide;
1-(((3-cyclopropylpyridin-2-yl)oxy)methyl)-N-(1-methylpiperidin-4-yl)cyclobutane-1-carboxamide;
3-((3-(difluoromethyl)pyridin-2-yl)oxy)-2,2-dimethyl-N-(1-methylpiperidin-4-yl)propanamide;
2,2-dimethyl-3-((3-methyl-5-(trifluoromethyl)pyridin-2-yl)oxy)-N-(1-methylpiperidin-4-yl)propanamide;
2,2-dimethyl-N-(1-methylpiperidin-4-yl)-3-((3-(trifluoromethoxy)pyridin-2-yl)oxy)propanamide;
trans-N-(4-(4-chlorophenyl)-1-methylpyrrolidin-3-yl)-3-((3,5-dimethylpyridin-2-yl)oxy)-2,2-dimethylpropanamide;
trans-N-(4-(4-chlorophenyl)-1-methylpyrrolidin-3-yl)-3-((3-cyclopropylpyridin-2-yl)oxy)-2,2-dimethylpropanamide;
trans-N-(4-ethoxy-1-methylpyrrolidin-3-yl)-3-(2-ethylphenoxy)-2,2-dimethylpropanamide;
trans-3-(2-ethylphenoxy)-N-(4-methoxy-1-methylpyrrolidin-3-yl)-2,2-dimethylpropanamide;
3-(2-ethylphenoxy)-2,2-dimethyl-N-(1-methyl-4-phenylpyrrolidin-3-yl)propanamide;
3-((6-chloro-4-(trifluoromethyl)pyridazin-3-yl)oxy)-2,2-dimethyl-N-(1-methylpiperidin-4-yl)propanamide;
3-(furo[3,2-c]pyridin-4-yloxy)-2,2-dimethyl-N-(1-methylpiperidin-4-yl)propanamide;
3-((5-bromo-3-(trifluoromethyl)pyridin-2-yl)oxy)-2,2-dimethyl-N-(1-methylpiperidin-4-yl)propanamide;
2,2-dimethyl-3-((5-methyl-3-(trifluoromethyl)pyridin-2-yl)oxy)-N-(1-methylpiperidin-4-yl)propanamide;
2,2-dimethyl-N-(1-methylpiperidin-4-yl)-3-(2-(trifluoromethoxy)phenoxy)propanamide;
trans-N-(1-(cyanomethyl)-4-(6-methylpyridin-3-yl)pyrrolidin-3-yl)-2,2-dimethyl-3-((3-(trifluoromethyl)pyridin-2-yl)oxy)propanamide;
N-((3S,4S)-1,3-dimethylpiperidin-4-yl)-2,2-dimethyl-3-((3-(trifluoromethyl)pyridin-2-yl)oxy)propanamide;
N-((3R,4R)-1,3-dimethylpiperidin-4-yl)-2,2-dimethyl-3-((3-(trifluoromethyl)pyridin-2-yl)oxy)propanamide;
N-((3S,4S)-1,3-dimethylpiperidin-4-yl)-2,2-dimethyl-3-((3-(trifluoromethoxy)pyridin-2-yl)oxy)propanamide;

N-((3R,4R)-1,3-dimethylpiperidin-4-yl)-2,2-dimethyl-3-((3-(trifluoromethoxy)pyridin-2-yl)oxy)propanamide;
trans-N-(1,3-dimethylpiperidin-4-yl)-2,2-dimethyl-3-((3-(trifluoromethyl)pyridin-2-yl)oxy)propanamide;
trans-N-(3-ethyl-1-methylpiperidin-4-yl)-2,2-dimethyl-3-((3-(trifluoromethyl)pyridin-2-yl)oxy)propanamide;
cis-N-(3-ethyl-1-methylpiperidin-4-yl)-2,2-dimethyl-3-((3-(trifluoromethyl)pyridin-2-yl)oxy)propanamide;
2,2-dimethyl-3-(trifluoromethyl)pyridin-2-yl)oxy)-N-(1,3,3-trimethylpiperidin-4-yl)propanamide;
N-(3-fluoro-1-methylpiperidin-4-yl)-2,2-dimethyl-3-(trifluoromethyl)pyridin-2-yl)oxy)propanamide;
2,2-dimethyl-N-(5-methyl-5-azaspiro[2.5]octan-8-yl)-3-((3-(trifluoromethyl)pyridin-2-yl)oxy)propanamide;
N-(trans-3-ethyl-1-methylpiperidin-4-yl)-2,2-dimethyl-3-(trifluoromethoxy)pyridin-2-yl)oxy)propanamide;
N-(cis-3-ethyl-1-methylpiperidin-4-yl)-2,2-dimethyl-3-((3-(trifluoromethoxy)pyridin-2-yl)oxy)propanamide;
N-((3 S,4S)-3-fluoro-1-methylpiperidin-4-yl)-2,2-dimethyl-3-(trifluoromethyl)pyridin-2-yl)oxy)propanamide;
N-(3,3-difluoro-1-methylpiperidin-4-yl)-2,2-dimethyl-3-((3-(trifluoromethyl)pyridin-2-yl)oxy)propanamide;
2,2-dimethyl-N-(5-methyl-5-azaspiro[2.5]octan-8-yl)-3-(trifluoromethoxy)pyridin-2-yl)oxy)propanamide;
N-(3-chloro-1-methylpiperidin-4-yl)-2,2-dimethyl-3-((3-(trifluoromethyl)pyridin-2-yl)oxy)propanamide;
N-((3 S,4S)-3-fluoro-1-methylpiperidin-4-yl)-2,2-dimethyl-3-((3-methylpyridin-2-yl)oxy)propanamide;
3-((3,5-dimethylpyridin-2-yl)oxy)-N-((3S,4S)-3-fluoro-1-methylpiperidin-4-yl)-2,2-dimethylpropanamide;
3-((3-cyclopropylpyridin-2-yl)oxy)-N-((3 S,4 S)-3-fluoro-1-methylpiperidin-4-yl)-2,2-dimethylpropanamide;
N-((3 S,4S)-3-fluoro-1-methylpiperidin-4-yl)-2,2-dimethyl-3-(trifluoromethoxy)pyridin-2-yl)oxy)propanamide;
trans-N-(3-(1-(difluoromethyl)-1H-pyrazol-4-yl)-1-methylpiperidin-4-yl)-2,2-dimethyl-3-(trifluoromethyl)pyridin-2-yl)oxy)propanamide;
trans-N-(3-(1-(difluoromethyl)-1H-pyrazol-4-yl)-1-methylpiperidin-4-yl)-2,2-dimethyl-3-(trifluoromethoxy)pyridin-2-yl)oxy)propanamide;
trans-N-(3-ethyl-1-methylpiperidin-4-yl)-2,2-dimethyl-3-((3-methylpyridin-2-yl)oxy)propanamide;
trans-3-((3,5-dimethylpyridin-2-yl)oxy)-N-(3-ethyl-1-methylpiperidin-4-yl)-2,2-dimethylpropanamide;
cis-N-(1,2-dimethylpiperidin-4-yl)-2,2-dimethyl-3-((3-(trifluoromethyl)pyridin-2-yl)oxy)propanamide;
trans-N-(4-fluoropyrrolidin-3-yl)-2,2-dimethyl-3-((3-(trifluoromethyl)pyridin-2-yl)oxy)propanamide;
N-(4,4-difluoropyrrolidin-3-yl)-2,2-dimethyl-3-((3-(trifluoromethyl)pyridin-2-yl)oxy)propanamide;
2,2-dimethyl-3-((3-(trifluoromethyl)pyridin-2-yl)oxy)-N-(1,2,2-trimethylpiperidin-4-yl)propanamide;
trans-N-(1,5-dimethylpyrrolidin-3-yl)-2,2-dimethyl-3-((3-(trifluoromethyl)pyridin-2-yl)oxy)propanamide;
cis-N-(1,5-dimethylpyrrolidin-3-yl)-2,2-dimethyl-3-((3-(trifluoromethyl)pyridin-2-yl)oxy)propanamide;
trans-N-(1,2-dimethylpiperidin-4-yl)-2,2-dimethyl-3-((3-(trifluoromethoxy)pyridin-2-yl)oxy)propanamide;
cis-N-(1,2-dimethylpiperidin-4-yl)-2,2-dimethyl-3-((3-(trifluoromethoxy)pyridin-2-yl)oxy)propanamide;
N-(2-ethyl-1-methylpiperidin-4-yl)-2,2-dimethyl-3-((3-(trifluoromethyl)pyridin-2-yl)oxy)propanamide;
2,2-dimethyl-N-(5-methyl-5-azaspiro[2.4]heptan-7-yl)-3-((3-(trifluoromethyl)pyridin-2-yl)oxy)propanamide;
trans-N-(1,2-dimethylpiperidin-4-yl)-2,2-dimethyl-3-((3-(trifluoromethyl)pyridin-2-yl)oxy)propanamide;
N-((3R,4R)-1,3-dimethylpiperidin-4-yl)-3-((3,5-dimethylpyridin-2-yl)oxy)-2,2-dimethylpropanamide;
N-((3S,4S)-1,3-dimethylpiperidin-4-yl)-3-((3,5-dimethylpyridin-2-yl)oxy)-2,2-dimethylpropanamide;
N-((3R,4R)-1,3-dimethylpiperidin-4-yl)-2,2-dimethyl-3-((3-methylpyridin-2-yl)oxy)propanamide;
N-((3S,4S)-1,3-dimethylpiperidin-4-yl)-2,2-dimethyl-3-((3-methylpyridin-2-yl)oxy)propanamide;
N-((3R,4R)-3-ethyl-1-methylpiperidin-4-yl)-2,2-dimethyl-3-((3-(trifluoromethyl)pyridin-2-yl)oxy)propanamide;
N-((3S,4S)-3-ethyl-1-methylpiperidin-4-yl)-2,2-dimethyl-3-((3-(trifluoromethyl)pyridin-2-yl)oxy)propanamide;
N-(2-ethyl-1-methylpiperidin-4-yl)-2,2-dimethyl-3-((3-(trifluoromethoxy)pyridin-2-yl)oxy)propanamide;
3-((3-cyclopropylpyridin-2-yl)oxy)-N-((2R,4R)-1,2-dimethylpiperidin-4-yl)-2,2-dimethylpropanamide;
(R)-2,2-dimethyl-N-(5-methyl-5-azaspiro[2.4]heptan-7-yl)-3-((3-(trifluoromethyl)pyridin-2-yl)oxy)propanamide;
trans-N-(2-ethyl-1-methylpyrrolidin-3-yl)-2,2-dimethyl-3-((3-(trifluoromethyl)pyridin-2-yl)oxy)propanamide;
(R)-2,2-dimethyl-N-(5-methyl-5-azaspiro[2.4]heptan-7-yl)-3-((3-(trifluoromethoxy)pyridin-2-yl)oxy)propanamide;
2,2-dimethyl-N-(5-methyl-5-azaspiro[3.4]octan-8-yl)-3-((3-(trifluoromethyl)pyridin-2-yl)oxy)propanamide;
N-((2S,4S)-1,2-dimethylpiperidin-4-yl)-2,2-dimethyl-3-((3-(trifluoromethoxy)pyridin-2-yl)oxy)propanamide;
(R)-2,2-dimethyl-N-(5-methyl-5-azaspiro[2.4]heptan-7-yl)-3-(3-methylpyridin-2-yl)oxy)propanamide;
(R)-3-((3,5-dimethylpyridin-2-yl)oxy)-2,2-dimethyl-N-(5-methyl-5-azaspiro[2.4]heptan-7-yl)propanamide;
N,2,2-trimethyl-N-(trans-3-(o-tolyl)piperidin-4-yl)-3-((3-(trifluoromethyl)pyridin-2-yl)oxy)propanamide;
N,2,2-trimethyl-N-(cis-3-(o-tolyl)piperidin-4-yl)-3-((3-(trifluoromethyl)pyridin-2-yl)oxy)propanamide;
2,2-dimethyl-N-(trans-3-(o-tolyl)piperidin-4-yl)-3-((3-(trifluoromethyl)pyridin-2-yl)oxy)propanamide;
N-((3S,4S)-3-fluoropiperidin-4-yl)-2,2-dimethyl-3-((3-(trifluoromethyl)pyridin-2-yl)oxy)propanamide;
N-(3,3-difluoropiperidin-4-yl)-2,2-dimethyl-3-((3-(trifluoromethyl)pyridin-2-yl)oxy)propanamide;
N-((3S,4S)-3-fluoropiperidin-4-yl)-N,2,2-trimethyl-3-((3-(trifluoromethyl)pyridin-2-yl)oxy)propanamide;
2,2-dimethyl-N-(trans-1-methyl-3-(o-tolyl)piperidin-4-yl)-3-((3-(trifluoromethyl)pyridin-2-yl)oxy)propanamide;
trans-N,2,2-trimethyl-N-(3-phenylpiperidin-4-yl)-3-((3-(trifluoromethyl)pyridin-2-yl)oxy)propanamide;
2,2-dimethyl-N-(cis-1-methyl-3-phenylpiperidin-4-yl)-3-((3-(trifluoromethyl)pyridin-2-yl)oxy)propanamide;
2,2-dimethyl-N-(trans-1-methyl-3-phenylpiperidin-4-yl)-3-((3-(trifluoromethyl)pyridin-2-yl)oxy)propanamide;
N-(trans-1,4-dimethylpyrrolidin-3-yl)-2,2-dimethyl-3-((3-(trifluoromethyl)pyridin-2-yl)oxy)propanamide;
2,2-dimethyl-N-(cis-1-methyl-3-phenylpiperidin-4-yl)-3-((3-(trifluoromethoxy)pyridin-2-yl)oxy)propanamide;
2,2-dimethyl-N-(trans-1-methyl-3-phenylpiperidin-4-yl)-3-((3-(trifluoromethoxy)pyridin-2-yl)oxy)propanamide;
trans-3-(o-tolyl)piperidin-4-yl 2,2-dimethyl-3-((3-(trifluoromethyl)pyridin-2-yl)oxy)propanoate;

2,2-dimethyl-N-(trans-1-methyl-4-(1-methyl-1H-pyrazol-4-yl)piperidin-3-yl)-3-((3-(trifluoromethyl)pyridin-2-yl)oxy)propanamide;
trans-3-(2-methylpyridin-3-yl)piperidin-4-yl 2,2-dimethyl-3-((3-(trifluoromethyl)pyridin-2-yl)oxy)propanoate;
trans-3-phenylpiperidin-4-yl 2,2-dimethyl-3-((3-(trifluoromethyl)pyridin-2-yl)oxy)propanoate;
N,2,2-trimethyl-N-(trans-3-(2-methylpyridin-3-yl)piperidin-4-yl)-3-((3-(trifluoromethyl)pyridin-2-yl)oxy)propanamide;
(S)-2,2-dimethyl-N-(5-methyl-5-azaspiro[2.4]heptan-7-yl)-3-((3-(trifluoromethyl)pyridin-2-yl)oxy)propanamide;
2,2-dimethyl-N-(4-methyl-4-azaspiro[2.5]octan-7-yl)-3-((3-(trifluoromethoxy)pyridin-2-yl)oxy)propanamide;
2,2-dimethyl-N-(4-methyl-4-azaspiro[2.5]octan-7-yl)-3-((3-(trifluoromethyl)pyridin-2-yl)oxy)propanamide;
N-((2R,4R)-1,2-dimethylpiperidin-4-yl)-2,2-dimethyl-3-((3-(trifluoromethyl)pyridin-2-yl)oxy)propanamide;
N-((2R,4S)-1,2-dimethylpiperidin-4-yl)-2,2-dimethyl-3-((3-(trifluoromethyl)pyridin-2-yl)oxy)propanamide;
N-((2S,4S)-1,2-dimethylpiperidin-4-yl)-2,2-dimethyl-3-((3-(trifluoromethyl)pyridin-2-yl)oxy)propanamide;
N-((2R,4R)-1,2-dimethylpiperidin-4-yl)-2,2-dimethyl-3-((3-(trifluoromethoxy)pyridin-2-yl)oxy)propanamide;
N-(trans-1,4-dimethylpyrrolidin-3-yl)-2,2-dimethyl-3-((3-(trifluoromethoxy)pyridin-2-yl)oxy)propanamide;
3-((3-cyclopropylpyridin-2-yl)oxy)-N-(trans-1,4-dimethylpyrrolidin-3-yl)-2,2-dimethylpropanamide;
N-(trans-1,4-dimethylpyrrolidin-3-yl)-2,2-dimethyl-3-((3-methylpyridin-2-yl)oxy)propanamide;
3-((3,5-dimethylpyridin-2-yl)oxy)-N-(trans-1,4-dimethylpyrrolidin-3-yl)-2,2-dimethylpropanamide;
trans-N-(1-(cyanomethyl)-3-methylpiperidin-4-yl)-2,2-dimethyl-3-((3-(trifluoromethoxy)pyridin-2-yl)oxy)propanamide;
3-((3-(chlorodifluoromethoxy)pyridin-2-yl)oxy)-N-((3S,4S)-1,3-dimethylpiperidin-4-yl)-2,2-dimethylpropanamide;
trans-3-(2-chlorophenoxy)-N-(1,3-dimethylpiperidin-4-yl)-2,2-dimethylpropanamide;
3-(2-chlorophenoxy)-N-((3S,4S)-3-fluoropiperidin-4-yl)-2,2-dimethylpropanamide;
3-(2-chlorophenoxy)-N-((3S,4S)-3-fluoro-1-methylpiperidin-4-yl)-2,2-dimethylpropanamide;
trans-N-(1,3-dimethylpiperidin-4-yl)-2,2-difluoro-3-((3-(trifluoromethyl)pyridin-2-yl)oxy)propanamide;
3-(2-chlorophenoxy)-2,2-dimethyl-N-((3S,4S)-3-methylpiperidin-4-yl)propanamide;
cis-N-(1,2-dimethylpiperidin-4-yl)-2,2-difluoro-3-((3-(trifluoromethyl)pyridin-2-yl)oxy)propanamide;
trans-3-((3-cyclopropylpyridin-2-yl)oxy)-N-(1,3-dimethylpiperidin-4-yl)-2,2-difluoropropanamide;
3-(2-chlorophenoxy)-N-((3S,4S)-1,3-dimethylpiperidin-4-yl)-2,2-dimethylpropanamide;
3-((3-cyclopropylpyridin-2-yl)oxy)-N-((2R,4R)-1,2-dimethylpiperidin-4-yl)-2,2-difluoropropanamide;
3-(2-fluorophenoxy)-2,2-dimethyl-N-(1-methylpiperidin-4-yl)propanamide;
3-(2-fluorophenoxy)-2,2-dimethyl-N-((3S,4S)-3-methylpiperidin-4-yl)propanamide;
2,2-difluoro-N-((3S,4S)-3-fluoropiperidin-4-yl)-3-((3-(trifluoromethyl)pyridin-2-yl)oxy)propanamide;
3-((3-cyclopropylpyridin-2-yl)oxy)-2,2-difluoro-N-((3S,4S)-3-fluoropiperidin-4-yl)propanamide;
N-(trans-1,3-dimethylpiperidin-4-yl)-2,2-difluoro-3-((3-methylpyridin-2-yl)oxy)propanamide;
N-(trans-1,3-dimethylpiperidin-4-yl)-2,2-difluoro-3-((3-(trifluoromethoxy)pyridin-2-yl)oxy)propanamide;
2,2-difluoro-N-((3S,4S)-3-fluoropiperidin-4-yl)-3-((3-methylpyridin-2-yl)oxy)propanamide;
N-((3S,4S)-1,3-dimethylpiperidin-4-yl)-3-(2-fluorophenoxy)-2,2-dimethylpropanamide;
3-(3-fluorophenoxy)-2,2-dimethyl-N-(1-methylpiperidin-4-yl)propanamide;
3-(4-fluorophenoxy)-2,2-dimethyl-N-(1-methylpiperidin-4-yl)propanamide;
N-((2R,4R)-1,2-dimethylpiperidin-4-yl)-2,2-difluoro-3-((3-methylpyridin-2-yl)oxy)propanamide;
N-((2R,4R)-1,2-dimethylpiperidin-4-yl)-2,2-difluoro-3-((3-(trifluoromethoxy)pyridin-2-yl)oxy)propanamide;
2,2-difluoro-N-((3S,4S)-3-fluoropiperidin-4-yl)-3-((3-(trifluoromethoxy)pyridin-2-yl)oxy)propanamide;
2,2-difluoro-N-((3S,4S)-3-methylpiperidin-4-yl)-3-((3-(trifluoromethyl)pyridin-2-yl)oxy)propanamide;
3-((3-cyclopropylpyridin-2-yl)oxy)-2,2-difluoro-N-((3S,4S)-3-methylpiperidin-4-yl)propanamide;
2,2-difluoro-N-((3S,4S)-3-methylpiperidin-4-yl)-3-((3-(trifluoromethoxy)pyridin-2-yl)oxy)propanamide;
3-((3-cyclopropylpyridin-2-yl)oxy)-2,2-difluoro-N-((2R,4R)-2-methylpiperidin-4-yl)propanamide;
2,2-difluoro-N42R,4R)-2-methylpiperidin-4-yl)-3-((3-(trifluoromethoxy)pyridin-2-yl)oxy)propanamide;
3-(2-chlorophenoxy)-2,2-dimethyl-N-(piperidin-4-yl)propanamide;
3-((3,5-dimethylpyridin-2-yl)oxy)-N43R,4R)-3-fluoropiperidin-4-yl)-2,2-dimethylpropanamide;
3-(2-chlorophenoxy)-2,2-difluoro-N-(1-methylpiperidin-4-yl)propanamide;
3-(2-chlorophenoxy)-2,2-difluoro-N43S,4S)-3-methylpiperidin-4-yl)propanamide;
3-(4-chlorophenoxy)-2,2-dimethyl-N-(1-methylpiperidin-4-yl)propanamide;
N-((2R,4R)-1,2-dimethylpiperidin-4-yl)-3-((3,5-dimethylpyridin-2-yl)oxy)-2,2-dimethylpropanamide; and
a pharmaceutically acceptable salt of any one of the aforementioned compounds.

19. A method of treating a disease, disorder or condition in a subject, the method comprising administering to the subject a pharmaceutical composition comprising:
a compound or pharmaceutically acceptable salt as defined in claim 1; and
a pharmaceutically acceptable excipient;
wherein the disease, disorder or condition is pain.

* * * * *